(12) United States Patent
Sakai et al.

(10) Patent No.: US 7,183,276 B2
(45) Date of Patent: Feb. 27, 2007

(54) AZOLE COMPOUNDS

(75) Inventors: Nozomu Sakai, Kobe (JP); Yu Momose, Takarazuka (JP); Katsuhito Murase, Suita (JP); Masatoshi Hazama, Ikeda (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 99 days.

(21) Appl. No.: 10/505,742

(22) PCT Filed: Feb. 27, 2003

(86) PCT No.: PCT/JP03/02217

§ 371 (c)(1),
(2), (4) Date: Aug. 25, 2004

(87) PCT Pub. No.: WO03/072554

PCT Pub. Date: Sep. 4, 2003

(65) Prior Publication Data

US 2005/0090534 A1    Apr. 28, 2005

(30) Foreign Application Priority Data

Feb. 28, 2002  (JP) .............................. 2002-053933

(51) Int. Cl.
| | |
|---|---|
| A61K 31/5377 | (2006.01) |
| A61K 31/421 | (2006.01) |
| A61K 31/454 | (2006.01) |
| A61K 31/541 | (2006.01) |
| C07D 413/04 | (2006.01) |
| C07D 279/12 | (2006.01) |
| C07F 9/653 | (2006.01) |
| C07D 211/46 | (2006.01) |

(52) U.S. Cl. ............................... 514/228.2; 514/236.8; 514/377; 514/322; 544/58.4; 544/137; 546/199; 548/113

(58) Field of Classification Search ............... 544/58.4, 544/137; 546/199; 548/113
See application file for complete search history.

(56) References Cited

U.S. PATENT DOCUMENTS

2002/0103185 A1* 8/2002 Sanner et al. .......... 514/217.09

FOREIGN PATENT DOCUMENTS

| EP | 0526877 A2 | 2/1993 |
|---|---|---|
| EP | 0630894 A1 | 12/1994 |
| EP | 0987265 A1 | 3/2000 |
| GB | 1425505 A | 2/1976 |
| JP | 52-083747 | 7/1977 |
| JP | 71014458 | 8/1993 |
| WO | WO 97/36882 | 10/1997 |
| WO | WO 99/02505 | 1/1999 |
| WO | WO 00/01679 | 1/2000 |
| WO | WO 01/10866 A1 | 2/2001 |
| WO | WO 01/14372 A2 | 3/2001 |
| WO | WO 01/77101 A1 | 10/2001 |
| WO | WO 02/20484 A1 | 3/2002 |
| WO | WO 03/000257 A1 | 1/2003 |

OTHER PUBLICATIONS

Ushijima et al. Analytical Science & Technology 1995, 8(4), 545-51. *CAS Abstract attached.*
Saito et al. Journal of Chromatography, B: Biomedical Applications 1995, 674(2), 167-75. *CAS Abstract attached.*
Saito et al. Analytical Sciences 1994, 10(4), 679-81. *CAS Abstract attached.*
T. Jakobiec, et al., "Synthesis of Derivatives of 2-Amino-4-P-Chlorophenylthiazole-5-Acetic Acid", Archivum Immunologiae et Thereapiae Experimentalis, (1978), pp. 935-941, vol. 26.
S. Bengtsson, et al., "Compounds Related to Clomethiazole—VI. Synthesis of Some Reference Compounds in Connection with Biotransformation Studies", Acta Pharm. Suec., (1982, pp. 37-42, vol. 19, No. 1.

* cited by examiner

Primary Examiner—Joseph K. McKane
Assistant Examiner—Jason M. Nolan
(74) Attorney, Agent, or Firm—Elaine M. Ramesh; Mark Chao

(57) ABSTRACT

The present invention provides a compound represented by the formula (I)

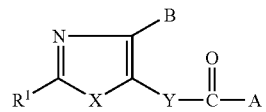

wherein $R^1$ is a hydrogen atom, a halogen atom, an optionally substituted hydrocarbon group, an optionally substituted heterocyclic group, an optionally substituted hydroxy group, an optionally substituted thiol group or an optionally substituted amino group, A is an optionally substituted cyclic amino group or —$NR^2$—W—D wherein $R^2$ is a hydrogen atom or an alkyl group, W is a bond or a divalent acyclic hydrocarbon group, and D is an optionally substituted cyclic group, an optionally substituted amino group or an optionally substituted acyl group, B is an optionally substituted hydrocarbon group or an optionally substituted heterocyclic group, X is an oxygen atom, a sulfur atom or an optionally substituted nitrogen atom, and Y is a bond or a divalent acyclic hydrocarbon group, or a salt thereof, which is useful for the prophylaxis or treatment of diabetic neuropathy and the like.

10 Claims, No Drawings

AZOLE COMPOUNDS

This application is the National Phase filing of International Patent Application No. PCT/JP03/02217, filed Feb. 27, 2003.

TECHNICAL FIELD

The present invention relates to an azole compound having a promoting action on the production or secretion of a neurotrophic factor and useful for the prophylaxis or treatment of diabetic neuropathy and the like.

BACKGROUND ART

Azole compounds are described in, for example, the following references.

(1) WO97/36882 describes that a compound represented by the formula

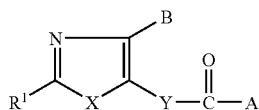

wherein $R^1$ is a halogen atom, an optionally substituted heterocyclic group, an optionally substituted hydroxy group, an optionally substituted thiol group or an optionally substituted amino group, A is an optionally substituted acyl group, an optionally substituted heterocyclic group, an optionally substituted hydroxy group or an optionally esterified or amidated carboxyl group, B is an optionally substituted aromatic group and Y is a divalent aliphatic hydrocarbon group is useful as an agent for the prophylaxis or treatment of diabetes.

(2) WO01/14372 describes that a compound represented by the formula

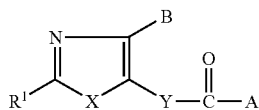

wherein $R^1$ is a halogen atom, an optionally substituted heterocyclic group, an optionally substituted hydroxy group, an optionally substituted thiol group or an optionally substituted amino group, A is an optionally substituted acyl group, an optionally substituted heterocyclic group, an optionally substituted hydroxy group or an optionally esterified or amidated carboxyl group, B is an optionally substituted aromatic group, X is an oxygen atom, a sulfur atom or an optionally substituted nitrogen atom, and Y is a divalent hydrocarbon group or heterocyclic group is useful as a neurotrophin production or secretion promoter.

(3) WO00/01679 describes that a compound represented by the formula

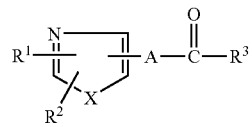

wherein $R^1$ is an aromatic hydrocarbon group or an aromatic heterocyclic group, each of which is optionally substituted; $R^2$ is a hydrogen or an optionally substituted hydrocarbon group;
X is O, S or a group represented by $-NR^4-$ wherein $R^4$ is a hydrogen or an optionally substituted alkyl group; A is an aromatic hydrocarbon group or an aromatic heterocyclic group, each of which is optionally substituted; $R^3$ is a group represented by the formula $-OR^5$ wherein $R^5$ is a hydrogen or an optionally substituted hydrocarbon group or $-NR^6R^7$ wherein $R^6$ and $R^7$ are the same or different and each is a hydrogen or an optionally substituted hydrocarbon group, and $R^6$ and $R^7$ may form a ring together with the adjacent nitrogen atom is useful as a retinoid-related receptor function regulator.

DISCLOSURE OF THE INVENTION

An object of the present invention is to provide an azole compound having a superior promoting action on the production or secretion of a neurotrophic factor and is of lower toxicity.

The present inventors have found that a compound represented by the formula (I)

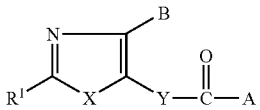

wherein $R^1$ is a hydrogen atom, a halogen atom, an optionally substituted hydrocarbon group, an optionally substituted heterocyclic group, an optionally substituted hydroxy group, an optionally substituted thiol group or an optionally substituted amino group, B is an optionally substituted hydrocarbon group or an optionally substituted heterocyclic group, X is an oxygen atom, a sulfur atom or an optionally substituted nitrogen atom, A is an optionally substituted cyclic amino group or $-NR^2-W-D$ wherein $R^2$ is a hydrogen atom or an alkyl group, W is a bond or a divalent acyclic hydrocarbon group, and D is an optionally substituted cyclic group, an optionally substituted amino group or an optionally substituted acyl group, and Y is a bond or a divalent acyclic hydrocarbon group, which is structurally characterized in that a group represented by the formula: $-Y-CO-A$ wherein A and Y are as defined above, is bonded at the 5-position of an azole ring has, based on the characteristic chemical structure, a superior neurotrophic factor producing or secreting action, and completed the present invention based on this finding.

Accordingly, the present invention relates to
1) a compound represented by the formula (I) or a salt thereof (hereinafter sometimes to be abbreviated as compound (I));
2) the compound (I) wherein $R^1$ is an optionally substituted heterocyclic group;
3) the compound (I) wherein A is an optionally substituted cyclic amino group;
4) the compound (I) wherein A is —$NR^2$—W—D wherein $R^2$ is a hydrogen atom or an alkyl group, W is a bond or a divalent acyclic hydrocarbon group, and D is an optionally substituted cyclic group, an optionally substituted amino group or an optionally substituted acyl group;
5) the compound of the aforementioned 4), wherein D is an optionally substituted cyclic group;
6) the compound (I) wherein B is an optionally substituted $C_{6-14}$ aryl group;
7) the compound (I) wherein X is an oxygen atom;
8) the compound (I) wherein Y is $C_{1-4}$ alkylene;
9) the compound (I) which is 3-[2-(1H-benzimidazol-1-yl)-4-(4-chlorophenyl)-5-oxazolyl]-N-[4-(diethylphosphonomethyl)phenyl]propionamide,
3-[4-(4-chlorophenyl)-2-(4-morpholinyl)-5-oxazolyl]-N-[4-(diethylphosphonomethyl)phenyl]propionamide,
3-[4-(4-chlorophenyl)-2-phenyl-5-oxazolyl]-N-[4-(dimethylphosphonomethyl)phenyl]propionamide,
3-[2-(1H-benzimidazol-1-yl)-4-(4-chlorophenyl)-5-oxazolyl]-N-{4-[(2-oxide-1,3,2-dioxaphosphinan-2-yl)methyl]phenyl}propionamide,
4-[2-(1H-benzimidazol-1-yl)-4-(4-chlorophenyl)-5-oxazolyl]-N-[(4-dimethylphosphonomethyl)phenyl]butanamide,
1-{3-[2-(1H-benzimidazol-1-yl)-4-(4-chlorophenyl)-5-oxazolyl]propanoyl}-4-piperidinol,
4-{3-[2-(1H-benzimidazol-1-yl)-4-(4-chlorophenyl)-5-oxazolyl]propanoyl}thiomorpholine-1,1-dioxide,
4-[2-(1H-benzimidazol-1-yl)-4-(4-chlorophenyl)-5-oxazolyl]-N-[(4-diethylphosphonomethyl)phenyl]butanamide, or
4-{3-[4-(4-chlorophenyl)-2-(1-methyl-1H-indol-3-yl)-5-oxazolyl]propanoyl}thiomorpholine-1,1-dioxide; 10) a pharmaceutical agent comprising compound (I) or a prodrug thereof;
11) the pharmaceutical agent of the aforementioned 10), which is an agent for the prophylaxis or treatment of diabetic neuropathy;
12) the pharmaceutical agent of the aforementioned 10), which is an agent for ameliorating pain;
13) an agent for promoting production or secretion of a neurotrophic factor which comprises compound (I) or a prodrug thereof;
14) use of compound (I) or a prodrug thereof for the production of an agent for the prophylaxis or treatment of diabetic neuropathy;
15) a method for the prophylaxis or treatment of diabetic neuropathy in a mammal, which comprises administering an effective amount of compound (I) or a prodrug thereof to the mammal;
16) use of compound (I) or a prodrug thereof for the production of an agent for ameliorating pain;
17) a method for ameliorating pain in a mammal, which comprises administering an effective amount of compound (I) or a prodrug thereof to the mammal;
18) use of compound (I) or a prodrug thereof for the production of an agent for promoting production or secretion of a neurotrophic factor;
19) a method for promoting production or secretion of a neurotrophic factor in a mammal, which comprises administering an effective amount of compound (I) or a prodrug thereof to the mammal; and the like.

The compound represented by the formula (I) is described in detail in the following.

In the formula (I), as the "halogen atom" for $R^1$, for example, a fluorine atom, a chlorine atom, a bromine atom and an iodine atom can be mentioned. Of these, a fluorine atom and a chlorine atom are preferable.

As the "hydrocarbon group" in the "optionally substituted hydrocarbon group" for $R^1$, for example, an aliphatic hydrocarbon group, an alicyclic hydrocarbon group, an aromatic hydrocarbon group, an aromatic aliphatic hydrocarbon group, an alicyclic aliphatic hydrocarbon group and the like can be mentioned.

As the aliphatic hydrocarbon group, for example, a straight-chain or branched aliphatic hydrocarbon group having 1 to 15 carbon atoms, specifically an alkyl group, an alkenyl group, an alkynyl group and the like can be mentioned.

As preferable examples of the alkyl group, $C_{1-10}$ alkyl groups such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As preferable examples of the alkenyl group, $C_{2-10}$ alkenyl groups such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As preferable examples of the alkynyl groups, $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the alicyclic hydrocarbon group, for example, a saturated or unsaturated alicyclic hydrocarbon group having 3 to 12 carbon atoms, specifically a cycloalkyl group, a cycloalkenyl group, a cycloalkadienyl group and the like, can be mentioned.

As preferable examples of the cycloalkyl group, $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like can be mentioned.

As preferable examples of the cycloalkenyl group, $C_{3-10}$ cycloalkenyl groups such as 2-cyclopenten-1-yl, 3-cyclopenten-1-yl, 2-cyclohexen-1-yl, 3-cyclohexen-1-yl and the like can be mentioned.

As preferable examples of the cycloalkadienyl group, $C_{4-10}$ cycloalkadienyl groups such as 2,4-cyclopentadien-1-yl, 2,4-cyclohexadien-1-yl, 2,5-cyclohexadien-1-yl and the like can be mentioned.

As the aromatic hydrocarbon group, for example, a $C_{6-14}$ aryl group and the like can be mentioned. As preferable examples of the aryl group, phenyl, naphthyl, anthryl, phenanthryl, acenaphthylenyl, biphenylyl, indenyl and the like can be mentioned. Of these, phenyl, naphthyl and the like are preferable. The aryl group may be partially saturated and as the partially saturated aryl group, for example, dihydroindenyl, tetrahydronaphthyl and the like can be mentioned.

As the aromatic aliphatic hydrocarbon group, for example, a $C_{7-14}$ aromatic aliphatic hydrocarbon group, and concretely, an aralkyl group, an arylalkenyl group, an arylalkynyl group and the like can be mentioned.

As preferable examples of the aralkyl group, $C_{7-14}$ aralkyl groups such as benzyl, phenethyl, naphthylmethyl, benzhydryl, phenylpropyl, phenylbutyl, diphenylethyl and the like can be mentioned.

As preferable examples of the arylalkenyl group, $C_{8-13}$ arylalkenyl groups such as styryl and the like can be mentioned.

As preferable examples of the arylalkynyl group, $C_{8-13}$ arylalkynyl groups such as phenylethynyl and the like can be mentioned.

As the alicyclic aliphatic hydrocarbon group, for example, a $C_{4-13}$ alicyclic aliphatic hydrocarbon group, and concretely, a cycloalkylalkyl group, a cycloalkylalkenyl group, a cycloalkenylalkyl group and the like can be mentioned.

As preferable examples of the cycloalkylalkyl group, $C_{4-13}$ cycloalkylalkyl groups such as cyclopropylmethyl, cyclopropylethyl, cyclopentylmethyl, cyclopentylethyl, cyclohexylmethyl, cyclohexylethyl and the like can be mentioned.

As preferable examples of the cycloalkylalkenyl group, $C_{5-13}$ cycloalkylalkenyl groups such as cyclopropylethenyl, cyclopentylethenyl, cyclohexylethenyl and the like can be mentioned.

As preferable examples of the cycloalkenylalkyl group, $C_{4-13}$ cycloalkenylalkyl groups such as cyclopentenylmethyl, cyclopentenylethyl, cyclohexenylmethyl, cyclohexenylethyl and the like can be mentioned.

The above-mentioned "optionally substituted hydrocarbon group" for $R^1$ may have 1 to 3 substituent(s) at substitutable position(s). As such substituent, for example, a halogen atom, a nitro, an oxo, a $C_{1-3}$ alkylenedioxy, an optionally substituted aromatic heterocyclic group, an optionally substituted non-aromatic heterocyclic group, an optionally substituted amino group, an optionally substituted hydroxy group, an optionally substituted thiol group, an optionally substituted acyl group and the like can be mentioned.

As the halogen atoms, for example, a fluorine atom, a chlorine atom, a bromine atom and an iodine atom can be mentioned. Especially preferred are a fluorine atom and a chlorine atom.

As the $C_{1-3}$ alkylenedioxy, for example, methylenedioxy, ethylenedioxy and the like can be mentioned.

As the "aromatic heterocyclic group" of the "optionally substituted aromatic heterocyclic group", for example, a 5- to 7-membered monocyclic aromatic heterocyclic group which contains, as a ring-constituting atom besides carbon atoms, 1 to 4 heteroatoms selected from an oxygen atom, a sulfur atom and a nitrogen atom, and a condensed aromatic heterocyclic group can be mentioned. As the condensed aromatic heterocyclic group, for example, a group wherein the 5- to 7-membered monocyclic aromatic heterocyclic group is condensed with a 6-membered ring containing 1 or 2 nitrogen atom(s), a benzene ring, a 5-membered ring containing 1 sulfur atom, and the like can be mentioned.

As preferable examples of the "aromatic heterocyclic group", furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), oxazolyl (e.g., 2-oxazolyl, 4-oxazolyl, 5-oxazolyl), isoxazolyl, thiazolyl (e.g., 2-thiazolyl, 4-thiazolyl, 5-thiazolyl), isothiazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), quinolyl (e.g., 2-quinolyl, 3-quinolyl, 4-quinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl), benzimidazolyl (e.g., benzimidazol-1-yl, benzimidazol-2-yl), indolyl (e.g., indol-1-yl, indol-3-yl), 1H-indazolyl (e.g., 1H-indazol-3-yl), 1H-pyrrolo[2,3-b]pyrazinyl (e.g., 1H-pyrrolo[2,3-b]pyrazin-2-yl), 1H-pyrrolopyridinyl (e.g., 1H-pyrrolo[2,3-b]pyridin-6-yl), 1H-imidazopyridinyl (e.g., 1H-imidazo[4,5-b]pyridin-2-yl, 1H-imidazo[4,5-c]pyridin-2-yl), 1H-imidazopyrazinyl (e.g., 1H-imidazo[4,5-b]pyrazin-2-yl), triazinyl, isoquinolyl, benzoxadiazolyl, benzothiadiazolyl, benztriazolyl and the like can be mentioned.

As the "non-aromatic heterocyclic group" of the "optionally substituted non-aromatic heterocyclic group", for example, a 5- to 7-membered monocyclic non-aromatic heterocyclic group which contains, as a ring-constituting atom besides carbon atoms, 1 to 4 heteroatoms selected from an oxygen atom, a sulfur atom and a nitrogen atom, and a condensed non-aromatic heterocyclic group can be mentioned. As the condensed non-aromatic heterocyclic group, for example, a group wherein the 5- to 7-membered monocyclic non-aromatic heterocyclic group is condensed with a 6-membered ring containing 1 or 2 nitrogen atom(s), a benzene ring, a 5-membered ring containing 1 sulfur atom, and the like can be mentioned.

As preferable examples of the non-aromatic heterocyclic group, pyrrolidinyl (e.g., 1-pyrrolidinyl), piperidinyl (e.g., piperidino), morpholinyl (e.g., morpholino), thiomorpholinyl (e.g., thiomorpholino), piperazinyl (e.g., 1-piperazinyl), hexamethyleniminyl (e.g., hexamethylenimin-1-yl), oxazolidinyl (e.g., oxazolidin-3-yl), thiazolidinyl (e.g., thiazolidin-3-yl), imidazolidinyl (e.g., imidazolidin-3-yl), imidazolinyl (e.g., imidazolin-1-yl, imidazolin-2-yl), oxazolinyl (e.g., oxazolin-2-yl), thiazolinyl (e.g., thiazolin-2-yl), oxazinyl (e.g., oxazin-2-yl), tetrahydrofuranyl, azepanyl, tetrahydropyridinyl (e.g., 1,2,3,6-tetrahydropyridin-1-yl), dihydrobenzofuranyl, dioxolanyl, dithiolanyl, tetrahydroisoquinolyl and the like can be mentioned.

The above-mentioned aromatic heterocyclic group and non-aromatic heterocyclic group may have 1 to 3 substituent(s) at substitutable position(s). As such substituent, for example, a nitro, a hydroxy, an amino, an oxo, a halogen atom (e.g., fluorine, chlorine, bromine, iodine), a $C_{1-6}$ alkyl (e.g., methyl, ethyl) optionally substituted by 1 to 3 halogen atom(s) (e.g., fluorine, chlorine, bromine, iodine), a $C_{1-6}$ alkoxy group (e.g., methoxy, ethoxy) optionally substituted by 1 to 3 halogen atom(s) (e.g., fluorine, chlorine, bromine, iodine), a $C_{6-14}$ aryl (e.g., phenyl) and the like can be mentioned.

As the "optionally substituted amino group", for example, an amino group optionally mono- or di-substituted by a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl, a $C_{1-15}$ acyl group or a heteroaryl group, each of which is optionally substituted can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group and $C_{7-14}$ aralkyl, those exemplified for the "hydrocarbon group" of the "optionally substituted hydrocarbon group" for $R^1$ can be mentioned.

As the $C_{1-15}$ acyl group, those exemplified for the acyl group of the "optionally substituted acyl group" to be mentioned later can be mentioned. The acyl group is preferably a formyl, a $C_{1-10}$ alkyl-carbonyl, a $C_{1-6}$ alkoxy-carbonyl, a $C_{6-14}$ aryl-carbonyl, a $C_{7-13}$ aralkyl-carbonyl, an aromatic heterocyclic-carbonyl, a 5- to 7-membered non-aromatic heterocyclic-carbonyl, a $C_{3-10}$ cycloalkyl-carbonyl (e.g., cyclopentanecarbonyl, cyclohexanecarbonyl); a $C_{8-13}$ arylalkenyl-carbonyl (e.g., styrylcarbonyl); a $C_{8-13}$ arylalkynyl-carbonyl (e.g., phenylethynylcarbonyl); a $C_{6-14}$ arylsulfonyl (e.g., phenylsulfonyl); a mono- or di-$C_{1-6}$ alkyl-carbamoyl (e.g., methylcarbamoyl, tert-butylcarbamoyl); a $C_{3-10}$ cycloalkyl-carbamoyl (e.g., cyclopropylcarbamoyl, cyclopentylcarbamoyl, cyclohexylcarbamoyl); a $C_{6-14}$ aryl-carbamoyl (e.g., phenylcarbamoyl); a $C_{7-14}$ aralkyl-carbamoyl (e.g., benzylcarbamoyl, phenethylcarbamoyl, diphenylethylcarbamoyl); a $C_{4-13}$ cycloalkylalkyl-carbamoyl (e.g., cyclohexylmethylcarbamoyl); an aromatic heterocyclic carbamoyl (e.g., isoxazolylcarbamoyl, benzothiazolylcarbamoyl); a non-aromatic heterocyclic carbamoyl (e.g., pyrrolidinylcarbamoyl); a $C_{7-14}$ aralkyloxy-carbamoyl (e.g., benzyloxycarbamoyl); and the like. As the $C_{1-15}$ acyl group, moreover, a $C_{1-6}$ alkoxy-carbamoyl (e.g., methoxycarbamoyl), a $C_{1-6}$ alkoxy-carbonylcarbamoyl (e.g., methoxycarbonylcarbamoyl, ethoxycarbonylcarbamoyl) and the like can be also mentioned.

As preferable examples of the $C_{1-10}$ alkyl-carbonyl, acetyl, propionyl, butyryl, isobutyryl, valeryl, isovaleryl, pivaloyl, hexanoyl, heptanoyl, octanoyl and the like can be mentioned.

As preferable examples of the $C_{1-6}$ alkoxy-carbonyl, for example, tert-butoxycarbonyl and the like can be mentioned.

As preferable examples of the $C_{6-14}$ aryl-carbonyl, benzoyl and the like can be mentioned.

As preferable examples of the $C_{7-13}$ aralkyl-carbonyl, benzylcarbonyl, phenethylcarbonyl and the like can be mentioned.

As preferable examples of the aromatic heterocyclic-carbonyl, furylcarbonyl, pyrrolylcarbonyl, thienylcarbonyl, pyridylcarbonyl, pyrimidinylcarbonyl, 1H-indazolylcarbonyl, benzofuranylcarbonyl, quinolylcarbonyl and the like can be mentioned.

As preferable examples of the 5 to 7-membered non-aromatic heterocyclic-carbonyl, tetrahydrofurylcarbonyl, thiomorpholinocarbonyl, piperidinocarbonyl, piperazinocarbonyl, hexamethyleniminylcarbonyl, thiazolidinylcarbonyl and the like can be mentioned.

As the heteroaryl group, for example, the aromatic heterocyclic groups exemplified for the substituents of the "optionally substituted heterocyclic group" for $R^1$ can be mentioned. Of these, pyridyl, imidazolyl, triazolyl, pyrimidinyl and the like are preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-14}$ aralkyl, $C_{1-15}$ acyl group and heteroaryl group may have 1 or 2 substituent(s) at substitutable position(s). As such substituent, for example, a halogen atom (e.g., fluorine, chlorine, bromine, iodine); a $C_{1-6}$ alkyl group (e.g., methyl, trifluoromethyl) optionally substituted by 1 to 3 halogen atom(s) (e.g., fluorine, chlorine, bromine, iodine); a $C_{1-6}$ alkoxy group (e.g., methoxy, ethoxy) optionally substituted by 1 to 3 halogen atom(s) (e.g., fluorine, chlorine, bromine, iodine); a hydroxy; a nitro; an amino group optionally mono- or di-substituted by $C_{1-6}$ alkyl group (e.g., methyl); a $C_{1-6}$ alkylsulfonyl group (e.g., methylsulfonyl); oxo; cyano; a $C_{7-13}$ aralkyl group (e.g., benzyl); a $C_{1-6}$ alkoxy-carbonylamino-$C_{1-6}$ alkyl group (e.g., methoxycarbonylaminomethyl, ethoxycarbonylaminomethyl); a mono- or di-$C_{1-10}$ alkylphosphono-$C_{1-6}$ alkyl group (e.g., dimethylphosphonomethyl, diethylphosphonomethyl); a mono- or di-$C_{1-6}$ alkylamino-$C_{1-6}$ alkyl group (e.g., dimethylaminomethyl); a $C_{1-6}$ alkoxy-$C_{6-14}$ aryl group (e.g., methoxyphenyl); a $C_{1-6}$ alkyl-carbonyl-$C_{6-14}$ aryl group (e.g., acetylphenyl); a heterocyclic group (e.g., thienyl, furyl, oxazolyl, isoxazolyl, imidazolyl, triazolyl, tetrazolyl, pyridyl, indolyl, 1H-indazolyl, benzimidazolyl, tetrahydrofuryl, pyrrolidinyl, piperidinyl, morpholinyl, thiomorpholinyl) optionally substituted by 1 to 3 substituent(s) selected from oxo, $C_{1-6}$ alkyl (e.g., methyl, ethyl) and $C_{1-6}$ alkoxy (e.g., methoxy, ethoxy); a $C_{6-14}$ aryloxy group (e.g., phenyloxy); a $C_{7-13}$ aralkyloxy group (e.g., benzyloxy); a $C_{1-6}$ alkylthio group (e.g., methylthio); a $C_{6-14}$ arylthio group (e.g., phenylthio) optionally substituted by 1 to 3 halogen atom(s); a heterocyclic thio group (e.g., pyrimidinylthio) optionally substituted by $C_{1-6}$ alkyl; a $C_{1-6}$ alkoxy-carbonyl group (e.g., methoxycarbonyl, ethoxycarbonyl); a heterocyclic carbonyl group (e.g., dihydroindolylcarbonyl); a $C_{1-6}$ alkylsulfonyl group (e.g., methylsulfonyl); a $C_{6-14}$ arylsulfonyl group (e.g., phenylsulfonyl); a carbamoyl; a $C_{1-6}$ alkoxy-carboxamide group (e.g., methoxycarboxamide, ethoxycarboxamide); a sulfamoyl group (e.g., sulfamoyl, acetylsulfamoyl) optionally substituted by $C_{1-6}$ alkyl-carbonyl; and the like can be mentioned. Of these substituents, a halogen atom (e.g., fluorine, chlorine, bromine, iodine); a $C_{1-6}$ alkyl group (e.g., methyl, trifluoromethyl) optionally substituted by 1 to 3 halogen atom(s) (e.g., fluorine, chlorine, bromine, iodine); a $C_{1-6}$ alkoxy group (e.g., methoxy, ethoxy) optionally substituted by 1 to 3 halogen atom(s) (e.g., fluorine, chlorine, bromine, iodine); a hydroxy; a nitro; an amino; a $C_{1-6}$ alkylsulfonyl group (e.g., methylsulfonyl) and the like are preferable.

As the substituted amino group, for example, a mono- or di-$C_{1-10}$ alkylamino (e.g., methylamino, dimethylamino, ethylamino, diethylamino, ethylmethylamino, propylamino, dibutylamino); a mono- or di-$C_{2-10}$ alkenylamino (e.g., diallylamino) [optionally substituted by $C_{1-6}$ alkoxy-carbonyl]; a mono- or di-$C_{3-10}$ cycloalkylamino (e.g., cyclohexylamino) ; a mono- or di-$C_{1-10}$ alkyl-carboxamide (e.g., acetylamino, propionylamino) [optionally substituted by 1 to 3 substituent(s) selected from a heterocyclic thio optionally substituted $C_{1-6}$ alkyl (e.g., pyrimidinylthio), $C_{6-14}$ arylthio optionally substituted by 1 to 3 halogen atom(s), cyano, $C_{1-6}$ alkylthio, halogen atom, heterocyclic carbonyl (e.g., dihydroindolylcarbonyl)]; a $C_{6-14}$ aryl-carboxamide (e.g., benzoylamino); a $C_{6-14}$ arylamino (e.g., phenylamino) ; a N-$C_{1-10}$ alkyl-N-$C_{6-14}$ arylamino (e.g., N-methyl-N-phenylamino) ; a N-$C_{1-10}$ alkyl-N-$C_{7-13}$ aralkylamino (e.g., N-methyl-N-benzylamino); a mono- or di-$C_{1-6}$ alkoxy-carboxamide (e.g., tert-butoxycarboxamide); a mono- or di-$C_{6-14}$ aryl-carboxamide (e.g., phenylcarboxamide) [optionally substituted by 1 to 3 substituent(s) selected from $C_{1-6}$ alkoxy, $C_{6-14}$ aryloxy and a heterocyclic group (e.g., triazolyl, tetrazolyl)]; a mono- or di-$C_{7-13}$ aralkyl-carboxamide (e.g., benzylcarboxamide, phenethylcarboxamide, phenylpropylcarboxamide, phenylbutylcarboxamide) [optionally substituted by 1 to 3 substituent(s) selected from $C_{1-6}$ alkoxy and a halogen atom]; an aromatic heterocyclic-carboxamide (e.g., furylcarboxamide, pyrrolylcarboxamide, thienylcarboxamide, pyridylcarboxamide, pyrimidinylcarboxamide, 1H-indazolylcarboxamide, benzofuranylcarboxamide, quinolylcarboxamide) [optionally substituted by 1 to 3 substituent(s) selected from a halogen atom and $C_{1-6}$ alkyl]; a 5 to 7-membered non-aromatic heterocyclic-carboxamide (e.g., tetrahydrofurylcarboxamide, thiomorpholinocarboxamide, piperidinocarboxamide, piperazinocarboxamide, hexamethyleniminylcarboxamide, thiazolidinylcarboxamide) [optionally substituted by 1 to 3 substituent(s) selected from oxo, $C_{1-6}$ alkoxy-carbonyl, $C_{1-6}$ alkoxy-$C_{6-14}$ aryl (e.g., methoxyphenyl), $C_{1-6}$ alkyl-carbonyl-$C_{6-14}$ aryl (e.g., acetylphenyl), carbamoyl, $C_{7-13}$ aralkyl (e.g., benzyl), heterocyclic group (e.g., piperidino)]; a $C_{3-10}$ cycloalkyl-carboxamide (e.g., cyclopentylcarboxamide, cyclohexylcarboxamide) [optionally substituted by $C_{1-6}$ alkyl optionally substituted by $C_{1-6}$ alkoxy-carboxamide (e.g., methoxycarboxamide, ethoxycarboxamide)]; a $C_{8-13}$ arylalkenyl-carboxamide (e.g., styrylcarboxamide) [optionally substituted by a halogen atom]; a $C_{8-13}$ arylalkynyl-carboxamide (e.g., phenylethynylcarboxamide); an aromatic heterocyclic (e.g., thienyl, furyl, indolyl)-$C_{1-6}$ alkyl-carboxamide; a $C_{6-14}$ arylsulfonylamino (e.g., phenylsulfonylamino); a mono- or di-$C_{1-6}$ alkyl-carbamoylamino (e.g., methylcarbamoylamino, tert-butylcarbamoylamino) [optionally substituted by 1 to 3 substituent(s) selected from hydroxy, $C_{1-6}$ alkoxy, $C_{1-6}$ alkylthio, halogen atom, $C_{1-6}$ alkoxy-carbonyl, $C_{1-6}$ alkoxy-carboxamide, cyano, $C_{1-6}$ alkylsulfonyl and carbamoyl]; a $C_{3-10}$ cycloalkyl-carbamoylamino (e.g., cyclopropylcarbamoylamino, cyclopentylcarbamoylamino, cyclohexylcarbamoylamino) [optionally substituted by hydroxy]; a $C_{6-14}$ aryl-carbamoylamino (e.g., phenylcarbamoylamino) [optionally substituted by 1 to 3 substituent(s) selected from $C_{1-6}$ alkyl optionally substituted by 1 to 3 halogen atom(s), sulfamoyl optionally substituted by $C_{1-6}$ alkyl-carbonyl, mono- or di-$C_{1-6}$ alkylamino, mono- or di-$C_{1-10}$ alkylphosphono-$C_{1-6}$ alkyl group, halogen atom, $C_{6-14}$ arylsulfonyl (e.g., phenylsulfonyl), $C_{7-13}$ aralkyloxy (e.g., benzyloxy) and $C_{1-6}$ alkoxy]; a $C_{7-14}$ aralkyl-carbamoylamino (e.g., benzylcarbamoylamino, phenethylcarbamoylamino, diphenylethylcarbamoylamino) [optionally substituted by 1 to 3 substituent(s) selected from $C_{1-6}$ alkyl optionally substituted by 1 to 3 substituent(s) selected from mono- or di-$C_{1-6}$ alkylamino and halogen atom, a halogen atom, a sulfamoyl, a hydroxyl, and $C_{1-6}$ alkoxy]; a $C_{1-6}$ alkoxy-carbonylcarbamoylamino (e.g., methoxycarbonylcarbamoylamino, ethoxycarbonylcarbamoylamino); a $C_{4-13}$ cycloalkylalkyl-carbamoylamino (e.g., cyclohexylmethylcarbamoylamino); a heterocyclic (e.g., thienyl, furyl, oxazolyl, isoxazolyl, imidazolyl, triazolyl, tetrazolyl, pyridyl, indolyl, 1H-indazolyl, benzimidazolyl, tetrahydrofuryl, pyrrolidinyl, piperidinyl, morpholinyl, thiomorpholinyl)-$C_{1-10}$ alkyl-carbamoylamino (e.g., methylcarbamoylamino, ethylcarbamoylamino) [optionally substituted by 1 to 3 substituent(s) selected from oxo, $C_{1-6}$ alkyl, hydroxy and $C_{1-6}$ alkoxy]; an aromatic heterocyclic carbamoylamino (e.g., isoxazolylcarbamoylamino, benzothiazolylcarbamoylamino) [optionally substituted by 1 to 3 substituent(s) selected from $C_{1-6}$ alkyl and $C_{1-6}$ alkoxy]; a non-aromatic heterocyclic carbamoylamino (e.g., pyrrolidinylcarbamoylamino) [optionally substituted by $C_{1-6}$ alkyl]; a $C_{7-14}$ aralkyloxy-carbamoylamino (e.g., benzyloxycarbamoylamino); and the like can be mentioned.

As the "optionally substituted hydroxy group", for example, a hydroxy group optionally substituted by a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl, a $C_{1-15}$ acyl group or a heteroaryl group, each of which is optionally substituted can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group and $C_{7-14}$ aralkyl, those exemplified for the "hydrocarbon group" of the "optionally substituted hydrocarbon group" for $R^1$ can be mentioned.

As the $C_{1-15}$ acyl group, those exemplified for the substituent of the aforementioned "optionally substituted amino group" can be mentioned.

As the "heteroaryl group", for example, aromatic heterocyclic groups exemplified for the substituents of the "optionally substituted heterocyclic group" for $R^1$ can be mentioned. Of these, pyridyl, imidazolyl, triazolyl, pyrimidinyl and the like are preferable.

These "$C_{1-10}$ alkyl group", "$C_{2-10}$ alkenyl group", "$C_{3-10}$ cycloalkyl group", "$C_{3-10}$ cycloalkenyl group", "$C_{6-14}$ aryl group", "$C_{7-14}$ aralkyl", "$C_{1-15}$ acyl group" and "heteroaryl group" may have 1 or 2 substituent(s) at substitutable position(s). As such substituent, for example, a halogen atom (e.g., fluorine, chlorine, bromine, iodine), a $C_{1-6}$ alkyl group (e.g., methyl, trifluoromethyl) optionally substituted by 1 to 3 halogen atom(s) (e.g., fluorine, chlorine, bromine, iodine), a $C_{1-6}$ alkoxy group (e.g., methoxy, ethoxy) optionally substituted by 1 to 3 halogen atom(s) (e.g., fluorine, chlorine, bromine, iodine), a hydroxy, a nitro, an amino, a $C_{1-6}$ alkylsulfonyl group (e.g., methylsulfonyl) and the like can be mentioned.

As the substituted hydroxy group, for example, an alkoxy group, an alkenyloxy group, a cycloalkyloxy group, a cycloalkenyloxy group, an aryloxy group, an aralkyloxy group, an acyloxy group, a heteroaryloxy group, each of which is optionally substituted and the like, can be mentioned.

As preferable examples of the alkoxy group, a $C_{1-10}$ alkoxy group, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy and the like, can be mentioned.

As preferable examples of the alkenyloxy group, a $C_{2-10}$ alkenyloxy group, such as allyloxy, crotyloxy, 2-pentenyloxy, 3-hexenyloxy and the like, can be mentioned.

As preferable examples of the cycloalkyloxy group, a $C_{3-10}$ cycloalkyloxy group, such as cyclobutoxy, cyclopentyloxy, cyclohexyloxy and the like, can be mentioned.

As preferable examples of the cycloalkenyloxy group, $C_{3-10}$ cycloalkenyloxy group, such as 2-cyclopentenyloxy, 2-cyclohexenyloxy and the like, can be mentioned.

As preferable examples of the aryloxy group, a $C_{6-14}$ aryloxy group, such as phenoxy, naphthyloxy and the like, can be mentioned.

As preferable examples of the aralkyloxy group, a $C_{7-14}$ aralkyloxy group, such as benzyloxy, phenethyloxy, naphthylmethyloxy and the like, can be mentioned.

As preferable examples of the acyloxy group, a $C_{2-13}$ acyloxy group, such as $C_{1-6}$ alkyl-carbonyloxy (e.g., acetyloxy, propionyloxy, butyryloxy, isobutyryloxy) and the like, can be mentioned.

As preferable examples of the heteroaryloxy group, a 5- to 7-membered monocyclic heteroaryloxy group, such as 2-pyridyloxy, 3-pyridyloxy, 2-imidazolyloxy, 2-pyrimidinyloxy, 1,2,4-triazol-5-yloxy and the like, can be mentioned.

The above-mentioned alkoxy group, alkenyloxy group, cycloalkyloxy group, cycloalkenyloxy group, aryloxy group, aralkyloxy group, acyloxy group and heteroaryloxy group may have 1 or 2 substituent(s) at substitutable position(s). As such substituent, for example, a halogen atom (e.g., fluorine, chlorine, bromine, iodine), a $C_{1-6}$ alkyl group (e.g., methyl, trifluoromethyl) optionally substituted by 1 to 3 halogen atom(s) (e.g., fluorine, chlorine, bromine, iodine), a $C_{1-6}$ alkoxy group (e.g., methoxy, ethoxy) optionally substituted by 1 to 3 halogen atom(s) (e.g., fluorine, chlorine, bromine, iodine), a hydroxy, a nitro, an amino, a $C_{1-6}$ alkylsulfonyl group (e.g., methylsulfonyl) and the like can be mentioned.

As the optionally substituted thiol group, for example, a thiol group optionally substituted by "$C_{1-10}$ alkyl group", "$C_{2-10}$ alkenyl group", "$C_{3-10}$ cycloalkyl group", "$C_{3-10}$ cycloalkenyl group", "$C_{6-14}$ aryl group", "$C_{7-14}$ aralkyl", "$C_{1-15}$ acyl group" or "heteroaryl group", each of which is optionally substituted, and the like can be mentioned.

Here, as the "$C_{1-10}$ alkyl group", "$C_{2-10}$ alkenyl group", "$C_{3-10}$ cycloalkyl group", "$C_{3-10}$ cycloalkenyl group", "$C_{6-14}$ aryl group", "$C_{7-14}$ aralkyl", "$C_{1-15}$ acyl group" and "heteroaryl group", those respectively exemplified for the aforementioned "optionally substituted hydroxy group" can be mentioned. These groups may have 1 or 2 substituent(s) at substitutable position(s). As such substituent, for example, a halogen atom (e.g., fluorine, chlorine, bromine, iodine), a $C_{1-6}$ alkyl group (e.g., methyl, trifluoromethyl) optionally substituted by 1 to 3 halogen atom(s) (e.g., fluorine, chlorine, bromine, iodine), a $C_{1-6}$ alkoxy group (e.g., methoxy, ethoxy) optionally substituted by 1 to 3 halogen atom(s) (e.g., fluorine, chlorine, bromine, iodine), a hydroxy, a nitro, an amino, a $C_{1-6}$ alkylsulfonyl group (e.g., methylsulfonyl), an oxo, a pyridyl and the like can be mentioned.

As the substituted thiol group, for example, an alkylthio, an alkenylthio, a cycloalkylthio, a cycloalkenylthio, an arylthio, an aralkylthio, an acylthio, a heteroarylthio, each of which is optionally substituted, and the like, can be mentioned.

As preferable examples of the alkylthio group, a $C_{1-10}$ alkylthio group, such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio and the like, can be mentioned.

As preferable examples of the alkenylthio group, a $C_{2-10}$ alkenylthio group, such as allylthio, crotylthio, 2-pentenylthio, 3-hexenylthio and the like can be mentioned.

As preferable examples of the cycloalkylthio group, a $C_{3-10}$ cycloalkylthio group, such as cyclobutylthio, cyclopentylthio, cyclohexylthio and the like, can be mentioned.

As preferable examples of the cycloalkenylthio group, a $C_{3-10}$ cycloalkenylthio group, such as 2-cyclopentenylthio, 2-cyclohexenylthio and the like, can be mentioned.

As preferable examples of the arylthio group, a $C_{6-14}$ arylthio group, such as phenylthio, naphthylthio and the like, can be mentioned.

As preferable examples of the aralkylthio group, a $C_{7-14}$ aralkylthio group, such as benzylthio, phenethylthio, naphthylmethylthio and the like can be mentioned.

As preferable examples of the acylthio group, a $C_{2-13}$ acylthio group, such as a $C_{1-6}$ alkyl-carbonylthio group (e.g., acetylthio, propionylthio, butyrylthio, isobutyrylthio), and the like can be mentioned.

As preferable examples of the heteroarylthio group, a 5- to 7-membered monocyclic heteroarylthio group, such as 2-pyridylthio, 3-pyridylthio, 2-imidazolylthio, 2-pyrimidinylthio, 1,2,4-triazol-5-ylthio, 1,2,4-triazol-3-ylthio and the like, can be mentioned.

The above-mentioned alkylthio group, alkenylthio group, cycloalkylthio group, cycloalkenylthio group, arylthio group, aralkylthio group, acylthio group and heteroarylthio group may have 1 or 2 substituent(s) at substitutable position(s). As such substituent, for example, a halogen atom (e.g., fluorine, chlorine, bromine, iodine), a $C_{1-6}$ alkyl (e.g., methyl, trifluoromethyl) optionally substituted by 1 to 3 halogen atom(s) (e.g., fluorine, chlorine, bromine, iodine), a $C_{1-6}$ alkoxy (e.g., methoxy, ethoxy) optionally substituted by 1 to 3 halogen atom(s) (e.g., fluorine, chlorine, bromine, iodine), a hydroxy, a nitro, an amino, a $C_{1-6}$ alkylsulfonyl (e.g., methylsulfonyl), an oxo, pyridyl and the like can be mentioned.

As the acyl group of the "optionally substituted acyl group", for example, a group represented by the formula: —$COR^3$, —CO—OR, —$SO_2R^3$, —$SOR^3$, —$PO_3R^3R^4$, —CO—$NR^{3a}R^{4a}$, —CS—$NR^{3a}R^{4a}$ wherein $R^3$ and $R^4$ are the same or different and each is a hydrogen atom, a hydrocarbon group or a heterocyclic group, or $R^3$ and $R^4$ may form a heterocycle together with the adjacent oxo-substituted phosphorus atom and 2 oxygen atoms; $R^{3a}$ and $R^{4a}$ are the same or different and each is a hydrogen atom, a hydrocarbon group or a heterocyclic group, or $R^{4a}$ and $R^{5a}$ may form a nitrogen-containing heterocycle together with the adjacent nitrogen atom, and the like can be mentioned.

As the "hydrocarbon group" for $R^3$, $R^4$, $R^{3a}$ or $R^{4a}$, those exemplified for the "hydrocarbon group" of the "optionally substituted hydrocarbon group" for $R^1$ can be mentioned.

The hydrocarbon group is preferably a $C_{1-10}$ alkyl group (preferably methyl, ethyl, propyl, butyl, tert-butyl, pentyl, 1-ethylpropyl, 2,2-dimethylpropyl, isopentyl, hexyl); a $C_{2-10}$ alkenyl group (preferably 1-propenyl); a $C_{2-10}$ alkynyl group (preferably 2-propynyl); a $C_{3-10}$ cycloalkyl group (preferably cyclopropyl, cyclopentyl, cyclohexyl, tetrahydronaphthyl) which may be condensed with a benzene ring; a $C_{3-10}$ cycloalkenyl group (preferably 2-cyclohexenyl); a $C_{6-14}$ aryl group (preferably phenyl, dihydroindenyl, biphenylyl) which may be condensed with a $C_{3-10}$ cycloalkane (preferably cyclopentane); a $C_{7-14}$ aralkyl group (preferably benzyl, phenethyl, phenylpropyl, phenylbutyl, naphthylmethyl, benzhydryl, diphenylethyl); a $C_{8-13}$ arylalkenyl group (preferably styryl); a $C_{8-13}$ arylalkynyl group (preferably phenylethynyl); a $C_{4-13}$ cycloalkylalkyl group (preferably cyclohexylmethyl); a $C_{4-13}$ cycloalkenylalkyl group (preferably cyclohexenylmethyl, cyclohexenylethyl) and the like.

As the "heterocyclic group" for $R^3$, $R^4$, $R^{3a}$ or $R^{4a}$, the aromatic heterocyclic group and the non-aromatic heterocyclic group exemplified for the substituents of the "optionally substituted hydrocarbon group" for $R^1$ can be mentioned.

The heterocyclic group is preferably thiazolyl, oxazolyl, isothiazolyl, isoxazolyl, pyrazolyl, pyridyl, pyrazinyl, benzoxazolyl, benzothiazolyl, benzothiadiazolyl, quinolyl, isoquinolyl, pyrrolidinyl, piperidinyl, piperazinyl, furyl, thienyl, pyrimidinyl, benzofuryl, 1H-indazolyl, morpholinyl, thiomorpholinyl, hexamethyleniminyl, tetrahydroisoquinolyl, oxazolidinyl, thiazolidinyl and the like.

As the heterocycle formed by $R^3$ and $R^4$ together with the adjacent oxo-substituted phosphorus atom and 2 oxygen atoms, for example, a 4- to 7-membered heterocycle containing an oxo-substituted phosphorus atom and 2 oxygen atoms besides carbon atoms as a ring-constituting atom, which may further contain 1 or 2 heteroatom(s) selected from an oxygen atom, a nitrogen atom and a sulfur atom, and the like can be mentioned. As preferable examples of such heterocycle, 2-oxide-1,3,2-dioxaphosphinane; 2-oxide-1,3,2-dioxaphosphorane and the like can be mentioned.

As the "nitrogen-containing heterocycle" formed by $R^{3a}$ and $R^{4a}$ together with the adjacent nitrogen atom, for example, a 5- to 7-membered nitrogen-containing heterocycle containing at least one nitrogen atom besides carbon atoms as a ring-constituting atom, which may further contain 1 or 2 heteroatom(s) selected from an oxygen atom, a sulfur atom and a nitrogen atom, and the like can be mentioned. As preferable examples of such nitrogen-containing heterocycle, pyrrolidine, imidazolidine, pyrazolidine, piperidine, piperazine, morpholine, thiomorpholine and the like can be mentioned.

Preferable examples of the "acyl group" include formyl; carboxyl; carbamoyl; thiocarbamoyl; $C_{1-10}$ alkyl-carbonyl (e.g., acetyl, propionyl, butyryl, isobutyryl, valeryl, isovaleryl, pivaloyl, hexanoyl, heptanoyl, octanoly); $C_{2-10}$ alkenyl-carbonyl (e.g., crotonyl); $C_{3-10}$ cycloalkyl-carbonyl (e.g., cyclobutanecarbonyl, cyclopentanecarbonyl, cyclohexanecarbonyl, cycloheptanecarbonyl); $C_{3-10}$ cycloalkenyl-carbonyl (e.g., 2-cyclohexenecarbonyl); $C_{6-14}$ aryl-carbonyl (e.g., benzoyl, 1-naphthoyl, 2-naphthoyl); $C_{7-14}$ aralkyl-carbonyl (e.g., benzylcarbonyl, phenethylcarbonylphenylpropylcarbonyl, phenylbutylcarbonyl); $C_{8-13}$ aralkenyl-carbonyl (e.g., styrylcarbonyl); $C_{8-13}$ arylalkynyl-carbonyl (e.g., phenylethynylcarbonyl); aromatic heterocyclic carbonyl (e.g., nicotinoyl, isonicotinoyl, furylcarbonyl, thienylcarbonyl, pyrimidinylcarbonyl, benzofuranylcarbonyl, 1H-indazolylcarbonyl, quinolylcarbonyl); non-aromatic heterocyclic carbonyl (e.g., pyrrolidinylcarbonyl, piperidinocarbonyl, morpholinocarbonyl, thiomorpholinocarbonyl, piperazinocarbonyl, thiazolidinylcarbonyl, hexamethyleniminylcarbonyl, tetrahydroisoquinolylcarbonyl); $C_{1-6}$ alkoxy-carbonyl (e.g., methoxycarbonyl, ethoxycarbonyl, propoxycarbonyl, butoxycarbonyl, tert-butoxycarbonyl); $C_{6-14}$ aryloxy-carbonyl (e.g., phenyloxycarbonyl, naphthyloxycarbonyl); $C_{7-14}$ aralkyloxy-carbonyl (e.g., benzyloxycarbonyl, phenethyloxycarbonyl); mono- or di-$C_{1-6}$ alkyl-carbamoyl (e.g., methylcarbamoyl, ethylcarbamoyl, dimethylcarbamoyl, diethylcarbamoyl, ethylmethylcarbamoyl, propylcarbamoyl, butylcarbamoyl, tert-butylcarbamoyl, pentylcarbamoyl, hexylcarbamoyl); mono- or di-$C_{1-6}$ alkyl-thiocarbamoyl (e.g., methylthiocarbamoyl, ethylthiocarbamoyl); $C_{6-14}$ aryl-carbamoyl (e.g., phenylcarbamoyl); $C_{3-10}$ cycloalkyl-carbamoyl (e.g., cyclopropylcarbamoyl, cyclopentylcarbamoyl, cyclohexylcarbamoyl); $C_{7-14}$ aralkyl-carbamoyl (e.g., benzylcarbamoyl, phenethylcarbamoyl, diphenylethylcarbamoyl); $C_{4-13}$ cycloalkylalkyl-carbamoyl (e.g., cyclohexylmethylcarbamoyl); aromatic heterocyclic carbamoyl (e.g., isoxazolylcarbamoyl, benzothiazolylcarbamoyl); non-aromatic heterocyclic carbamoyl (e.g., pyrrolidinylcarbamoyl); $C_{1-10}$ alkylsulfinyl group (e.g., methylsulfinyl, ethylsulfinyl); $C_{1-10}$ oalkylsulfonyl group (e.g., methylsulfonyl, ethylsulfonyl); $C_{6-14}$ arylsulfonyl (e.g., phenylsulfonyl); (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); mono- or di-($C_{1-6}$ alkyl optionally substituted by 1 to 3 halogen(s))-sulfamoyl (e.g., methylsulfamoyl, ethylsulfamoyl) and the like can be mentioned.

The acyl group may have 1 to 3 substituent(s) at substitutable position(s). As such substituent, for example, a $C_{1-6}$ alkyl (e.g., methyl, ethyl) optionally substituted by 1 to 3 halogen atom(s) (e.g., fluorine, chlorine, bromine, iodine); a $C_{1-6}$ alkoxy (e.g., methoxy, ethoxy) optionally substituted by 1 to 3 halogen atom(s) (e.g., fluorine, chlorine, bromine, iodine); a halogen atom (e.g., fluorine, chlorine, bromine, iodine); a nitro; a hydroxy; an amino optionally mono- or di-substituted by $C_{1-6}$ alkyl (e.g., methyl, ethyl); a cyano; a mono- or di-$C_{1-10}$ alkylphosphono-$C_{1-6}$ alkyl group (e.g., dimethylphosphonomethyl, diethylphosphonomethyl, dimethylphosphonoethyl); a $C_{6-14}$ aryl (e.g., phenyl) optionally substituted by 1 to 3 substituent(s) selected from a halogen atom (e.g., fluorine, chlorine, bromine, iodine), $C_{1-6}$ alkyl (e.g., methyl, ethyl), $C_{1-6}$ alkoxy (e.g., methoxy, ethoxy) and $C_{1-6}$ alkyl-carbonyl (e.g., acetyl); a $C_{7-13}$ aralkyl (e.g., benzyl); a $C_{1-6}$ alkylthio (e.g., methylthio) optionally substituted by 1 to 3 halogen atom(s) (e.g., fluorine, chlorine, bromine, iodine); a $C_{6-14}$ aryloxy (e.g., phenoxy) optionally substituted by 1 to 3 halogen atom(s) (e.g., fluorine, chlorine, bromine, iodine); a $C_{6-14}$ arylthio (e.g., phenylthio) optionally substituted by 1 to 3 halogen atom(s) (e.g., fluorine, chlorine, bromine, iodine); a $C_{7-13}$ aralkyloxy (e.g., benzyloxy); a heterocyclic thio (e.g., pyrimidinylthio) optionally substituted by $C_{1-6}$ alkyl (e.g., methyl, ethyl); a $C_{1-6}$ alkoxy-carbonyl (e.g., methoxycarbonyl, ethoxycarbonyl, propoxycarbonyl, butoxycarbonyl, tert-butoxycarbonyl); a $C_{1-6}$ alkylsulfonyl (e.g., methylsulfonyl, ethylsulfonyl); a $C_{6-14}$ arylsulfonyl (e.g., phenylsulfonyl); a carbamoyl; a sulfamoyl optionally substituted by $C_{1-6}$ alkyl-carbonyl (e.g., acetyl); a heterocyclic carbonyl (e.g., dihydroindolylcarbonyl); a $C_{1-6}$ alkoxy-carboxamide (e.g., tert-butoxycarboxamide); a $C_{7-13}$ aralkyloxy-carboxamide (e.g., benzyloxycarboxamide) a heterocyclic group (e.g., thienyl, furyl, oxazolyl, isoxazolyl, imidazolyl, triazolyl, tetrazolyl, pyridyl, indolyl, 1H-indazolyl, benzimidazolyl, tetrahydrofuryl, pyrrolidinyl, piperidinyl, morpholinyl, thiomorpholinyl) optionally substituted by 1 to 3 substituent(s) selected from oxo, $C_{1-6}$ alkyl (e.g., methyl, ethyl) and $C_{1-6}$ alkoxy (e.g., methoxy, ethoxy); and the like can be mentioned.

As preferable examples of the "acyl group", formyl; carboxyl; carbamoyl; thiocarbamoyl; $C_{1-10}$ alkyl-carbonyl (e.g., acetyl, propionyl, butyryl, isobutyryl, valeryl, isovaleryl, pivaloyl, hexanoyl, heptanoyl, octanoly); $C_{2-10}$ alkenyl-carbonyl (e.g., crotonyl); $C_{3-10}$ cycloalkyl-carbonyl (e.g., cyclobutanecarbonyl, cyclopentanecarbonyl, cyclohexanecarbonyl, cycloheptanecarbonyl); $C_{3-10}$ cycloalkenyl-carbonyl (e.g., 2-cyclohexenecarbonyl); $C_{6-14}$ aryl-carbonyl (e.g., benzoyl, 1-naphthoyl, 2-naphthoyl); $C_{7-14}$ aralkyl-carbonyl (e.g., benzylcarbonyl, phenethylcarbonyl, phenylpropylcarbonyl, phenylbutylcarbonyl); $C_{8-13}$ arylalkenyl-carbonyl (e.g., styrylcarbonyl); $C_{8-13}$ arylalkynyl-carbonyl (e.g., phenylethynylcarbonyl); aromatic heterocyclic carbonyl (e.g., nicotinoyl, isonicotinoyl, furylcarbonyl, thienylcarbonyl, pyrimidinylcarbonyl, benzofuranylcarbonyl, 1H-indazolylcarbonyl, quinolylcarbonyl); non-aromatic heterocyclic carbonyl (e.g., pyrrolidinylcarbonyl, piperidinocarbonyl, morpholinocarbonyl, thiomorpholinocarbonyl, piperazinocarbonyl, thiazolidinylcarbonyl, hexamethyleniminylcarbonyl, tetrahydroisoquinolylcarbonyl); $C_{1-6}$ alkoxy-carbonyl (e.g., methoxycarbonyl, ethoxycarbonyl, propoxycarbonyl, butoxycarbonyl, tert-butoxycarbonyl); $C_{6-14}$ aryloxy-carbonyl (e.g., phenyloxycarbonyl, naphthyloxycarbonyl); $C_{7-14}$ aralkyloxy-carbonyl (e.g., benzyloxycarbonyl, phenethyloxycarbonyl); mono- or di-($C_{1-6}$ alkyl optionally having 1 to 3 substituent(s) selected from halogen atom and $C_{1-6}$ alkoxy-carbonyl)-carbamoyl (e.g., methylcarbamoyl, ethylcarbamoyl, dimethylcarbamoyl, diethylcarbamoyl, ethylmethylcarbamoyl, propylcarbamoyl, trifluoroethylcarbamoyl, butylcarbamoyl, tert-butylcarbamoyl, pentylcarbamoyl, hexylcarbamoyl); mono- or di-($C_{1-6}$ alkyl optionally substituted by 1 to 3 halogen(s))-thiocarbamoyl (e.g., methylthiocarbamoyl, ethylthiocarbamoyl); $C_{6-14}$ aryl-carbamoyl (e.g., phenylcarbamoyl); $C_{3-10}$ cycloalkyl-carbamoyl (e.g., cyclopropylcarbamoyl, cyclopentylcarbamoyl, cyclohexylcarbamoyl); $C_{7-14}$ aralkyl-carbamoyl (e.g., benzylcarbamoyl, phenethylcarbamoyl, diphenylethylcarbamoyl); $C_{4-13}$ cycloalkylalkyl-carbamoyl (e.g., cyclohexylmethylcarbamoyl); aromatic heterocyclic carbamoyl (e.g., isoxazolylcarbamoyl, benzothiazolylcarbamoyl); non-aromatic heterocyclic carbamoyl (e.g., pyrrolidinylcarbamoyl); $C_{1-10}$ alkylsulfinyl group (e.g., methylsulfinyl, ethylsulfinyl); $C_{1-10}$ alkylsulfonyl group (e.g., methylsulfonyl, ethylsulfonyl); $C_{6-14}$ arylsulfonyl (e.g., phenylsulfonyl); (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); mono- or di-($C_{1-6}$ alkyl optionally substituted by 1 to 3 halogen(s))-sulfamoyl (e.g., methylsulfamoyl, ethylsulfamoyl) and the like can be mentioned.

In addition, as the "optionally substituted acyl group". $C_{1-6}$ alkoxy-carbamoyl (e.g., methoxycarbamoyl), $C_{1-6}$ alkoxy-carbonylcarbamoyl (e.g., methoxycarbonylcarbamoyl, ethoxycarbonylcarbamoyl), $C_{7-14}$ aralkyloxy-carbamoyl (e.g., benzyloxycarbamoyl) and the like can be also mentioned.

The "hydrocarbon group" of the "optionally substituted hydrocarbon group" for $R^1$ is preferably a $C_{1-10}$ alkyl group, a $C_{6-14}$ aryl group, a $C_{3-10}$ cycloalkyl group, a $C_{7-14}$ aralkyl group, a $C_{8-13}$ arylalkenyl group, a $C_{4-13}$ cycloalkylalkyl group and the like. The hydrocarbon group is more preferably a $C_{6-14}$ aryl group, and phenyl, naphthyl and the like are particularly preferable.

The substituent of the "optionally substituted hydrocarbon group" for $R^1$ is preferably a $C_{1-6}$ alkoxy group (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{1-3}$ alkylenedioxy (e.g., methylenedioxy, ethylenedioxy) and the like. The number of the substituent is, for example, 1 to 3.

As the "heterocyclic group" of the "optionally substituted heterocyclic group" for $R^1$, those exemplified for the aforementioned "heterocyclic group" for the aforementioned $R^3$ can be mentioned.

The heterocyclic group is preferably an azolyl group optionally condensed with a benzene ring, such as pyrrolyl, imidazolyl, pyrazolyl, oxazolyl, isoxazolyl, thiazolyl, isothiazolyl, oxadiazolyl, thiadiazolyl, triazolyl, tetrazolyl, and the like.

Of these, imidazolyl, benzimidazolyl, indolyl, 1H-indazolyl and the like are preferable, and imidazolyl, benzimidazolyl and the like are particularly preferable.

The heterocyclic group for $R^1$ may have 1 to 3 substituent(s) at substitutable position(s). As such substituent, for example, an optionally substituted aliphatic hydrocarbon group, an optionally substituted alicyclic hydrocarbon group, an optionally substituted aromatic hydrocarbon group, an optionally substituted aromatic heterocyclic group, an optionally substituted non-aromatic heterocyclic group, a halogen atom, a nitro, an optionally substituted amino group, an optionally substituted acyl group, optionally substituted hydroxy group, an optionally substituted thiol group, an optionally substituted acyl group, a $C_{1-3}$ alkylenedioxy, an oxo and the like can be mentioned.

Here, as the "aliphatic hydrocarbon group", "alicyclic hydrocarbon group" and "aromatic hydrocarbon group" of the "optionally substituted aliphatic hydrocarbon group", "optionally substituted alicyclic hydrocarbon group" and "optionally substituted aromatic hydrocarbon group", those exemplified for the "hydrocarbon group" of the "optionally substituted hydrocarbon group" for $R^1$ can be mentioned.

As the "aromatic heterocyclic group" and "non-aromatic heterocyclic group" of the "optionally substituted aromatic heterocyclic group" and "optionally substituted non-aromatic heterocyclic group", those exemplified for the substituent of the "optionally substituted hydrocarbon group" for $R^1$ can be mentioned.

Moreover, as the "halogen atom", "optionally substituted amino group", "optionally substituted acyl group", "optionally substituted hydroxy group", "optionally substituted thiol group", "optionally substituted acyl group" and "$C_{1-3}$ alkylenedioxy", those exemplified for the substituent of the "optionally substituted hydrocarbon group" for $R^1$ can be mentioned.

In the aforementioned "optionally substituted aliphatic hydrocarbon group", as the substituent, for example,
1) a hydroxy;
2) a cyano;
3) a halogen atom (e.g., fluorine, chlorine, bromine, iodine);
4) an amidino;
5) a carboxyl;
6) a sulfo;
7) an azide;
8) a nitro;
9) a nitroso;
10) a $C_{3-10}$ cycloalkyl;
11) a $C_{6-14}$ aryl (e.g., phenyl, naphthyl);
12) a 5- or 6-membered aromatic heterocyclic group (e.g., thienyl, furyl, pyridyl, oxazolyl, thiazolyl);
13) a 5- or 6-membered non-aromatic heterocyclic group (e.g., tetrahydrofuryl, morpholino, thiomorpholino, piperidino, pyrrolidinyl, piperazinyl);
14) a $C_{1-6}$ alkoxy optionally substituted by 1 to 3 halogen atom(s) (e.g., fluorine, chlorine, bromine, iodine);
15) a $C_{2-6}$ alkenyloxy optionally substituted by 1 to 3 halogen atom(s) (e.g., fluorine, chlorine, bromine, iodine);
16) a $C_{3-10}$ cycloalkyloxy;
17) a $C_{6-14}$ aryloxy (e.g., phenyloxy, naphthyloxy);
18) a $C_{7-13}$ aralkyloxy;
19) a thiol;
20) a $C_{1-6}$ alkylthio optionally substituted by 1 to 3 halogen atom(s) (e.g., fluorine, chlorine, bromine, iodine);
21) a $C_{2-6}$ alkenylthio optionally substituted by 1 to 3 halogen atom(s) (e.g., fluorine, chlorine, bromine, iodine);
22) a $C_{3-10}$ cycloalkylthio;
23) a $C_{6-14}$ arylthio (e.g., phenylthio, naphthylthio);
24) a $C_{7-13}$ aralkylthio;
25) a $C_{1-6}$ alkyl-carbonyl;
26) a $C_{1-6}$ alkoxy-carbonyl (e.g., methoxycarbonyl, ethoxycarbonyl, propoxycarbonyl, butoxycarbonyl, tert-butoxycarbonyl);
27) a (mono- or di-$C_{1-10}$ alkyl)phosphono group optionally forming a ring (e.g., dimethylphosphono, diethylphosphono, diisopropylphosphono, dibutylphosphono, 2-oxide-1,3,2-dioxaphosphinanyl);
28) a carbamoyl (e.g., carbamoyl, methylcarbamoyl, ethylcarbamoyl, dimethylcarbamoyl, diethylcarbamoyl, ethylmethylcarbamoyl, propylcarbamoyl) optionally mono- or di-substituted by $C_{1-6}$ alkyl optionally substituted by 1 to 3 halogen(s);
29) a sulfamoyl (e.g., sulfamoyl, methylsulfamoyl, ethylsulfamoyl) optionally mono- or di-substituted by $C_{1-6}$ alkyl optionally substituted by 1 to 3 halogen(s);
30) a thiocarbamoyl;
31) an amino optionally mono- or di-substituted by substituent selected from $C_{1-6}$ alkyl and $C_{1-6}$ alkyl-carbonyl; and the like can be mentioned. The number of substituents is, for example, 1 to 3.

In the aforementioned "optionally substituted alicyclic hydrocarbon group", "optionally substituted aromatic hydrocarbon group", "optionally substituted aromatic heterocyclic group" and "optionally substituted non-aromatic heterocyclic group", as the substituent, for example, 1) a hydroxy;
2) a cyano;
3) a halogen atom (e.g., fluorine, chlorine, bromine, iodine);
4) an amidino;
5) a carboxyl;
6) a sulfo;
7) an azide;
8) a nitro;
9) a nitroso;
10) a $C_{1-6}$ alkyl optionally substituted by 1 to 3 halogen atom(s) (e.g., fluorine, chlorine, bromine, iodine);
11) a $C_{2-6}$ alkenyl optionally substituted by 1 to 3 halogen atom(s) (e.g., fluorine, chlorine, bromine, iodine);
12) a $C_{7-13}$ aralkyl;
13) a $C_{3-10}$ cycloalkyl;
14) a $C_{6-14}$ aryl (e.g., phenyl, naphthyl);
15) a 5- or 6-membered aromatic heterocyclic group (e.g., thienyl, furyl, pyridyl, oxazolyl, thiazolyl);
16) a 5- or 6-membered non-aromatic heterocyclic group (e.g., tetrahydrofuryl, morpholino, thiomorpholino, piperidino, pyrrolidinyl, piperazinyl);
17) a $C_{1-6}$ alkoxy optionally substituted by 1 to 3 halogen atom(s) (e.g., fluorine, chlorine, bromine, iodine);
18) a $C_{2-6}$ alkenyloxy optionally substituted by 1 to 3 halogen atom(s) (e.g., fluorine, chlorine, bromine, iodine);
19) a $C_{3-10}$ cycloalkyloxy;
20) a $C_{6-14}$ aryloxy (e.g., phenyloxy, naphthyloxy);
21) a $C_{7-13}$ aralkyloxy;
22) a thiol;
23) a $C_{1-6}$ alkylthio optionally substituted by 1 to 3 halogen atom(s) (e.g., fluorine, chlorine, bromine, iodine);
24) a $C_{2-6}$ alkenylthio optionally substituted by 1 to 3 halogen atom(s) (e.g., fluorine, chlorine, bromine, iodine);
25) a $C_{3-10}$ cycloalkylthio;
26) a $C_{6-14}$ arylthio (e.g., phenylthio, naphthylthio);
27) a $C_{7-13}$ aralkylthio;
28) a $C_{1-6}$ alkyl-carbonyl;
29) a $C_{1-6}$ alkoxy-carbonyl (e.g., methoxycarbonyl, ethoxycarbonyl, propoxycarbonyl, butoxycarbonyl, tert-butoxycarbonyl);
30) a (mono- or di-$C_{1-10}$ alkyl)phosphono group optionally forming a ring (e.g., dimethylphosphono, diethylphosphono, diisopropylphosphono, dibutylphosphono, 2-oxide-1,3,2-dioxaphosphinanyl);
31) a carbamoyl (e.g., carbamoyl, methylcarbamoyl, ethylcarbamoyl, dimethylcarbamoyl, diethylcarbamoyl, ethylmethylcarbamoyl, propylcarbamoyl) optionally mono- or di-substituted by $C_{1-6}$ alkyl optionally substituted by 1 to 3 halogen(s);
32) a sulfamoyl (e.g., sulfamoyl, methylsulfamoyl, ethylsulfamoyl) optionally mono- or di-substituted by $C_{1-6}$ alkyl optionally substituted by 1 to 3 halogen(s);
33) a thiocarbamoyl;
34) an amino optionally mono- or di-substituted by substituent selected from $C_{1-6}$ alkyl and $C_{1-6}$ alkyl-carbonyl; and the like can-be mentioned. The number of substituents is, for example, 1 to 3.

The substituent of the "optionally substituted heterocyclic group" for $R^1$ preferably includes a $C_{1-6}$ alkyl (e.g., methyl, ethyl) optionally substituted by 1 to 3 halogen atom(s) (e.g., fluorine, chlorine, bromine, iodine), a $C_{1-6}$ alkoxy (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{6-14}$ aryl (e.g., phenyl), a $C_{1-3}$ alkylenedioxy (e.g., methylenedioxy, ethylenedioxy), a $C_{1-10}$ alkylsulfonyl group (e.g., methylsulfonyl, ethylsulfonyl), a hydroxy-$C_{1-6}$ alkyl (e.g., hydroxymethyl) and the like. The number of substituents is, for example, 1 to 3.

As the "optionally substituted hydroxy group", "optionally substituted thiol group" and "optionally substituted amino group" for $R^1$, those exemplified for the substituent of the "optionally substituted hydrocarbon group" for $R^1$ can be mentioned.

$R^1$ is preferably an "optionally substituted heterocyclic group". The heterocyclic group is preferably an azolyl group optionally condensed with a benzene ring (e.g., pyrrolyl, imidazolyl, pyrazolyl, oxazolyl, isoxazolyl, thiazolyl, isothiazolyl, oxadiazolyl, thiadiazolyl, triazolyl, tetrazolyl), and the like. Of these, imidazolyl, benzimidazolyl, indolyl, 1H-indazolyl and the like are preferable, and imidazolyl, benzimidazolyl and the like are particularly preferable.

$R^1$ is more preferably an "azolyl group optionally condensed with a benzene ring (e.g., pyrrolyl, imidazolyl, pyrazolyl, oxazolyl, isoxazolyl, thiazolyl, isothiazolyl, oxadiazolyl, thiadiazolyl, triazolyl, tetrazolyl)" which is optionally substituted by 1 to 3 substituent(s) selected from a $C_{1-6}$ alkyl (e.g., methyl, ethyl) optionally substituted by 1 to 3 halogen atom(s) (e.g., fluorine, chlorine, bromine, iodine), a $C_{1-6}$ alkoxy (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{6-14}$ aryl (e.g., phenyl), a $C_{1-3}$ alkylenedioxy (e.g., methylenedioxy, ethylenedioxy), a $C_{1-10}$ alkylsulfonyl group (e.g., methylsulfonyl, ethylsulfonyl) and a hydroxy-$C_{1-6}$ alkyl (e.g., hydroxymethyl), and the like. Of these, imidazolyl and benzimidazolyl, each of which is optionally substituted by $C_{1-6}$ alkyl group (e.g., methyl, ethyl) optionally substituted by 1 to 3 halogen atom(s) (e.g., fluorine, chlorine, bromine, iodine), are preferable. $R^1$ is particularly preferably benzimidazolyl.

A is an "optionally substituted cyclic amino group" or "—$NR^2$—W—D ($R^2$ is a hydrogen atom or an alkyl group, W is a bond or a divalent acyclic hydrocarbon group, and D is an optionally substituted cyclic group, an optionally substituted amino group or an optionally substituted acyl group)".

As the "cyclic amino group" of the "optionally substituted cyclic amino group", for example, a 5- to 8-membered nitrogen-containing heterocyclic group containing at least one nitrogen atom besides carbon atoms as ring-constituting atoms and optionally further containing 1 or 2 heteroatom(s) selected from an oxygen atom, a sulfur atom and a nitrogen atom can be mentioned. Preferable examples of the nitrogen-containing heterocyclic group include 1-pyrrolidinyl, 1-imidazolidinyl, 1-pyrazolidinyl, 1-piperidinyl, 1-piperazinyl, 4-morpholinyl, 4-thiomorpholinyl, 1-azepanyl, 1-azocanyl, 3-thiazolidinyl, 3-oxazolidinyl and the like. Of these, 1-piperidinyl, 1-piperazinyl, 4-morpholinyl, 4-thiomorpholinyl and the like are preferable.

The "cyclic amino group" optionally has 1 to 3 substituent(s) at substitutable position(s). As such substituent, for example, 1) an oxo;
2) a hydroxy;
3) a cyano;
4) a halogen atom (e.g., fluorine, chlorine, bromine, iodine);

5) a $C_{1-6}$ alkylenedioxy (e.g., methylenedioxy, ethylenedioxy);
6) a $C_{1-6}$ alkyl group (e.g., methyl, ethyl) optionally substituted by 1 to 3 substituent(s) selected from a halogen atom (e.g., fluorine, chlorine, bromine, iodine), a hydroxy, a cyano, a $C_{1-6}$ alkoxy (e.g., methoxy), an amino (e.g., amino, methylamino, dimethylamino) optionally mono- or di-substituted by $C_{1-6}$ alkyl, a 5- or 6-membered aromatic heterocyclic group (e.g., thiazolyl) optionally substituted by $C_{1-6}$ alkyl, a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl, a carboxamide, an optionally halogenated mono- or di-$C_{1-6}$ alkyl-carboxamide (e.g., acetylamino, trifluoroacetylamino), and a ono- or di-$C_{1-6}$ alkoxy-carboxamide (e.g., tert-butoxycarboxamide);
7) a $C_{6-14}$ aryl (e.g., phenyl) optionally substituted by 1 to 3 substituent(s) selected from a halogen atom (e.g., fluorine, chlorine, bromine, iodine), an optionally halogenated $C_{1-6}$ alkyl and a $C_{1-6}$ alkoxy;
8) a $C_{7-13}$ aralkyl group (e.g., benzyl, benzhydryl) optionally substituted by $C_{1-6}$ alkylenedioxy;
9) a 5- or 6-membered nitrogen-containing heterocyclic group (e.g., pyridyl, piperidinyl, pyrimidinyl, pyrrolidinyl) optionally substituted by $C_{1-6}$ alkyl group;
10) an amino (e.g., amino, methylamino, dimethylamino) optionally mono- or di-substituted by $C_{1-6}$ alkyl;
11) a $C_{1-6}$ alkyl-carbonyl (e.g., acetyl);
12) a $C_{1-6}$ alkyl-sulfonyl (e.g., methylsulfonyl, ethylsulfonyl);
13) a $C_{3-10}$ cycloalkyl-carbonyl (e.g., cyclohexylcarbonyl);
14) a $C_{6-14}$ aryl-carbonyl (e.g., benzoyl);
15) a $C_{7-13}$ aralkyl-carbonyl (e.g., benzylcarbonyl, phenethylcarbonyl);
16) a $C_{6-14}$ aryl-$C_{2-6}$ alkenyl-carbonyl (e.g., styrylcarbonyl);
17) a $C_{1-6}$ alkoxy-carbonyl (e.g., methoxycarbonyl, ethoxycarbonyl, propoxycarbonyl, butoxycarbonyl, tert-butoxycarbonyl);
18) a 5- or 6-membered aromatic heterocyclic-carbonyl (e.g., furoyl, pyrrolylcarbonyl, thenoyl, pyridylcarbonyl) optionally substituted by $C_{1-6}$ alkyl;
19) a 5- or 6-membered non-aromatic heterocyclic-carbonyl (e.g., tetrahydrofuroyl) optionally substituted by $C_{1-6}$ alkyl;
20) a carboxamide;
21) a mono- or di-$C_{1-6}$ alkyl-carboxamide optionally substituted by 1 to 3 substituent(s) selected from a halogen atom (e.g., fluorine, chlorine, bromine, iodine) and a $C_{1-6}$ alkyl, such as acetylamino, hexanoylamino, trifluoroacetylamino, N-acetyl-N-methylamino and pentafluoropropionylamino;
22) a $C_{3-10}$ cycloalkyl-carboxamide (e.g., cyclohexylcarboxamide);
23) a $C_{6-14}$ aryl-carboxamide (e.g., phenylcarboxamide) optionally substituted by $C_{1-6}$ alkylenedioxy;
24) a $C_{7-13}$ aralkyl-carboxamide (e.g., benzylcarboxamide, phenethylcarboxamide);
25) a $C_{6-14}$ aryl-$C_{2-6}$ alkenyl-carboxamide (e.g., styrylcarboxamide);
26) a $C_{1-6}$ alkoxy-carboxamide (e.g., tert-butoxycarboxamide);
27) a 5- or 6-membered aromatic heterocyclic-carboxamide (e.g., furylcarboxamide, pyrrolylcarboxamide, thienylcarboxamide, pyridylcarboxamide) optionally substituted by $C_{1-6}$ alkyl;
28) a 5- or 6-membered non-aromatic heterocyclic-carboxamide (e.g., tetrahydrofurylcarboxamide) optionally substituted by $C_{1-6}$ alkyl; and the like can be mentioned.

The "optionally substituted cyclic amino group" for A is preferably 1-piperidinyl, 1-piperazinyl, 4-morpholinyl or 4-thiomorpholinyl, each optionally having 1 to 3 substituent(s) selected from 1) an oxo;
2) a hydroxy;
3) a cyano;
4) a halogen atom (e.g., fluorine, chlorine, bromine, iodine);
5) a $C_{1-6}$ alkylenedioxy (e.g., methylenedioxy, ethylenedioxy);
6) a $C_{1-6}$ alkyl group (e.g., methyl, ethyl) optionally substituted by 1 to 3 substituent(s) selected from halogen atom (e.g., fluorine, chlorine, bromine, iodine), hydroxy, cyano, $C_{1-6}$ alkoxy (e.g., methoxy), amino (e.g., amino, methylamino, dimethylamino) optionally mono- or di-substituted by $C_{1-6}$ alkyl, 5- or 6-membered aromatic heterocyclic group (e.g., tetrazolyl) optionally substituted by $C_{1-6}$ alkyl, a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl, carboxamide, optionally halogenated mono- or di-$C_{1-6}$ alkyl-carboxamide (e.g., acetylamino, trifluoroacetylamino), and mono- or di-$C_{1-6}$ alkoxy-carboxamide (e.g., tert-butoxycarboxamide);
7) a $C_{6-14}$ aryl (e.g., phenyl) optionally substituted by 1 to 3 substituent(s) selected from a halogen atom (e.g., fluorine, chlorine, bromine, iodine), an optionally halogenated $C_{1-6}$ alkyl and a $C_{1-6}$ alkoxy;
8) a $C_{7-13}$ aralkyl group (e.g., benzyl, benzhydryl) optionally substituted by $C_{1-6}$ alkylenedioxy;
9) a 5- or 6-membered nitrogen-containing heterocyclic group (e.g., pyridyl, piperidinyl, pyrimidinyl, pyrrolidinyl) optionally substituted by $C_{1-6}$ alkyl group;
10) an amino (e.g., amino, methylamino, dimethylamino) optionally mono- or di-substituted by $C_{1-6}$ alkyl;
11) a $C_{1-6}$ alkyl-carbonyl (e.g., acetyl);
12) a $C_{1-6}$ alkyl-sulfonyl (e.g., methylsulfonyl, ethylsulfonyl);
13) a $C_{3-10}$ cycloalkyl-carbonyl (e.g., cyclohexylcarbonyl);
14) a $C_{6-14}$ aryl-carbonyl (e.g., benzoyl);
15) a $C_{7-13}$ aralkyl-carbonyl (e.g., benzylcarbonyl, phenethylcarbonyl);
16) a $C_{6-14}$ aryl-$C_{2-6}$ alkenyl-carbonyl (e.g., styrylcarbonyl);
17) a $C_{1-6}$ alkoxy-carbonyl (e.g., methoxycarbonyl, ethoxycarbonyl, propoxycarbonyl, butoxycarbonyl, tert-butoxycarbonyl);
18) a 5- or 6-membered aromatic heterocyclic-carbonyl (e.g., furoyl, pyrrolylcarbonyl, thenoyl, pyridylcarbonyl) optionally substituted by $C_{1-6}$ alkyl;
19) a 5- or 6-membered non-aromatic heterocyclic-carbonyl (e.g., tetrahydrofuroyl) optionally substituted by $C_{1-6}$ alkyl;
20) a carboxamide;

21) a mono- or di-$C_{1-6}$ alkyl-carboxamide optionally substituted by 1 to 3 substituent(s) selected from a halogen atom (e.g., fluorine, chlorine, bromine, iodine) and a $C_{1-6}$ alkyl, such as acetylamino, hexanoylamino, trifluoroacetylamino, N-acetyl-N-methylamino and pentafluoropropionylamino;
22) a $C_{3-10}$ cycloalkyl-carboxamide (e.g., cyclohexylcarboxamide);
23) a $C_{6-14}$ aryl-carboxamide (e.g., phenylcarboxamide) optionally substituted by $C_{1-6}$ alkylenedioxy;
24) a $C_{7-13}$ aralkyl-carboxamide (e.g., benzylcarboxamide, phenethylcarboxamide);
25) a $C_{6-14}$ aryl-$C_{2-6}$ alkenyl-carboxamide (e.g., styrylcarboxamide);
26) a $C_{1-6}$ alkoxy-carboxamide (e.g., tert-butoxycarboxamide)
27) a 5- or 6-membered aromatic heterocyclic-carboxamide (e.g., furylcarboxamide, pyrrolylcarboxamide, thienylcarboxamide, pyridylcarboxamide) optionally substituted by $C_{1-6}$ alkyl;
28) a 5- or 6-membered non-aromatic heterocyclic-carboxamide (e.g., tetrahydrofurylcarboxamide) optionally substituted by $C_{1-6}$ alkyl.

As the alkyl group for $R^2$, for example, a $C_{1-6}$ alkyl group (e.g., methyl, ethyl, propyl, isopropyl) can be mentioned. Particularly, methyl is preferable. $R^2$ is preferably a hydrogen atom.

The "divalent acyclic hydrocarbon group" for W may be straight-chain or branched and saturated or unsaturated, as long as it is an acyclic divalent hydrocarbon group.

As the "divalent acyclic hydrocarbon group", for example, a "divalent aliphatic hydrocarbon group" can be mentioned. Particularly, a divalent $C_{1-8}$ aliphatic hydrocarbon group is preferable.

Preferable examples of the "divalent acyclic hydrocarbon group" include:
(1) a $C_{1-8}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH(CH$_3$)—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$— and the like);
(2) a $C_{2-8}$ alkenylene (e.g., —CH=CH—, —CH$_2$—CH=CH—, —C(CH$_3$)$_2$—CH=CH—, —CH$_2$—CH=CH—CH$_2$—, —CH$_2$—CH=CH—, —CH=CH—CH=CH—, —CH=CH—CH$_2$—CH$_2$—CH$_2$— and the like) and the like.

The "divalent acyclic hydrocarbon group" is preferably a divalent aliphatic hydrocarbon group having 1 to 4 carbon atoms, and is more preferably a $C_{1-4}$ alkylene. Particularly, —CH$_2$—, —(CH$_2$)$_2$—, —(CH$_2$)$_3$—, —(CH$_2$)$_4$— and the like are preferable, and specifically, —(CH$_2$)$_2$—, —(CH$_2$)$_3$—, —(CH$_2$)$_4$— and the like are preferable.

W is preferably a bond or a divalent aliphatic hydrocarbon group having 1 to 4 carbon atoms and is more preferably a bond or a $C_{1-4}$ alkylene. Particularly, a bond, —CH$_2$—, —(CH$_2$)$_2$—, —(CH$_2$)$_3$—, —(CH$_2$)$_4$— and the like are preferable, and specifically, a bond, —(CH$_2$)$_2$—, —(CH$_2$)$_3$—, —(CH$_2$)$_4$— and the like are preferable.

As the "cyclic group" of the "optionally substituted cyclic group" for D is, for example, an alicyclic hydrocarbon group, an aromatic hydrocarbon group, an aromatic heterocyclic group, a non-aromatic heterocyclic group and the like can be mentioned.

Here, as the "alicyclic hydrocarbon group" and "aromatic hydrocarbon group", those exemplified for the "hydrocarbon group" of the "optionally substituted hydrocarbon group" for $R^1$ can be mentioned.

As the "aromatic heterocyclic group" and "non-aromatic heterocyclic group", those exemplified for the substituents of the "optionally substituted hydrocarbon group" for $R^1$ can be mentioned.

The cyclic group is preferably a $C_{6-14}$ aryl group (preferably phenyl, biphenylyl), a $C_{3-10}$ cycloalkyl group (preferably cyclopropyl, cyclobutyl, cyclopentyl, cyclohexyl, cycloheptyl, cyclooctyl), a $C_{3-10}$ cycloalkenyl group (preferably cyclohexenyl), a 5- or 6-membered aromatic heterocyclic group optionally condensed with a benzene ring (preferably furyl, thienyl, thiazolyl, imidazolyl, pyrazolyl, pyridyl, pyrazinyl, indolyl, quinolyl, isoquinolyl, benzothiazolyl, benzothiadiazolyl, isoxazolyl), a 5- or 6-membered non-aromatic heterocyclic group optionally condensed with a benzene ring (preferably pyrrolidinyl, tetrahydrofuranyl, thiazolinyl, oxazolinyl, thiazolidinyl, oxazolidinyl, dioxolanyl, piperidinyl, piperazinyl, morpholino, thiomorpholino, dihydrobenzofuranyl) and the like. The cyclic group is more preferably a $C_{6-14}$ aryl group, and phenyl is particularly preferable.

The "cyclic group" for D may have 1 to 3 substituent(s) at the substitutable position(s). As such substituent, for example,
(1) an oxo;
(2) a hydroxy;
(3) a cyano;
(4) a halogen atom (e.g., fluorine, chlorine, bromine, iodine);
(5) a $C_{1-6}$ alkylenedioxy (e.g., methylenedioxy, ethylenedioxy);
(6) a carboxyl;
(7) a $C_{1-6}$ alkyl group (e.g., methyl, ethyl, propyl, isopropyl, butyl, isobutyl) optionally substituted by 1 to 3 substituent(s) selected from a halogen atom (e.g., fluorine, chlorine, bromine, iodine); a hydroxyl; a cyano; a $C_{1-6}$ alkoxy (e.g., methoxy); an amino optionally mono- or di-substituted by $C_{1-6}$ alkyl, such as amino, methylamino, dimethylamino; a 5- or 6-membered aromatic heterocyclic group (e.g., thiazolyl) optionally substituted by $C_{1-6}$ alkyl; a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl; carboxyl group; $C_{1-6}$ alkoxy-carbonyl (e.g., methoxycarbonyl, ethoxycarbonyl, propoxycarbonyl, butoxycarbonyl, tert-butoxycarbonyl); a (mono- or di-$C_{1-10}$ alkyl)phosphono group optionally forming a ring (e.g., dimethylphosphono, diethylphosphono, diisopropylphosphono, dibutylphosphono, 2-oxide-1,3,2-dioxaphosphinanyl); a carbamoyl; a mono- or di-$C_{1-6}$ alkyl-carbamoyl optionally substituted by 1 to 3 substituent(s) selected from a halogen atom, a hydroxy and a $C_{1-6}$ alkoxy-carbonyl, such as methylcarbamoyl, ethylcarbamoyl, dimethylcarbamoyl, diethylcarbamoyl, ethylmethylcarbamoyl, propylcarbamoyl, trifluoroethylcarbamoyl, methoxycarbonylethylcarbamoyl, 2-hydroxy-1-methoxycarbonyl-ethylcarbamoyl and 2-hydroxy-1-methoxycarbonyl-propylcarbamoyl; a mono- or di-$C_{6-14}$ aryl-carbamoyl optionally substituted by 1 to 3 substituent(s) selected from an optionally halogenated $C_{1-6}$ alkyl and a $C_{1-6}$ alkoxy, such as phenylcarbamoyl, methoxyphenylcarbamoyl and trifluoromethylphenylcarbamoyl; a mono- or di-$C_{7-13}$ aralkyl-carbamoyl optionally substituted by 1 to 3 substituent(s) selected from an amino optionally mono- or di-substituted by $C_{1-6}$ alkyl, an optionally halogenated $C_{1-6}$ alkyl, a hydroxy and a $C_{1-6}$ alkoxy-carbonyl, such as benzylcarbamoyl, phenethylcarbamoyl, dimethylaminobenzylcarbamoyl, methoxycarbonylphenethylcarbamoyl and trifluoromethylbenzylcarbamoyl; a sulfamoyl; and an optionally halogenated mono- or di-$C_{1-6}$ alkylsulfamoyl (e.g., methylsulfamoyl, ethylsulfamoyl);

(8) a $C_{3-10}$ cycloalkyl group (e.g., cyclohexyl);
(9) a $C_{6-14}$ aryl (e.g., phenyl);
(10) a $C_{7-13}$ aralkyl (e.g., benzyl);
(11) a 5- or 6-membered aromatic heterocyclic group (e.g., thiadiazolyl);
(12) a $C_{1-6}$ alkoxy group, (e.g., methoxy, ethoxy) optionally substituted by 1 to 3 halogen atom(s) (e.g., fluorine, chlorine, bromine, iodine);
(13) a $C_{1-6}$ alkylthio (e.g., methylthio) optionally substituted by 1 to 3 halogen atom(s) (e.g., fluorine, chlorine, bromine, iodine);
(14) a $C_{6-14}$ aryloxy (e.g., phenoxy);
(15) an amino optionally mono- or di-substituted by $C_{1-6}$ alkyl, such as amino, methylamino, dimethylamino, ethylamino, diethylamino, ethylmethylamino, propylamino and dibutylamino;
(16) a phosphono-$C_{1-6}$ alkylamino optionally mono- or di-substituted by $C_{1-10}$ alkyl, such as phosphonomethylamino and diethylphosphonomethylamino;
(17) a mono- or di-$C_{1-6}$ alkyl-carboxamide optionally substituted by 1 to 3 substituent(s) selected from a halogen atom (e.g., fluorine, chlorine, bromine, iodine) and a $C_{1-6}$ alkyl, such as acetylamino, hexanoylamino, trifluoroacetylamino, N-acetyl-N-methylamino and pentafluoropropionylamino;
(18) a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl);
(19) a $C_{1-6}$ alkyl-carbonyl (e.g., acetyl);
(20) a $C_{1-6}$ alkyl-sulfonyl (e.g., methylsulfonyl and ethylsulfonyl);
(21) a $C_{3-10}$ cycloalkyl-carbonyl (e.g., cyclohexylcarbonyl);
(22) a $C_{6-14}$ aryl-carbonyl (e.g., benzoyl);
(23) a $C_{7-13}$ aralkyl-carbonyl (e.g., benzylcarbonyl and phenethylcarbonyl);
(24) a $C_{6-14}$ aryl-$C_{2-6}$ alkenyl-carbonyl (e.g., styrylcarbonyl);
(25) a $C_{1-6}$ alkoxy-carbonyl (e.g., methoxycarbonyl and tert-butoxycarbonyl);
(26) a 5- or 6-membered aromatic heterocyclic-carbonyl (e.g., furoyl, pyrrolylcarbonyl and pyridylcarbonyl) optionally substituted by $C_{1-6}$ alkyl;
(27) a 5- or 6-membered non-aromatic heterocyclic-carbonyl (e.g., tetrahydrofuroyl) optionally substituted by $C_{1-6}$ alkyl;
(28) a carbamoyl optionally mono- or di-substituted by $C_{1-6}$ alkyl, such as carbamoyl and dimethylcarbamoyl;
(29) a sulfamoyl optionally mono- or di-substituted by $C_{1-6}$ alkyl, such as sulfamoyl and dimethylsulfamoyl; and the like can be mentioned.

As the "optionally substituted amino group" and "optionally substituted acyl group" for D, those exemplified for the substituents of the "optionally substituted hydrocarbon group" for $R^1$ can be mentioned.

As preferable examples of the "optionally substituted amino group" for D,
1) an amino optionally mono- or di-substituted by substituents selected from a $C_{1-6}$ alkyl optionally substituted by hydroxy, a $C_{6-14}$ aryl, and a 5- or 6-membered aromatic heterocyclic group (e.g., pyridyl) optionally substituted by nitro, such as amino, methylamino, dimethylamino, diisopropylamino, phenylamino and N-phenyl-N-methylamino;
2) a mono- or di-$C_{1-6}$ alkyl-carboxamide optionally substituted by 1 to 3 substituent(s) selected from halogen atom(s) (e.g., fluorine, chlorine, bromine, iodine) and a $C_{1-6}$ alkyl, such as acetylamino, hexanoylamino, trifluoroacetylamino, N-acetyl-N-methylamino and pentafluoropropionylamino;
3) a $C_{1-6}$ alkoxy-carboxamide optionally substituted by $C_{1-6}$ alkyl, such as tert-butoxycarboxamide and N-tert-butoxycarbonyl-N-methylamino;
4) a $C_{6-14}$ aryl-carboxamide (e.g., phenylcarboxamide) optionally substituted by $C_{1-6}$ alkyl;
5) a $C_{7-13}$ aralkyl-carboxamide (e.g., benzylcarboxamide and phenethylcarboxamide) optionally substituted by $C_{1-6}$ alkyl;
6) a 5- or 6-membered aromatic heterocyclic-carboxamide (e.g., furylcarboxamide, pyrrolylcarboxamide, thienylcarboxamide, pyridylcarboxamide) optionally substituted by $C_{1-6}$ alkyl;
7) a 5- or 6-membered non-aromatic heterocyclic-carboxamide (e.g., tetrahydrofurylcarboxamide) optionally substituted by $C_{1-6}$ alkyl; and the like can be mentioned.

As preferable examples of the "optionally substituted acyl group" for D,
(1) a carboxyl;
(2) a $C_{1-6}$ alkyl-carbonyl (e.g., acetyl);
(3) a $C_{1-6}$ alkoxy-carbonyl (e.g., methoxycarbonyl, ethoxycarbonyl);
(4) a $C_{1-6}$ alkylsulfonyl (e.g., methylsulfonyl, ethylsulfonyl);
(5) a carbamoyl optionally mono- or di-substituted by $C_{1-6}$ alkyl, such as carbamoyl and dimethylcarbamoyl;
(6) a sulfamoyl optionally mono- or di-substituted by $C_{1-6}$ alkyl, such as sulfamoyl and dimethylsulfamoyl;
(7) a mono- or di-$C_{6-14}$ aryl-carbamoyl (e.g., phenylcarbamoyl);
(8) a mono- or di-$C_{7-13}$ aralkyl-carbamoyl (e.g., benzylcarbamoyl);
(9) a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl; and the like can be mentioned.

D is preferably an optionally substituted cyclic group, and more preferably "a $C_{6-14}$ aryl group (preferably phenyl, biphenylyl)", "a 5- or 6-membered aromatic heterocyclic group optionally condensed with a benzene ring (preferably furyl, thienyl, thiazolyl, imidazolyl, pyrazolyl, pyridyl, pyrazinyl, indolyl, quinolyl, isoquinolyl, benzothiazolyl, benzothiadiazolyl, isoxazolyl)" or "a 5- or 6-membered non-aromatic heterocyclic group optionally condensed with a benzene ring (preferably pyrrolidinyl, tetrahydrofuranyl, thiazolinyl, oxazolinyl, thiazolidinyl, oxazolidinyl, dioxolanyl, piperidinyl, piperazinyl, morpholino, thiomorpholino, dihydrobenzofuranyl)", each of which is optionally substituted by 1 to 3 substituent(s) selected from
(1) an oxo;
(2) a hydroxy;
(3) a cyano;
(4) a halogen atom;
(5) a $C_{1-6}$ alkylenedioxy;
(6) a carboxyl;

(7) a $C_{1-6}$ alkyl group optionally substituted by 1 to 3 substituent(s) selected from a halogen atom; a hydroxy; a cyano; a $C_{1-6}$ alkoxy; an amino optionally mono- or di-substituted by $C_{1-6}$ alkyl; a 5- or 6-membered aromatic heterocyclic group (e.g., tetrazolyl) optionally substituted by $C_{1-6}$ alkyl; a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl; a carboxyl group; a $C_{1-6}$ alkoxy-carbonyl; a (mono- or di-$C_{1-10}$ alkyl) phosphono group optionally forming a ring; a carbamoyl; a mono- or di-$C_{1-6}$ alkyl-carbamoyl optionally substituted by 1 to 3 substituent(s) selected from a halogen atom, a hydroxy and a $C_{1-6}$ alkoxy-carbonyl; a mono- or di-$C_{6-14}$ aryl-carbamoyl optionally substituted by 1 to 3 substituent(s) selected from an optionally halogenated $C_{1-6}$ alkyl and a $C_{1-6}$ alkoxy; a mono- or di-$C_{7-13}$ aralkyl-carbamoyl optionally substituted by 1 to 3 substituent(s) selected from an amino optionally mono- or di-substituted by $C_{1-6}$ alkyl, an optionally halogenated $C_{1-6}$ alkyl, a hydroxy and a $C_{1-6}$ alkoxy-carbonyl; a sulfamoyl; and an optionally halogenated mono- or di-$C_{1-6}$ alkylsulfamoyl;

(8) a $C_{3-10}$ cycloalkyl group;

(9) a $C_{6-14}$ aryl;

(10) a $C_{7-13}$ aralkyl;

(11) a 5- or 6-membered aromatic heterocyclic group (e.g., thiadiazolyl);

(12) a $C_{1-6}$ alkoxy group optionally substituted by 1 to 3 halogen atom(s);

(13) a $C_{1-6}$ alkylthio optionally substituted by 1 to 3 halogen atom(s);

(14) a $C_{6-14}$ aryloxy;

(15) an amino optionally mono- or di-substituted by $C_{1-6}$ alkyl;

(16) a phosphono-$C_{1-6}$ alkylamino optionally mono- or di-substituted by $C_{1-10}$ alkyl;

(17) a mono- or di-$C_{1-6}$ alkyl-carboxamide optionally substituted by 1 to 3 substituent(s) selected from a halogen atom and a $C_{1-6}$ alkyl;

(18) a (mono- or di-$C_{1-10}$ alkyl)phosphono group optionally forming a ring;

(19) a $C_{1-6}$ alkyl-carbonyl;

(20) a $C_{1-6}$ alkyl-sulfonyl;

(21) a $C_{3-10}$ cycloalkyl-carbonyl;

(22) a $C_{6-14}$ aryl-carbonyl;

(23) a $C_{7-13}$ aralkyl-carbonyl;

(24) a $C_{6-14}$ aryl-$C_{2-6}$ alkenyl-carbonyl;

(25) a $C_{1-6}$ alkoxy-carbonyl;

(26) a 5- or 6-membered aromatic heterocyclic-carbonyl (e.g., furoyl, pyrrolylcarbonyl and pyridylcarbonyl) optionally substituted by $C_{1-6}$ alkyl;

(27) a 5- or 6-membered non-aromatic heterocyclic-carbonyl (e.g., tetrahydrofuroyl) optionally substituted by $C_{1-6}$ alkyl;

(28) a carbamoyl optionally mono- or di-substituted by $C_{1-6}$ alkyl; and

(29) a sulfamoyl optionally mono- or di-substituted by $C_{1-6}$ alkyl.

D is particularly preferably a $C_{6-14}$ aryl group (preferably phenyl) optionally substituted by $C_{1-6}$ alkyl group (preferably methyl, ethyl) optionally substituted by (mono- or di-$C_{1-10}$ alkyl)phosphono group optionally forming a ring (preferably dimethylphosphono; diethylphosphono; diisopropylphosphono; dibutylphosphono; 2-oxide-1,3,2-dioxaphosphinanyl).

As the "optionally substituted hydrocarbon group" and "optionally substituted heterocyclic group" for B, those exemplified for $R^1$ can be mentioned.

B is preferably an "optionally substituted hydrocarbon group", and is more preferably a $C_{1-10}$ alkyl group (e.g., methyl, isopropyl, t-butyl) or an optionally substituted $C_{6-14}$ aryl group. Particularly, an optionally substituted $C_{6-14}$ aryl group is preferable.

Preferable examples of B include a $C_{6-14}$ aryl group (preferably phenyl or biphenylyl, more preferably phenyl) optionally substituted by 1 to 3 substituent(s) selected from a $C_{1-6}$ alkyl (e.g., methyl, ethyl, trifluoromethyl) optionally substituted by 1 to 3 halogen atom(s) (e.g., fluorine, chlorine, bromine, iodine), a $C_{1-6}$ alkoxy (e.g., methoxy, ethoxy, trifluoromethoxy) optionally substituted by 1 to 3 halogen atom(s) (e.g., fluorine, chlorine, bromine, iodine), a halogen atom (e.g., fluorine, chlorine, bromine, iodine), a nitro, a formyl, a $C_{1-3}$ alkylenedioxy (e.g., methylenedioxy) and an aromatic heterocyclic group (e.g., benzofuryl).

Particularly, a $C_{6-14}$ aryl group (preferably phenyl) optionally substituted by 1 to 3 halogen atom(s) (e.g., chlorine, bromine) is preferable.

X is an oxygen atom, a sulfur atom or an optionally substituted nitrogen atom.

As the optionally substituted nitrogen atom for X, for example, —$NR^5$— wherein R5 is a hydrogen atom, an optionally substituted hydrocarbon group, an optionally substituted heterocyclic group or an optionally substituted acyl group, and the like can be mentioned.

Here, as the "optionally substituted hydrocarbon group" and "optionally substituted heterocyclic group" for $R^5$, those exemplified for $R^1$ can be mentioned.

As the optionally substituted acyl group for $R^5$, those exemplified for the substituent of the "optionally substituted hydrocarbon group" for $R^1$ can be mentioned.

$R^5$ is preferably a hydrogen atom, an optionally substituted hydrocarbon group and the like, more preferably a hydrogen atom, an optionally substituted alkyl group and the like, and particularly, a hydrogen atom, a $C_{1-4}$ alkyl group and the like are preferable.

X is preferably an oxygen atom or a sulfur atom, more preferably an oxygen atom.

As the "divalent acyclic hydrocarbon group" for Y, those exemplified for the aforementioned W can be mentioned.

Y is preferably a divalent acyclic hydrocarbon group, more preferably a divalent aliphatic hydrocarbon group having 1 to 4 carbon atoms, particularly preferably a $C_{1-4}$ alkylene (preferably —$CH_2$—, —$(CH_2)_2$—, —$(CH_2)_3$—, —$(CH_2)_4$—). Of these, —$(CH_2)_2$—, —$(CH_2)_3$—, —$(CH_2)_4$— and the like are preferable, particularly, —$(CH_2)_2$— and the like are preferable.

As the preferable examples of the compounds represented y the formula (I), the following compounds (A)–(F) and the like can be mentioned.

Compound (A)

A compound wherein $R^1$ is an "azolyl group optionally condensed with a benzene ring (e.g., pyrrolyl, imidazolyl, pyrazolyl, oxazolyl, isoxazolyl, thiazolyl, isothiazolyl, oxadiazolyl, thiadiazolyl, triazolyl, tetrazolyl)" optionally substituted by 1 to 3 substituent(s) selected from a $C_{1-6}$ alkyl optionally substituted by 1 to 3 halogen atom(s), a $C_{1-6}$alkoxy optionally substituted by 1 to 3 halogen atom(s), a halogen atom, a nitro, a hydroxy, an amino, a $C_{6-14}$ aryl and a $C_{1-3}$ alkylenedioxy;

A is an optionally substituted cyclic amino group;

B is a $C_{6-14}$ aryl group (preferably phenyl) optionally substituted by 1 to 3 substituent(s) selected from a $C_{1-6}$ alkyl optionally substituted by 1 to 3 halogen atom(s), a $C_{1-6}$ alkoxy, a halogen atom, nitro, formyl and a $C_{1-3}$ alkylenedioxy;

X is an oxygen atom or a sulfur atom; and

Y is a divalent aliphatic hydrocarbon group having 1 to 4 carbon atoms (preferably $C_{1-4}$ alkylene).

Compound (B)

A compound wherein $R^1$ is an "azolyl group optionally condensed with a benzene ring (e.g., pyrrolyl, imidazolyl, pyrazolyl, oxazolyl, isoxazolyl, thiazolyl, isothiazolyl, oxadiazolyl, thiadiazolyl, triazolyl, tetrazolyl)" optionally substituted by 1 to 3 substituent(s) selected from a $C_{1-6}$ alkyl optionally substituted by 1 to 3 halogen atom(s), a $C_{1-6}$ alkoxy optionally substituted by 1 to 3 halogen atom(s), a halogen atom, a nitro, a hydroxy, an amino, a $C_{6-14}$ aryl and a $C_{1-3}$ alkylenedioxy;

A is —$NR^2$—W—D wherein $R^2$ is a hydrogen atom or a $C_{1-6}$ alkyl group, W is a bond or $C_{1-4}$ alkylene, and D is an optionally substituted cyclic group;

B is a $C_{6-14}$ aryl group (preferably phenyl) optionally substituted by 1 to 3 substituent(s) selected from a $C_{1-6}$ alkyl optionally substituted by 1 to 3 halogen atom(s), a $C_{1-6}$ alkoxy, a halogen atom, nitro, formyl and a $C_{1-3}$ alkylenedioxy;

X is an oxygen atom or a sulfur atom; and

Y is a divalent aliphatic hydrocarbon group having 1 to 4 carbon atoms (preferably $C_{1-4}$ alkylene).

Compound (C)

A compound wherein $R^1$ is (1) imidazolyl, benzimidazolyl, indolyl or 1H-indazolyl, each of which is optionally substituted by 1 to 3 substituent(s) selected from a $C_{1-6}$ alkyl (e.g., methyl, ethyl) optionally substituted by 1 to 3 halogen atom(s) (e.g., fluorine, chlorine, bromine, iodine), a $C_{1-6}$ alkoxy (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{6-14}$ aryl (e.g., phenyl), a $C_{1-3}$ alkylenedioxy (e.g., methylenedioxy, ethylenedioxy), a $C_{1-10}$ alkylsulfonyl group (e.g., methylsulfonyl, ethylsulfonyl) and a hydroxy-$C_{1-6}$ alkyl (e.g., hydroxymethyl); or (2) a $C_{1-10}$ alkyl group, a $C_{6-14}$ aryl group, a $C_{3-10}$ cycloalkyl group, a $C_{7-14}$ aralkyl group, a $C_{8-13}$ aralkenyl group, a $C_{4-13}$ cycloalkylalkyl group (preferably a $C_{6-14}$ aryl group), each of which is optionally substituted by 1 to 3 substituent(s) selected from a $C_{1-6}$ alkoxy group (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{1-3}$ alkylenedioxy (e.g., methylenedioxy, ethylenedioxy);

[$R^1$ is preferably imidazolyl or benzimidazolyl, each of which is optionally substituted by a $C_{1-6}$ alkyl group optionally substituted by 1 to 3 halogen atom(s); more preferably benzimidazolyl];

A is 1-piperidinyl, 1-piperazinyl, 4-morpholinyl or 4-thiomorpholinyl, each optionally having 1 to 3 substituent(s) selected from 1) an oxo;
2) a hydroxy;
3) a cyano;
4) a halogen atom (e.g., fluorine, chlorine, bromine, iodine);
5) a $C_{1-6}$ alkylenedioxy (e.g., methylenedioxy, ethylenedioxy);
6) a $C_{1-6}$ alkyl group (e.g., methyl, ethyl) optionally substituted by 1 to 3 substituent(s) selected from a halogen atom (e.g., fluorine, chlorine, bromine, iodine); a hydroxy; a cyano; a $C_{1-6}$ alkoxy (e.g., methoxy); amino (e.g., amino, methylamino, dimethylamino) optionally mono- or di-substituted by $C_{1-6}$ alkyl; a 5- or 6-membered aromatic heterocyclic group (e.g., tetrazolyl) optionally substituted by $C_{1-6}$ alkyl; a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl; a carboxamide; an optionally halogenated mono- or di-$C_{1-6}$ alkyl-carboxamide (e.g., acetylamino, trifluoroacetylamino); and a mono- or di-$C_{1-6}$ alkoxy-carboxamide (e.g., tert-butoxycarboxamide);
7) a $C_{6-14}$ aryl (e.g., phenyl) optionally substituted by 1 to 3 substituent(s) selected from a halogen atom (e.g., fluorine, chlorine, bromine, iodine), optionally halogenated $C_{1-6}$ alkyl and $C_{1-6}$ alkoxy;
8) a $C_{7-13}$ aralkyl group (e.g., benzyl, benzhydryl) optionally substituted by $C_{1-6}$ alkylenedioxy;
9) a 5- or 6-membered nitrogen-containing heterocyclic group (e.g., pyridyl, piperidinyl, pyrimidinyl, pyrrolidinyl) optionally substituted by $C_{1-6}$ alkyl group;
10) an amino (e.g., amino, methylamino, dimethylamino) optionally mono- or di-substituted by $C_{1-6}$ alkyl;
11) a $C_{1-6}$ alkyl-carbonyl (e.g., acetyl);
12) a $C_{1-6}$ alkyl-sulfonyl (e.g., methylsulfonyl, ethylsulfonyl);
13) a $C_{3-10}$ cycloalkyl-carbonyl (e.g., cyclohexylcarbonyl);
14) a $C_{6-14}$ aryl-carbonyl (e.g., benzoyl);
15) a $C_{7-13}$ aralkyl-carbonyl (e.g., benzylcarbonyl, phenethylcarbonyl);
16) a $C_{6-14}$ aryl-$C_{2-6}$ alkenyl-carbonyl (e.g., styrylcarbonyl);
17) a $C_{1-6}$ alkoxy-carbonyl (e.g., methoxycarbonyl, ethoxycarbonyl, propoxycarbonyl, butoxycarbonyl, tert-butoxycarbonyl);
18) a 5- or 6-membered aromatic heterocyclic-carbonyl (e.g., furoyl, pyrrolylcarbonyl, thenoyl, pyridylcarbonyl) optionally substituted by $C_{1-6}$ alkyl;
19) a 5- or 6-membered non-aromatic heterocyclic-carbonyl (e.g., tetrahydrofuroyl) optionally substituted by $C_{1-6}$ alkyl;
20) a carboxamide;
21) a mono- or di-$C_{1-6}$ alkyl-carboxamide (e.g., acetylamino, hexanoylamino, trifluoroacetylamino, N-acetyl-N-methylamino, pentafluoropropionylamino) optionally substituted by 1 to 3 substituent(s) selected from a halogen atom (e.g., fluorine, chlorine, bromine, iodine) and $C_{1-6}$ alkyl;
22) a $C_{3-10}$ cycloalkyl-carboxamide (e.g., cyclohexylcarboxamide);
23) a $C_{6-14}$ aryl-carboxamide (e.g., phenylcarboxamide) optionally substituted by $C_{1-6}$ alkylenedioxy;
24) a $C_{7-13}$ aralkyl-carboxamide (e.g., benzylcarboxamide, phenethylcarboxamide);
25) a $C_{6-14}$ aryl-$C_{2-6}$ alkenyl-carboxamide (e.g., styrylcarboxamide);

26) a $C_{1-6}$ alkoxy-carboxamide (e.g., tert-butoxycarboxamide);
27) a 5- or 6-membered aromatic heterocyclic-carboxamide (e.g., furylcarboxamide, pyrrolylcarboxamide, thienylcarboxamide, pyridylcarboxamide) optionally substituted by $C_{1-6}$ alkyl;
28) a 5- or 6-membered non-aromatic heterocyclic-carboxamide (e.g., tetrahydrofurylcarboxamide) optionally substituted by $C_{1-6}$ alkyl;

B is (1) a $C_{6-14}$ aryl group (preferably phenyl) optionally substituted by 1 to 3 substituent(s) selected from a $C_{1-6}$ alkyl (e.g., methyl, ethyl, trifluoromethyl) optionally substituted by 1 to 3 halogen atom(s) (e.g., fluorine, chlorine, bromine, iodine), a $C_{1-6}$ alkoxy (e.g. methoxy, ethoxy, trifluoromethoxy) optionally substituted by 1 to 3 halogen atom(s) (e.g., fluorine, chlorine, bromine, iodine), a halogen atom (e.g., fluorine, chlorine, bromine, iodine), a nitro, a formyl, a $C_{1-3}$ alkylenedioxy (e.g., methylenedioxy), an aromatic heterocyclic group (e.g., benzofuryl) or (2) a $C_{1-10}$ alkyl group (e.g., methyl, isopropyl, t-butyl);

[B is preferably a $C_{6-14}$ aryl group (preferably phenyl) optionally substituted by 1 to 3 halogen atom(s)(preferably chlorine, bromine)];

X is an oxygen atom or a sulfur atom; and

Y is a divalent aliphatic hydrocarbon group having 1 to 4 carbon atoms (preferably $C_{1-4}$ alkylene).

Compound (D)

A compound wherein $R^1$ is (1) imidazolyl, benzimidazolyl, indolyl or 1H-indazolyl, each of which is optionally substituted by 1 to 3 substituent(s) selected from a $C_{1-6}$ alkyl (e.g., methyl, ethyl) optionally substituted by 1 to 3 halogen atom(s) (e.g., fluorine, chlorine, bromine, iodine), a $C_{1-6}$ alkoxy (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino, a $C_{6-14}$ aryl (e.g., phenyl), a $C_{1-3}$ alkylenedioxy (e.g., methylenedioxy, ethylenedioxy), a $C_{1-10}$ alkylsulfonyl group (e.g., methylsulfonyl, ethylsulfonyl) and a hydroxy-$C_{1-6}$ alkyl (e.g., hydroxymethyl); or (2) a $C_{1-10}$ alkyl group, a $C_{6-14}$ aryl group, a $C_{3-10}$ cycloalkyl group, a $C_{7-14}$ aralkyl group, a $C_{8-13}$ arylalkenyl group, a $C_{4-13}$ cycloalkylalkyl group (preferably a $C_{6-14}$ aryl group), each of which is optionally substituted by 1 to 3 substituent(s) selected from a $C_{1-6}$ alkoxy group (e.g., methoxy, ethoxy) optionally substituted by 1 to 3 halogen atom(s) (e.g., fluorine, chlorine, bromine, iodine), a halogen atom (e.g., fluorine, chlorine, bromine, iodine), a nitro, a hydroxy, an amino and a $C_{1-3}$ alkylenedioxy (e.g., methylenedioxy, ethylenedioxy);

[$R^1$ is preferably imidazolyl or benzimidazolyl, each of which is optionally substituted by a $C_{1-6}$ alkyl group optionally substituted by 1 to 3 halogen atom(s); more preferably benzimidazolyl];

A is —$NR^2$—W—D;

$R^2$ is a hydrogen atom or a $C_{1-6}$ alkyl group, W is a bond or a $C_{1-4}$ alkylene, D is "a $C_{6-14}$ aryl group (preferably phenyl, biphenylyl)", "a 5- or 6-membered aromatic heterocyclic group optionally condensed with a benzene ring (preferably furyl, thienyl, thiazolyl, imidazolyl, pyrazolyl, pyridyl, pyrazinyl, indolyl, quinolyl, isoquinolyl, benzothiazolyl, benzothiadiazolyl, isoxazolyl)" or "a 5- or 6-membered non-aromatic heterocyclic group optionally condensed with a benzene ring (preferably pyrrolidinyl, tetrahydrofuranyl, thiazolinyl, oxazolinyl, thiazolidinyl, oxazolidinyl, dioxolanyl, piperidinyl, piperazinyl, morpholino, thiomorpholino, dihydrobenzofuranyl)", each of which is optionally substituted by 1 to 3 substituent(s) selected from (1) an oxo;
(2) a hydroxy;
(3) a cyano;
(4) a halogen atom;
(5) a $C_{1-6}$ alkylenedioxy;
(6) a carboxyl;
(7) a $C_{1-6}$ alkyl group optionally substituted by 1 to 3 substituent(s) selected from a halogen atom; a hydroxy; a cyano; a $C_{1-6}$ alkoxy; an amino optionally mono- or di-substituted by $C_{1-6}$ alkyl; a 5- or 6-membered aromatic heterocyclic group (e.g., tetrazolyl) optionally substituted by $C_{1-6}$ alkyl; a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl; a carboxyl group; a $C_{1-6}$ alkoxy-carbonyl; a (mono- or di-$C_{1-10}$ alkyl) phosphono group optionally forming a ring; a carbamoyl; a mono- or di-$C_{1-6}$alkyl-carbamoyl optionally substituted by 1 to 3 substituent(s) selected from a halogen atom, hydroxy and $C_{1-6}$ alkoxy-carbonyl; a mono- or di-$C_{6-14}$ aryl-carbamoyl optionally substituted by 1 to 3 substituent(s) selected from optionally halogenated $C_{1-6}$ alkyl and $C_{1-6}$ alkoxy; a mono- or di-$C_{7-13}$ aralkyl-carbamoyl optionally substituted by 1 to 3 substituent(s) selected from amino optionally mono- or di-substituted by $C_{1-6}$ alkyl, optionally halogenated $C_{1-6}$ alkyl, hydroxy and $C_{1-6}$ alkoxy-carbonyl; a sulfamoyl; an optionally halogenated mono- or di-$C_{1-6}$ alkylsulfamoyl;

(8) a $C_{3-10}$ cycloalkyl group;
(9) a $C_{6-14}$ aryl;
(10) a $C_{7-13}$ aralkyl;
(11) a 5- or 6-membered aromatic heterocyclic group (e.g., thiadiazolyl);
(12) a $C_{1-6}$ alkoxy group optionally substituted by 1 to 3 halogen atom(s);
(13) a $C_{1-6}$ alkylthio optionally substituted by 1 to 3 halogen atom(s)
(14) a $C_{6-14}$ aryloxy;
(15) an amino optionally mono- or di-substituted by $C_{1-6}$ alkyl;
(16) a phosphono-$C_{1-6}$ alkylamino optionally mono- or di-substituted by $C_{1-10}$ alkyl;
(17) a mono- or di-$C_{1-6}$ alkyl-carboxamide optionally substituted by 1 to 3 substituent(s) selected from a halogen atom and $C_{1-6}$ alkyl;
(18) a (mono- or di-$C_{1-10}$ alkyl)phosphono group optionally forming a ring;
(19) a $C_{1-6}$ alkyl-carbonyl;
(20) a $C_{1-6}$ alkyl-sulfonyl;
(21) a $C_{3-10}$ cycloalkyl-carbonyl;
(22) a $C_{6-14}$ aryl-carbonyl;
(23) a $C_{7-13}$ aralkyl-carbonyl;
(24) a $C_{6-14}$ aryl-$C_{2-6}$ alkenyl-carbonyl;
(25) a $C_{1-6}$ alkoxy-carbonyl;
(26) a 5- or 6-membered aromatic heterocyclic-carbonyl (e.g., furoyl, pyrrolylcarbonyl, pyridylcarbonyl) optionally substituted by $C_{1-6}$ alkyl;

(27) a 5- or 6-membered non-aromatic heterocyclic-carbonyl (e.g., tetrahydrofuroyl) optionally substituted by $C_{1-6}$ alkyl;

(28) a carbamoyl optionally mono- or di-substituted by $C_{1-6}$ alkyl;

(29) a sulfamoyl optionally mono- or di-substituted by $C_{1-6}$ alkyl;

[D is preferably a $C_{6-14}$ aryl group (preferably phenyl) optionally substituted by $C_{1-6}$ alkyl group (preferably methyl, ethyl) optionally substituted by (mono- or di-$C_{1-10}$ alkyl)phosphono group optionally forming a ring (preferably dimethylphosphono; diethylphosphono; diisopropylphosphono; dibutylphosphono; and 2-oxide-1,3,2-dioxaphosphinanyl)];

B is (1) a $C_{6-14}$ aryl group (preferably phenyl) optionally substituted by 1 to 3 substituent(s) selected from a $C_{1-6}$ alkyl (e.g., methyl, ethyl, trifluoromethyl) optionally substituted by 1 to 3 halogen atom(s) (e.g., fluorine, chlorine, bromine, iodine), a $C_{1-6}$ alkoxy (e.g., methoxy, ethoxy, trifluoromethoxy) optionally substituted by 1 to 3 halogen atom(s) (e.g., fluorine, chlorine, bromine, iodine), a halogen atom (e.g., fluorine, chlorine, bromine, iodine), a nitro, a formyl, a $C_{1-3}$ alkylenedioxy (e.g., methylenedioxy), an aromatic heterocyclic group (e.g., benzofuryl) or (2) a $C_{1-10}$ alkyl group (e.g., methyl, isopropyl, t-butyl);

[B is preferably a $C_{6-14}$ aryl group (preferably phenyl) optionally substituted by 1 to 3 halogen atom(s) (preferably chlorine, bromine)];

X is an oxygen atom or a sulfur atom; and

Y is a divalent aliphatic hydrocarbon group having 1 to 4 carbon atoms (preferably $C_{1-4}$ alkylene)

Compound (E)

A compound wherein $R^1$ is a mono- or di-$C_{1-10}$ alkylamino (e.g., methylamino, dimethylamino, ethylamino, diethylamino, ethylmethylamino, propylamino, dibutylamino); a mono- or di-$C_{2-10}$ alkenylamino (e.g., diallylamino) [optionally substituted by $C_{1-6}$ alkoxy-carbonyl]; a mono- or di-$C_{3-10}$ cycloalkylamino (e.g., cyclohexylamino); a mono- or di-$C_{1-10}$ alkyl-carboxamide (e.g., acetylamino, propionylamino) [optionally substituted by 1 to 3 substituent(s) selected from heterocyclic thio (e.g., pyrimidinylthio) optionally substituted by $C_{1-6}$ alkyl, $C_{6-14}$ arylthio optionally substituted by 1 to 3 halogen atom(s), cyano, $C_{1-6}$ alkylthio, halogen atom and heterocyclic carbonyl (e.g., dihydroindolylcarbonyl)]; a $C_{6-14}$ aryl-carboxamide (e.g., benzoylamino); a $C_{6-14}$ arylamino (e.g., phenylamino); a N-$C_{1-10}$ alkyl-N-$C_{6-14}$ arylamino (e.g., N-methyl-N-phenylamino) ; N-$C_{1-10}$ alkyl-N-$C_{7-13}$ aralkylamino (e.g., N-methyl-N-benzylamino); a mono- or di-$C_{1-6}$ alkoxy-carboxamide (e.g., tert-butoxycarboxamide); a mono- or di-$C_{6-14}$ arylcarboxamide (e.g., phenylcarboxamide) [optionally substituted by 1 to 3 substituent(s) selected from $C_{1-6}$ alkoxy, $C_{6-14}$ aryloxy and heterocyclic group (e.g., triazolyl, tetrazolyl)]; mono- or di-$C_{7-13}$ aralkyl-carboxamide (e.g., benzylcarboxamide, phenethylcarboxamide, phenylpropylcarboxamide, phenylbutylcarboxamide) [optionally substituted by 1 to 3 substituent(s) selected from $C_{1-6}$ alkoxy and halogen atom]; an aromatic heterocyclic-carboxamide (e.g., furylcarboxamide, pyrrolylcarboxamide, thienylcarboxamide, pyridylcarboxamide, pyrimidinylcarboxamide, 1H-indazolylcarboxamide, benzofuranylcarboxamide, quinolylcarboxamide) [optionally substituted by 1 to 3 substituent(s) selected from halogen atom and $C_{1-6}$ alkyl]; a 5- to 7-membered non-aromatic heterocyclic-carboxamide (e.g., tetrahydrofurylcarboxamide, thiomorpholinocarboxamide, piperidinocarboxamide, piperazinocarboxamide, hexamethyleniminylcarboxamide, thiazolidinylcarboxamide) [optionally substituted by 1 to 3 substituent(s) selected from oxo, $C_{1-6}$ alkoxy-carbonyl, $C_{1-6}$ alkoxy-$C_{6-14}$ aryl (e.g., methoxyphenyl), $C_{1-6}$ alkyl-carbonyl-$C_{6-14}$ aryl (e.g., acetylphenyl), carbamoyl, $C_{7-13}$ aralkyl (e.g., benzyl) and heterocyclic group (e.g., piperidino)]; a $C_{3-10}$ cycloalkyl-carboxamide (e.g., cyclopentylcarboxamide, cyclohexylcarboxamide) [optionally substituted by $C_{1-6}$ alkyl optionally substituted by $C_{1-6}$ alkoxy-carboxamide (e.g., methoxycarboxamide, ethoxycarboxamide)]; a $C_{8-13}$ arylalkenyl-carboxamide (e.g., styrylcarboxamide) [optionally substituted by halogen atom]; a $C_{8-13}$ arylalkynyl-carboxamide (e.g., phenylethynylcarboxamide); an aromatic heterocyclic (e.g., thienyl, furyl, indolyl)-$C_{1-6}$ alkyl-carboxamide; a $C_{6-14}$ arylsulfonylamino (e.g., phenylsulfonylamino); mono- or di-$C_{1-6}$ alkyl-carbamoylamino (e.g., methylcarbamoylamino, tert-butylcarbamoylamino) [optionally substituted by 1 to 3 substituent(s) selected from hydroxy, $C_{1-6}$ alkoxy, $C_{1-6}$ alkylthio, halogen atom, $C_{1-6}$ alkoxycarbonyl, $C_{1-6}$ alkoxy-carboxamide, cyano, $C_{1-6}$ alkylsulfonyl and carbamoyl]; a $C_{3-10}$ cycloalkyl-carbamoylamino (e.g., cyclopropylcarbamoylamino, cyclopentylcarbamoylamino, cyclohexylcarbamoylamino) [optionally substituted by hydroxy]; a $C_{6-14}$ aryl-carbamoylamino (e.g., phenylcarbamoylamino) [optionally substituted by 1 to 3 substituent(s) selected from $C_{1-6}$ alkyl optionally substituted by 1 to 3 halogen atom(s), sulfamoyl optionally substituted by $C_{1-6}$ alkyl-carbonyl, mono- or di-$C_{1-6}$ alkylamino, mono- or di-$C_{1-10}$ alkylphosphono-$C_{1-6}$ alkyl group, halogen atom, $C_{6-14}$ arylsulfonyl (e.g., phenylsulfonyl), a $C_{7-13}$ aralkyloxy (e.g., benzyloxy) and $C_{1-6}$ alkoxy]; a $C_{7-14}$ aralkyl-carbamoylamino (e.g., benzylcarbamoylamino, phenethylcarbamoylamino, diphenylethylcarbamoylamino) [optionally substituted by 1 to 3 substituent(s) selected from $C_{1-6}$ alkyl optionally substituted by 1 to 3 substituent(s) selected from mono- or di-$C_{1-6}$ alkylamino and halogen atom; halogen atom; sulfamoyl; hydroxyl; and $C_{1-6}$ alkoxy]; $C_{1-6}$ alkoxy-carbonylcarbamoylamino (e.g., methoxycarbonylcarbamoylamino, ethoxycarbonylcarbamoylamino); a $C_{4-13}$ cycloalkylalkyl-carbamoylamino (e.g., cyclohexylmethylcarbamoylamino); a heterocyclic (e.g., thienyl, furyl, oxazolyl, isoxazolyl, imidazolyl, triazolyl, tetrazolyl, pyridyl, indolyl, 1H-indazolyl, benzimidazolyl, tetrahydrofuryl, pyrrolidinyl, piperidinyl, morpholinyl, thiomorpholinyl)-$C_{1-10}$ alkyl-carbamoylamino (e.g., methylcarbamoylamino, ethylcarbamoylamino) [optionally substituted by 1 to 3 substituent(s) selected from oxo, $C_{1-6}$ alkyl, hydroxy and $C_{1-6}$ alkoxy]; an aromatic heterocyclic carbamoylamino (e.g., isoxazolylcarbamoylamino, benzothiazolylcarbamoylamino) [optionally substituted by 1 to 3 substituent(s) selected from $C_{1-6}$ alkyl and $C_{1-6}$ alkoxy]; a non-aromatic heterocyclic carbamoylamino (e.g., pyrrolidinylcarbamoylamino) [optionally substituted by $C_{1-6}$ alkyl]; or a $C_{7-14}$ aralkyloxy-carbamoylamino (e.g., benzyloxycarbamoylamino);

A is (1) —$NR^2$—W—D;

$R^2$ is a hydrogen atom or $C_{1-6}$ alkyl group, W is a bond or $C_{1-4}$ alkylene, D is a $C_{6-14}$ aryl group (preferably phenyl) optionally substituted by $C_{1-6}$ alkyl group (preferably methyl, ethyl) optionally substituted by (mono- or di-$C_{1-10}$ alkyl)phosphono group optionally forming a ring (preferably, dimethylphosphono; diethylphosphono; diisopropylphosphono; dibutylphosphono; 2-oxide-1,3,2-dioxaphosphinanyl); or (2) 1-piperidinyl, 1-piperazinyl, 4-morpholinyl or 4-thiomorpholinyl, each optionally having 1 to 3 substituent(s) selected from 1) an oxo;
2) a hydroxy;
3) a cyano;
4) a halogen atom (e.g., fluorine, chlorine, bromine, iodine);
5) a $C_{1-6}$ alkylenedioxy (e.g., methylenedioxy, ethylenedioxy)
6) a $C_{1-6}$ alkyl group (e.g., methyl, ethyl) optionally substituted by 1 to 3 substituent(s) selected from a halogen atom (e.g., fluorine, chlorine, bromine, iodine), hydroxyl, cyano, $C_{1-6}$ alkoxy (e.g., methoxy); an amino (e.g., amino, methylamino, dimethylamino) optionally mono- or di-substituted by $C_{1-6}$ alkyl; a 5- or 6-membered aromatic heterocyclic group (e.g., tetrazolyl) optionally substituted by $C_{1-6}$ alkyl; a 5- or 6-membered non-aromatic heterocyclic group (e.g., tetrahydrofuryl, morpholino, thiomorpholino, piperidinyl, pyrrolidinyl, piperazinyl, dioxothiazolidinyl, dioxooxazolidinyl) optionally substituted by $C_{1-6}$ alkyl; carboxamide; optionally halogenated mono- or di-$C_{1-6}$ alkyl-carboxamide (e.g., acetylamino, trifluoroacetylamino); and mono- or di-$C_{1-6}$ alkoxy-carboxamide (e.g., tert-butoxycarboxamide);
7) a $C_{6-14}$ aryl (e.g., phenyl) optionally substituted by 1 to 3 substituent(s) selected from a halogen atom (e.g., fluorine, chlorine, bromine, iodine), optionally halogenated $C_{1-6}$ alkyl and $C_{1-6}$ alkoxy;
8) a $C_{7-13}$ aralkyl group (e.g., benzyl, benzhydryl) optionally substituted by $C_{1-6}$ alkylenedioxy;
9) a 5- or 6-membered nitrogen-containing heterocyclic group (e.g., pyridyl, piperidinyl, pyrimidinyl, pyrrolidinyl) optionally substituted by a $C_{1-6}$ alkyl group;
10) an amino (e.g., amino, methylamino, dimethylamino) optionally mono- or di-substituted by $C_{1-6}$ alkyl;
11) a $C_{1-6}$ alkyl-carbonyl (e.g., acetyl);
12) a $C_{1-6}$ alkyl-sulfonyl (e.g., methylsulfonyl, ethylsulfonyl);
13) a $C_{3-10}$ cycloalkyl-carbonyl (e.g., cyclohexylcarbonyl);
14) a $C_{6-14}$ aryl-carbonyl (e.g., benzoyl);
15) a $C_{7-13}$ aralkyl-carbonyl (e.g., benzylcarbonyl, phenethylcarbonyl);
16) a $C_{6-14}$ aryl-$C_{2-6}$ alkenyl-carbonyl (e.g., styrylcarbonyl);
17) a $C_{1-6}$ alkoxy-carbonyl (e.g., methoxycarbonyl, ethoxycarbonyl, propoxycarbonyl, butoxycarbonyl, tert-butoxycarbonyl);
18) a 5- or 6-membered aromatic heterocyclic-carbonyl (e.g., furoyl, pyrrolylcarbonyl, thenoyl, pyridylcarbonyl) optionally substituted by $C_{1-6}$ alkyl;
19) a 5- or 6-membered non-aromatic heterocyclic-carbonyl (e.g., tetrahydrofuroyl) optionally substituted by $C_{1-6}$ alkyl;
20) a carboxamide;
21) a mono- or di-$C_{1-6}$ alkyl-carboxamide (e.g., acetylamino, hexanoylamino, trifluoroacetylamino, N-acetyl-N-methylamino, pentafluoropropionylamino) optionally substituted by 1 to 3 substituent(s) selected from a halogen atom (e.g., fluorine, chlorine, bromine, iodine) and $C_{1-6}$ alkyl;
22) a $C_{3-10}$ cycloalkyl-carboxamide (e.g., cyclohexylcarboxamide);
23) a $C_{6-14}$ aryl-carboxamide (e.g., phenylcarboxamide) optionally substituted by $C_{1-6}$ alkylenedioxy;
24) a $C_{7-13}$ aralkyl-carboxamide (e.g., benzylcarboxamide, phenethylcarboxamide);
25) a $C_{6-14}$ aryl-$C_{2-6}$ alkenyl-carboxamide (e.g., styrylcarboxamide);
26) a $C_{1-6}$ alkoxy-carboxamide (e.g., tert-butoxycarboxamide)
27) a 5- or 6-membered aromatic heterocyclic-carboxamide (e.g., furylcarboxamide, pyrrolylcarboxamide, thienylcarboxamide, pyridylcarboxamide) optionally substituted by $C_{1-6}$ alkyl;
28) a 5- or 6-membered non-aromatic heterocyclic-carboxamide (e.g., tetrahydrofurylcarboxamide) optionally substituted by $C_{1-6}$ alkyl;

[A is preferably the aforementioned (1)];

B is (1) a $C_{6-14}$ aryl group (preferably phenyl) optionally substituted by 1 to 3 substituent(s) selected from a $C_{1-6}$ alkyl (e.g., methyl, ethyl, trifluoromethyl) optionally substituted by 1 to 3 halogen atom(s) (e.g., fluorine, chlorine, bromine, iodine), a $C_{1-6}$ alkoxy (e.g., methoxy, ethoxy, trifluoromethoxy) optionally substituted by 1 to 3 halogen atom(s) (e.g., fluorine, chlorine, bromine, iodine), a halogen atom (e.g., fluorine, chlorine, bromine, iodine), a nitro, a formyl, a $C_{1-3}$ alkylenedioxy (e.g., methylenedioxy), and an aromatic heterocyclic group (e.g., benzofuryl) or (2) a $C_{1-10}$ alkyl group (e.g., methyl, isopropyl, t-butyl);

[B is preferably a $C_{6-14}$ aryl group (preferably phenyl) optionally substituted by 1 to 3 halogen atom(s) (preferably chlorine, bromine)];

X is an oxygen atom or a sulfur atom; and

Y is a divalent aliphatic hydrocarbon group having 1 to 4 carbon atoms (preferably $C_{1-4}$ alkylene).

Compound (F)

3-[2-(1H-benzimidazol-1-yl)-4-(4-chlorophenyl)-5-oxazolyl]-N-[4-(diethylphosphonomethyl)phenyl]propionamide;

3-[4-(4-chlorophenyl)-2-(4-morpholinyl)-5-oxazolyl]-N-[4-(diethylphosphonomethyl)phenyl]propionamide;

3-[4-(4-chlorophenyl)-2-phenyl-5-oxazolyl]-N-[4-(dimethylphosphonomethyl)phenyl]propionamide;

3-[2-(1H-benzimidazol-1-yl)-4-(4-chlorophenyl)-5-oxazolyl]-N-{4-[(2-oxide-1,3,2-dioxaphosphinan-2-yl)methyl]phenyl)propionamide;

4-[2-(1H-benzimidazol-1-yl)-4-(4-chlorophenyl)-5-oxazolyl]-N-[(4-dimethylphosphonomethyl)phenyl]butanamide;

1-{3-[2-(1H-benzimidazol-1-yl)-4-(4-chlorophenyl)-5-oxazolyl]propanoyl}-4-piperidinol;

4-(3-[2-(1H-benzimidazol-1-yl)-4-(4-chlorophenyl)-5-oxazolyl]propanoyl}thiomorpholine-1,1-dioxide;

4-[2-(1H-benzimidazol-1-yl)-4-(4-chlorophenyl)-5-oxazolyl]-N-[(4-diethylphosphonomethyl)phenyl]butanamide; or 4-{3-[4-(4-chlorophenyl)-2-(1-methyl-1H-indol-3-yl)-5-oxazolyl]propanoyl}thiomorpholine-1,1'-dioxide.

As the salts of a compound represented by the formula (I), pharmacologically acceptable salts are preferable. As such salts, for example, a salt with an inorganic base, a salt with an organic base, a salt with an inorganic acid, a salt with an organic acid and a salt with a basic or acidic amino acid can be mentioned.

Preferable examples of the salt with an inorganic base include alkali metal salts such as sodium salt, potassium salt and the like; alkaline earth metal salts such as calcium salt, magnesium salt and the like; and aluminum salt, ammonium salt and the like.

Preferable examples of the salt with an organic base include salts with trimethylamine, triethylamine, pyridine, picoline, ethanolamine, diethanolamine, triethanolamine, dicyclohexylamine, N,N-dibenzylethylenediamine, and the like.

Preferable examples of the salt with an inorganic acid include salts with hydrochloric acid, hydrobromic acid, nitric acid, sulfuric acid, and phosphoric acid and the like.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salt with a basic amino acid include salts with arginine, lysine and ornithine and the like.

Preferable examples of the salt with an acidic amino acid include salts with aspartic acid, glutamic acid, and the like.

Of these salts, a sodium salt, a potassium salt, hydrochloride and the like are preferred.

A prodrug of the compound (I) means a compound capable of being converted to the compound (I) in vivo by the reaction of an enzyme or gastric juice and the like under physiological conditions, namely a compound capable of being converted to the compound (I) upon enzymatic oxidation, reduction or hydrolysis and the like, or a compound capable of being converted to the compound (I) upon hydrolysis and the like by gastric juice and the like. As the prodrug of the compound (I), compounds derived by acylation, alkylation or phosphorylation of the amino group of the compound (I) (e.g. compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of the compound (I), and the like); compounds derived by acylation, alkylation, phosphorylation or boration of the hydroxy group of the compound (I) (e.g. compounds derived by acetylation, palmitoylation, propanoylation, pivaloylation, succinylation, fumarylation, alanylation or dimethylaminomethylcarbonylation of the hydroxy group of the compound (I), and the like); and compounds derived by esterification or amidation of the carboxyl group of the compound (I) (e.g. compounds derived by ethyl esterification, phenyl esterification; carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of the compound (I), and the like), and the like can be mentioned. These compounds can be produced from the compound (I) by methods known per se.

The prodrug of the compound (I) may be one capable of being converted to the compound (I) under physiological conditions, as described in "Iyakuhin no Kaihatsu (Development of Drugs)", vol. 7, Molecular Designing, published by Hirokawa Shoten, 1990, pages 163–198.

The compound (I) may be labeled with an isotope (e.g., $^3$H, $^{14}$C, $^{35}$S, $^{125}$I, and the like) and the like.

Furthermore, the compound (I) may be an anhydride or a hydrate.

The compound (I) and a prodrug thereof (hereinafter sometimes to be simply abbreviated as the compound of the present invention) are of lower toxicity and can be used for mammals (e.g. human, mouse, rat, rabbit, dog, cat, cattle, horse, swine, monkey and the like), as an agent for promoting production or secretion of a neurotrophic factor and the like, either as such or by admixing with a pharmacologically acceptable carrier or the like to give a pharmaceutical composition.

Here, as the above-mentioned pharmacologically acceptable carrier, various organic or inorganic carrier substances which are conventionally used as pharmaceutical preparation materials can be mentioned. They are incorporated as excipients, lubricants, binders, disintegrants or the like in solid preparations; as solvents, solubilizers, suspending agents, isotonizing agents, buffers, soothing agents or the like in liquid preparations. Where necessary, additives such as preservatives, antioxidants, coloring agents, sweeteners and the like may be used.

As preferable examples of the excipients, lactose, sucrose, D-mannitol, D-sorbitol, starch, pre-gelatinized starch, dextrin, crystalline cellulose, low-substituted hydroxypropylcellulose, carboxymethylcellulose sodium, acacia, dextrin, pullulan, light silicic anhydride, synthetic aluminum silicate, magnesium aluminometasilicate and the like can be mentioned.

As preferable examples of the lubricants, magnesium stearate, calcium stearate, talc, colloidal silica and the like can be mentioned.

As preferable examples of the binders, pre-gelatinized starch, sucrose, gelatin, acacia, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like can be mentioned.

As preferable examples of the disintegrants, lactose, sucrose, starch, carboxymethylcellulose, carboxymethylcellulose calcium, croscarmellose sodium, carboxymethylstarch sodium, light silicic anhydride, low-substituted hydroxypropylcellulose and the like can be mentioned.

As preferable examples of the solvents, water for injection, physiological saline, Ringer's solution, alcohol, propylene glycol, polyethylene glycol, sesame oil, corn oil, olive oil, cotton seed oil and the like can be mentioned.

As preferable examples of the solubilizers, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As preferable examples of the suspending agents, surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene-hardened castor oil, and the like can be mentioned.

As preferable examples of the isotonizing agents, sodium chloride, glycerol, D-mannitol, D-sorbitol, glucose and the like can be mentioned.

As preferable examples of the buffers, buffer solutions of phosphate, acetate, carbonate, citrate and the like can be mentioned.

As preferable examples of the soothing agents, benzyl alcohol and the like can be mentioned.

As preferable examples of the preservatives, para-oxybenzoates, chlorobutanol, benzyl alcohol, phenethyl alcohol, dehydroacetic acid, sorbic acid and the like can be mentioned.

As preferable examples of the antioxidants, sulfites, ascorbates and the like can be mentioned.

As preferable examples of the coloring agents, water-soluble edible tar dyes (e.g. food colors such as Food Color Red No. 2 and No. 3, Food Color Yellow No. 4 and No. 5, Food Color Blue No. 1 and No. 2), water-insoluble lake colors (e.g. the aluminum salt of the above water-soluble edible tar dyes and the like), natural colors (e.g. β-carotene, chlorophyll, red iron oxide and the like), and the like can be mentioned.

As preferable examples of the sweeteners, saccharin sodium, dipotassium glycyrrhizinate, aspartame, stevia and the like can be mentioned.

As the dosage form of the aforementioned pharmaceutical composition, oral preparations such as tablets (including sublingual tablet and intraorally disintegrating tablet), capsules (including soft capsules and microcapsules), granules, powders, troches, syrups, emulsions, suspensions and the like; or parenteral preparations such as injections (e.g. subcutaneous injection, intravenous injection, intramuscular injection, intraperitoneal injection, drip infusions and the like), external preparations (e.g. transdermal preparations, ointments and the like), suppositories (e.g. rectal suppositories, vaginal suppositories and the like), pellets, transnasal agents, transpulmonary agents (inhalant), eye drops etc., and the like can be mentioned, and these preparations can be safely administered orally or parenterally.

These preparations may be controlled-release preparations (e.g., sustained-release microcapsules and the like) such as rapid release preparations, sustained-release preparations and the like.

The pharmaceutical composition can be produced by the methods well established in fields of the pharmaceutical manufacturing techniques, for example, by the methods described in the Japanese Pharmacopoeia and the like. In the following, some concrete methods for producing such preparations are described in detail. The content of the compound of the invention in a pharmaceutical composition varies depending on the dosage form, dose of the compound of the invention and the like, but it is, for example, about 0.1–100 wt %.

For example, an oral preparation can be produced by adding an excipient (e.g., lactose, sucrose, starch, D-mannitol and the like), a disintegrant (e.g., carboxymethylcellulose calcium and the like), a binder (e.g., pre-gelatinized starch, acacia, carboxymethylcellulose, hydroxypropylcellulose, polyvinylpyrrolidone and the like), a lubricant (e.g., talc, magnesium stearate, polyethylene glycol 6000 and the like) and the like to the active ingredient and compression-molding the mixture, and then, if desirable, by coating the molded product by a method known per se with a coating base for the purpose of masking of taste, or imparting enteric property or durability.

As the coating base, for example, a sugar coating base, a water-soluble film coating base, an enteric film coating base, a sustained-release film coating base and the like can be mentioned.

As the sugar coating base, sucrose is used and, further, one or more kinds of ingredients selected from talc, precipitated calcium carbonate, gelatin, acacia, pullulan, carnauba wax and the like may be used in combination.

As the water-soluble film coating base, for example, cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trademark), Roehm Pharma], polyvinylpyrrolidone and the like; polysaccharides such as pullulan and the like, and the like can be mentioned.

As the enteric film coating base, for example, cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trademark), Roehm Pharma], methacrylic acid copolymer LD [Eudragit L-30D55 (trademark), Roehm Pharma], methacrylic acid copolymer S [Eudragit S (trademark), Roehm Pharma] and the like; natural products such as shellac and the like, and the like can be mentioned.

As the sustained-release film coating base, for example, cellulose polymers such as ethylcellulose and the like; acrylic acid polymers such as aminoalkyl methacrylate copolymer RS [Eudragit RS (trademark), Roehm Pharma], an ethyl acrylate-methyl methacrylate copolymer suspension [Eudragit NE (trademark), Roehm Pharma] and the like; and the like can be mentioned.

Two or more of the above coating bases may be used in admixture in appropriate proportions. On the occasion of coating, a shading agent such as titanium oxide, ferric oxide and the like may be used.

Injections are produced by dissolving, suspending or emulsifying the active ingredient in an aqueous solvent (e.g. distilled water, physiological saline, Ringer's solution) or an oleaginous solvent (e.g. vegetable oils such as olive oil, sesame oil, cotton seed oil, corn oil and the like; propylene glycol and the like), together with dispersants (e.g. polysorbate 80, polyoxyethylene-hardened castor oil 60, polyethylene glycol, carboxymethylcellulose, sodium alginate and the like), preservatives (e.g. methylparaben, propylparaben, benzyl alcohol, chlorobutanol, phenol and the like), isotonizing agents (e.g. sodium chloride, glycerol, D-mannitol, D-sorbitol, glucose and the like) and the like. If desirable, additives such as solubilizers (e.g. sodium salicylate, sodium acetate and the like), stabilizers (e.g. human serum albumin and the like), soothing agents (e.g. benzyl alcohol and the like) and the like, may be used.

The compound of the present invention has superior neurotrophic factor production or secretion promoting action.

As the neurotrophic factor, for example, neurotrophin, TGF-β superfamily, neurokine family, growth factor and the like can be mentioned.

The neurotrophin is a general name of the nerve growth factor (NGF) gene family, and refers to a protein that plays an important role in differentiation and functional homeostasis of the cells of the central and peripheral nervous systems, formation of synapse, regeneration and repair of damage and the like. As concrete examples of the neurotrophin, NGF, BDNF (brain-derived neurotrophic factor), NT-3 (neurotrophin-3), NT-4/5 (neurotrophin-4/5), NT-6 (neurotrophin-6) and the like can be mentioned. The neurotrophin preferably includes NGF, BDNF, NT-3 and the like.

The TGF-β superfamily means a protein group known to have a structure characterized by the position of cysteine in a mature molecule, and exhibit a great diversity of actions on various cells and tissues. As concrete examples thereof, TGF-β1, TGF-β2, TGF-β3, BMP (bone morphogenetic protein)-2, BMP-3, BMP-4, BMP-5, BMP-6, BMP-7, BMP- 8A, BMP-8B, BMP-14 (GDF-5), GDNF (glial cell line-derived neurotrophic factor), neurturin, artemin, persephin, GDF-1, GDF-8, GDF (growth/differentiation factor)-15, inhibin α, inhibin β, DAF (dauer formation) 7 and the like can be mentioned. The TGF-β superfamily is preferably GDNF, GDF-15 and the like.

As the neurokine family, for example, ciliary neurotrophic factor (CNTF), interleukin 6 (IL-6) and the like can be mentioned.

As the growth factor, for example, insulin growth factor-1 (IGF-1), basic fibroblast growth factor and the like can be mentioned.

The neurotrophic factor is preferably neurotrophin, TGF-β superfamily and the like, more preferably NGF, BDNF, NT-3, GDNF, GDF-15 and the like.

Moreover, the compound of the present invention has a motor nerve or sensory nerve conduction velocity improving action, pain (e.g., neuropathic pain) ameliorating action.

The compound of the present invention is useful as an agent for the prophylaxis or treatment of, for example, neurodegenerative diseases (e.g., Alzheimer's senile dementia, Parkinson's syndrome, Huntington's chorea, amyotrophic lateral sclerosis (ALS), Down's syndrome and the like); peripheral neuropathies (e.g., diabetic neuropathy, cancer treatment-induced neuropathy and the like); diabetic cardiac myopathy; peripheral nerve injury; spinal injury; multiple sclerosis; cerebral ischemic disease; epilepsy; depression; inflammatory bowel disease (e.g., inflammatory colitis and the like); chronic pain (e.g., cancer pain and the like); behavioral abnormalities accompanied by dementia (e.g., wandering, aggressive behavior and the like); anxiety disorder; numbness caused by wound; pain; autonomic abnormalities (e.g., diabetic autonomic disorder, asymptomatic hypoglycemia, gastroparesis, neuropathic diarrhea and constipation, erectile dysfunction, orthostatic hypotension, arrhythmia, heart failure, painless cardiac infarction, dyshidrosis, neuropathic bladder and the like); bladder dysfunction (e.g., bladder reflex disorder and the like); hearing impairment; diabetic foot lesion; bone disease (e.g., osteoporosis and the like); joint disease (e.g., Charcot's joint, osteoarthritis, rheumatism and the like); Hirschsprung's disease; neuropathic pains (e.g., painful neuropathy, postherpetic neuralgia, back pain, trigeminal neuralgia, carpal tunnel syndrome, phantom limb pain, spinal injury, multiple sclerosis); and the like.

In addition, the compound of the present invention is also useful as an agent for the prophylaxis or treatment of diseases such as diabetes (e.g., type-1 diabetes, type-2 diabetes, gestational diabetes etc.), impaired glucose tolerance (IGT), hyperlipidemia (e.g., hypertriglyceridemia, hypercholesterolemia, hypo-HDL-emia, postprandial hyperlipidemia and the like), hyperinsulinemia, obesity, hyperphagia, hypertension, cardiovascular disease (e.g., atherosclerosis and the like) and the like; or a syndrome (e.g., syndrome X, visceral obesity syndrome and the like) comprising combination of some of these diseases.

Moreover, the compound of the present invention is used for secondary prophylaxis or suppression of progression (e.g., suppression of progression of impaired glucose tolerance into diabetes) of the above-mentioned various diseases (e.g., cardiac infarction and the like).

Furthermore, the compound of the present invention is useful as an agent for ameliorating peripheral neuropathy or brain metabolic disorder; a promoter of curing skin injury caused by metabolic or endocrine system disease such as diabetes, and by wound; pancreatic regeneration agent (pancreatic function recovering agent); renal regeneration agent (renal function recovering agent); an agent for ameliorating or suppressing pain (e.g., neuropathic pain); prophylactic agent of amputation of lower limb; a prophylactic agent of sudden death and the like.

While the dose of the compound of the present invention varies depending on the administration subject, administration route, target disease, condition and the like, it is, for example, in the case of oral administration to an adult patient with peripheral neuropathy (e.g., diabetic neuropathy), generally about 0.01–100 mg/kg body weight, preferably 0.05–30 mg/kg body weight, more preferably 0.1–2 mg/kg body weight, per dose, which amount is desirably administered once to 3 times a day.

The compound of the present invention can be used in combination with a pharmaceutical agent (hereinafter to be abbreviated as a combination drug) such as a therapeutic agent of diabetes, a therapeutic agent of diabetic complications, an antihyperlipemic agent, a hypotensive agent, an antiobesity agent, a diuretic, a chemotherapeutic agent, an immunotherapeutic agent, an antithrombotic agent, a therapeutic agent of osteoporosis, an antidementia agent, an agent for ameliorating erectile dysfunction, a therapeutic agent of incontinentia or pollakiuria, an antiepileptic agent, an antidepressant, an opioid agonist, a non-steroidal anti-inflammatory drug, a local anesthetic, vitamins and the like. These combination drugs may be a low molecular weight compound, or may be a high molecular weight protein, polypeptide, antibody, vaccine and the like.

The time of administration of the compound of the present invention and a combination drug is not limited, and these may be administered to an administration subject simultaneously or in a staggered manner. As a concrete mode of administration, for example, (1) administration of a single preparation obtained by simultaneous formulation of the compound of the present invention and a combination drug, (2) simultaneous administration of two kinds of preparations obtained by separate formulation of the compound of the present invention and a combination drug, by the same administration route, (3) time staggered administration of two kinds of preparations obtained by separate formulation of the compound of the present invention and a combination drug, by the same administration route, (4) simultaneous administration of two kinds of preparations obtained by separate formulation of the compound of the present invention and a combination. drug, by different administration routes, (5) time staggered administration of two kinds of preparations obtained by separate formulation of the compound of the present invention and a combination drug, by different administration routes, such as administration in the order of the compound of the present invention and then the combination drug, or administration in a reversed order, and the like can be mentioned.

The dose of the combination drug can be appropriately determined based on the dose clinically employed. In addition, the mixing ratio of the compound of the present invention and a combination drug can be appropriately determined according to the administration subject, administration route, target disease, condition, combination and the like. For example, when the administration subject is a human, 0.01–100 parts by weight of a combination drug can be used relative to 1 part by weight of the compound of the present invention.

As the therapeutic agent of diabetes, insulin preparations (e.g. animal insulin preparations obtained by extraction from the bovine or swine pancreas; human insulin preparations synthesized by a genetic engineering technique using *Escherichia coli* or a yeast; insulin-zinc; protamine-insulinzinc, a fragment or derivative of insulin (e.g., INS-1 etc.), insulin sensitizers (e.g. pioglitazone hydrochloride, rosiglitazone (maleate), GI-262570, reglixane (JTT-501), netoglitazone (MCC-555), YM-440, KRP-297, CS-011, FK-614, the compounds described in WO99/58510 (e.g., (E)-4-[4-(5-methyl-2-phenyl-4-oxazolylmethoxy)benzyloxyimino]-4-phenylbutyric acid), ragaglitazar (NN-622), AR-H-039242, BMS-298585, EML-16336, tesaglitazar (AZ-242), balaglitazone (NN-2344), ONO-5816, BM-13-1258, LM-4156, MBX-102, LY-519818, MX-6054, LY-510929 etc.), α-glucosidase inhibitors (e.g., voglibose, acarbose, miglitol, emiglitate etc.), biguanides (e.g., phenformin, metformin, buformin etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, senaglinide, nateglinide, mitiglinide or its calcium salt hydrate etc.], GLP-1 receptor agonists [e.g., GLP-1, NN-2211, AC-2993 (exendin-4), BIM-51077, Aib(8,35)hGLP-1(7,37)$NH_2$, etc.], amyrin agonists (e.g., pramlintide etc.), phosphotyrosine phosphatase inhibitors (e.g., vanadic acid etc.), dipeptidylpeptidase IV inhibitors (e.g., NVP-DPP-278, PT-100, P32/98 etc.), β3 agonists (e.g., CL-316243, SR-58611-A, UL-TG-307, SB-226552, AJ-9677, BMS-196085, AZ40140 etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.) and the like can be mentioned.

As the therapeutic agent of diabetic complications, aldose reductase inhibitors (e.g., tolrestat, epalrestat, zenarestat, zopolrestat, minalrestat, fidarestat, SNK-860, CT-112 and the like), neurotrophic factors and increasing drugs thereof (e.g., NGF, NT-3, BDNF, neurotrophin production or secretion promoters described in WO01/14372 (e.g., 4-(4-chlorophenyl)-2-(2-methyl-1-imidazolyl)-5-[3-(2-methylphenoxy)propyl]oxazole and the like) and the like), nerve regeneration enhancers (e.g., Y-128 and the like), PKC inhibitors (e.g., LY-333531 and the like), AGE inhibitors (e.g., ALT946, pimagedine, pyratoxanthine, N-phenacylthiazolium bromide (ALT766), EXO-226 and the like), active oxygen scavengers (e.g., thioctic acid and the like), cerebral vasodilators (e.g., tiapride, mexiletine and the like), and the like can be mentioned.

As the antihyperlipemic agent, statin compounds (e.g., cerivastatin, pravastatin, simvastatin, lovastatin, atorvastatin, fluvastatin, itavastatin and salts thereof (e.g., sodium salt) and the like) which are cholesterol synthesis inhibitors, squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]-piperidine-4-acetic acid and the like), fibrate compounds (e.g., bezafibrate, clofibrate, simfibrate, clinofibrate and the like) having a triglyceride lowering action, and the like can be mentioned.

As the hypotensive agent, angiotensin converting enzyme inhibitors (e.g., captopril, enalapril, delapril and the like) r angiotensin II antagonists (e.g., candesartan cilexetil, losartan, eprosartan, valsartan, telmisartan, irbesartan, asosartan etc.), calcium antagonists (e.g., manidipine, nifedipine, amlodipine, efonidipine, nicardipine and the like), clonidine and the like can be mentioned.

As the antiobesity agent, for example, antiobesity drugs acting on the central nervous system (e.g. dexfenfluramine, fenfluramine, phentermine, sibutramine, anfepramon, dexamphetamine, mazindol, phenylpropanolamine, clobenzorex, and the like), pancreatic lipase inhibitors (e.g., orlistat etc.), β3 agonists (e.g., CL-316243, SR-58611-A, UL-TG-307, SB-226552, AJ-9677, BMS-196085, AZ40140 etc.), anorectic peptides (e.g., leptin, CNTF (ciliary neurotrophic factor) etc.), cholecystokinin agonists (e.g., lintitript, FPL-15849 etc.) and the like can be mentioned.

As the diuretic, for example, xanthine derivatives (e.g., sodium salicylate and theobromine, calcium salicylate and theobromine, and the like), thiazide preparations (e.g., ethiazide, cyclopenthiazide., trichloromethyazide, hydrochlorothiazide, hydroflumethiazide, benzylhydrochlorothiazide, penflutizide, polythiazide, methyclothiazide and the like), antialdosterone preparations (e.g., spironolactone, triamterene and the like), carbonic anhydrase inhibitors (e.g., acetazolamide and the like), chlorobenzenesulfonamide preparations (e.g., chlortalidone, mefruside, indapamide and the like), azosemide, isosorbide, etacrynic acid, piretanide, bumetanide, furosemide and the like can be mentioned.

As the chemotherapeutic agent, for example, alkylation agents (e.g., cyclophosphamide, ifosfamide and the like), metabolic antagonists (e.g., methotrexate, 5-fluorouracil and the like), anti-cancer antibiotics (e.g., mitomycin, adriamycin and the like), plant-derived anti-cancer agents (e.g., vincristin, vindesine, taxol and the like), cisplatin, carboplatin, etopoxide and the like can be mentioned. Of these, furtulon and neofurtulon, which are 5-fluorouracil derivatives, and the like are preferable.

As the immunotherapeutic agent, for example, microorganism or bacterial components (e.g., a muramyl dipeptide derivative, picibanil and the like), polysaccharides having immunity potentiating activity (e.g., lentinan, sizofiran, krestin and the like), cytokines obtained by genetic engineering techniques (e.g., interferon, interleukin (IL) and the like), colony stimulating factors (e.g., granulocyte colony stimulating factor, erythropoietin and the like) and the like can be mentioned, with preference given to IL-1, IL-2, IL-12 and the like.

As the antithrombotic agent, for example, heparin (e.g., heparin sodium, heparin calcium, dalteparin sodium and the like), warfarin (e.g., warfarin potassium and the like), antithrombin drugs (e.g., aragatroban and the like), thrombolytic agents (e.g., urokinase, tisokinase, alteplase, nateplase, monteplase, pamiteplase and the like), platelet aggregation inhibitors (e.g., ticlopidine hydrochloride, cilostazol, ethyl icosapentate, beraprost sodium, sarpogrelate hydrochloride and the like) and the like can be mentioned.

As the therapeutic agent of osteoporosis, for example, alfacalcidol, calcitriol, elcatonin, calcitonin salmon, estriol, ipriflavone, pamidronate disodium, alendronate sodium hydrate, incadronate disodium and the like can be mentioned.

As the antidementia agent, for example, tacrine, donepezil, rivastigmine, galantamine and the like can be mentioned.

As the agent for ameliorating erectile dysfunction, for example, apomorphine, sildenafil citrate and the like can be mentioned.

As the therapeutic agent of incontinentia or pollakiuria, for example, flavoxate hydrochloride, oxybutynin hydrochloride, propiverine hydrochloride and the like can be mentioned.

As the antiepileptic agent, for example, gabapentin, carbamazepine and the like can be mentioned.

As the antidepressant, for example, amitriptyline, imipramine and the like can be mentioned.

As the opioid agonist, for example, morphine and the like can be mentioned.

As the non-steroidal anti-inflammatory drug, for example, aspirin, acetaminophen, indomethacin and the like can be mentioned.

As the local anesthetic, for example, lidocaine, capsaicin and the like can be mentioned.

As vitamins, for example, vitamin B1, vitamin B12 and the like can be mentioned.

Furthermore, drugs having a cachexia-ameliorating action established in animal models or clinical situations, such as cyclooxygenase inhibitors (e.g., indomethacin and the like) [*Cancer Research*, Vol. 49, 5935–5939, 1989], progesterone derivatives (e.g., megesterol acetate) [*Journal of Clinical Oncology*, Vol. 12, 213–225, 1994], glucosteroid (e.g., dexamethasone and the like), metoclopramide agents, tetrahydrocannabinol agents (ibid.), fat metabolism improving agents (e.g., eicosapentaenoic acid and the like) [*British Journal of Cancer*, Vol. 68, 314–318, 1993], growth hormones, IGF-1, or antibodies to a cachexia-inducing factor such as TNF-α, LIF, IL-6, Oncostatin M and the like, can be also used in combination with the compound of the present invention.

The combination drug is preferably an insulin preparation, an insulin sensitizer, α-glucosidase inhibitor, a biguanide, an insulin secretagogue (preferably a sulfonylurea), an aldose reductase inhibitor, a PKC inhibitor, an antiepileptic agent, an antidepressant, an opioid agonist, a non-steroidal anti-inflammatory drug and the like.

The above-mentioned combination drugs may be used in combination of two or more kinds at an appropriate ratio. As preferable combinations when two or more kinds of the combination drugs are used, for example, the following can be mentioned.

1) an insulin secretagogue (preferably a sulfonylurea) and an α-glucosidase inhibitor;
2) an insulin secretagogue (preferably a sulfonylurea) and a biguanide;
3) an insulin secretagogue (preferably a sulfonylurea), a biguanide and an a-glucosidase inhibitor;
4) an insulin sensitizer and an α-glucosidase inhibitor;
5) an insulin sensitizer and a biguanide;
6) an insulin sensitizer, a biguanide and an α-glucosidase inhibitor.

When the compound of the present invention is used in combination with a combination drug, the dose of the both components can be reduced within a safe range in consideration of the opposing effect of the components. Particularly, a combination drug such as an insulin sensitizer, an insulin secretagogue (preferably a sulfonylurea) and a biguanide can be reduced from the normal dose. Therefore, the opposing effect caused by these agents can be safely prevented. In addition, the doses of a therapeutic agent of diabetic complications, an antihyperlipemic agent and a hypotensive agent can be reduced, and as a result, the side effects that would be caused by these agents can be prevented effectively.

The production methods of the compound of the present invention are explained in the following.

The compound (I) can be produced by, for example, the following Methods A–G, or a method analogous thereto.

[Method A]

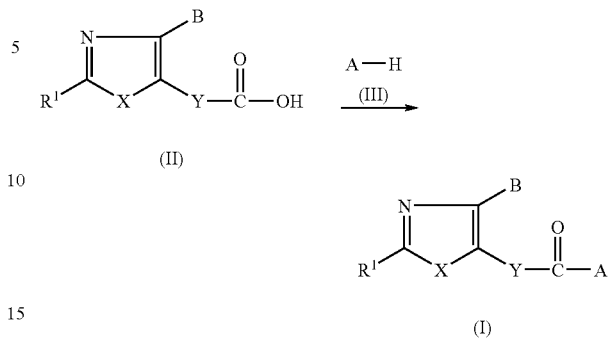

wherein the symbols are as defined above.

In this method, compound (II) is subjected to an amidation reaction to produce compound (I). This reaction is carried out according to a method known per se, such as a method for directly condensing compound (II) with compound (III) using a condensation agent, a method for appropriately reacting a reactive derivative of compound (II) with compound (III) and the like.

As the condensation agent, one such as carbodiimide type condensation reagents such as dicyclohexylcarbodiimide, diisopropylcarbodiimide, 1-ethyl-3-dimethylaminopropylcarbodiimide or its hydrochloride and the like; phosphoric acid type condensation reagents such as diethyl cyanophosphate, diphenylphosphoryl azide and the like; carbonyl diimidazole, 2-chloro-1,3-dimethylimidazolium tetrafluoroborate and the like can be mentioned.

As a solvent to be used for the reaction using a condensation agent, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like can be mentioned. Two or more kinds of these solvents may be used in a mixture at appropriate ratios.

The amount of compound (III) to be used is generally 0.1–10 molar equivalents, preferably 0.3–3 molar equivalents, relative to compound (II).

The amount of the condensation agent to be used is generally 0.1–10 molar equivalents, preferably 0.3–3 molar equivalents, relative to compound (II).

When the aforementioned carbodiimide type condensation reagent is used as the condensation agent, the reaction efficiency can be improved by the use of a suitable condensation promoter (e.g., 1-hydroxy-7-azabenzotriazole, 1-hydroxybenzotriazole, N-hydroxysuccinimide, N-hydroxyphthalimide and the like) where necessary. When the above-mentioned phosphoric acid type condensation reagent is used as the condensation agent, the reaction efficiency can be improved by generally adding an organic amine type base such as triethylamine and the like.

The amount of the above-mentioned condensation promoter and the organic amine type base to be used is generally 0.1–10 molar equivalents, preferably 0.3–3 molar equivalents, relative to compound (II).

The reaction temperature is generally −30° C. to 100° C.

The reaction time is generally 0.5–60 hrs.

In the method using a reactive derivative of compound (II), as the reactive derivative of compound (II), for example, acid anhydride, acid halide (acid chloride, acid bromide), imidazolide, or mixed acid anhydride (e.g., anhydride with methyl carbonate, ethyl carbonate or isobutyl carbonate, and the like can be mentioned.

For example, when an acid anhydride or an acid halide is used as the reactive derivative, the reaction is generally carried out in the presence of a base, in a solvent that does not exert an influence on the reaction.

As the base, for example, amines such as triethylamine, pyridine, N-methylmorpholine, N,N-dimethylaniline, 4-dimethylaminopyridine and the like; alkali metal salts such as lithium hydroxide, sodium hydroxide, potassium hydroxide, sodium hydrogen carbonate, sodium carbonate, potassium carbonate, cesium carbonate and the like can be mentioned.

The amount of the base to be used is generally 0.1–10 molar equivalents, preferably 0.3–3 molar equivalents, relative to compound (II).

As the solvent that does not exert an influence on the reaction, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like can be mentioned. Two or more kinds of these solvents may be used in a mixture at appropriate ratios. When the above-mentioned amides are used as the solvent that does not exert an influence on the reaction, the reaction can be also carried out in the absence of a base.

The amount of compound (III) to be used is generally 0.1–10 molar equivalents, preferably 0.3–3 molar equivalents, relative to compound (II).

The reaction temperature is generally −30° C. to 100° C.

The reaction time is generally 0.5–20 hrs.

When a mixed acid anhydride is used, compound (II) is reacted with chlorocarbonic acid esters (e.g., methyl chlorocarbonate, ethyl chlorocarbonate, isobutyl chlorocarbonate and the like) in the presence of a base and then reacted with compound (III).

As the base, for example, amines such as triethylamine, aniline, N-methylmorpholine, N,N-dimethylaniline, 4-dimethylaminopyridine and the like; alkali metal salts such as sodium hydroxide, potassium hydroxide, lithium hydroxide, sodium hydrogen carbonate, sodium carbonate, potassium carbonate, cesium carbonate and the like can be mentioned.

The amount of the base to be used is generally 0.1–10 molar equivalents, preferably 0.3–3 molar equivalents, relative to compound (II).

The amount of the compound (III) to be used is generally 0.1–10 molar equivalents, preferably 0.3–3 molar equivalents, relative to compound (II).

The reaction temperature is generally −30° C. to 100° C.

The reaction time is generally 0.5–20 hrs.

The compound (I) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (II) to be used as a starting compound in the above-mentioned Method A can be produced by a method described in, for example, WO97/36882, WO01/14372 and the like, or a method analogous thereto. In addition, compound (III) can be produced by a method known per se.

[Method B] (Substitution Reaction)

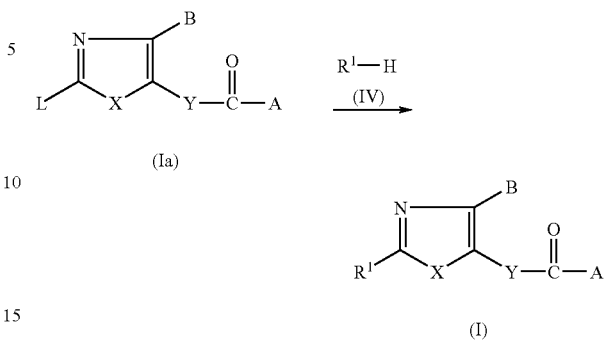

wherein L is a leaving group, and other symbols are as defined above.

As the leaving group for L, for example, a halogen atom (e.g., fluorine, chlorine, bromine, iodine); an oxygen functional group such as alkoxy group, phenoxy group and the like; a sulfur functional group such as sulfanyl group, sulfinyl group, sulfonyl group and the like; an amino group; an acyl group and the like can be mentioned.

In this method, compound (Ia) is reacted with compound (IV) to give compound (I).

This reaction is carried out according to a conventional method generally in the presence of a base in a solvent that does not exert an adverse influence on the reaction.

As the base, for example, alkali metal salts such as lithium hydroxide, potassium hydroxide, sodium hydroxide, sodium hydrogen carbonate, sodium carbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and the like; metal hydrides such as potassium hydride, sodium hydride and the like; alkali metal alkoxides such as sodium methoxide, sodium ethoxide, potassium tert-butoxide and the like; and the like can be mentioned.

The amount of the base to be used is preferably about 1–about 5 molar equivalents., relative to compound (Ia).

As the solvent that does not exert an adverse influence on the reaction, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like, water and the like can be mentioned. These solvents may be used in a mixture at appropriate ratios.

The reaction temperature is generally about −50° C. to about 150° C., preferably about −10° C. to about 100° C.

The reaction time is generally about 0.5–about 20 hrs.

The compound (I) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (Ia) to be used as a starting compound in the above-mentioned Method B can be produced according to the aforementioned Method A. In addition, compound (IV) can be produced by a method known per se.

The compound (Ib) having an optionally substituted aryl group for $R^1$ in the formula (I) can be also produced by the following Method C.

[Method C] (Suzuki Coupling Reaction)

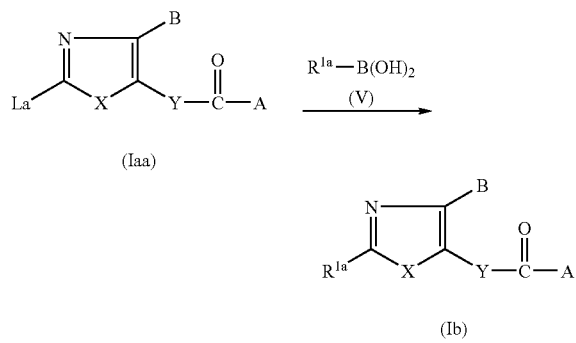

wherein La is a halogen atom, $R^{1a}$ is an optionally substituted aryl, and other symbols are as defined above.

As the halogen atom for La, fluorine, chlorine, bromine and iodine can be mentioned.

As the "optionally substituted aryl group" for R a, one from those exemplified for the "optionally substituted hydrocarbon group" for $R^1$, wherein the "hydrocarbon group" is an aryl group, can be mentioned. Particularly, phenyl optionally substituted by 1 or 2 substituent(s) selected from $C_{1-6}$ alkyl and halogen atom, and the like are preferable.

Specific examples of compound (V) include phenylboronic acid, tolylboronic acid, 4-fluorophenylboronic acid and the like.

This method is performed according to known Suzuki reaction (*Journal of Organometalic Chemistry*, vol. 576, p. 147 (1999)).

That is, in this method, compound (Iaa) and compound (V) are reacted in the presence of a suitable base as necessary and using a palladium catalyst to give compound (Ib).

This reaction is performed according to a conventional method generally in the presence of a base in a solvent that does not exert an adverse influence on the reaction.

As the base, for example, alkali metal salts such as lithium hydroxide, potassium hydroxide, sodium hydroxide, sodium hydrogen carbonate, sodium carbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and; metal hydrides such as potassium hydride, sodium hydride and the like; alkali metal alkoxides such as sodium methoxide, sodium ethoxide, potassium t.-butoxide and the like; and the like can be mentioned.

The amount of the base to be used is preferably about 1–about 5 molar equivalents, relative to compound (Iaa).

The amount of compound (V) to be used is preferably about 1–about 5 molar equivalents, relative to compound (Iaa).

As the solvent that does not exert an adverse influence on the reaction, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like, water and the like can be mentioned. These solvents may be used in a mixture at appropriate ratios.

The reaction temperature is generally about −50° C. to about 150° C., preferably about −10° C. to about 100° C.

The reaction time is generally about 0.5–about 20 hrs.

The compound (Ib) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (Iaa) to be used as a starting compound in the above-mentioned Method C can be produced by, for example, the aforementioned Method A. In addition, compound (V) can be produced by a method known per se.

The compound (Id) wherein, in the formula (I), $R^1$ is an amino group optionally substituted by carbamoyl or thiocarbamoyl can be also produced by the following Method D.

[Method D] (Reaction Between Aminoazole and Isocyanate Derivative)

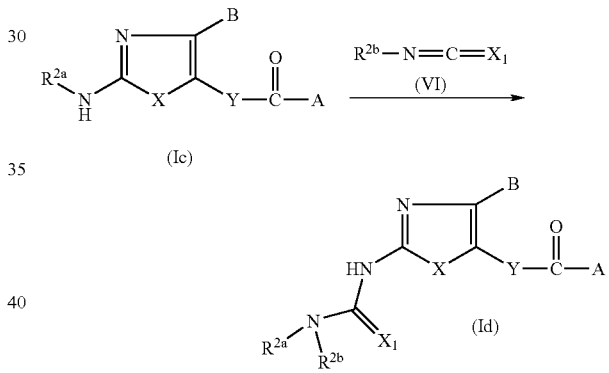

wherein $X_1$ is an oxygen atom or a sulfur atom, $R^{2a}$ is a hydrogen atom or an optionally substituted alkyl group, $R^{2b}$ is an optionally substituted alkyl group or an optionally substituted aryl group, and other symbols are as defined above.

As the "optionally substituted alkyl group" for $R^{2a}$ or $R^{2b}$, one from those exemplified for the "optionally substituted hydrocarbon group" for $R^1$, wherein the "hydrocarbon group" is an alkyl group, can be mentioned. Particularly, $C_{1-6}$ alkyl and the like are preferable.

As the "optionally substituted aryl group" for $R^{2b}$, one from those exemplified for the "optionally substituted hydrocarbon group" for $R^1$, wherein the "hydrocarbon group" is an aryl group, can be mentioned. Particularly, phenyl and the like are preferable.

Specific examples of compound (VI) include, phenyl isocyanate, isopropyl isocyanate, phenylthio isocyanate and the like.

In this method, compound (Ic) and compound (IV) are reacted to give compound (Id).

This reaction is performed according to a conventional method generally under neutral conditions and where necessary, in the presence of a suitable base in a solvent that does not exert an adverse influence on the reaction.

As the base, for example, alkali metal salts such as lithium hydroxide, potassium hydroxide, sodium hydroxide, sodium hydrogen carbonate, sodium carbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and; metal hydrides such as potassium hydride, sodium hydride and the like; alkali metal alkoxides such as sodium methoxide, sodium ethoxide, potassium tert-butoxide and the like and the like can be mentioned.

The amount of the base to be used is preferably about 1–about 5 molar equivalents, relative to compound (Ic).

The amount of compound (VI) to be used is preferably about 1–about 5 molar equivalents, relative to compound (Ic).

As the solvent that does not exert an adverse influence on the reaction, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like and the like can be mentioned. These solvents may be used in a mixture at appropriate ratios.

The reaction temperature is generally about −50° C. to about 150° C., preferably about −10° C. to about 100° C.

The reaction time is generally about 0.5–about 20 hrs.

The compound (Id) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (Ic) to be used as a starting compound in the above-mentioned Method D can be produced by, for example, the aforementioned Method A or Method B. In addition, compound (VI) can be produced by a method known per se.

[Method E] (Reaction Between Aminoazole and Acetal Derivative)

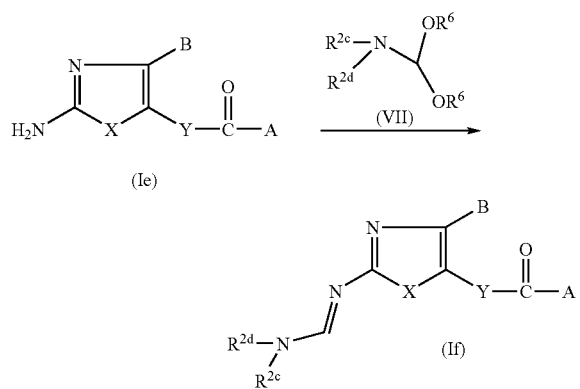

wherein $R^{2c}$ and $R^{2d}$ are the same or different and each is a hydrogen atom, an optionally substituted alkyl group or an optionally substituted aryl group, $R^6$ is a $C_{1-6}$ alkyl group, and other symbols are as defined above.

As the "optionally substituted alkyl group" and "optionally substituted aryl group" for $R^{2c}$ and $R^{2d}$, those exemplified for the aforementioned $R^{2b}$ can be mentioned.

As the $C_{1-6}$ alkyl group for $R^6$, those exemplified for the aforementioned $R^2$ can be mentioned.

In this method, compound (Ie) and compound (VII) are reacted to give compound (If).

This reaction is performed according to a conventional method generally under neutral conditions and where necessary, in the presence of a suitable base, in a solvent that does not exert an adverse influence on the reaction.

As the base, for example, alkali metal salts such as lithium hydroxide, potassium hydroxide, sodium hydroxide, sodium hydrogen carbonate, sodium carbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and; metal hydrides such as potassium hydride, sodium hydride and the like; alkali metal alkoxides such as sodium methoxide, sodium ethoxide, potassium tert-butoxide and the like; and the like can be mentioned.

The amount of the base to be used is preferably about 1–about 5 molar equivalents, relative to compound (Ie).

The amount of compound (VII) to be used is preferably about 1–about 5 molar equivalents, relative to compound (Ie).

As the solvent that does not exert an adverse influence on the reaction, for example, aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like;

amides such as N,N-dimethylformamide and the like; sulfoxides such as dimethyl sulfoxide and the like, water and the like can be mentioned. These solvents may be used in a mixture at appropriate ratios.

The reaction temperature is generally about −50° C. to about 150° C., preferably about −10° C. to about 100° C.

The reaction time is generally about 0.5–about 20 hrs.

The compound (If) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (Ie) to be used as a starting compound in the above-mentioned Method E can be produced by, for example, the aforementioned Method A or Method B. In addition, compound (VII) can be produced by a method known per se.

[Method F] (Reaction Between Aminoazole and Carboxylic Acid Derivative)

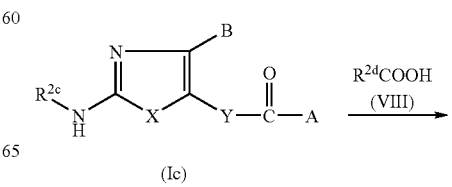

-continued $$\underset{(Ig)}{\overset{R^{2d}}{\underset{}{\bigvee}}\overset{O}{\underset{}{\bigvee}}\overset{}{\underset{R^{2c}}{N}}\overset{N}{\underset{X}{\bigvee}}\overset{B}{\underset{Y-C-A}{\bigvee}}\overset{O}{\underset{}{\parallel}}}$$

(Ig)

wherein the symbols are as defined above.

In this method, compound (Ic) and compound (VIII) are reacted to give compound (Ig).

This method can be performed in the same manner as in the aforementioned Method A.

The compound (Ig) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

The compound (Ic) to be used as a starting compound in the above-mentioned Method F can be produced by, for example, the aforementioned Method A or Method B. In addition, compound (VIII) can be produced by a method known per se.

Of the compound (Ia) used as a starting compound in the aforementioned Method B, compound (Iaa) wherein the leaving group for L is a halogen atom, and compound (Iaa) to be used as a starting compound in Method C can be produced by, for example, the following Method G.

[Method G] Sandmeyer Reaction of Aminoazole $$\underset{(Ie)}{H_2N\overset{N}{\underset{X}{\bigvee}}\overset{B}{\underset{Y-C-A}{\bigvee}}\overset{O}{\underset{}{\parallel}}} \longrightarrow$$

(Ie)

$$\underset{(Iaa)}{L^a\overset{N}{\underset{X}{\bigvee}}\overset{B}{\underset{Y-C-A}{\bigvee}}\overset{O}{\underset{}{\parallel}}}$$

(Iaa)

wherein the symbols are as defined above.

This reaction is performed according to, for example, a known Sandmeyer reaction.

That is, compound (Ie) is subjected to diazotization reaction, the obtained diazonium salt and a monovalent or divalent copper salt and hydrochloric acid or hydrobromic acid are reacted in a solvent that does not exert an adverse influence on the reaction to give compound (Iaa).

The diazotization reaction is carried out using a diazotization reagent according to a known method. As the diazotization reagent, for example, nitrous acid, nitrites such as sodium nitrite and the like; nitrosyl halides such as nitrosyl chloride and the like; and the like are used.

The amount of the diazotization reagent to be used is generally about 1–about 5 molar equivalents, relative to compound (Ie).

As the monovalent or divalent copper salt, copper(I) chloride, copper(I) bromide, copper(I) iodide, copper(II) chloride, copper(II) bromide, copper(II) iodide and the like can be mentioned.

The amount of the copper salt to be used is generally about 1–5 molar equivalents, relative to compound (Ie).

As the solvent that does not exert an adverse influence on the reaction, for example, alcohols such as methanol, ethanol and the like; ethers such as tetrahydrofuran, dioxane and the like; aromatic amines such as quinoline, pyridine and the like; acetone, dimethyl sulfoxide, phosphoric acid, acetic acid, water and the like can be mentioned. These solvents may be used in a mixture at appropriate ratios.

The reaction temperature is generally about −20° C. to 200° C., preferably about 0° C. to 150° C.

The reaction time is generally about 0.5–about 20 hrs.

This reaction can be also carried out by reacting compound (Ie) with alkyl nitrite in the presence of a monovalent or divalent copper salt in a solvent that does not exert an influence on the reaction.

As the monovalent or divalent copper salt, those similar to the aforementioned examples can be mentioned. The amount of copper salt to be used is generally about 1–5 molar equivalents, relative to compound (Ie).

As the solvent that does not exert an influence on the reaction, for example, ethers such as tetrahydrofuran, dioxane and the like; acetonitrile, acetone, dimethyl sulfoxide and the like can be mentioned. These solvents may be used in a mixture at appropriate ratios.

As the alkyl nitrite, for example, t-butyl nitrite, isoamyl nitrite and the like can be mentioned. The amount of alkyl nitrite to be used is generally about 1–5 molar equivalents, relative to compound (Ie).

The reaction temperature is generally about −20° C. to 200° C., preferably about 0° C. to 150° C.

The reaction time is generally about 0.5–about 20 hrs.

The compound (Iaa) thus obtained can be isolated and purified by a known separation and purification means, such as concentration, concentration under reduced pressure, solvent extraction, crystallization, recrystallization, phase transfer, chromatography, a method using an ion exchange resin and a scavenger resin and the like.

In each of the aforementioned reactions, when the starting compound has amino, carboxy, hydroxy or carbonyl as a substituent, these groups may have a protecting group introduced therein, such as one generally used in peptide chemistry and the like. The objective compound can be obtained by removing the protecting group as necessary after the reaction.

As the amino-protecting group, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atom(s) (e.g., fluorine, chlorine, bromine, iodine and the like), $C_{1-6}$ alkoxy (e.g., methoxy, ethoxy, propoxy and the like) or nitro and the like.

As the carboxy-protecting group, for example, $C_{1-6}$ alkyl (e.g., methyl, ethyl, propyl, isopropyl, butyl, tert-butyl and the like), $C_{7-13}$ aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atom(s) (e.g., fluorine, chlorine, bromine, iodine and the like), $C_{1-6}$ alkoxy (e.g., methoxy, ethoxy, propoxy and the like) or nitro and the like.

As the hydroxy-protecting group, for example, $C_{1-6}$ alkyl (e.g., methyl, ethyl, propyl, isopropyl, butyl, tert-butyl and the like), phenyl, trityl, $C_{7-13}$ aralkyl (e.g., benzyl and the like), formyl, $C_{1-6}$ alkyl-carbonyl (e.g., acetyl, propionyl and the like), benzoyl, $C_{7-13}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atom(s) (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like) or nitro and the like.

As the carbonyl-protecting group, for example, cyclic acetal (e.g., 1,3-dioxane and the like), non-cyclic acetal (e.g., di-$C_{1-6}$ alkyl acetal and the like) and the like can be mentioned.

The removing method of these protecting groups may be carried out by methods known per se, for example, the methods described in *Protective Groups in Organic Synthesis,* published by John Wiley and Sons, 1980, and the like. For example, employed are the methods using acids, bases, ultraviolet ray, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide, etc.), etc.; and reduction method, and the like.

When the starting compound can form a salt in each of the aforementioned reactions, the compound may be used in the form of a salt. As such salt, for example, those exemplified for the salt of the compound represented by the formula (I) can be used.

Where the compound (I) includes optical isomers, stereoisomers, regioisomers and rotational isomers, those are also encompassed in the compound (I), and can be obtained as a single compound by synthetic methods and separation methods known per se. For example, when optical isomers of the compound (I) exist, optical isomers resolved from the compound are also encompassed in the compound (I).

The optical isomers can be produced by a method known per se. Concretely, an optically active isomer can be obtained using an optically active synthetic intermediate or by optical resolution of a final racemate by a conventional method.

For optical resolution, a method known per se, such as a fractional recrystallization method, a chiral column method, a diastereomer method, and the like can be used.

1) Fractional Recrystallization Method

The method which comprises allowing a racemate and an optically-active compound (e.g., (+)-mandelic acid, (−)-andelic acid, (+)-tartaric acid, (−)-tartaric acid, (+)-1-phenethylamine, (−)-1-phenethylamine, cinchonine, (−)-cinchonidine, brucine, etc.) to form a salt, which is then separated through fractional recrystallization method, followed by, when desired, subjecting the salt to a neutralization step to give a free optical isomer.

2) Chiral Column Method

The method of separating by applying a racemate or a salt thereof, to a column for fractionating optical isomers (chiral column). In the case of, for example, liquid chromatography, the optical isomers are separated by applying a mixture of optical isomers to a chiral column, such as ENANTIO-OVM (manufactured by Tosoh Corp.), CHIRAL SERIES (manufactured by Daicel Co.), etc., and developing with water, various buffers (e.g., phosphate buffer) and organic solvents (e.g., ethanol, methanol, isopropanol, acetonitrile, trifluoroacetic acid, diethylamine, etc.), singly or as a suitable mixture of them. In the case of, for example, gas chromatography, a chiral column such as CP-Chirasil-DeX CB (manufactured by GL Science Co.), etc. is used for separation.

3) Diastereomer Method

The method that a racemic mixture is chemically reacted with an optically-active reagent to give a mixture of diastereomers, which is subjected to an ordinary separation means (e.g., fractional recrystallization, chromatography, etc.) to give a single compound, which is then subjected to a chemical treatment (e.g., hydrolysis reaction etc.) to separate the optically-active reagent site from the compound to give an optical isomer. For example, where compound (I) has a hydroxy or a primary or secondary amino in the molecule, the compound and an optically-active organic acid (e.g., MTPA [α-methoxy-α-(trifluoromethyl)phenylacetic acid], (−)-menthoxyacetic acid, etc.) or the like are subjected to condensation reaction to give the respectively corresponding ester or amide diastereomer. On the other hand, where compound (I) has a carboxylic acid group, the compound and an optically-active amine or alcohol reagent are subjected to condensation reaction to give an amide or ester diastereomer. The separated diastereomer is then subjected to acidic or basic hydrolysis reaction, through which it is converted into the optical isomer of the original compound.

The present invention is explained in detail in the following by referring to Reference Examples, Examples, Experimental Examples and Formulation Examples, which are not to be construed as limitative.

In the following Reference Examples and Examples, "%" means percent by weight unless specifically indicated. In addition, room temperature means a temperature of 1–30° C.

EXAMPLES

Reference Example 1

Ethyl 2-chloro-4-isopropyl-5-thiazolecarboxylate (30.0 g) was dissolved in toluene (200 mL) and to the solution was added dropwise a 70% solution (59.1 g) of sodium dihydrido bis(2-methoxyethoxy)aluminate in toluene at 0° C. To the reaction mixture was added a 10% aqueous solution (100 mL) of potassium sodium tartrate tetrahydrate, and the mixture was extracted with ethyl acetate. The ethyl acetate layer was washed with saturated brine, dried over anhydrous magnesium sulfate and concentrated to give a yellow oil (23.2 g). This oil was dissolved in tetrahydrofuran (150 mL) and manganese dioxide (60 g) was added, and the mixture was stirred at room temperature for 12 hrs. Manganese dioxide was removed by filtration and the organic layer was concentrated. The residue was purified by silica gel column chromatography. 2-Chloro-4-isopropyl-5-thiazolecarbaldehyde (12.0 g, 54%) was obtained as a yellow oil from a fraction eluted with hexane-ethyl acetate (9:1, volume ratio).

NMR(CDCl$_3$) delta:1.39(6H,t,d,J=7 Hz),3.45–3.65(1H, m),10.06(1H,s).

In the same manner as in Reference Example 1 except that an ethyl 2-chloro-5-thiazolecarboxylate derivative having a different substituent at the 4-position was used as a starting material, the compound of Reference Example 2–4 was synthesized.

Reference Example 2

4-tert-butyl-2-chloro-5-thiazolecarbaldehyde yield: 69%. a yellow oil. NMR(CDCl$_3$) delta: 1.52(9H, s),10.31(1H,s).

Reference Example 3

2-chloro-4-phenyl-5-thiazolecarbaldehyde yield 70%. pale-yellow solid

Reference Example 4

2-chloro-4-methyl-5-thiazolecarbaldehyde yield 82%. a yellow oil. NMR(CDCl$_3$) delta: 2.31(3H,s),10.31(1H,s).

Reference Example 5

A mixture of 2-chloro-4-isopropyl-5-thiazolecarbaldehyde (2.0 g), ethyl diethylphosphonoacetate (2.47 g), sodium hydride (0.44 g) and N,N-dimethylformamide (10 mL) was stirred at room temperature for 1 hr. Benzimidazole (1.54 g) and sodium hydride (0.44 g) were added to the reaction mixture and the mixture was further stirred at room temperature for 1 hr. The reaction mixture was poured into water, the precipitated crystals were collected by filtration and washed with water. Recrystallization from acetone-hexane gave ethyl (2E)-3-[2-(1H-benzimidazol-1-yl)-4-isopropyl-5-thiazolyl]propenoate (3.01 g, 84%) as a pale-yellow prism crystal. melting point: 229–230° C.

In the same manner as in Reference Example 5, the compounds of Reference Examples 6–8 were synthesized.

Reference Example 6 ethyl (2E)-3-[2-(1H-benzimidazol-1-yl)-4-tert-butyl-5-thiazolyl]propenoate yield: 84%. pale-yellow prism crystal, melting point: 129–130° C. (recrystallized from acetone-hexane).

Reference Example 7 ethyl (2E)-3-[2-(1H-benzimidazol-1-yl)-4-phenyl-5-thiazolyl]propenoate yield: 84%. amorphous solid NMR(CDCl$_3$) delta: 1.33 (3H,t,J=7 Hz), 4.27(2H,q,J=7 Hz), 6.25(1H,d,J=15 Hz), 7.4–7.6(6H,m), 7.7–7.9(2H,m), 7.95(1H,d,J=15 Hz), 8.1–8.2(1H,m), 8.63(1H,s).

Reference Example 8 ethyl (2E)-3-[2-(1H-benzimidazol-1-yl)-4-methyl-5-thiazolyl]propenoate yield: 81%. pale-yellow prism crystal, melting point: 109–112° C. (recrystallized from acetone-hexane).

Reference Example 9

A mixture of ethyl (2E)-3-[2-(1H-benzimidazol-1-yl)-4-isopropyl-5-thiazolyl]propenoate (1.50 g), 5% palladium-carbon (1.0 g), tetrahydrofuran (20 mL) and ethanol (20 mL) was stirred at room temperature under an atmospheric pressure of hydrogen for 14 hrs. The catalyst was removed by filtration, and the organic layer was concentrated to give ethyl 3-[2-(1H-benzimidazol-1-yl)-4-isopropyl-5-thiazolyl]propionate (1.50 g, 99%) as a yellow oil.

NMR(CDCl$_3$) delta: 1.24(3H,t,J=7 Hz), 1.34(6H,d,J=7 Hz), 2.66(2H,t,J=7 Hz), 3.1–3.2(1H,m), 3.14(2H,t,J=7 Hz), 4.18(2H,q,J=7 Hz), 7.35–7.5(2H,m), 7.8–7.9(1H,m), 8.05–8.15(1H,m), 8.46(1H,s).

In the same manner as in Reference Example 9, the compounds of Reference Examples 10 and 11 were synthesized.

Reference Example 10 ethyl 3-[2-(1H-benzimidazol-1-yl)-4-tert-butyl-5-thiazolyl]propionate yield: 99%. a yellow oil. NMR(CDCl$_3$) delta:1.29(3H,t, J=7 Hz), 1.48(9H,s), 2.71(2H,t,J=7 Hz), 3.32(2H,t,J=7 Hz), 4.19(2H,q,J=7 Hz), 7.3–7.5(2H,m), 7.8–7.9(1H,m), 8.05–8.15(1H,m), 8.43(1H,s).

Reference Example 11 ethyl 3-[2-(1H-benzimidazol-1-yl)-4-phenyl-5-thiazolyl]propionate yield: 88%. pale-yellow prism crystal, melting point: 81–82° C. (recrystallized from acetone-hexane).

Reference Example 12

A mixture of methyl 3-[2-chloro-4-(4-chlorophenyl)-5-oxazolyl]propionate (1.50 g), dihydroxyphenylborane (650 mg), sodium hydrogen carbonate (1.68 g), tetrakis(triphenylphosphine)palladium (250 mg), toluene (50 mL), ethanol (25 mL) and water (25 mL) was stirred under an argon atmosphere with heating under reflux for 12 hrs. The reaction mixture was concentrated and the residue was purified by silica gel column chromatography. Methyl 3-[4-(4-chlorophenyl)-2-phenyl-5-oxazolyl]propionate (1.50 g, 88%) was obtained as a yellow oil from a fraction eluted with hexane-ethyl acetate (6:1, volume ratio).

NMR(CDCl$_3$) delta:2.82(2H,t,J=7.5 Hz), 3.29(2H,t,J=7.5 Hz), 3.70(3H,s), 7.3–7.5(5H,m), 7.69(2H,d,J=8.5 Hz), 8.0–8.1(2H,m).

In the same manner as in Reference Example 12, the compounds of Reference Examples 13–15 were synthesized.

Reference Example 13 ethyl 4-[4-(4-chlorophenyl)-2-phenyl-5-oxazolyl]butanoate yield: 90%. a yellow oil NMR(CDCl$_3$) delta:1.24(3H,t,J=7 Hz), 2.0–2.3(2H,m), 2.43(2H,t,J=7 Hz), 3.00(2H,t,J=7 Hz), 4.12(2H,q,J=7 HZ), 7.3–7.5(5H,m), 7.66(2H,d,J=8.5 Hz), 8.0–8.1(2H,m).

Reference Example 14 methyl 3-[4-(3,4-dichlorophenyl)-2-phenyl-5-oxazolyl]propionate yield: 69%. a yellow oil NMR(CDCl$_3$) delta: 2.83 (2H,t, J=7 Hz), 3.29 (2H,t,J=7 Hz), 3.71 (3H,s), 7.4–7.7(5H,m), 7.91 (1H,d,J=2 Hz), 8.0–8.1 (2H,m).

Reference Example 15 methyl 6-[4-(4-chlorophenyl)-2-phenyl-5-oxazolyl]hexanoate yield: 90%. a yellow oil NMR(CDCl$_3$) delta: 1.4–1.6 (2H,m), 1.6–1.9 (4H,m), 2.33 (2H,t,J=7 Hz), 2.93 (2H,t,J=7 Hz), 3.66 (3H,s), 7.4–7.5 (5H,m), 7.65 (2H,d,J=8.5 Hz), 8.0–8.1 (2H,m).

Reference Example 16

A mixture of ethyl 5-[2-chloro-4-chlorophenyl-5-oxazolyl]pentanoate (6.30 g), potassium carbonate (5.08 g), benzimidazole (4.34 g) and N,N-dimethylformamide (50 mL) was stirred at 120° C. for 1 hr. The reaction mixture was poured into water. The precipitated crystals were collected by filtration, washed with water and dried to give ethyl 5-[2-(1H-benzimidazol-1-yl)-4-(4-chlorophenyl)-5-oxazolyl]pentanoate (7.20 g, yield 90%).

NMR(CDCl$_3$) delta: 1.25 (3H,t,J=7 Hz), 1.7–2.0 (4H,m), 2.39 (2H,t,J=7 Hz), 3.00 (2H,t,J=7 Hz), 4.14 (2H,q,J=7 Hz), 7.4–7.5(4H,m), 7.67(2H,d,J=8.5 Hz), 7.88 (1H,d,J=7.5 Hz), 8.26 (1H,d,J=7.5 Hz), 8.59(1H,s).

In the same manner as in Reference Example 16, the compounds of Reference Examples 17–21 were synthesized.

Reference Example 17 methyl 3-[2-(1H-benzimidazol-1-yl)-4-(3,4-dichlorophenyl)-5-oxazolyl]propionate yield: 62%. pale-yellow prism crystal, melting point: 81–82° C. (recrystallized from acetone-isopropyl ether).

Reference Example 18 ethyl 4-[4-(4-chlorophenyl)-2-(5,6-dimethyl-1H-benzimidazol-1-yl)-5-oxazolyl]butanoate yield: 90%. pale-yellow prism crystal, melting point: 119–120° C. (recrystallized from acetone-hexane).

Reference Example 19 methyl 3-[4-(4-chlorophenyl)-2-(5,6-dimethyl-1H-benzimidazol-1-yl)-5-oxazolyl]propionate yield: 88%. pale-yellow prism crystal, melting point: 151–152° C. (recrystallized from acetone-ethyl acetate).

Reference Example 20 ethyl 4-[2-(1H-benzimidazol-1-yl)-4-(4-chlorophenyl)-5-thiazolyl]butanoate yield: 55%. pale-yellow solid.

NMR(CDCl$_3$) delta:1.26(3H,t,J=7 Hz), 2.0–2.2(2H,m), 2.42(2H,t,J=7 Hz), 3.05(2H,t,J=7 Hz), 4.13(2H,q,J=7 Hz), 7.4–7.5(4H,m), 7.64(2H,d,J=8.5 Hz), 7.85–7.9(1H,m), 8.05–8.1 (1H,m), 8.54 (1H,s).

Reference Example 21 ethyl 3-[2-(1H-benzimidazol-1-yl)-4-(4-chlorophenyl)-5-thiazolyl]propionate yield: 33%. pale-yellow prism crystal, melting point: 121–122° C. (recrystallized from acetone-ethyl acetate).

Reference Example 22

A mixture of ethyl 2-[2-chloro-4-chlorophenyl-5-oxazolyl]-2-oxoacetate (5.0 g), benzimidazole (2.26 g), sodium hydride (0.76 g) and N,N-dimethylformamide (50 mL) was stirred at 0° C. for 1 hr. The reaction mixture was poured into water, and the mixture was extracted with ethyl acetate, washed with water, dried over anhydrous magnesium sulfate, and concentrated to give ethyl 2-[2-(1H-benzimidazol-1-yl)-4-(4-chlorophenyl)-5-oxazolyl]-2-oxoacetate (4.57 g, 73%) as crystals. Recrystallization from ethyl acetate-isopropyl ether gave pale-yellow prism crystals. melting point: 143–144° C.

Reference Example 23

Ethyl 2-[2-(1H-benzimidazol-1-yl)-4-(4-chlorophenyl)-5-oxazolyl]-2-oxoacetate (3.50 g) was dissolved in a mixed solvent of tetrahydrofuran (60 mL)-ethanol (20 mL), sodium borohydride (100 mg) was added at 0° C. and the mixture was stirred at 0° C. for 1 hr. The reaction mixture was poured into water, and the precipitated solid was collected by filtration and dried. The obtained solid was added to thionyl chloride (10 mL) at 0° C., and the mixture was stirred at room temperature for 1 hr. The reaction mixture was concentrated and poured into 10% aqueous sodium hydrogen carbonate solution and the mixture was extracted with ethyl acetate. The organic layer was washed with water, dried over anhydrous magnesium sulfate, and concentrated. The residue was dissolved in acetic acid (50 mL) and zinc powder (10 g) was added. The mixture was stirred with heating under reflux for 30 min. Insoluble material was removed by filtration, and the filtrate was concentrated and poured into 10% aqueous sodium hydrogen carbonate solution. The mixture was extracted with ethyl acetate, and the organic layer was washed with water, dried over anhydrous magnesium sulfate, and concentrated. The residue was purified by silica gel column chromatography and ethyl 2-[2-(1H-benzimidazol-1-yl)-4-(4-chlorophenyl)-5-oxazolyl]acetate (2.07 g, 61%) was obtained as crystals from a fraction eluted with acetone-hexane (1:2, volume ratio). Recrystallization from acetone-isopropyl ether gave colorless needle crystals. melting point: 152–153° C.

Reference Example 24

A mixture of ethyl(2E)-3-[2-(1H-benzimidazol-1-yl)-4-isopropyl-5-thiazolyl]propenoate (1.00 g), 2N aqueous sodium hydroxide solution (5 mL), tetrahydrofuran (5 mL), ethanol (5 mL) was stirred at room temperature for 1 hr. The reaction mixture was poured into dilute hydrochloric acid and the precipitated solid was collected by filtration, washed with water and dried to give (2E)-3-[2-(1H-benzimidazol-1-yl)-4-isopropyl-5-thiazolyl]propenoic acid (0.90 g, 98%) as crystals. Recrystallization from acetone-hexane gave pale-yellow prism crystals. melting point: 262–264° C.

In the same manner as in Reference Example 24, the compounds of Reference Examples 25–38 were synthesized by alkaline hydrolysis of the corresponding ester.

Reference Example 25

(2E)-3-[2-(1H-benzimidazol-1-yl)-4-tert-butyl-5-thiazolyl]propenoic acid yield: 93%. pale-yellow prism crystal, melting point: 256–257° C. (recrystallized from acetone-hexane).

Reference Example 26

(2E)-3-[2-(1H-benzimidazol-1-yl)-4-phenyl-5-thiazolyl]propenoic acid yield: 89%. pale-yellow prism crystal, melting point: dec. 285° C. (recrystallized from acetone-hexane)

Reference Example 27

(2E)-3-[2-(1H-benzimidazol-1-yl)-4-methyl-5-thiazolyl]propenoic acid yield: 81%. pale-yellow prism crystal, melting point: 247–251° C. (recrystallized from acetone-hexane).

Reference Example 28

3-[2-(1H-benzimidazol-1-yl)-4-isopropyl-5-thiazolyl]propionic acid yield: 88%. pale-yellow prism crystal, melting point: 187–188° C. (recrystallized from acetone-hexane).

Reference Example 29

3-[2-(1H-benzimidazol-1-yl)-4-tert-butyl-5-thiazolyl]propionic acid yield: 85%. pale-yellow prism crystal, melting point: 193–194° C. (recrystallized from acetone-hexane).

Reference Example 30

3-[2-(1H-benzimidazol-1-yl)-4-methyl-5-thiazolyl]propionic acid yield: 82%. pale-yellow prism crystal, melting point: 175–179° C. (recrystallized from acetone-hexane).

Reference Example 31

3-[2-(1H-benzimidazol-1-yl)-4-(4-chlorophenyl)-5-thiazolyl]propionic acid yield: 85%. pale-yellow prism crystal, melting point: 300° C. or above (recrystallized from acetone-hexane).

Reference Example 32

4-[2-(1H-benzimidazol-1-yl)-4-(4-chlorophenyl)-5-thiazolyl]butanoic acid yield: 71%. pale-yellow prism crystal, melting point: 199–200° C. (recrystallized from acetone-hexane).

Reference Example 33

2-[2-(1H-benzimidazol-1-yl)-4-(4-chlorophenyl)-5-oxazolyl]acetic acid yield: 82%. colorless needle crystal, melting point: 256–257° C. (recrystallized from methanol-ethyl acetate).

Reference Example 34

3-[4-(4-chlorophenyl)-2-(5,6-dimethyl-1H-benzimidazol-1-yl)-5-oxazolyl]propionic acid yield: 80%. colorless needle crystal, melting point: 238–240° C. (recrystallized from ethanol-hexane).

Reference Example 35

4-[4-(4-chlorophenyl)-2-(5,6-dimethyl-1H-benzimidazol-1-yl)-5-oxazolyl]butanoic acid yield: 97%. colorless needle crystal, melting point: 205–206° C. (recrystallized from tetrahydrofuran-hexane).

Reference Example 36

4-[4-(4-chlorophenyl)-2-phenyl-5-oxazolyl]butanoic acid yield: 87%. colorless prism crystal, melting point: 158–159° C. (recrystallized from ethyl acetate-hexane).

Reference Example 37

3-[4-(4-chlorophenyl)-2-phenyl-5-oxazolyl]propionic acid yield: 80%. colorless prism crystal, melting point: 166–167° C. (recrystallized from ethyl acetate-hexane).

Reference Example 38

5-[2-(1H-benzimidazol-1-yl)-4-(4-chlorophenyl)-5-oxazolyl]pentanoic acid yield: 93%. pale-yellow solid. NMR(CDCl$_3$) delta: 1.7–2.0(4H,m), 2.46 (2H,t,J=7 Hz), 3.01(2H,t,J=7 Hz), 7.2–7.3(4H,m), 7.68(2H,d,J=8.5 Hz), 7.87(1H,d,J=7.5 Hz), 8.27(1H,d,J=7.5 Hz), 8.63(1H,s).

Reference Example 39

A mixture of 3-[2-chloro-4-(4-chlorophenyl)-5-oxazolyl]butanoic acid (2.03 g), potassium carbonate (2.76 g), benzimidazole (1.18 g) and N,N-dimethylformamide (30 mL) was stirred at 120° C. for 4 hrs. The reaction mixture was poured into water, and the precipitated crystals were collected by filtration, washed with water and dried to give 4-[2-(1H-benzimidazol-1-yl)-4-(4-chlorophenyl)-5-oxazolyl]butanoic acid (2.22 g, yield 82%). Recrystallization from tetrahydrofuran-ethanol gave colorless needle crystals. melting point: 199–200° C.

Reference Example 40

In the same manner as in Reference Example 39, 6-[2-(1H-benzimidazol-1-yl)-4-(4-chlorophenyl)-5-oxazolyl]hexanoic acid was produced.

yield: 86%. pale-yellow prism crystal, melting point: 158–159° C. (recrystallized from acetone-isopropyl ether).

Reference Example 41

A mixture of 2-bromo-4'-chloropropiophenone (45.0 g), thiobenzamide (24.7 g), sodium acetate (14.8 g) and ethanol (400 mL) was stirred with heating under reflux for 3 hrs. The reaction mixture was poured into water, and the mixture was extracted with ethyl acetate. The organic layer was washed with water, dried over anhydrous magnesium sulfate and concentrated to give 4-(4-chlorophenyl)-5-methyl-2-phenylthiazole (35.1 g, 68%) as crystals. Recrystallization from ethyl acetate-hexane gave colorless prism crystals. melting point: 90–91° C.

Reference Example 42

A mixture of 4-(4-chlorophenyl)-5-methyl-2-phenylthiazole (35.1 g), N-bromosuccinimide (24.0 g), azobisisobutyronitrile (4.11 g) and carbon tetrachloride (400 mL) was stirred with heating under reflux for 3 hrs. The precipitated solid was removed by filtration and the organic layer was concentrated. The residue was purified by silica gel column chromatography. 5-(Bromomethyl)-4-(4-chlorophenyl)-2-phenylthiazole (30.8 g, 69%) was obtained as crystals from a fraction eluted with hexane-ethyl acetate (19:1, volume ratio). Recrystallization from ethyl acetate gave colorless prism crystals. melting point: 108–109° C.

Reference Example 43

To a solution of ethyl malonate (17.5 g) in N,N-dimethylformamide (50 mL) was added sodium hydride (4.38 g) and the mixture was stirred at 0° C. for 30 min, after which a solution of 5-(bromomethyl)-4-(4-chlorophenyl)-2-phenylthiazole (8.0 g) in N,N-dimethylformamide (200 mL) was added at 0° C. The mixture was stirred at 0° C. for 2 hrs. and poured into dilute hydrochloric acid. The mixture was extracted with ethyl acetate and the organic layer was washed with water, dried over anhydrous magnesium sulfate and concentrated to give a yellow oil. This oil was dissolved in ethanol (140 mL) and 10% aqueous sodium hydroxide solution (140 mL) was added. The mixture was stirred at 60° C. for 2 hrs. and the reaction mixture was poured into water. The mixture was washed with diethyl ether and the aqueous layer was acidified with dilute hydrochloric acid. The mixture was extracted with ethyl acetate, and the organic layer was washed with saturated brine, dried over anhydrous magnesium sulfate and concentrated to give a yellow powder. This powder was dissolved in pyridine (140 mL) and the mixture was stirred at 100° C. for 2 hrs. The reaction mixture was concentrated and diluted with dilute hydrochloric acid. The mixture was extracted with ethyl acetate, and the organic layer was washed with water, dried over anhydrous magnesium sulfate and concentrated to give 3-[4-(4-chlorophenyl)-2-phenyl-5-thiazolyl]propionic acid (5.71 g, 75%) as a yellow powder. Recrystallization from ethyl acetate-hexane gave colorless prism crystals, melting point: 142–143° C.

Reference Example 44

A mixture of methyl 3-{2-chloro-4-[4-(trifluoromethyl)]phenyl-5-oxazolyl}propionate (1.33 g), potassium carbonate (1.38 g), benzimidazole (1.18 g) and N-methylpyrrolidone (10 mL) was stirred at 120° C. for 1 hr. The reaction mixture was poured into water, and the precipitated crystals were collected by filtration, washed with water, dried and recrystallized from ethyl acetate-hexane to give methyl 3-{2-(1H-benzimidazol-1-yl)-4-[4-(trifluoromethyl)phenyl]-5-oxazolyl}propionate (1.15 g, yield 70%) as pale-yellow prism crystals. melting point: 129–130° C.

Reference Example 45

A mixture of methyl 3-{2-(1H-benzimidazol-1-yl)-4-[4-(trifluoromethyl)phenyl]-5-oxazolyl}propionate (1.00 g), 1N aqueous sodium hydroxide solution (10 mL), tetrahydrofuran (10 mL) and ethanol (10 mL) was stirred at room temperature for 1 hr. The reaction mixture was poured into dilute hydrochloric acid, and the precipitated crystals were collected by filtration, washed with water, dried and recrystallized from tetrahydrofuran-ethanol to give 3-{2-(1H-benzimidazol-1-yl)-4-[4-(trifluoromethyl)phenyl]-5-oxazolyl}propionic acid (1.00 g, yield 83%) as pale-yellow prism crystals. melting point: 224–226° C.

Reference Example 46

To a mixture of 2-(ethylsulfanyl)ethylamine (0.94 g) and tetrahydrofuran (10 mL) was added dropwise di-tert-butyl dicarbonate (2.14 g) with stirring under ice-cooling. The mixture was stirred at room temperature for 30 min and the reaction mixture was concentrated, diluted with ethyl acetate and washed with water. The organic layer was dried over anhydrous magnesium sulfate and concentrated and the residue was subjected to silica gel column chromatography. tert-Butyl 2-(ethylsulfanyl)ethylcarbamate was obtained as a colorless oil from a fraction eluted with ethyl acetate-hexane (1:4, volume ratio). (1.83 g, yield 100%).

NMR(CDCl$_3$) delta:1.26(3H, t, J=7.5 Hz), 1.45(9H, s), 2.55(2H, q, J=7.5 Hz), 2.66(2H, t, J=6.5 Hz), 3.24–3.36(2H, m), 4.94(1H, brs).

Reference Example 47

To a mixture of tert-butyl 2-(ethylsulfanyl)ethylcarbamate (1.83 g) and tetrahydrofuran (15 mL) was added m-chloroperbenzoic acid (4.84 g) with stirring under ice-cooling. The reaction mixture was diluted with ethyl acetate and washed successively with saturated aqueous sodium hydrogen carbonate, water and saturated brine. The organic layer was dried over anhydrous magnesium sulfate and concentrated to give tert-butyl 2-(ethylsulfonyl)ethylcarbamate as a colorless oil. (2.07 g, yield 98%).

MR (CDCl$_3$) delta:1.42(3H, t, J=8 Hz), 1.45(9H, s), 3.04(2H, q, J=8 Hz), 3.19(2H, t, J=6.5 Hz), 3.58–3.70(2H, m), 5.22(1H, brs).

Reference Example 48

To a mixture of tert-butyl 2-(ethylsulfonyl)ethylcarbamate (1.5 g) and ethyl acetate (15 mL) was added dropwise 4N hydrochloric acid•ethyl acetate solution (4 mL) with stirring under ice-cooling. The mixture was stirred at room temperature for 4 hrs., and the precipitated crystals were collected by filtration and washed with ethyl acetate to give 2-(ethylsulfonyl)ethylamine hydrochloride as crystals. (0.76 g, yield 69%). Recrystallization from ethanol gave colorless prism crystals. melting point: 103–104° C.

Reference Example 49

To a mixture of 2-(methylsulfanyl)ethylamine (3.01 g) and tetrahydrofuran (30 mL) was added dropwise di-tert-butyl dicarbonate (8.16 g) with stirring under ice-cooling. After stirring at room temperature for 30 min, the reaction mixture was concentrated, diluted with ethyl acetate and washed with water. The organic layer was dried over anhydrous magnesium sulfate and concentrated. The residue was subjected to silica gel column chromatography and tert-butyl 2-(methylsulfanyl)ethylcarbamate (5.62 g, 89%) was obtained as a colorless oil from a fraction eluted with ethyl acetate-hexane (1:4, volume ratio).

NMR(CDCl$_3$) delta:1.45(9H, s), 2.11(3H, s), 2.62(2H, t, J=6.5 Hz), 3.33(2H, q, J=6.5 Hz), 4.94(1H, brs).

Reference Example 50

To a mixture of tert-butyl 2-(methylsulfanyl)ethylcarbamate (2.0 g) and tetrahydrofuran (20 mL) was added m-chloroperbenzoic acid (5.67 g) with stirring under ice-cooling. The reaction mixture was diluted with ethyl acetate and washed successively with saturated aqueous sodium hydrogen carbonate, water and saturated brine. The organic layer was dried over anhydrous magnesium sulfate, and concentrated to give tert-butyl 2-(methylsulfonyl)ethylcarbamate as crystals. The crystals were recrystallized from ethyl acetate-hexane to give colorless prism crystals. (1.78 g, yield 76%). melting point: 85–86° C.

Reference Example 51

To a mixture of tert-butyl 2-(methylsulfonyl)ethylcarbamate (1.5 g) and ethyl acetate (10 mL) was added dropwise 4N hydrochloric acid.ethyl acetate solution (3 mL) with stirring under ice-cooling. After stirring at room temperature overnight, the precipitated crystals were collected by filtration and washed with ethyl acetate to give 2-(methylsulfonyl)ethylamine hydrochloride as crystals (1.04 g, yield 97%). Recrystallization from ethanol gave colorless prism crystal. melting point: 169–170° C.

Reference Example 52

To a mixture of tert-butyl 2-(methylsulfanyl)ethylcarbamate (3.5 g) and tetrahydrofuran (20 mL) was added lithium aluminum hydride (1.39 g) with stirring under ice-cooling and the mixture was heated under reflux for 2 hrs. After cooling the reaction mixture, sodium sulfate 10 hydrate (5 g) was added, and the solid was filtered off. The filtrate was concentrated and diluted with tetrahydrofuran, and di-tert-butyl dicarbonate was added dropwise with stirring under ice-cooling. After stirring at room temperature for 30 min, the reaction mixture was concentrated, diluted with ethyl acetate and washed with water. The organic layer was dried over anhydrous magnesium sulfate and concentrated. The residue was subjected to silica gel column chromatography, and tert-butyl N-methyl-N-[2-(methylsulfanyl)ethyl]carbamate was obtained as a colorless oil (0.82 g, yield 22%) from a fraction eluted with ethyl acetate-hexane (1:4, volume ratio).

NMR(CDCl$_3$) delta:1.46(9H, s), 2.14(3H, s), 2.56–2.68 (2H, m), 2.89(3H, s), 3.34–3.46(2H, m).

Reference Example 53

To a mixture of tert-butyl N-methyl-N-[2-(methylsulfanyl)ethyl]carbamate (0.8 g) and tetrahydrofuran (10 mL) was added m-chloroperbenzoic acid (2.11 g) with stirring under ice-cooling. The reaction mixture was diluted with ethyl acetate and washed successively with saturated aqueous sodium hydrogen carbonate, water and saturated brine. The organic layer was dried over anhydrous magnesium sulfate to give tert-butyl N-methyl-N-[2-(methylsulfonyl)ethyl]carbamate as a colorless oil. (0.83 g, yield 89%).

NMR(CDCl$_3$) delta:1.47(9H, s), 2.93(3H, s), 2.94(3H, s), 3.20–3.36(2H, m), 3.64–3.74(2H, m).

Reference Example 54

To a mixture of tert-butyl N-methyl-N-[2-(methylsulfonyl)ethyl]carbamate (0.81 g) and ethyl acetate (10 mL) was added dropwise a 4N hydrochloric acid.ethyl acetate solution (2 mL) with stirring under ice-cooling. After stirring at room temperature overnight, the precipitated crystals were collected by filtration and washed with ethyl acetate to give N-methyl-N-[2-(methylsulfonyl)ethyl]amine hydrochloride as crystals (0.38 g, yield 64%). Recrystallization from ethanol gave colorless prism crystals. melting point: 259–260° C.

Reference Example 55

To a mixture of tetrahydrothiopyran-4-one (5.0 g), hydroxylamine hydrochloride (15 g) and ethanol (400 mL) was added sodium acetate (29.3 g) and the mixture was stirred overnight at room temperature. The reaction mixture was cooled to 0° C., and the precipitated crystals were collected by filtration and washed with water at 0° C. to give tetrahydrothiopyran-4-one oxime as crystals. Recrystallization from petroleum ether gave white prism crystals. (2.36 g, yield 66%). melting point: 85–86° C.

Reference Example 56

To a mixture of lithium aluminum hydride (5.42 g) and tetrahydrofuran (400 mL) was added a solution of tetrahydrothiopyran-4-one oxime (3.75 g) in tetrahydrofuran (30 mL) with stirring under ice-cooling, and the mixture was stirred with heating under reflux overnight. After cooling the reaction mixture, a 2N aqueous sodium hydroxide solution was added, and the precipitated solid was filtered off. The filtrate was concentrated until the liquid amount became half, and di-tert-butyl dicarbonate (7.5 g) was added dropwise with stirring under ice-cooling. The mixture was stirred at room temperature for 2 hrs., and the reaction mixture was concentrated, diluted with ethyl acetate and washed with water. The organic layer was dried over anhydrous magnesium sulfate and concentrated to give tert-butyl(tetrahydrothiopyran-4-yl)carbamate as crystals (4.68 g, yield 75%). Recrystallization from ethyl acetate-hexane gave white prism crystals. melting point: 141–142° C.

Reference Example 57

To a mixture of tert-butyl(tetrahydrothiopyran-4-yl)carbamate (2.0 g) and tetrahydrofuran (20 mL) was added m-chloroperbenzoic acid (5.0 g) with stirring under ice-cooling. The reaction mixture was diluted with ethyl acetate, and washed successively with saturated aqueous sodium hydrogen carbonate, water and saturated brine. The organic layer was dried over anhydrous magnesium sulfate and concentrated to give tert-butyl(1,1-dioxidetetrahydro-2H-thiopyran-4-yl)carbamate as crystals (1.63 g, yield 71%). Recrystallization from diisopropyl ether-hexane gave white prism crystals. melting point: 207–208° C.

Reference Example 58

To a mixture of tert-butyl(1,1-dioxidetetrahydrothiopyran-4-yl)carbamate (1.5 g) and ethyl acetate (10 mL) was added dropwise a 4N hydrochloric acid.ethyl acetate solution (3 mL) with stirring under ice-cooling. After stirring at room temperature overnight, the precipitated crystals were collected by filtration and washed with ethyl acetate to give (1,1-dioxidetetrahydrothiopyran-4-yl)amine hydrochloride as crystals (0.78 g, yield 95%). Recrystallization from ethanol gave colorless prism crystals. melting point: 288–289° C.

Reference Example 59

To a mixture of tert-butyl 4-hydroxypiperidine-1-carboxylate (10 g) and tetrahydrofuran (100 mL) were successively added methanesulfonyl chloride (5.98 g) and triethylamme (5.53 g) at 0° C. The mixture was stirred at room temperature for 2 hrs., and the reaction mixture was diluted with ethyl acetate and washed successively with 1N aqueous sodium hydroxide solution, water and saturated brine. The organic layer was dried over anhydrous magnesium sulfate and concentrated to give tert-butyl 4-(methylsulfonyl)oxypiperidine-1-carboxylate as crystals. Recrystallization from ethyl acetate-hexane gave white prism crystals (13.2 g, yield 95%). melting point: 94–95° C.

Reference Example 60

A mixture of tert-butyl 4-(methylsulfonyl)oxypiperidine-1-carboxylate (12.5 g), methylmercaptan sodium salt (3.31 g), tetra-n-butylammonium iodide (1.66 g) and tetrahydrofuran (50 mL) was stirred at room temperature for 72 hrs. The insoluble material was filtered through celite and the filtrate was concentrated. The residue was subjected to silica gel column chromatography, and tert-butyl 4-(methylthio)piperidine-1-carboxylate was obtained as a colorless oil from a fraction eluted with ethyl acetate-hexane (1:4, volume ratio) (6.89 g, yield 67%).

NMR (CDCl$_3$) delta:1.45(9H, s), 1.40–1.60(2H, m), 1.82–2.00 (2H, m), 2.10(3H, s), 2.60–2.80(1H, m), 2.80–3.00 (2H, m), 3.92–4.08(2H, m).

Reference Example 61

To a mixture of tert-butyl 4-(methylthio)piperidine-1-carboxylate (3.0 g) and tetrahydrofuran (30 mL) was added m-chloroperbenzoic acid (7.03 g) with stirring under ice-cooling. The reaction mixture was stirred at room temperature for 6 hrs., diluted with ethyl acetate, and washed successively with 2N aqueous sodium hydroxide solution, water and saturated brine. The organic layer was dried over anhydrous magnesium sulfate to give tert-butyl 4-(methylsulfonyl)piperidine-1-carboxylate as crystals (2.00 g, yield 59%). Recrystallization from ethyl acetate-hexane gave colorless prism crystals. melting point: 107–108° C.

Reference Example 62

To a mixture of tert-butyl 4-(methylsulfonyl)piperidine-1-carboxylate (1.5 g) and ethyl acetate (10 mL) was added dropwise a 4N hydrochloric acid.ethyl acetate solution (2.5 mL) with stirring under ice-cooling. After stirring overnight at room temperature, the precipitated crystals were collected by filtration and washed with ethyl acetate to give 4-(methylsulfonyl)piperidine hydrochloride as crystals (1.08 g, yield 95%). Recrystallization from ethanol gave colorless prism crystals. melting point: 271–272° C.

Reference Example 63

To a mixture of tetrahydrothiopyran-4-one (5.14 g) and conc. hydrochloric acid (20 mL) was added sodium azide (4.31 g) under ice-cooling. The reaction mixture was stirred at room temperature for 4 hrs., and sodium carbonate was added. The mixture was diluted with iced water and extracted with chloroform. The organic layer was washed successively with water and saturated brine, dried over anhydrous magnesium sulfate, and concentrated to give 1,4-thiazepan-5-one as crystals (3.62 g, yield 62%). Recrystallization from ethyl acetate-hexane gave colorless prism crystals. melting point: 120–121° C.

Reference Example 64

To a mixture of lithium aluminum hydride (2.31 g) and tetrahydrofuran (100 mL) was added a solution of 1,4-thiazepan-5-one (4.0 g) in tetrahydrofuran (30 mL) with stirring under ice-cooling and the mixture was stirred at room temperature for 30 min. 2N Sodium hydroxide was added to the reaction mixture until aluminum hydroxide precipitated, and the solid was filtered off. The filtrate was concentrated until the liquid amount became half, and di-tert-butyl dicarbonate (7.32 g) was added dropwise with stirring under ice-cooling. The mixture was stirred at room temperature for 2 hrs., and the reaction mixture was concentrated, diluted with ethyl acetate and washed with water. The organic layer was dried over anhydrous magnesium sulfate and concentrated. The residue was subjected to silica gel column chromatography, and tert-butyl 1,4-thiazepan-4-carboxylate was obtained as a colorless oil (6.00 g, yield 91%) from a fraction eluted with ethyl acetate-hexane (1:4,volume ratio).

NMR(CDCl$_3$) delta: 1.46 (9H, s), 1.92–2.10 (2H, m), 2.60–2.76 (4H, m), 3.50–3.68 (4H, m).

Reference Example 65

To a mixture of tert-butyl 1,4-thiazepan-4-carboxylate (3.0 g) and tetrahydrofuran (20 mL) was added m-chloroperbenzoic acid (7.48 g) with stirring under ice-cooling. The mixture was stirred at room temperature for 1 hr., diluted with ethyl acetate, and washed successively with saturated aqueous sodium hydrogen carbonate, water and saturated brine. The organic layer was dried over anhydrous magnesium sulfate and concentrated to give tert-butyl 1,1-dioxide-1,4-thiazepan-4-carboxylate as crystals (1.19 g, yield 35%). Recrystallization from ethyl acetate-hexane gave colorless prism crystals. melting point: 120–121° C.

Reference Example 66

To a mixture of tert-butyl 1,1-dioxide-1,4-thiazepan-4-carboxylate (1.0 g) and ethyl acetate (10 mL) was added dropwise a 4N hydrochloric acid.ethyl acetate solution (2.5 mL) with stirring under ice-cooling. After stirring at room temperature for 16 hrs., the precipitated crystals were collected by filtration and washed with ethyl acetate to give 1,1-dioxide-1,4-thiazepan hydrochloride as crystals (0.61 g, yield 81%). Recrystallization from ethanol gave colorless prism crystals. melting point: 196–200° C.

Reference Example 67

To a solution of 4-iodoaniline (10 g) in tetrahydrofuran (200 mL) was added di-tert-butyl dicarbonate (11 g), and the reaction mixture was heated under reflux for 16 hrs. The reaction mixture was concentrated and the residue was subjected to silica gel column chromatography, and tert-butyl 4-iodophenylcarbamate was obtained as crystals from a fraction eluted with ethyl acetate-hexane (1:4, volume ratio). Recrystallization from ethyl acetate-hexane gave colorless prism crystals (10.7 g, yield 73%). melting point: 148–149° C.

Reference Example 68

To a mixture of 4-nitrobenzaldehyde (8.56 g) and ethyl hypophosphite (7.81 g) was gradually added triethylamine (1.5 mL). After stirring for 1 hr., the reaction mixture was diluted with ethyl acetate and washed successively with 1N hydrochloric acid and water. The organic layer was dried over anhydrous magnesium sulfate, and concentrated. The residue was subjected to silica gel column chromatography, and diethyl α-hydroxy-4-nitrobenzylphosphonate was obtained as crystals from a fraction eluted with ethyl acetate-hexane (1:1, volume ratio). Recrystallization from ethyl acetate-hexane gave yellow prism crystals (4.62 g, yield 28%). melting point: 94–95° C.

Reference Example 69

To a mixed solution of diethyl α-hydroxy-4-nitrobenzylphosphonate (1.42 g) and methanol (30 mL) was added 10% palladium-carbon (0.14 g) and the mixture was stirred at room temperature under an atmospheric hydrogen pressure for 3 hrs. Palladium-carbon was removed from the reaction mixture by filtration and the filtrate was concentrated to give diethyl 4-amino-α-hydroxybenzylphosphonate as a solid (1.02 g, yield 80%).
NMR(CDCl$_3$) delta: 1.18–1.34 (6H, m), 2.98 (1H, brs), 3.72 (2H, brs), 3.82–4.16 (4H, m), 4.87 (1H, d, J=10 Hz), 6.68 (2H, d, J=8.5 Hz), 7.20–7.34 (2H, m).

Reference Example 70

To a mixture of diethyl α-hydroxy-4-nitrobenzylphosphonate (1.0 g) and chloroform (10 mL) was added diethylaminosulfur trifluoride (1.4 mL) at −78° C. and the reaction mixture was warmed to room temperature. Saturated brine was added to the reaction mixture and the mixture was extracted with ethyl acetate. The extract was concentrated and the residue was purified by preparative HPLC to give 4-[(diethylphosphono)(fluoro)methyl]nitrobenzene (0.1 g, yield 10%) as yellow oil.
NMR(CDCl$_3$) delta: 1.22–1.42 (6H, m), 4.00–4.34 (4H, m), 5.86 (1H, dd, J=45, 9 Hz), 7.64 (2H, d, J=7 Hz), 8.28 (2H, d, J=9 Hz).

Reference Example 71

A mixed solution of 4-nitrobenzaldehyde (2.0 g), trimethyl orthoformate (2 mL), p-toluenesulfonic acid (20 mg) and methanol (20 mL) was heated under reflux for 30 min. The reaction mixture was concentrated, diluted with ethyl acetate, and washed successively with saturated aqueous sodium hydrogen carbonate, water and saturated brine. The organic layer was dried over anhydrous magnesium sulfate and concentrated. Triethyl hypophosphite (2.12 g) and dichloromethane (30 mL) were added to the residue and a boron trifluoride diethyl ether complex (5.2 mL) was gradually added under an argon atmosphere at −20° C. The mixture was stirred overnight at room temperature. Saturated aqueous sodium hydrogen carbonate was added to the reaction mixture and extracted with ethyl acetate. The organic layer was washed successively with water and saturated brine, dried over anhydrous magnesium sulfate and concentrated. The residue was subjected to silica gel column chromatography, and diethyl α-methoxy-4-nitrobenzylphosphonate (3.8 g, yield 95%) was obtained as a yellow oil from a fraction eluted with ethyl acetate.
NMR(CDCl$_3$) delta: 1.20–1.30 (6H, m), 3.45 (3H, s), 4.02–4.20 (4H, m), 4.63 (1H, d, J=17 Hz), 7.58–7.66 (2H, m), 8.24 (2H, d, J=8.8 Hz).

Reference Example 72

To a mixed solution of diethyl α-methoxy-4-nitrobenzylphosphonate (3.7 g) and methanol (50 mL) was added 10% palladium-carbon (0.5 g) and the mixture was stirred overnight at room temperature under an atmospheric hydrogen pressure. Palladium-carbon was removed by filtration and the filtrate was concentrated to give diethyl 4-amino-α-methoxybenzylphosphonate as crystals. Recrystallization from ethyl acetate-isopropyl ether gave yellow prism crystals (2.0 g, yield 60%). melting point: 100–101° C.

Reference Example 73

To a mixed solution of 1-(3-chlorophenyl)-2-hydroxyethanone (21.8 g), potassium cyanide (20.8 g) and 2-propanol (100 mL) was added acetic acid (18 mL) at room temperature. After stirring for 30 min, water was added, and the precipitated crystals were collected by filtration and recrystallized from methanol-diisopropyl ether to give 4-(3-chlorophenyl)oxazol-2(3H)-one (6.7 g, yield 41%) as a solid.
NMR(CDCl$_3$) delta: 7.15 (1H, s), 7.22–7.42 (4H, m), 10.54 (1H, brs).

Reference Example 74

To a solution of 4-(3-chlorophenyl)oxazol-2(3H)-one (3.31 g) and acetonitrile (15 mL) was gradually added conc. sulfuric acid (5.01 g) at 0° C. To the reaction mixture was added methyl acrylate (3.05 mL) at 0° C. and the mixture was stirred at room temperature for 5 hrs. Water was added to the reaction mixture and the mixture was extracted with ethyl acetate-tetrahydrofuran (1:1). The organic layer was washed successively with water and saturated brine, dried over anhydrous magnesium sulfate and concentrated. The residue was subjected to silica gel column chromatography, and methyl 3-[4-(3-chlorophenyl)-2-oxo-2,3-dihydro-5-oxazolyl]propionate (3.0 g, 63%) was obtained as an oil from a fraction eluted with ethyl acetate-hexane (1:1, volume ratio).

NMR(CDCl$_3$) delta: 2.71 (2H, t, J=7.5 Hz), 2.98 (2H, t, J=7.5 Hz), 3.61 (3H, s), 7.24–7.50 (4H, m).

In the same manner as in Reference Example 74, the compounds of Reference Examples 75–77 were synthesized.

Reference Example 75 methyl 3-[2-oxo-4-phenyl-2,3-dihydro-5-oxazolyl]propionate yield: 71%. colorless prism crystal melting point: 166–167° C. (recrystallized from isopropyl ether-hexane)

Reference Example 76 methyl 3-[2-oxo-4-(4-methoxyphenyl)-2,3-dihydro-5-oxazolyl]propionate yield: 5.7g(yield: 42%)pale-yellow solid
NMR(CDCl$_3$) delta: 2.68 (2H, t, J=7 Hz), 2.96 (2H, t, J=7 Hz), 3.68 (3H, s), 3.84 (3H, s), 7.34–7.42 (2H, m), 8.08–8.16 (2H, m)

Reference Example 77 methyl 3-[2-oxo-4-(4-fluorophenyl)-2,3-dihydro-5-oxazolyl]propionate yield:5.9 g(yield: 65%)solid NMR(CDCl$_3$) delta: 2.70 (2H, t, J=7 Hz), 2.97 (2H, t, J=7 Hz), 3.68 (3H, s), 7.10–7.20 (2H, m), 7.40–7.50 (2H, m).

Reference Example 78

To a solution of methyl 3-[4-(3-chlorophenyl)-2-oxo-2,3-dihydro-5-oxazolyl]propionate (3.0 g), phosphorus oxychloride (4 mL) was gradually added pyridine (0.86 mL) at room temperature and the mixture was stirred at 90° C. for 3 hrs. The reaction mixture was cooled and acetonitrile was added. The mixture was poured into water and the mixture was extracted with ethyl acetate. The organic layer was washed successively with water and saturated brine, dried over anhydrous magnesium sulfate and concentrated. The residue was subjected to silica gel column chromatography, and methyl 3-[2-chloro-4-(3-chlorophenyl)-5-oxazolyl]propionate (2.3 g, 72%) was obtained as an oil from a fraction eluted with ethyl acetate-hexane (4:1, volume ratio).

NMR(CDCl$_3$) delta: 2.76 (2H, t, J=7.5 Hz), 3.21 (2H, t, J=7.5 Hz), 3.70 (3H, s), 7.30–7.40 (2H, m), 7.48–7.54 (1H, m), 7.66 (1H, s).

In the same manner as in Reference Example 78, the compounds of Reference Examples 79–81 were synthesized.

Reference Example 79 ethyl 3-[2-chloro-4-phenyl-5-oxazolyl]propionate yield: 63%. an oil
MR (CDCl$_3$) delta: 2.74 (2H, t, J=7.5 Hz), 3.22 (2H, t, J=7.5 Hz), 3.69 (3H, s), 7.28–7.48 (3H, m), 7.58–7.66 (2H, m).

Reference Example 80 methyl 3-[2-chloro-4-(4-methoxyphenyl)-5-oxazolyl]propionate yield: 12%. an oil NMR(CDCl$_3$) delta: 2.73 (2H, t, J=7 Hz), 3.18 (2H, t, J=7 Hz), 3.69 (3H, s), 3.84 (3H, s), 6.90–7.00 (2H, m), 7.50–7.60 (2H, m).

Reference Example 81 methyl 3-[2-chloro-4-(4-fluorophenyl)-5-oxazolyl]propionate yield: 72%. an oil NMR(CDCl$_3$) delta: 2.76 (2H, t, J=7.5 Hz), 3.21 (2H, t, J=7.5 Hz), 3.70 (3H, s), 7.30–7.40 (2H, m), 7.48–7.54 (1H, m), 7.66 (1H, s).

Reference Example 82

A mixture of methyl 3-[2-chloro-4-(3-chlorophenyl)-5-oxazolyl]propionate (2.31 g), 1H-benzoimidazole (1.82 g), potassium carbonate (3.19 g) and N,N-dimethylformamide (12 mL) was stirred at 120° C. for 2 hrs. Water was added to the reaction mixture and the mixture was extracted with ethyl acetate. The organic layer was washed successively with water and saturated brine, dried over anhydrous magnesium sulfate and concentrated. The residue was subjected to silica gel column chromatography, and methyl 3-[2-(1H-benzoimidazol-1-yl)-4-(3-chlorophenyl)-5-oxazolyl]propionate (1.85 g, 63%) was obtained as a solid from a fraction eluted with ethyl acetate-hexane (1:1, volume ratio).

NMR(CDCl$_3$) delta: 2.86 (2H, t, J=7 Hz), 3.36 (2H, t, J=7 Hz), 3.73 (3H, s), 7.38–7.56 (4H, m), 7.60–7.66 (1H, m), 7.76–7.82 (1H, m), 7.86–7.90(1H, m), 8.20–8.26(1H, m), 8.57(1H, s).

In the same manner as in Reference Example 82, the compounds of Reference Examples 83–85 were synthesized.

Reference Example 83 methyl 3-[2-(1H-benzoimidazol-1-yl)-4-phenyl-5-oxazolyl]propionate yield: 72%. solid NMR(CDCl$_3$) delta: 2.85 (2H, t, J=7.5 Hz), 3.36 (2H, t, J=7.5 Hz), 3.72(3H, s), 7.38–7.52(5H, m), 7.76(2H, d, J=7 Hz), 7.88(1H, d, J=7 Hz), 8.26(1H, d, J=7 Hz), 8.58(1H, s).

Reference Example 84 methyl 3-[2-(1H-benzoimidazol-1-yl)-4-(4-methoxyphenyl)-5-oxazolyl]propionate yield: 61%. solid NMR(CDCl$_3$) delta: 2.83 (2H, t, J=7.5 Hz), 3.33 (2H, t, J=7.5 Hz), 3.72 (3H, s), 3.87 (3H, s), 7.02 (2H, d, J=9 Hz), 7.38–7.50 (2H, m), 7.68 (2H, d, J=9 Hz), 7.87 (1H, d, J=8 Hz), 8.24 (1H, d, J=8 Hz), 8.57 (1H, s).

Reference Example 85 methyl 3-[2-(1H-benzoimidazol-1-yl)-4-(4-fluorophenyl)-5-oxazolyl]propionate yield: 70%. solid NMR(CDCl₃) delta: 2.85 (2H, t, J=8 Hz), 3.33 (2H, t, J=8 Hz), 3.72 (3H, s), 7.14–7.22 (2H, m), 7.38–7.50 (2H, m), 7.70–7.80 (2H, m), 7.84–7.90 (1H, m), 8.20–8.26 (1H, m), 8.57 (1H, s).

Reference Example 86

To a mixed solution of methyl 3-[2-chloro-4-(4-chlorophenyl)-5-oxazolylpropionate (1.5 g), 4-tert-butylphenol (0.9 g) and N,N-dimethylformamide (20 mL) was added sodium hydride (60% in oil, 0.24 g) and the mixture was stirred at room temperature for 2 hrs., and further stirred at 70° C. for 30 min. The reaction mixture was diluted with methanol (20 mL) and 2N aqueous sodium hydroxide solution (5 mL) was added. The mixture was stirred at room temperature for 30 min. The reaction mixture was diluted with water, acidified with 2N aqueous hydrochloric acid solution, and extracted with ethyl acetate. The organic layer was washed successively with water and saturated brine, dried over anhydrous magnesium sulfate and concentrated to give 3-[2-(4-tert-butylphenoxy)-4-(4-chlorophenyl)-5-oxazolyl]propionic acid (1.6 g, yield 80%) as crystals. Recrystallization from ethanol gave colorless prism crystals. melting point: 166–167° C.

Reference Example 87

A mixed solution of 3-[2-chloro-4-(4-chlorophenyl)-5-oxazolyl]propionic acid (1.43 g), cyclohexylmercaptan (0.6 g) and N,N-dimethylformamide (20 mL) was stirred at 100° C. for 1.5 hrs. The reaction mixture was diluted with water, and washed with diethyl ether. The aqueous layer was acidified with 2N aqueous hydrochloric acid solution, and the mixture was extracted with ethyl acetate. The organic layer was washed successively with water and saturated brine, dried over anhydrous magnesium sulfate and concentrated to give 3-[4-(4-chlorophenyl)-2-(cyclohexylsulfanyl)-5-oxazolyl]propionic acid (0.95 g, yield 52%) as crystals. Recrystallization from ethanol gave colorless prism crystals. melting point: 136–137° C.

Reference Example 88

A mixed solution of 3-[2-chloro-4-(4-chlorophenyl)-5-oxazolyl]propionic acid (1.43 g), 1-methylpiperazine (2.5 g) and isopropyl alcohol (20 mL) was heated under reflux for 10 hrs. The reaction mixture was concentrated, diluted with water, and acidified with 2N aqueous hydrochloric acid solution. The precipitated crystals were collected by filtration and recrystallized from ethanol to give 3-[4-(4-chlorophenyl)-2-(4-methyl-1-piperazinyl)-5-oxazolyl]propionic acid (1.37 g, yield 70%) as colorless prism crystals. melting point: 157–160° C.

Reference Example 89

A mixed solution of 3-[2-chloro-4-(4-chlorophenyl)-5-oxazolyl]propionic acid (1.43 g), 2-mercapto-4-methylpyrimidine hydrochloride (1.05 g), potassium carbonate (2.76 g) and N,N-dimethylformamide (20 mL) was stirred at 110° C. under a nitrogen atmosphere for 10 hrs. The reaction mixture was diluted with water, and acidified with 2N aqueous hydrochloric acid solution. The precipitated crystals were collected by filtration and recrystallized from methanol to give 3-[4-(4-chlorophenyl)-2-[(4-methylpyrimidin-2-yl)sulfanyl]-5-oxazolepropionic acid (1.65 g, yield 88%) as colorless prism crystals. melting point: 174–175° C.

Reference Example 90

To a mixed solution of methyl 3-[2-chloro-4-(4-chlorophenyl)-5-oxazolyl]propionate (3.0 g), imidazole (0.82 g) and N,N-dimethylformamide (20 mL) was added sodium hydride (60% in oil, 0.5 g), and the mixture was stirred at room temperature for 1 hr. The reaction mixture was poured into iced water, and the precipitated crystals were collected by filtration to give methyl 3-[4-(4-chlorophenyl)-2-(1H-imidazol-1-yl)-5-oxazolyl]propionate (1.6 g, yield 80%) as crystals. Recrystallization from methanol gave colorless prism crystals. melting point: 95–96° C.

Reference Example 91

Methyl 3-[4-(4-chlorophenyl)-2-(1H-imidazol-1-yl)-5-oxazolyl]propionate (1.6 g) and p-formaldehyde (37% aqueous solution, 4 mL) were stirred in a sealed tube at 100° C. for 16 hrs. The reaction mixture was cooled, diluted with water and extracted with ethyl acetate. The organic layer was washed successively with water and saturated brine, dried over anhydrous magnesium sulfate and concentrated. The residue was subjected to silica gel column chromatography, and methyl 3-{4-(4-chlorophenyl)-2-[2-(hydroxymethyl)-1H-imidazol-1-yl]-5-oxazolyl}propionate was obtained from a fraction eluted with chloroform-ethyl acetate-methanol (8:1:4, volume ratio). 2N Aqueous sodium hydroxide solution (2 mL) and methanol (4 mL) were added to this ester form, and the mixture was stirred at 80° C. for 10 min. The reaction mixture was diluted with water and acidified with 2N aqueous hydrochloric acid solution. The precipitated crystals were collected by filtration and recrystallized from methanol-chloroform to give 3-{4-(4-chlorophenyl)-2-[2-(hydroxymethyl)-1H-imidazol-1-yl]-5-oxazolyl}propionic acid (0.65 g, yield 38%) as colorless prism crystals. melting point: 171–173° C.

Reference Example 92

To a solution of 1-propylmercaptan (0.54 mL) in methanol (20 mL) was added sodium methoxide (1.1 g) and then methyl 3-[2-chloro-4-(4-chlorophenyl)-5-oxazolyl]propionate (1.5 g) was added. The mixture was stirred with heating under reflux for 30 min. The reaction mixture was concentrated, diluted with water, and extracted with ethyl acetate. The organic layer was washed successively with water and saturated brine, dried over anhydrous magnesium sulfate and concentrated. The residue was subjected to silica gel column chromatography, and methyl 3-[4-(4-chlorophenyl)-2-(1-propylsulfanyl)-5-oxazolyl]propionate was obtained from a fraction eluted with hexane-acetone (9:1, volume ratio). 2N Aqueous sodium hydroxide solution (5 mL) and methanol (15 mL) were added to this ester form, and the mixture was stirred at room temperature for 1 hr. The reaction mixture was diluted with water and acidified with 2N aqueous hydrochloric acid solution. The precipitated crystals were collected by filtration and recrystallized from isopropyl ether to give 3-[4-(4-chlorophenyl)-2-(1-propylsulfanyl)-5-oxazolyl]propionic acid (1.0 g, yield 63%) as colorless prism crystals. melting point: 128–129° C.

Reference Example 93

To a mixture of 2-(methylsulfanyl)-1H-imidazole (1.09 g), methyl 3-[2-chloro-4-(4-chlorophenyl)-5-oxazolepropionate (2.4 g) and N,N-dimethylformamide (24 mL) was added sodium hydride (60% in oil, 0.4 g), and the mixture was stirred at room temperature for 2 hrs. The reaction mixture was diluted with water and extracted with ethyl acetate. The organic layer was washed successively with water and saturated brine, dried over anhydrous magnesium sulfate and concentrated to give methyl 3-{4-(4-chlorophenyl)-2-[2-(methylsulfanyl)-1H-imidazol-1-yl]-5-oxazolyl}propionate (1.9 g, yield 63%) as crystals. Recrystallization from methanol gave pale-brown prism crystals. melting point: 88–89° C.

Reference Example 94

To a solution of methyl 3-{4-(4-chlorophenyl)-2-[2-(methylsulfanyl)-1H-imidazol-1-yl]-5-oxazolyl}propionate (2.0 g) in dichloromethane (40 mL) was added m-chloroperbenzoic acid (70% purity, 2.6 g) at 0° C. The reaction mixture was. stirred at room temperature for 1 hr., washed successively with aqueous sodium sulfite solution and saturated aqueous sodium hydrogen carbonate, dried over anhydrous magnesium sulfate and concentrated to give methyl 3-{4-(4-chlorophenyl)-2-[2-(methylsulfonyl)-1H-imidazol-1-yl]-5-oxazolyl}propionate (1.65 g, yield 76%) as crystals. Recrystallization from methanol gave colorless prism crystals. melting point: 112–113° C.

Reference Example 95

To a solution of methyl 3-{4-(4-chlorophenyl)-2-[2-(methylsulfonyl)-1H-imidazol-1-yl]-5-oxazolyl}propionate (1.4 g) in 1,4-dioxane (7 mL) was added 2N aqueous sodium hydroxide solution (3.5 mL) and the mixture was stirred at room temperature for 30 min. The reaction mixture was diluted with water, and acidified with 2N aqueous hydrochloric acid solution. The precipitated crystals were collected by filtration and recrystallized from methanol to give 3-{4-(4-chlorophenyl)-2-[2-(methylsulfonyl)-1H-imidazol-1-yl]-5-oxazolyl}propionic acid (1.22 g, yield 90%) as colorless prism crystals. melting point: 166–167° C.

Reference Example 96

A mixture of 1-(chloroacetyl)-5,6,7,8-tetrahydronaphthalene (12.0 g) and acetamide (34 g) was stirred at 135° C. for 3.5 hrs. The reaction mixture was poured into water, and saturated aqueous sodium hydrogen carbonate was added. The mixture was extracted with ethyl acetate. The organic layer was washed successively with water and saturated brine, dried over anhydrous magnesium sulfate and concentrated. The residue was subjected to silica gel column chromatography, and 2-methyl-4-(5,6,7,8-tetrahydronaphthalen-2-yl)oxazole (9.57 g, yield 78%) was obtained as crystals from a fraction eluted with ethyl acetate-hexane (1:9, volume ratio). Recrystallization from hexane-ethyl acetate gave colorless prism crystals. melting point: 53–54° C.

Reference Example 97

To a solution of 2-methyl-4-(5,6,7,8-tetrahydronaphthalen-2-yl)oxazole (9.0 g) in dichloromethane (90 mL) was added dropwise a solution of bromine (2.2 mL) in dichloromethane (5 mL) at room temperature. After stirring the mixture at room temperature for 30 min, saturated aqueous sodium hydrogen carbonate was added, and the mixture was extracted with dichloromethane. The organic layer was dried over anhydrous magnesium sulfate and concentrated to give 5-bromo-2-methyl-4-(5,6,7,8-tetrahydronaphthalen-2-yl) oxazole (11.7 g, yield 95%) as crystals. Recrystallization from ethanol gave colorless plate crystals. melting point: 97–98° C.

Reference Example 98

To a mixed solution of 5-bromo-2-methyl-4-(5,6,7,8-tetrahydronaphthalen-2-yl)oxazole (11.0 g) and tetrahydrofuran (100 mL) was added dropwise a 1.6N n-butyllithium hexane solution (24 mL) at −78° C. under a nitrogen atmosphere. After stirring the reaction mixture at −78° C. for 10 min, $CO_2$ gas was blown into the reaction mixture for 30 min. The reaction mixture was poured into water and washed with ether. The aqueous layer was acidified with conc. hydrochloric acid, and the mixture was extracted with ethyl acetate. The organic layer was dried over anhydrous magnesium sulfate and concentrated to give [2-methyl-4-(5,6,7,8-tetrahydronaphthalen-2-yl)-5-oxazolyl]carboxylic acid (7.4 g, yield 76%) as crystals. Recrystallization from ethyl acetate gave colorless crystals. melting point: 183–185° C.

Reference Example 99

To a solution of [2-methyl-4-(5,6,7,8-tetrahydronaphthalen-2-yl)-5-oxazolyl]carboxylic acid (6.0 g) in methanol (120 mL) was added conc. sulfuric acid (6.0 mL) and the mixture was stirred with heating under reflux for 18 hrs. The reaction mixture was concentrated and the residue was diluted with water. The mixture was extracted with ethyl acetate. The organic layer was washed successively with saturated aqueous sodium hydrogen carbonate, water and saturated brine, dried over anhydrous magnesium sulfate, and concentrated to give methyl [2-methyl-4-(5,6,7,8-tetrahydronaphthalen-2-yl)-5-oxazolyl]carboxylate (4.75 g, yield 76%) as crystals. Recrystallization from ethanol gave colorless crystals. melting point: 96–97° C.

Reference Example 100

To a solution of methyl [2-methyl-4-(5,6,7,8-tetrahydronaphthalen-2-yl)-5-oxazolyl]carboxylate (4.5 g) in diethyl ether (90 mL) was added lithium aluminum hydride (0.63 g) at 0° C. After stirring the reaction mixture at room temperature for 30 min, water (3.2 mL) was added, and the precipitated solid was removed by filtration. The filtrate was concentrated and the obtained solid was washed with isopropyl ether to give [2-methyl-4-(5,6,7,8-tetrahydronaphthalen-2-yl)-5-oxazolyl]methanol (3.63 g, yield 90%) as crystals. Recrystallization from ethanol gave colorless crystals. melting point: 132–133° C.

Reference Example 101

To a solution of [2-methyl-4-(5,6,7,8-tetrahydronaphthalen-2-yl)-5-oxazolyl]methanol (3.3 g) in (40 mL) was added thionyl chloride (1.5 mL) at 0° C. After stirring at room temperature for 15 min, the reaction mixture was concentrated. To the residue was added saturated aqueous sodium hydrogen carbonate, and the mixture was extracted with ethyl acetate. The organic layer was washed successively with water and saturated brine, dried over anhydrous magnesium sulfate, and concentrated to give an oil. To a mixed solution of 2-chloroethyl acetate (2.68 g) and N,N-dimethylformamide (40 mL) was added sodium hydride (60% in oil, 0.6 g) and the mixture was stirred at 0° C. for 5 min. To this the reaction mixture was added a solution of the aforementioned oil in N,N-dimethylformamide (10 mL) at room temperature and the mixture was stirred at room temperature for 2.5 hrs. Water was poured into the reaction mixture, and the mixture was extracted with ethyl acetate. The organic layer was washed successively with water and saturated brine, dried over anhydrous magnesium sulfate and concentrated. The residue was diluted with ethanol (30 mL) and a 2N aqueous sodium hydroxide solution (16 mL) was added at 0° C. and the mixture was stirred for 20 min. Water was added to the reaction mixture and the mixture was washed with diethyl ether. The aqueous layer was acidified with 2N aqueous hydrochloric acid solution, and the mixture was extracted with ethyl acetate. The organic layer was washed successively with water and saturated brine, dried over anhydrous magnesium sulfate and concentrated. The precipitated crystals were collected by filtration and recrystallized from ethanol to give 2-chloro-3-[2-methyl-4-(5,6,7,8-tetrahydronaphthalen-2-yl)-5-oxazolyl]propionic acid (3.93 g, yield 91%) as colorless prism crystals. melting point: 141–142° C.

Reference Example 102

To a solution of 2-chloro-3-[2-methyl-4-(5,6,7,8-tetrahydronaphthalen-2-yl)-5-oxazolyl]propionic acid (3.2 g) in acetic acid (30 mL) was added zinc powder (3.25 g) at 90° C. and the mixture was stirred at 90° C. for 15 min. The insoluble material was removed by filtration and the filtrate was concentrated. Water was added to the residue, and the precipitated crystals were collected by filtration and recrystallized from methanol to give 3-[2-methyl-4-(5,6,7,8-tetrahydronaphthalen-2-yl)-5-oxazolyl]propionic acid (2.25 g, yield 79%) as colorless prism crystals. melting point: 135–136° C.

Reference Example 103

A mixture of 2,4-dibromo-1-phenylbutan-1-one (30.6 g) and acetamide (47.2 g) was stirred at 130° C. for 1 hr. The reaction mixture was poured into iced water, and the mixture was extracted with ethyl acetate. The organic layer was washed successively with water and saturated brine, dried over anhydrous magnesium sulfate and concentrated. The residue was subjected to silica gel column chromatography, and 2-(2-methyl-4-phenyl-5-oxazolyl)ethyl acetate (16.6 g, yield 68%) was obtained as an oil from a fraction eluted with acetone-hexane (1:4, volume ratio). A solution of this oil (16.6 g) in methanol (40 mL) was added a 2N aqueous sodium hydroxide solution (40 mL). After stirring at room temperature for 30 min, the reaction mixture was acidified with conc. hydrochloric acid, and the mixture was extracted with ethyl acetate. The organic layer was dried over anhydrous magnesium sulfate and concentrated. The residue (10.5 g) was dissolved in chloroform (100 mL), N,N-dimethylformamide (4 mL) was added, and thionyl chloride (11.4 mL) was added dropwise at 0° C.

After stirring with heating under reflux for 30 min, the reaction mixture was concentrated. To the residue was added saturated aqueous sodium hydrogen carbonate, and the mixture was extracted with ethyl acetate. The organic layer was washed successively with water and saturated brine, dried over anhydrous magnesium sulfate and concentrated to give 5-(2-chloroethyl)-2-methyl-4-phenyloxazole (11.0 g, yield 97%) as an oil. This oil (9.8 g) was dissolved in acetone (150 mL) and sodium iodide (12.3 g) was added. The mixture was heated under reflux for 26 hrs. The reaction mixture was concentrated and water was added, and the mixture was extracted with diethyl ether. The organic layer was washed successively with water and saturated brine, dried over anhydrous magnesium sulfate and concentrated to give 5-(2-iodoethyl)-2-methyl-4-phenyloxazole (11.5 g, yield 83%) as an oil. This oil (11.5 g) was dissolved in dimethyl sulfoxide (20 mL) and added dropwise to a solution of sodium cyanide (2.16 g) in dimethyl sulfoxide (80 mL) at room temperature. The reaction mixture was stirred at room temperature for 2 hrs. and iced water was added. The mixture was extracted with diethyl ether. The organic layer was washed successively with water and saturated brine, dried over anhydrous magnesium sulfate and concentrated. The residue was subjected to silica gel column chromatography, and 3-(2-methyl-4-phenyl-5-oxazolyl)propionitrile (3.3 g, yield 42%) was obtained as an oil from a fraction eluted with diethyl ether-hexane (1:1, volume ratio). To this oil (3.0 g) were added benzaldehyde (7.5 g) and zinc chloride (0.78 g), and the mixture was stirred at 170° C. for 5 hrs. The reaction mixture was cooled and water was added. The mixture was extracted with ethyl acetate. The organic layer was washed successively with water and saturated brine, dried over anhydrous magnesium sulfate and concentrated. The residue was subjected to silica gel column chromatography, and 3-[4-phenyl-2-((E)-2-phenylethenyl)-5-oxazolyl]propionitrile (1.45 g, yield 34%) was obtained as crystals from a fraction eluted with diethyl ether-hexane (3:7, volume ratio). Recrystallization from methanol gave pale-brown crystals. melting point: 117–118° C.

Reference Example 104

To a solution of 3-[4-phenyl-2-((E)-2-phenylethenyl)-5-oxazolyl]propionitrile (1.3 g) in ethanol (18 mL) was added 2N aqueous sodium hydroxide solution (9 mL) and the mixture was stirred with heating under reflux for 5 hrs. The reaction mixture was cooled and water was added. The mixture was acidified with 2N aqueous hydrochloric acid solution, and extracted with ethyl acetate. The organic layer was washed successively with water and saturated brine, dried over anhydrous magnesium sulfate and concentrated. The precipitated crystals were collected by filtration and recrystallized from ethanol to give 3-[4-phenyl-2-((E)-2-phenylethenyl)-5-oxazolyl]propionic acid (0.9 g, yield 65%) as colorless prism crystals. melting point: 138–139° C.

Reference Example 105

A mixture of 4-phenyl-2, 5-dimethyloxazole (6.21 g), N-bromosuccinimide (5.34 g), azobisisobutyronitrile (0.25 g) and carbon tetrachloride (90 mL) was stirred with heating under reflux for 15 min. The reaction mixture was cooled, washed successively with water, saturated aqueous sodium hydrogen carbonate and water, dried over anhydrous magnesium sulfate and concentrated. The residue was recrystallized from ethanol to give 5-bromomethyl-4-phenyl-2-methyloxazole (6.73 g, yield 78%) as colorless crystals. melting point: 75–76° C.

Reference Example 106

To a solution of diethyl 2-methylmalonate acid (3.13 g) in N,N-dimethylformamide (30 mL) was added sodium hydride (60% in oil, 0.6 g) at 0° C. and the mixture was stirred for 5 min. To the reaction mixture was added a solution of 5-bromomethyl-4-phenyl-2-methyloxazole (3.78 g) in N,N-dimethylformamide (20 mL). After stirring the reaction mixture for 30 min, iced water was added, and the mixture was extracted with diethyl ether. The organic layer was washed successively with water and saturated brine, dried over anhydrous magnesium sulfate and concentrated. The residue was diluted with ethanol (15 mL) and a 2N aqueous sodium hydroxide solution (10 mL) was added at 0° C., and the mixture was further stirred for 1.5 hrs. Water was added to the reaction mixture, and the mixture was washed with diethyl ether. The aqueous layer was acidified with 2N aqueous hydrochloric acid solution, and the mixture was extracted with ethyl acetate. The organic layer was washed successively with water and saturated brine (100 mL), dried over anhydrous magnesium sulfate and concentrated. The residue was dissolved in pyridine (30 mL) and the mixture was stirred with heating under reflux for 4 hrs. The reaction mixture was concentrated, dissolved in ethanol (15 mL) and 2N aqueous sodium hydroxide solution (15 mL) was added. The mixture was further stirred for 1 hr. Water was added to the reaction mixture, and the mixture was washed with diethyl ether. The aqueous layer was acidified with 2N aqueous hydrochloric acid solution, and the mixture was extracted with ethyl acetate.

The organic layer was washed successively with water and saturated brine, dried over anhydrous magnesium sulfate and concentrated. The precipitated crystals were collected by filtration and recrystallized from isopropyl ether to give 2-methyl-3-(4-phenyl-2-methyl-5-oxazolyl)propionic acid (2.25 g, yield 61%) as crystals. melting point: 109–110° C.

Reference Example 107

To a solution of diisopropylamine (2.02 g) in tetrahydrofuran (20 mL) was added dropwise a 1.6N n-butyllithium hexane solution (12.5 mL) at 0° C. After stirring the reaction mixture for 10 min, a solution of isobutyric acid (0.88 g) in tetrahydrofuran (5 mL) was added. After further stirring the reaction mixture for 30 min, a solution of 5-bromomethyl-4-(4-chlorophenyl)-2-methyloxazole (2.52 g) in tetrahydrofuran (15 mL) was added. After stirring for 1 hr., water was added, and the mixture was concentrated. The residue was washed with diethyl ether. The aqueous layer was acidified with 2N aqueous hydrochloric acid solution and extracted with diethyl ether. The organic layer was washed successively with water and saturated brine, dried over anhydrous magnesium sulfate and concentrated. The residue was dissolved in 10% hydrochloric acid methanol solution (30 mL) and the mixture was stirred with heating under reflux for 1.5 hrs. The reaction mixture was concentrated and saturated aqueous sodium hydrogen carbonate was added. The mixture was extracted with diethyl ether. The organic layer was washed successively with water and saturated brine, dried over anhydrous magnesium sulfate and concentrated. The residue was subjected to silica gel column chromatography, and an oil was obtained from a fraction eluted with diethyl ether-hexane (3:7, volume ratio).

This oil was dissolved in ethanol (5 mL) and 2N aqueous sodium hydroxide solution (5 mL) was added. The mixture was stirred at 80° C. for 15 min. The reaction mixture was acidified with 2N aqueous hydrochloric acid solution and extracted with diethyl ether. The organic layer was washed successively with water and saturated brine, dried over anhydrous magnesium sulfate and concentrated. The precipitated crystals were collected by filtration and recrystallized from isopropyl ether to give 2,2-dimethyl-3-(2-methyl-4-phenyl-5-oxazolyl)propionic acid (1.0 g, yield 39%) as crystals. melting point: 129–130° C.

Reference Example 108

To a solution of 1-(4-chlorophenyl)propan-1-one (6.5 g) in dichloromethane (60 mL) was added a solution of bromine (2.0 mL) in dichloromethane (5 mL) at room temperature. The reaction mixture was concentrated and 1-methylcyclohexanecarboxamide (5.44 g) was added and the mixture was stirred at 130° C. for 3 hrs. Water was added to the reaction mixture, and the mixture was extracted with diethyl ether. The organic layer was washed successively with water and saturated brine, dried over anhydrous magnesium sulfate, concentrated and purified by silica gel column chromatography (developing solvent: acetone-hexane (1:9, volume ratio)). To the obtained oil were added iodine (7.0 g), N-bromosuccinimide (4.3 g), azobisisobutyronitrile (0.2 g) and carbon tetrachloride (70 mL) and the mixture was heated under reflux for 30 min. The solid was removed by filtration and the filtrate was concentrated to give an oil. To a mixed solution of ethyl 2-chloroaceto acetate (1.65 g) and N,N-dimethylformamide (20 mL) was added sodium hydride (60% in oil, 0.4 g) at 0° C. and the mixture was stirred for 10 min. The aforementioned oil was added to the reaction mixture and the mixture was further stirred for 1 hr. The reaction mixture was poured into water, and extracted with diethyl ether. The organic layer was washed successively with water and saturated brine, dried over anhydrous magnesium sulfate and concentrated. The residue was dissolved in ethanol (10 mL) and a 2N aqueous sodium hydroxide solution (15 mL) was added. The mixture was further stirred for 1 hr. Water was added to the reaction mixture, and the mixture was washed with diethyl ether. The aqueous layer was acidified with 2N aqueous hydrochloric acid solution and extracted with diethyl ether. The organic layer was washed successively with water and saturated brine, dried over anhydrous magnesium sulfate and concentrated. The residue was diluted with acetic acid (10 mL) and zinc powder (0.68 g) was added at 90° C. The mixture was stirred at 90° C. for 15 min. Insoluble material was removed by filtration and the filtrate was concentrated. Water was added to the residue, and the mixture was extracted with ethyl acetate. The organic layer was washed successively with water and saturated brine, dried over anhydrous magnesium sulfate and concentrated. The residue purified by silica gel column chromatography (developing solvent:acetone-hexane (1:4, volume ratio)) to give 3-[4-(4-chlorophenyl)-2-(1-methylcyclohexyl)-5-oxazolyl]propionic acid (0.65 g, yield 5%) as crystals. Recrystallization from diisopropyl ether gave colorless prism crystals. melting point: 138–139° C.

Reference Example 109

A mixture of methyl 3-[2-chloro-4-(4-chlorophenyl)-5-oxazolyl]propionate (1.50 g), 1H-indazole (1.18 g), potassium carbonate (1.38 g) and N,N-dimethylformamide (20 mL) was stirred at 120° C. for 3 hrs. The reaction mixture was poured into water and extracted with ethyl acetate. The organic layer was washed with water, dried over anhydrous magnesium sulfate and concentrated. The obtained crystals were collected by filtration, dried and dissolved in a mixed solvent of tetrahydrofuran (20 mL) and ethanol (20 mL). A 1N aqueous sodium hydroxide solution (10 mL) was added, and the mixture was stirred at room temperature for 2 hrs. The reaction mixture was acidified with 1N aqueous hydrochloric acid solution, and the mixture was extracted with ethyl acetate. The organic layer was washed with water, dried over anhydrous magnesium sulfate and concentrated. The obtained crystals were collected by filtration using isopropyl ether and dried to give 3-[4-(4-chlorophenyl)-2-(1H-indazol-1-yl)-5-oxazolyl]propionic acid (824 mg, yield 45%) as pale-yellow prism crystal. melting point: 204–205° C.

Reference Example 110

A mixture of 3,4-(methylenedioxy)benzoic acid (3.24 g), oxalyl chloride (2.97 g), N,N-dimethylformamide (0.1 mL) and tetrahydrofuran (80 mL) and the mixture was stirred at room temperature for 2 hrs. The reaction mixture was concentrated and the residue was dissolved in pyridine (50 mL). To this solution was added a solution of methyl 5-(4-chlorophenyl)-4-hydroxy-5-oxopentanoate (5.0 g) in pyridine (25 mL) at 0° C. After stirring at room temperature for 1.5 hrs., the reaction mixture was poured into a 1N aqueous hydrochloric acid solution, and the mixture was extracted with ethyl acetate. The organic layer was washed successively with a 1N aqueous hydrochloric acid solution, water and saturated brine, dried over anhydrous magnesium sulfate, and concentrated to give a yellow oil. This oil was dissolved in acetic acid (100 mL). and ammonium acetate (7.52 g) was added. The mixture was stirred with heating under reflux for 2 hrs. The reaction mixture was concentrated, poured into water and extracted with ethyl acetate. The organic layer was washed with aqueous sodium hydrogen carbonate solution and saturated brine, dried over anhydrous magnesium sulfate and concentrated. The residue was purified by silica gel column chromatography and methyl 3-[4-(4-chlorophenyl)-2-[3,4-(methylenedioxy)phenyl]-5-oxazolyl]propionate (1.59 g, 21%) was obtained as a colorless powder from a fraction eluted with hexane-ethyl acetate (4:1). Recrystallization from ethanol gave colorless prism crystals. melting point: 123–124° C.

In the same manner as in Reference Example 110, the compounds of Reference Examples 111–122 were synthesized.

Reference Example 111 methyl 3-[4-(4-chlorophenyl)-2-(1-naphthyl)-5-oxazolyl]propionate yield: 44%. colorless prism crystal. melting point: 76–77° C. (recrystallized from isopropyl ether-hexane)

Reference Example 112 methyl 3-[4-(4-chlorophenyl)-2-(1-methyl-1H-indol-2-yl)-5-oxazolyl]propionate yield: 36%. an oil NMR(CDCl$_3$) delta: 2.42–2.80 (4H, m), 3.70 (3H, s), 4.02 (3H, s), 6.11 (1H, dd, J=9, 4 Hz), 7.10–7.20 (1H, m), 7.32–7.40 (2H, m), 7.42–7.54 (3H, m), 7.66–7.72 (1H, m), 8.02–8.10 (2H, m).

Reference Example 113 methyl 3-[4-(4-chlorophenyl)-2-(1-methyl-1H-indol-3-yl)-5-oxazolyl]propionate yield: 36%. colorless prism crystal. melting point: 132–133° C. (recrystallized from isopropyl ether-hexane)

Reference Example 114 methyl 3-[4-(4-chlorophenyl)-2-(1H-indazol-3-yl)-5-oxazolyl]propionate yield: 7%. colorless prism crystal. melting point: 180–181° C. (recrystallized from isopropyl ether-hexane)

Reference Example 115 methyl 3-[4-(4-chlorophenyl)-2-(2,3-dichlorophenyl)-5-oxazolyl]propionate yield: 23%. colorless prism crystal. melting point: 92–93° C. (recrystallized from isopropyl ether-hexane)

Reference Example 116 methyl 3-[4-(4-chlorophenyl)-2-cyclohexyl-5-oxazolyl]propionate yield: 65%. a yellow oil. NMR(CDCl$_3$) delta: 1.25–1.85 (8H,m), 2.05–2.1 (2H,m), 2.71 (2H,t,J=8 Hz), 3.17 (2H,t, J=8 Hz), 3.68 (3H,s), 7.37 (2H,d,J=8.5 Hz), 7.59 (2H,d, J=8.5 Hz).

Reference Example 117 methyl 3-[2-benzyl-4-(4-chlorophenyl)-5-oxazolyl]propionate yield: 41%. a yellow oil. NMR(CDCl$_3$) delta: 2.68 (2H, t,J=8 Hz), 3.15 (2H,t,J=8 Hz), 3.62 (3H,s), 4.11 (2H,s), 7.25–7.35 (5H,m), 7.37 (2H,d,J=8.5 Hz), 7.59 (2H,d,J=8.5 Hz).

Reference Example 118 methyl 3-[4-(4-chlorophenyl)-2-(4-fluorophenyl)-5-oxazolyl]propionate yield: 51%. colorless prism crystal, melting point: 97–98° C. (recrystallized from ethyl acetate-hexane).

Reference Example 119 methyl 3-[4-(4-chlorophenyl)-2-(2-naphthyl)-5-oxazolyl]propionate yield: 47%. colorless prism crystal, melting point:, 120–121° C. (recrystallized from ethyl acetate-hexane).

Reference Example 120 methyl 3-[4-(4-chlorophenyl)-2-(2-thienyl)-5-oxazolyl]propionate yield: 37%. colorless prism crystal, melting point: 66–67° C. (recrystallized from hexane).

Reference Example 121 methyl 3-[4-(4-chlorophenyl)-2-(4-methoxyphenyl)-5-oxazolyl]propionate yield: 53%. colorless prism crystal, melting point: 83–84° C. (recrystallized from methanol).

Reference Example 122 methyl 3-[4-(4-chlorophenyl)-2-(1-propyl)-5-oxazolyl]propionate yield: 62%. a yellow oil. NMR(CDCl$_3$) delta: 1.01 (3H, t,J=7.5 Hz), 1.75–1.85 (2H,m) 2.72 (2H,t,J=8 Hz), 2.73 (2H,t,J=7.5 Hz), 3.18 (2H,t,J=8 Hz), 3.68 (3H,s), 7.38 (2H,d,J=8.5 Hz), 7.59 (2H,d,J=8.5 Hz).

Reference Example 123

A mixture of methyl 3-[4-(4-chlorophenyl)-2-[3,4-(methylenedioxy)phenyl]-5-oxazolyl]propionate (1.29 g), potassium hydroxide (0.44 g), methanol (20 mL) and tetrahydrofuran (15 mL) was stirred at room temperature for 2 hrs. The reaction mixture was poured into dilute hydrochloric acid, and extracted with ethyl acetate. The organic layer was washed with water, dried over anhydrous magnesium sulfate, and concentrated to give 3-[4-(4-chlorophenyl)-2-[3,4-(methylenedioxy)phenyl]-5-oxazolyl]propionic acid (1.22 g, 98%) as a colorless powder. Recrystallization from ethyl acetate-hexane gave colorless prism crystals. melting point: 199–200° C.

In the same manner as in Reference Example 123, the compounds of Reference Examples 124–143 were synthesized.

Reference Example 124 ethyl 3-[2-(1H-benzimidazol-1-yl)-4-phenyl-5-thiazolyl]propionate yield: 88%. pale-yellow prism crystal, melting point: 81–82° C. (recrystallized from acetone-hexane).

Reference Example 125

3-[4-(3,4-dichlorophenyl)-2-phenyl-5-oxazolyl]propionic acid yield: 98%. pale-yellow prism crystal, melting point: 197–198° C. (recrystallized from acetone-hexane).

Reference Example 126

6-[4-(4-chlorophenyl)-2-phenyl-5-oxazolyl]hexanoic acid yield: 79%. colorless prism crystal, melting point: 123–124° C. (recrystallized from ethanol-hexane).

Reference Example 127

3-[2-(1H-benzimidazol-1-yl)-4-(3,4-dichlorophenyl)-5-oxazolyl]propionic acid yield: 91%. colorless prism crystal, melting point: 233–234° C. (recrystallized from acetone-hexane).

Reference Example 128

3-[4-(4-chlorophenyl)-2-cyclohexyl-5-oxazolyl]propionic acid yield: 98%. colorless prism crystal, melting point: 150–151° C. (recrystallized from ethyl acetate-hexane).

Reference Example 129

3-[2-benzyl-4-(4-chlorophenyl)-5-oxazolyl]propionic acid yield: 98%. colorless prism crystal, melting point: 175–176° C. (recrystallized from ethyl acetate).

Reference Example 130

3-[4-(4-chlorophenyl)-2-(4-fluorophenyl)-5-oxazolyl]propionic acid yield: 93%. colorless prism crystal, melting point: 162–163° C. (recrystallized from ethyl acetate-hexane).

Example 131

3-[4-(4-chlorophenyl)-2-(2-naphthyl)-5-oxazolyl]propionic acid yield: 97%. colorless prism crystal, melting point: 167–168° C. (recrystallized from ethyl acetate-hexane).

Reference Example 132

3-[4-(4-chlorophenyl)-2-(2-thienyl)-5-oxazolyl]propionic acid yield: 94%. colorless prism crystal, melting point: 160–161° C. (recrystallized from ethyl acetate-hexane).

Reference Example 133

3-[4-(4-chlorophenyl)-2-(4-methoxyphenyl)-5-oxazolylpropionic acid yield: 93%. colorless prism crystal, melting point: 152–153° C. (recrystallized from ethanol).

Reference Example 134

3-[4-(4-chlorophenyl)-2-(1-propyl)-5-oxazolepropionic acid yield: 84%. colorless prism crystal, melting point: 150–151° C. (recrystallized from ethanol).

Reference Example 135

3-[4-(4-chlorophenyl)-2-(1-naphthyl)-5-oxazolyl]propionic acid yield: 89%. colorless prism crystal melting point: 154–155° C. (recrystallized from isopropyl ether-hexane)

Reference Example 136

3-[4-(4-chlorophenyl)-2-(1-methyl-1H-indol-2-yl)-5-oxazolyl]propionic acid yield: 91%, colorless prism crystal
melting point: 195–196° C. (recrystallized from ethyl acetate-hexane)

Reference Example 137

3-[4-(4-chlorophenyl)-2-(1-methyl-1H-indol-3-yl)-5-oxazolyl]propionic acid yield: 98%. colorless prism crystal melting point: 209–210° C. (recrystallized from isopropyl ether-hexane)

Reference Example 138

3-[4-(4-chlorophenyl)-2-(1H-indazol-3-yl)-5-oxazolyl]propionic acid yield: 80%, colorless prism crystal melting point: 214–216° C. (recrystallized from isopropyl ether-hexane)

Reference Example 139

3-[4-(4-chlorophenyl)-2-(2,3-dichlorophenyl)-5-oxazolyl]propionic acid yield: 90%. colorless prism crystal melting point: 166–167° C. (recrystallized from isopropyl ether-hexane)

Reference Example 140

2-(1H-benzoimidazol-1-yl)-4-(3-chlorophenyl)-5-oxazolepropionic acid yield: 71%. pale-yellow solid NMR(CDCl$_3$) delta: 2.91 (2H, t, J=7.5 Hz), 3.37 (2H, t, J=7.5 Hz), 7.32–7.52 (4H, m), 7.60–7.64 (1H, m), 7.79 (1H, s), 7.87 (1H, d, J=8 Hz), 8.27 (1H, d, J=8.5 Hz), 8.62 (1H, s).

Reference Example 141

3-[2-(1H-benzoimidazol-1-yl)-4-phenyl-5-oxazolyl]propionic acid yield: 91%. solid NMR(CDCl$_3$) delta: 2.89 (2H, t, J=7.5 Hz), 3.38 (2H, t, J=7.5 Hz), 7.34–7.56 (5H, m), 7.76 (2H, d, J=8 Hz), 7.86 (1H, d, J=7.5 Hz), 8.28 (1H, d, J=7.5 Hz), 8.64 (1H, s).

Reference Example 142

3-[2-(1H-benzoimidazol-1-yl)-4-(4-methoxyphenyl)-5-oxazolyl]propionic acid yield: 81%, pale-yellow solid NMR(CDCl$_3$) delta: 2.88 (2H, t, J=7 Hz), 3.35 (2H, t, J=7 Hz), 3.87 (3H, s), 7.02 (2H, d, J=9 Hz), 7.34–7.52 (2H, m), 7.69 (2H, d, J=9 Hz), 7.86 (1H, d, J=8 Hz), 8.27 (1H, d, J=8 Hz), 8.62 (1H, s).

Reference Example 143

3-[2-(1H-benzoimidazol-1-yl)-4-(4-fluorophenyl)-5-oxazolyl]propionic acid yield: 70%. pale-yellow solid NMR(CDCl$_3$) delta: 2.89 (2H, t, J=7 Hz), 3.35 (2H, t, J=7 Hz), 7.10–7.24 (2H, m), 7.36–7.52 (2H, m), 7.68–7.80 (2H, m), 7.86 (1H, d, J=7 Hz), 8.26 (1H, d, J=7.5 Hz), 8.63 (1H, s).

Reference Example 144

A mixture of 3-[2-chloro-4-(4-chlorophenyl)-5-oxazolyl]propionic acid (1.0 g), 1-phenylpiperazine (2.27 g), potassium carbonate (2.42 g) and N,N-dimethylformamide (20 mL) was stirred at 100° C. for 3 hrs. The reaction mixture was poured into aqueous ammonium chloride solution and the mixture was extracted with ethyl acetate, washed with water, dried over anhydrous magnesium sulfate and concentrated. The residue was purified by silica gel column chromatography and 3-[4-(4-chlorophenyl)-2-(4-phenyl-1-piperazinyl)-5-oxazolyl]propionic acid (0.76 g, yield 53%) was obtained as a powder from a fraction eluted with ethyl acetate-chloroform-methanol (10:10:1, volume ratio). Recrystallization from ethyl acetate gave colorless prism crystals. melting point: 177–178° C.

In the same manner as in Reference Example 144, the compounds of Reference Examples 145 and 146 were synthesized.

Reference Example 145

3-[4-(4-chlorophenyl)-2-(2-pyrimidinylsulfanyl)-5-oxazolyl]propionic acid yield: 76%. colorless prism crystal, melting point: 198–199° C. (recrystallized from ethyl acetate).

Reference Example 146

3-[2-(N-benzylamino)-4-(4-chlorophenyl)-5-oxazolyl]propionic acid yield: 86%. colorless prism crystal, melting point: 178–179° C. (recrystallized from ethyl acetate-hexane).

Reference Example 147

A mixture of 4-(4-chlorophenyl)-2-phenyloxazole (14.43 g), phosphorus oxychloride (12.97 g), N,N-dimethylformamide (100 mL) was stirred at 90° C. for 1.5 hrs. The reaction mixture was poured into iced water, and the precipitated solid was collected by filtration, washed successively with aqueous sodium hydrogen carbonate solution and water and dried. The obtained crystals were recrystallized from acetone-hexane to give 4-(4-chlorophenyl)-2-phenyl-5-oxazolecarbaldehyde (7.90 g, 49%) as yellow prism crystals.

NMR(CDCl$_3$) delta: 7.45–7.65 (5H,m), 8.10 (2H,d,J=8.5 Hz), 8.2–8.25 (2H,m), 10.03 (1H,s).

A mixture of this compound (3.95 g), malonic acid (2.90 g), piperidine (0.36 g) and pyridine (80 mL) was stirred at 100° C. for 8 hrs. The reaction mixture was poured into iced water and acidified with 1N aqueous hydrochloric acid solution.

The mixture was extracted with ethyl acetate. The organic layer was washed successively with water and saturated brine, dried over anhydrous magnesium sulfate, and concentrated to give (2E)-3-[4-(4-chlorophenyl)-2-phenyl-5-oxazolyl]propenoic acid (4.36 g, 96%) as a yellow powder. Recrystallization from ethyl acetate gave yellow prism crystals. melting point: 255–257° C.

Reference Example 148

Ethyl 5-(4-chlorophenyl)-5-oxopentanoate (30 g) was dissolved in diethyl ether (300 ml) and bromine (6.55 g) was added dropwise at room temperature. An aqueous sodium sulfite solution was added to the reaction mixture, and the mixture was neutralized with aqueous sodium hydrogen carbonate solution. The organic layer was dried over anhydrous magnesium sulfate and concentrated. The residue was dissolved in ethanol (200 mL) and thiourea (8.85 g) and sodium acetate (14.3 g) were added. The mixture was stirred with heating under reflux for 2 hrs. The reaction mixture was poured into water, and the precipitated solid was collected by filtration to give ethyl 3-[2-amino-4-(4-chlorophenyl)-1,3-thiazol-5-yl]propionate (30.2 g, 80%) as a colorless powder.

NMR(CDCl$_3$) delta: 1.24 (3H,t,J=7.5 Hz), 2.58 (2H,t,J=7 Hz), 3.08 (2H,t,J=7 Hz), 4.13 (2H,q,J=7.5 Hz), 4.97 (2H,s), 7.3–7.5 (4H,m).

This compound (30 g) was dissolved in a mixed solvent of tetrahydrofuran (300 ml)-ethanol (150 ml) and 2N aqueous sodium hydroxide solution was added at 0° C. The mixture was stirred at 60° C. for 1 hr. The reaction mixture was poured into water and 1N hydrochloric acid was added. The precipitated solid was collected by filtration to give 3-[2-amino-4-(4-chlorophenyl)-5-thiazolyl]propionic acid (25.9 g, 94%) as a yellow powder. Recrystallization from ethanol gave yellow prism crystals. melting point: 116–118° C.

Reference Example 149

4-(4-chlorophenyl)-5-[3-(1,1-dioxide-4-thiomorpholinyl)-3-oxopropyl]-1,3-thiazole-2-amine In the same manner as in Reference Example 148, the title compound was produced.
yield: 22%. colorless prism crystal, melting point: 220–222° C. (recrystallized from ethanol-diisopropyl ether).

Example 1

A mixture of 3-[2-chloro-4-(4-chlorophenyl)-5-oxazolyl]propionic acid (0.50 g), oxalyl chloride (0.27 g), N,N-dimethylformamide (0.1 ml) and tetrahydrofuran (15 ml) was stirred at room temperature for 1 hr. The reaction mixture was concentrated and the residue was dissolved in tetrahydrofuran (15 ml). Thereto were added triethylamine (0.21 g) and diethyl 4-aminobenzylphosphonate (0.37 g) and the mixture was stirred at room temperature for 1.5 hrs. The reaction mixture was poured into water, and the mixture was extracted with ethyl acetate. The ethyl acetate layer was washed with dilute hydrochloric acid, saturated aqueous sodium hydrogen carbonate and then saturated brine, dried (MgSO$_4$) and concentrated to give a colorless powder (0.80 g). Recrystallization from ethanol gave 3-[2-chloro-4-(4-chlorophenyl)-5-oxazolyl]-N-[4-(diethylphosphonomethyl)phenyl]propionamide as colorless prism crystals (660 mg, 74%). melting point: 137–138° C.

In the same manner as in Example 1, the compounds of Examples 2–60 were synthesized.

Example 2

3-[2-chloro-4-(4-chlorophenyl)-5-oxazolyl]-N-{4-[(2-oxide-1,3,2-dioxaphosphinan-2-yl)methyl]phenyl}propionamide yield: 22%. colorless prism crystals, melting point: 172–173° C. (recrystallized from ethanol).

Example 3

3-[4-(4-chlorophenyl)-2-(2-methyl-1-imidazolyl)-5-oxazolyl]-N-[4-(diethylphosphonomethyl)phenyl]propionamide yield: 10%. pale-yellow prism crystals, melting point: 158–159° C. (recrystallized from ethanol).

Example 4

3-[4-(4-chlorophenyl)-2-(2-methyl-1-imidazolyl)-5-oxazolyl]-N-{4-[(2-oxide-1,3,2-dioxaphosphinan-2-yl)methyl]phenyl}propionamide yield: 33%. colorless prism crystals, melting point: 173–174° C. (recrystallized from ethanol).

Example 5

3-[2-(1H-benzimidazol-1-yl)-4-(4-chlorophenyl)-5-oxazolyl]-N-[4-(diethylphosphonomethyl)phenyl]propionamide yield: 63%. colorless prism crystals, melting point: 159–160° C. (recrystallized from ethyl acetate-hexane).

Example 6

3-[4-(4-chlorophenyl)-2-(4-morpholinyl)-5-oxazolyl]-N-[4-(diethylphosphonomethyl)phenyl]propionamide yield: 76%. pale-yellow prism crystals, melting point: 186–187° C. (recrystallized from ethyl acetate-hexane).

Example 7

3-{4-(4-chlorophenyl)-2-[(4-methylphenyl)sulfanyl]-5-oxazolyl)}}-N-[4-(diethylphosphonomethyl)phenyl}propionamide yield: 99%. a yellow oil. NMR(CDCl$_3$) delta: 1.23 (6H, t, J=7 Hz), 2.35 (3H,s),2.71 (2H, t, J=8.5 Hz), 3.09 (2H, d, J=22 Hz), 3.22 (2H, d, J=8.5 Hz), 3.95–4.05 (4H, m), 7.16 (2H, d, J=8 Hz), 7.15–7.2 (2H, m), 7.35–7.4 (2H, m), 7.36 (2H, d, J=8.5 Hz), 7.46 (2H, d, J=8 Hz), 7.61 (2H, d, J=8.5 Hz), 8.00 (1H, s).

Example 8

3-[2-(1H-benzimidazol-1-yl)-4-(4-chlorophenyl)-5-oxazolyl]propionamide yield: 47%. pale-yellow prism crystals, melting point: 265–266° C. (recrystallized from ethanol-chloroform).

Example 9

3-[4-(4-chlorophenyl)-2-(4-morpholinyl)-5-oxazolyl]propionamide yield: 70%. colorless prism crystal, melting point: 180–181° C. (recrystallized from ethyl acetate-hexane).

Example 10

3-[4-(4-chlorophenyl)-2-[(4-methylphenyl)sulfanyl]-5-oxazolyl]propionamide yield: 50%. colorless prism crystals, melting point: 155–156° C. (recrystallized from ethyl acetate).

Example 11

N-(4-{[bis(ethylamide)phosphoryl]methyl}phenyl)-3-[4-(4-chlorophenyl)-2-phenyl-5-oxazolyl]propionamide yield: 44%. colorless prism crystals, melting point: 122–123° C. (recrystallized from ethyl acetate-hexane).

Example 12

3-{4-(4-chlorophenyl)-2-[3,4-(methylenedioxy)phenyl]-5-oxazolyl}-N-[4-(diethylphosphonomethyl)phenyl]propionamide yield: 84%. colorless prism crystals, melting point: 155–156° C. (recrystallized from ethyl acetate-hexane).

Example 13

3-[4-(4-chlorophenyl)-2-cyclohexyl-5-oxazolyl]-N-[4-(diethylphosphonomethyl)phenyl]propionamide yield: 76%. colorless prism crystals, melting point: 133–134° C. (recrystallized from ethyl acetate-hexane).

Example 14

3-[2-benzyl-4-(4-chlorophenyl)-5-oxazolyl]-N-[4-(diethylphosphonomethyl)phenyl]propionamide yield: 76%. colorless prism crystals, melting point: 161–162° C. (recrystallized from ethyl acetate-hexane).

Example 15

3-[4-(4-chlorophenyl)-2-(4,5-dimethyl-1-imidazolyl)-5-oxazolyl]-N-[4-(diethylphosphonomethyl)phenyl]propionamide yield: 58%. colorless prism crystals, melting point: 179–180° C. (recrystallized from ethyl acetate-hexane).

Example 16

3-{4-(4-chlorophenyl)-2-[3,4-(methylenedioxy)phenyl]-5-oxazolyl}propionamide yield: 84%. colorless prism crystals, melting point: 210–211° C. (recrystallized from ethyl acetate).

Example 17

3-[4-(4-chlorophenyl)-2-cyclohexyl-5-oxazolyl]propionamide yield: 70%. colorless prism crystals, melting point: 142–143° C. (recrystallized from ethyl acetate-hexane).

Example 18

3-[2-benzyl-4-(4-chlorophenyl)-5-oxazolyl]propionamide yield: 74%. colorless prism crystals, melting point: 169–170° C. (recrystallized from ethyl acetate-hexane).

Example 19

3-[4-(4-chlorophenyl)-2-(4,5-dimethyl-1-imidazolyl)-5-oxazolyl]propionamide yield: 50%. colorless prism crystals, melting point: 232–233° C. (recrystallized from ethyl acetate-hexane).

Example 20

3-[4-(4-chlorophenyl)-2-(4-fluorophenyl)-5-oxazolyl]-N-[4-(diethylphosphonomethyl)phenyl]propionamide yield: 19%. colorless prism crystals, melting point: 148–149° C. (recrystallized from ethyl acetate-hexane).

Example 21

3-[4-(4-chlorophenyl)-2-(2-naphthyl)-5-oxazolyl]-N-[4-(diethylphosphonomethyl)phenyl]propionamide yield: 76%. colorless prism crystals, melting point: 191–192° C. (recrystallized from ethanol).

Example 22

3-[4-(4-chlorophenyl)-2-(2-thienyl)-5-oxazolyl]-N-[4-(diethylphosphonomethyl)phenyl]propionamide yield: 77%. colorless prism crystals, melting point: 164–165° C. (recrystallized from ethyl acetate-hexane).

Example 23

3-[4-(4-chlorophenyl)-2-(4-fluorophenyl)-5-oxazolyl]propionamide yield: 22%. colorless prism crystals, melting point: 212–213° C. (recrystallized from ethyl acetate).

Example 24

3-[4-(4-chlorophenyl)-2-(2-naphthyl)-5-oxazolyl]propionamide yield: 84%. colorless prism crystals, melting point: 206–207° C. (recrystallized from ethyl acetate).

Example 25

3-[4-(4-chlorophenyl)-2-(2-thienyl)-5-oxazolyl]propionamide yield: 78%. colorless prism crystals, melting point: 226–227° C. (recrystallized from ethanol).

Example 26

3-[4-(4-chlorophenyl)-2-(4-methoxyphenyl)-5-oxazolyl]-N-[4-(diethylphosphonomethyl)phenyl]propionamide yield: 85%. colorless prism crystals, melting point: 141–142° C. (recrystallized from ethyl acetate-hexane).

Example 27

3-[4-(4-chlorophenyl)-2-propyl-5-oxazolyl]-N-[4-(diethylphosphonomethyl)phenyl]propionamide yield: 64%. colorless prism crystals, melting point: 108–109° C. (recrystallized from ethyl acetate-hexane).

Example 28

3-[4-(4-chlorophenyl)-2-(4-methoxyphenyl)-5-oxazolyl]propionamide yield: 72%. colorless prism crystals, melting point: 215–216° C. (recrystallized from ethyl acetate).

Example 29

3-[4-(4-chlorophenyl)-2-propyl-5-oxazolyl]propionamide yield: 74%. colorless prism crystals, melting point: 150–151° C. (recrystallized from ethyl acetate-hexane).

Example 30

3-[4-(4-chlorophenyl)-2-(4-phenyl-1-piperazinyl)-5-oxazolyl]-N-[4-(diethylphosphonomethyl)phenyl]propionamide yield: 70%. a yellow oil. NMR(CDCl$_3$) delta: 1.22 (6H, t, J=7 Hz), 2.72 (2H, t, J=7.5 Hz), 3.09 (2H, d, J=22 Hz), 3.2–3.3 (6H, m), 3.64 (4H, t, J=5 Hz), 3.95–4.05 (4H, m), 6.9–7.0 (3H, m), 7.2–7.45 (8H, m), 7.59 (2H, d, J=8.5 Hz), 7.91 (1H, s).

Example 31

3-[4-(4-chlorophenyl)-2-(4-phenyl-1-piperazinyl)-5-oxazolyl]propionamide yield: 68%. colorless prism crystals, melting point: 187–188° C. (recrystallized from ethyl acetate).

Example 32

3-[4-(4-chlorophenyl)-2-(2-pyrimidinylsulfanyl)-5-oxazolyl]-N-[4-(diethylphosphonomethyl)phenyl]propionamide yield: 70%. colorless prism crystals, melting point: 146–147° C. (recrystallized from ethyl acetate).

Example 33

3-[4-(4-chlorophenyl)-2-(2-pyrimidinylsulfanyl)-5-oxazolyl]propionamide yield: 78%. colorless prism crystals, melting point: 194–195° C. (recrystallized from ethanol).

Example 34

3-[2-(benzylamino)-4-(4-chlorophenyl)-5-oxazolyl]-N-[4-(diethylphosphonomethyl)phenyl]propionamide yield: 21%. colorless prism crystals, melting point: 156–157° C. (recrystallized from ethyl acetate).

Example 35

3-[4-(4-chlorophenyl)-2-(2-pyridinylsulfanyl)-5-oxazolyl]-N-[4-(diethylphosphonomethyl)phenyl]propionamide yield: 72%. colorless prism crystals, melting point: 146–147° C. (recrystallized from ethyl acetate).

Example 36

3-[4-(4-chlorophenyl)-2-(2-pyridinylsulfanyl)-5-oxazolyl]propionamide yield: 67%. colorless prism crystals, melting point: 162–163° C. (recrystallized from ethyl acetate).

Example 37

3-[4-(4-chlorophenyl)-2-phenoxy-5-oxazolyl)-N-]4-(diethylphosphonomethyl)phenyl]propionamide yield: 76%. colorless prism crystals, melting point: 149–150° C. (recrystallized from ethyl acetate).

Example 38

3-[4-(4-chlorophenyl)-2-phenoxy-5-oxazolyl]propionamide yield: 60%. colorless prism crystals, melting point: 139–140° C. (recrystallized from ethyl acetate).

Example 39

3-[4-(4-chlorophenyl)-2-phenyl-5-oxazolyl]-N-{4-[(5,5-dimethyl-2-oxide-1,3,2-dioxaphosphinan-2-yl)methyl]phenyl}propionamide yield: 62%. colorless prism crystals, melting point: 193–194° C. (recrystallized from ethyl acetate-hexane).

Example 40

3-[4-(4-chlorophenyl)-2-phenyl-5-oxazolyl]-N-{4-[(2-oxide-1,3,2-dioxaphosphinan-2-yl)methyl]phenyl}propionamide yield: 18%. colorless prism crystals, melting point: 224–225° C. (recrystallized from chloroform-ethanol).

Example 41

3-[4-(4-chlorophenyl)-2-phenyl-5-oxazolyl]-N-(3-pyridinyl)propionamide yield: 80%. colorless prism crystals, melting point: 204–205° C. (recrystallized from chloroform-ethanol).

Example 42

3-[4-(4-chlorophenyl)-2-phenyl-5-oxazolyl]-N-[4-(methoxycarbonyl)phenyl]propionamide yield: 73%. colorless prism crystals, melting point: 198–200° C. (recrystallized from ethyl acetate-hexane).

Example 43

3-[4-(4-chlorophenyl)-2-phenyl-5-oxazolyl]propionamide yield: 79%. colorless prism crystals, melting point: 207–208° C. (recrystallized from ethanol-chloroform).

Example 44

3-[2-(1H-imidazol-1-yl)-4-(4-chlorophenyl)-5-oxazolyl]-N-(4-{[(methylamino)sulfonyl]methyl}phenyl)propionamide yield: 54%. colorless prism crystals, melting point: 224–225° C. (recrystallized from tetrahydrofuran-isopropyl ether).

Example 45

3-[4-(4-chlorophenyl)-2-phenyl-5-thiazolyl]-N-[4-(methoxycarbonyl)phenyl]propionamide yield: 91%. colorless prism crystals, melting point: 177–178° C. (recrystallized from ethyl acetate).

Example 46

3-[4-(4-chlorophenyl)-2-phenyl-5-thiazolyl]propionamide yield: 71%. colorless prism crystals, melting point: 175–176° C. (recrystallized from ethyl acetate).

Example 47

4-[4-(4-chlorophenyl)-2-phenyl-5-oxazolyl]-N-[4-(diethylphosphonomethyl)phenyl]butanamide yield: 73%. colorless prism crystals, melting point: 152–153° C. (recrystallized from ethyl acetate-ethanol).

Example 48

4-[4-(4-chlorophenyl)-2-phenyl-5-oxazolyl]-N-{4-[(2-oxide-1,3,2-dioxaphosphinan-2-yl)methyl]phenyl}butanamide yield: 50%. colorless prism crystals, melting point: 224–225° C. (recrystallized from ethanol-chloroform).

Example 49

N-ethyl-4-[4-(4-chlorophenyl)-2-phenyl-5-oxazolyl]butanamide yield: 78%. colorless prism crystals, melting point: 127–128° C. (recrystallized from ethyl acetate).

Example 50

4-[4-(4-chlorophenyl)-2-phenyl-5-oxazolyl]-N-[4-(methoxycarbonyl)phenyl]butanamide yield: 74%. colorless prism crystals, melting point: 170–171° C. (recrystallized from ethyl acetate).

Example 51

1-{4-[4-(4-chlorophenyl)-2-phenyl-5-oxazolyl]butanoyl}-4-phenylpiperazine yield: 30%. colorless prism crystals, melting point: 104–105° C. (recrystallized from ethyl acetate-hexane).

Example 52

4-[4-(4-chlorophenyl)-2-phenyl-5-oxazolyl]butanamide yield: 75%. colorless prism crystals, melting point: 168–169° C. (recrystallized from ethyl acetate).

Example 53

2-[4-(4-chlorophenyl)-2-phenyl-5-oxazolyl]-N-[4-(diethylphosphonomethyl)phenyl]acetamide yield: 41%. colorless prism crystals, melting point: 173–174° C. (recrystallized from ethanol).

Example 54

(2E)-3-[4-(4-chlorophenyl)-2-phenyl-5-oxazolyl]-N-[4-(diethylphosphonomethyl)phenyl]propenamide yield: 70%. pale-yellow prism crystals, melting point: 204–206° C. (recrystallized from ethanol).

Example 55

(2E)-3-[4-(4-chlorophenyl)-2-phenyl-5-oxazolyl]propenamide yield: 72%. colorless prism crystals, melting point: 240–241° C. (recrystallized from ethyl acetate-hexane).

Example 56

(2E)-3-[4-(4-chlorophenyl)-2-phenyl-5-oxazolyl]-N-[4-(ethoxycarbonyl)phenyl]propenamide yield: 98%. colorless prism crystals, melting point: 135–140° C. (recrystallized from ethyl acetate).

Example 57

3-[4-(4-chlorophenyl)-2-phenyl-5-oxazolyl]-N-[4-(dimethylphosphonomethyl)phenyl]propionamide yield: 74%. colorless prism crystals, melting point: 153–154° C. (recrystallized from ethanol-hexane).

Example 58

3-[4-(4-chlorophenyl)-2-phenyl-5-oxazolyl]-N-{4-[(2-oxide-1,3,2-dioxaphosphinan-2-yl)methyl]phenyl}propionamide yield: 77%. colorless prism crystals, melting point: 177–178° C. (recrystallized from ethanol-hexane).

Example 59

3-[4-(4-chlorophenyl)-2-phenyl-5-thiazolyl]-N-[4-(diethylphosphonomethyl)phenyl]propionamide yield: 89%. colorless prism crystals, melting point: 164–165° C. (recrystallized from dichloromethane-isopropyl ether).

Example 60

3-[4-(4-chlorophenyl)-2-phenyl-5-thiazolyl]-N-[4-(diethylphosphono)phenyl]propionamide yield: 83%. colorless prism crystals, melting point: 186–187° C. (recrystallized from dichloromethane-isopropyl ether).

Example 61

To a mixture of 4-(4-chlorophenyl)-2-phenyl-5-oxazolepropionic acid (500 mg), triethylamine (230 mg) and tetrahydrofuran (10 ml) was added ethyl chlorocarbonate (250 mg) at −40° C., and the mixture was stirred for 1 hr. Diethyl 4-aminophenylphosphonate (420 mg) was added, and the mixture was stirred at room temperature for 5 hrs. The reaction mixture was poured into water and extracted with ethyl acetate. The organic layer was washed with water, dried over anhydrous magnesium sulfate and concentrated. The residue was purified by silica gel column chromatography and 3-[4-(4-chlorophenyl)-2-phenyl-5-oxazolyl]-N-[4-(diethylphosphono)phenyl]propionamide (295 mg, yield 36%) was obtained as colorless prism crystals from a fraction eluted with ethyl acetate-chloroform (1:1, volume ratio). melting point: 139–140° C. (recrystallized from dichloromethane-isopropyl ether).

Example 62

In the same manner as in Example 61, 3-[4-(4-chlorophenyl)-2-phenyl-5-oxazolyl]-N-[4-(diethylphosphonomethyl)phenyl]propionamide was synthesized.

yield: 95%. colorless prism crystals, melting point: 143–144° C. (recrystallized from dichloromethane-isopropyl ether).

Example 63

A mixture of 3-[4-(4-chlorophenyl)-2-phenyl-5-oxazolyl]-N-[4-(ethoxycarbonyl)phenyl]propionamide (0.70 g), potassium hydroxide (0.26 g), ethanol (20 ml) and tetrahydrofuran (10 ml) was stirred at room temperature for 5 hrs and further stirred at 50° C. for 3 hrs. The reaction mixture was poured into water and acidified with 1N hydrochloric acid. The mixture was extracted with ethyl acetate. The ethyl acetate layer was washed with water and then with saturated brine, dried over anhydrous magnesium sulfate, and concentrated to give a colorless powder. Recrystallization from chloroform-ethanol gave 4-({3-[4-(4-chlorophenyl)-2-phenyl-5-oxazolyl]propanoyl}amino)benzoic acid as colorless prism crystals (0.51 g, 75%). melting point: 243–244° C.

In the same manner as in Example 63, the compounds of Examples 64 and 65 were synthesized.

Example 64

4-({3-[4-(4-chlorophenyl)-2-phenyl-5-thiazolyl]propanoyl}amino)benzoic acid yield: 95%. colorless prism crystals, melting point: 294–295° C. (recrystallized from ethanol-chloroform).

Example 65

4-({(2E)-3-[4-(4-chlorophenyl)-2-phenyl-5-oxazolyl]propenoyl}amino)benzoic acid yield: 40%. colorless prism crystals, melting point: 275–276° C. (recrystallized from ethyl acetate-hexane).

Example 66

A mixture of 4-({3-[4-(4-chlorophenyl)-2-phenyl-5-oxazolyl]propanoyl}amino)benzoic acid (0.30 g), oxalyl chloride (0.10 g), N,N-dimethylformamide (0.1 ml) and tetrahydrofuran (10 ml) was stirred at room temperature for 1 hr. The reaction mixture was concentrated and the residue was dissolved in tetrahydrofuran (15 ml). Thereto was added 25% aqueous ammonia (3 ml) and the mixture was stirred at room temperature for 1.5 hrs. The reaction mixture was poured into water, and the mixture was extracted with ethyl acetate. The ethyl acetate layer was washed with dilute hydrochloric acid, saturated aqueous sodium hydrogen carbonate, and then with saturated brine, dried (MgSO$_4$), and concentrated to give a colorless powder (0.27 g). Recrystallization from chloroform-ethanol gave 4-({3-[4-(4-chlorophenyl)-2-phenyl-5-oxazolyl]propanoyl}amino)benzamide as colorless prism crystals (0.15 g, 50%). melting point: 268–269° C.

In the same manner as in Example 66, the compounds of Examples 67 and 68 were synthesized.

Example 67

4-({3-[4-(4-chlorophenyl)-2-phenyl-5-thiazolyl]propanoyl}amino)benzamide yield: 55%. colorless prism crystals, melting point: 300° C. or above (dec.) (recrystallized from tetrahydrofuran).

Example 68

4-({(2E)-3-[4-(4-chlorophenyl)-2-phenyl-5-oxazolyl]propenoyl}amino)benzamide yield: 54%. colorless prism crystals, melting point: 274–275° C. (recrystallized from ethanol).

Example 69

A mixture of diethyl 4-aminobenzylphosphonate (0.73 g), 2-(1H-benzimidazol-1-yl)-4-[4-(trifluoromethyl)phenyl]-5-oxazolepropionic acid (0.85 g), 1-hydroxy-1H-1,2,3-benzotriazole hydrate (0.46 g), 1-ethyl-3-(3-dimethylaminopropyl)carbodiimide hydrochloride (0.56 g) and N,N-dimethylformamide (20 ml) was stirred at room temperature for 16 hrs. The reaction mixture was poured into water, and the mixture was extracted with ethyl acetate. The ethyl acetate layer was washed with dilute hydrochloric acid, saturated aqueous sodium hydrogen carbonate, and then with saturated brine, dried (MgSO$_4$) and concentrated. The residue was subjected to silica gel column chromatography, and 3-{2-(1H-benzimidazol-1-yl)-4-[4-(trifluoromethyl)phenyl]-5-oxazolyl}-N-[(4-diethylphosphonomethyl)phenyl]propionamide (0.70 g, yield 52%) was obtained as colorless crystals from a fraction eluted with ethyl acetate-hexane (2:1, volume ratio). Recrystallization from acetone-isopropyl ether gave colorless prism crystals. melting point: 208–209° C.

In the same manner as in Example 69, the compounds of Examples 70–223 were synthesized.

Example 70

3-[4-(4-chlorophenyl)-5-oxazolyl]-N-[4-(diethylphosphonomethyl)phenyl]propionamide yield: 92%. colorless prism crystals, melting point: 130–131° C. (recrystallized from ethyl acetate-hexane).

Example 71

3-[4-(4-chlorophenyl)-2-(2-methyl-1-imidazolyl)-5-oxazolyl]-N-(2-methoxyphenyl)propionamide yield: 90%. colorless prism crystals, melting point: 153–154° C. (recrystallized from ethyl acetate-hexane).

Example 72

3-[2-(1H-benzimidazol-1-yl)-4-(4-chlorophenyl)-5-oxazolyl]-N-[3-(diethylphosphono)propyl]propionamide yield: 80%. colorless prism crystals, melting point: 130–131° C. (recrystallized from ethyl acetate).

Example 73

3-[2-(1H-benzimidazol-1-yl)-4-(4-chlorophenyl)-5-oxazolyl]-N-[(4-dimethylphosphonomethyl)phenyl]propionamide yield: 65%. colorless prism crystals, melting point: 206–207° C. (recrystallized from ethanol-hexane).

Example 74

3-[2-(1H-benzimidazol-1-yl)-4-(4-chlorophenyl)-5-oxazolyl]-N-{4-[(2-oxide-1,3,2-dioxaphosphinan-2-yl)methyl]phenyl}propionamide yield: 67%. colorless prism crystals, melting point: 240–241° C. (recrystallized from tetrahydrofuran-ethanol).

Example 75

3-[2-(1H-benzimidazol-1-yl)-4-(4-chlorophenyl)-5-oxazolyl]-N-{4-[(5,5-dimethyl-2-oxide-1,3,2-dioxaphosphinan-2-yl)methyl]phenyl}propionamide yield: 58%. colorless prism crystals, melting point: 206–207° C. (recrystallized from tetrahydrofuran-ethanol).

Example 76

3-[2-(1H-benzimidazol-1-yl)-4-(4-chlorophenyl)-5-oxazolyl]-N-[4-(ethoxycarbonylmethyl)phenyl]propionamide yield: 53%. colorless prism crystals, melting point: 181–182° C. (recrystallized from tetrahydrofuran-ethanol).

Example 77

1-(4-chlorophenyl)-4-{4-[4-(4-chlorophenyl)-2-(2-methyl-1-imidazolyl)-5-oxazolyl]butanoyl}piperazine yield: 67%. amorphous. NMR(CDCl$_3$) delta: 2.05–2.2 (2H, m), 2.43 (2H,t, J=7 Hz),2.78 (3H, s), 3.0–3.1 (6H, m), 3.52 (2H, t, J=5 Hz), 3.75 (2H, t, J=5 Hz), 6.82 (2H, d, J=9 Hz), 7.00 (1H, d, J=2 Hz), 7.23 (2H, d, J=9 Hz), 7.41 (2H, d, J=9 Hz), 7.47 (1H, d, J=2 Hz), 7.66 (2H, d, J=9 Hz).

Example 78

4-[2-chloro-4-(4-chlorophenyl)-5-oxazolyl]-N-[(4-diethylphosphonomethyl)phenyl]butanamide yield: 57%. amorphous. NMR(CDCl$_3$) delta: 1.25 (6H, t, J=7 Hz), 2.1–2.2 (2H,m),2.44 (2H, t, J=7.5 Hz), 2.98 (2H, t,J=7 Hz), 3.11 (2H, d, J=21 Hz), 3.9–4.1 (4H, m), 7.15–7.25 (2H, m), 7.35 (2H, d, J=8.5 Hz), 7.35–7.5 (2H, m), 7.56 (2H, d, J=8.5 Hz), 7.68 (1H, s).

Example 79

3-[2-(1H-benzimidazol-1-yl)-4-(4-chlorophenyl)-5-oxazolyl]-N-(4-chlorophenyl)propionamide yield: 76%. colorless prism crystals, melting point: 248–249° C. (recrystallized from tetrahydrofuran-ethanol).

Example 80

3-[4-(4-chlorophenyl)-2-(4,5-dimethyl-1H-benzimidazol-1-yl)-5-oxazolyl]-N-[(4-diethylphosphonomethyl)phenyl]propionamide yield: 58%. colorless prism crystals, melting point: 198–199° C. (recrystallized from ethanol-hexane).

Example 81

3-[4-(4-chlorophenyl)-2-[4-(trifluoromethyl)phenyl]-N-[(4-dimethylphosphonomethyl)phenyl]propionamide yield: 81%. colorless prism crystals, melting point: 138–139° C. (recrystallized from ethanol-hexane).

Example 82

4-[2-(1H-benzimidazol-1-yl)-4-(4-chlorophenyl)-5-oxazolyl]-N-[(4-dimethylphosphonomethyl)phenyl]butanamide yield: 72%. colorless prism crystals, melting point: 172–174° C. (recrystallized from ethanol-hexane).

Example 83

4-[4-(4-chlorophenyl)-2-(4,5-dimethyl-1H-benzimidazol-1-yl)-5-oxazolyl]-N-[(4-diethylphosphonomethyl)phenyl]butanamide yield: 72%. colorless prism crystals, melting point: 172–174° C. (recrystallized from ethanol-hexane).

Example 84

4-[4-(4-chlorophenyl)-2-phenyl-5-oxazolyl]-N-[(4-dimethylphosphonomethyl)phenyl]butanamide yield: 54%. colorless prism crystals, melting point: 145–146° C. (recrystallized from ethanol-hexane).

Example 85

3-[2-(1H-benzimidazol-1-yl)-4-(3,4-dichlorophenyl)-5-oxazolyl]-N-[(4-diethylphosphonomethyl)phenyl]propionamide yield: 59%. pale-yellow prism crystals, melting point: 175–176° C. (recrystallized from ethanol-hexane).

Example 86

3-[4-(3,4-dichlorophenyl)-2-phenyl-5-oxazolyl]-N-[(4-dimethylphosphonomethyl)phenyl]propionamide yield: 85%. pale-yellow prism crystals, melting point: 162–163° C. (recrystallized from ethanol-hexane).

Example 87

3-[2-(1H-benzimidazol-1-yl)-4-(4-chlorophenyl)-5-oxazolyl)-N-(4-{[N-methyl-N-(4-tetrahydropyranyl)amino]methyl}phenyl)propionamide yield: 60%. colorless prism crystals, melting point: 182–184° C. (recrystallized from tetrahydrofuran-ethyl acetate).

Example 88

3-[2-(1H-benzimidazol-1-yl)-4-(4-chlorophenyl)-5-oxazolyl]-N-{4-[(1-piperidinyl)methyl]phenyl}propionamide yield: 73%. colorless prism crystals, melting point: 194–195° C. (recrystallized from acetone-isopropyl ether).

Example 89

3-[2-(1H-benzimidazol-1-yl)-4-(4-chlorophenyl)-5-oxazolyl]-N-[4-(cyanomethyl)phenyl]propionamide yield: 73%. pale-yellow prism crystals, melting point: 212–214° C. (recrystallized from tetrahydrofuran-hexane).

Example 90

4-({3-[2-(1H-benzimidazol-1-yl)-4-(4-chlorophenyl)-5-oxazolyl]propanoyl)amino}phenylacetic acid yield: 55%. pale-yellow prism crystals, melting point: 247–248° C. (recrystallized from tetrahydrofuran-hexane).

Example 91

3-[2-(1H-benzimidazol-1-yl)-4-(4-chlorophenyl)-5-oxazolyl]-N-[4-(methoxycarbonyl)phenyl]propionamide yield: 70%. pale-yellow prism crystals, melting point: 249–250° C. (recrystallized from tetrahydrofuran-hexane).

Example 92

3-[2-(1H-benzimidazol-1-yl)-4-(4-chlorophenyl)-5-oxazolyl]-N-[2-(2-pyridinyl)ethyl]propionamide yield: 70%. pale-yellow prism crystals, melting point: 150–151° C. (recrystallized from acetone-hexane).

Example 93

1-{3-[2-(1H-benzimidazol-1-yl)-4-(4-chlorophenyl)-5-oxazolyl]propanoyl}-4-(2-pyridinyl)piperazine yield: 79%. pale-yellow prism crystals, melting point: 174–176° C. (recrystallized from ethyl acetate-hexane).

Example 94

3-[4-(4-chlorophenyl)-2-phenyl-5-oxazolyl]-N-(4-{[N-methyl-N-(4-tetrahydropyranyl)amino]methyl}phenyl)propionamide yield: 89%. colorless prism crystals, melting point: 154–155° C. (recrystallized from ethyl acetate-isopropyl ether).

Example 95

3-[4-(4-chlorophenyl)-2-phenyl-5-oxazolyl]-N-{4-[(1-piperidinyl)methyl]phenyl}propionamide yield: 70%. pale-yellow prism crystals, melting point: 223–225° C. (recrystallized from tetrahydrofuran-ethyl acetate).

Example 96

3-[2-(1H-benzimidazol-1-yl)-4-(4-chlorophenyl)-5-oxazolyl]-N-{4-(methylsulfanyl)phenyl}propionamide yield: 47%. pale-yellow prism crystals, melting point: 276–277° C. (recrystallized from ethyl acetate-hexane).

Example 97

4-[2-(1H-benzimidazol-1-yl)-4-(4-chlorophenyl)-5-oxazolyl]-N-{4-(cyanomethyl)phenyl}butanamide yield: 85%. NMR(CDCl$_3$) delta: 2.0–2.2 (2H,m),2.49 (2H, t, J=7.5 Hz), 3.12 (2H, d, J=7.5 Hz), 3.70 (2H, s), 7.23 (2H, d, J=8.5 Hz), 7.35–7.5 (6H, m), 7.70 (2H, d, J=8.5 Hz), 7.85–7.90 (1H, m), 8.02 (1H, s) 8.2–8.3 (1H, m), 8.57 (1H, s).

Example 98

4-[2-(1H-benzimidazol-1-yl)-4-(4-chlorophenyl)-5-oxazolyl]-N-{4-[(2-oxide-1,3,2-dioxaphosphinan-2-yl)methyl]phenyl}butanamide yield: 59%. pale-yellow prism crystals, melting point: 206–207° C. (recrystallized from tetrahydrofuran-isopropyl ether).

Example 99

4-[2-(1H-benzimidazol-1-yl)-4-(4-chlorophenyl)-5-oxazolyl]-N-{4-[(5-methyl-2-oxide-1,3,2-dioxaphosphinan-2-yl)methyl]phenyl}butanamide yield: 43%. pale-yellow prism crystals, melting point: 202–203° C. (recrystallized from).

Example 100

4-[2-(1H-benzimidazol-1-yl)-4-(4-chlorophenyl)-5-oxazolyl]-N-[3-(diethylphosphonomethyl)phenyl]butanamide yield: 68%. pale-yellow prism crystals, melting point: 135–136° C. (recrystallized from ethanol-hexane).

Example 101

4-[2-(1H-benzimidazol-1-yl)-4-(4-chlorophenyl)-5-oxazolyl]-N-{4-[(4,6-dimethyl-2-oxide-1,3,2-dioxaphosphinan-2-yl)methyl]phenyl}butanamide yield: 89%. pale-yellow prism crystals, melting point: 149–150° C. (recrystallized from ethanol-hexane).

Example 102

4-[2-(1H-benzimidazol-1-yl)-4-(4-chlorophenyl)-5-oxazolyl]-N-[4-(diethylphosphonomethyl)-2-methylphenyl]butanamide yield: 46%. pale-yellow prism crystals, melting point: 118–119° C. (recrystallized from ethanol-hexane).

Example 103

4-[2-(1H-benzimidazol-1-yl)-4-(4-chlorophenyl)-5-oxazolyl]-N-[4-(diethylphosphono)phenyl]butanamide yield: 75%. pale-yellow prism crystals, melting point: 162–163° C. (recrystallized from ethanol-hexane).

Example 104

4-[2-(1H-benzimidazol-1-yl)-4-(4-chlorophenyl)-5-oxazolyl]-N-(4-{[(2-thiazolyl)amino]sulfonyl}phenyl)butanamide yield: 79%. pale-yellow prism crystals, melting point: 243–244° C. (recrystallized from tetrahydrofuran-ethyl acetate).

Example 105

3-[4-(4-chlorophenyl)-2-phenyl-5-oxazolyl]-N-[4-(cyanomethyl)phenyl]propionamide yield: 76%. pale-yellow prism crystals, melting point: 212–214° C. (recrystallized from ethyl acetate-hexane).

Example 106

2-[4-({3-[2-(1H-benzimidazol-1-yl)-4-(4-chlorophenyl)-5-oxazolyl]propanoyl}amino)phenyl]-N,N-diethylacetamide yield: 72%. colorless prism crystals, melting point: 209–210° C. (recrystallized from tetrahydrofuran-isopropyl ether).

Example 107

3-[2-(1H-benzimidazol-1-yl)-4-(4-chlorophenyl)-5-oxazolyl]-N-[4-(diethylphosphono)phenyl]propionamide yield: 69%. pale-yellow prism crystals, melting point: 249–250° C. (recrystallized from ethyl acetate-hexane).

Example 108

3-[2-(1H-benzimidazol-1-yl)-4-(4-chlorophenyl)-5-oxazolyl]-N-[3-(hydroxymethyl)phenyl]propionamide yield: 87%. pale-yellow prism crystals, melting point: 206–207° C. (recrystallized from ethanol-hexane).

Example 109

3-[2-(1H-benzimidazol-1-yl)-4-(4-chlorophenyl)-5-oxazolyl]-N-[2-(hydroxymethyl)phenyl]propionamide yield: 93%. pale-yellow prism crystals, melting point: 159–160° C. (recrystallized from ethanol-hexane).

Example 110

3-[2-(1H-benzimidazol-1-yl)-4-(4-chlorophenyl)-5-oxazolyl]-N-[3-(cyanomethyl)phenyl]propionamide yield: 75%. colorless prism crystals, melting point: 188–189° C. (recrystallized from acetone-hexane).

Example 111

3-[2-(1H-benzimidazol-1-yl)-4-(4-chlorophenyl)-5-oxazolyl]-N-[2-(cyanomethyl)phenyl]propionamide yield: 76%. pale-yellow prism crystals, melting point: 235–236° C. (recrystallized from acetone-hexane).

Example 112

3-[2-(1H-benzimidazol-1-yl)-4-(4-chlorophenyl)-5-oxazolyl]-N-(4-cyanophenyl)propionamide yield: 86%. pale-yellow prism crystals, melting point: 216–217° C. (recrystallized from ethyl acetate-hexane).

Example 113

3-[2-(1H-benzimidazol-1-yl)-4-(4-chlorophenyl)-5-oxazolyl]-N-(2-cyanophenyl)propionamide yield: 77%. pale-yellow prism crystals, melting point: 186–187° C. (recrystallized from ethyl acetate-hexane).

Example 114

3-[2-(1H-benzimidazol-1-yl)-4-(4-chlorophenyl)-5-oxazolyl]-N-(4-methoxyphenyl)propionamide yield: 77%. colorless prism crystals, melting point: 240–241° C. (recrystallized from ethanol-hexane).

Example 115

3-[2-(1H-benzimidazol-1-yl)-4-(4-chlorophenyl)-5-oxazolyl]-N-(2-methoxyphenyl)propionamide yield: 70%. colorless prism crystals, melting point: 194–195° C. (recrystallized from tetrahydrofuran-ethanol).

Example 116

3-[2-(1H-benzimidazol-1-yl)-4-(4-chlorophenyl)-5-oxazolyl]-N-(4-cyclohexylphenyl)propionamide yield: 66%. colorless prism crystals, melting point: 216–217° C. (recrystallized from ethanol-hexane).

Example 117

3-[2-(1H-benzimidazol-1-yl)-4-(4-chlorophenyl)-5-oxazolyl]-N-(4-tert-butylphenyl)propionamide yield: 74%. colorless prism crystals, melting point: 219–220° C. (recrystallized from ethanol-hexane

Example 118

3-[2-(1H-benzimidazol-1-yl)-4-(4-chlorophenyl)-5-oxazolyl]-N-{4-[(4,6-dimethyl-2-oxide-1,3,2-dioxaphosphinan-2-yl)methyl]phenyl}propionamide yield: 48%. colorless prism crystals, melting point: 190–191° C. (recrystallized from ethanol-hexane).

Example 119

3-[2-(1H-benzimidazol-1-yl)-4-(4-chlorophenyl)-5-oxazolyl]-N-{4-[(5-methyl-2-oxide-1,3,2-dioxaphosphinan-2-yl)methyl]phenyl}propionamide yield: 92%. pale-yellow prism crystals, melting point: 205–206° C. (recrystallized from ethanol-hexane).

Example 120

3-[2-(1H-benzimidazol-1-yl)-4-(4-chlorophenyl)-5-oxazolyl]-N-phenylpropionamide yield: 78%. pale-yellow prism crystals, melting point: 226–227° C. (recrystallized from ethanol-hexane).

Example 121

3-[2-(1H-benzimidazol-1-yl)-4-(4-chlorophenyl)-5-oxazolyl]-N-[4-(trifluoromethyl)phenyl]propionamide yield: 72%. colorless prism crystals, melting point: 259–263° C. (recrystallized from ethanol-hexane).

Example 122

3-[2-(1H-benzimidazol-1-yl)-4-(4-chlorophenyl)-5-oxazolyl]-N-[4-(trifluoromethoxy)phenyl]propionamide yield: 66%. colorless prism crystals, melting point: 174–175° C. (recrystallized from ethanol-hexane

Example 123

4-[2-(1H-benzimidazol-1-yl)-4-(4-chlorophenyl)-5-oxazolyl]-N-[4-(dibutylphosphonomethyl)phenyl]butanamide yield: 99%. a yellow oil. NMR(CDCl$_3$) delta: 0.89 (6H, t, J=7 Hz), 1.3–1.8 (8H,m), 2.2–2.4 (2H, m), 2.4–2.6 (2H, m), 3.0–3.2 (4H,m), 3.8–4.2 (4H, m), 7.1–7.3 (2H, m), 7.3–7.5 (7H, m), 7.71 (2H, d, J=8.5 Hz), 7.8–7.9 (1H,m), 8.2–8.3 (1H,m), 8.58 (1H, s).

Example 124

4-[2-(1H-benzimidazol-1-yl)-4-(4-chlorophenyl)-5-oxazolyl]-N-[2-(diethylphosphonomethyl)phenyl]butanamide yield: 66%. pale-yellow prism crystals, melting point: 133–136° C. (recrystallized from ethanol-hexane).

Example 125

3-[2-(1H-benzimidazol-1-yl)-4-(4-chlorophenyl)-5-oxazolyl]-N-(4-methylbenzyl)propionamide yield: 53%. colorless prism crystals, melting point: 241–242° C. (recrystallized from ethanol-hexane).

Example 126

3-[2-(1H-benzimidazol-1-yl)-4-(4-chlorophenyl)-5-oxazolyl]-N-(4-isopropylphenyl)propionamide yield: 82%. colorless prism crystals, melting point: 232–233° C. (recrystallized from ethanol-hexane).

Example 127

3-[2-(1H-benzimidazol-1-yl)-4-(4-chlorophenyl)-5-oxazolyl]-N-(3,4,5-trimethoxyphenyl)propionamide yield: 85%. colorless prism crystals, melting point: 228–229° C. (recrystallized from ethanol-hexane).

Example 128

3-[2-(1H-benzimidazol-1-yl)-4-(4-chlorophenyl)-5-oxazolyl]-N-(4-fluorophenyl)propionamide yield: 63%. colorless prism crystals, melting point: 221–222° C. (recrystallized from ethanol-hexane).

Example 129

3-[2-(1H-benzimidazol-1-yl)-4-(4-chlorophenyl)-5-oxazolyl]-N-{4-[(methoxycarbonyl)methyl]-2-thiazolyl}propionamide yield: 72%. pale-yellow prism crystals, melting point: 233–234° C. (recrystallized from acetone-isopropyl ether).

Example 130

3-[2-(1H-benzimidazol-1-yl)-4-(4-chlorophenyl)-5-oxazolyl]-N-[4-(dimethylamino)phenyl]propionamide yield: 61%. pale-yellow prism crystals, melting point: 212–214° C.

Example 131

4-[2-(1H-benzimidazol-1-yl)-4-(4-chlorophenyl)-5-oxazolyl]-N-{4-[2-(diethylphosphono)ethyl]phenyl}butanamide yield: 72%. pale-yellow prism crystal, melting point: 116–117° C. (recrystallized from acetone-isopropyl ether).

Example 132

3-[2-(1H-benzimidazol-1-yl)-4-(4-chlorophenyl)-5-oxazolyl]-N-benzylpropionamide yield: 76%. colorless prism crystals, melting point: 205–206° C. (recrystallized from tetrahydrofuran-ethanol).

Example 133

3-[2-(1H-benzimidazol-1-yl)-4-(4-chlorophenyl)-5-oxazolyl]-N-(2-methoxybenzyl)propionamide yield: 77%. colorless prism crystals, melting point: 210–211° C. (recrystallized from ethanol-hexane).

Example 134

3-[2-(1H-benzimidazol-1-yl)-4-(4-chlorophenyl)-5-oxazolyl]-N-(2-chlorobenzyl)propionamide yield: 56%. colorless prism crystals, melting point: 222–223° C. (recrystallized from ethanol-hexane).

Example 135

3-[2-(1H-benzimidazol-1-yl)-4-(4-chlorophenyl)-5-oxazolyl]-N-[4-(dimethylamino)benzyl]propionamide yield: 60%. colorless prism crystals, melting point: 184–185° C. (recrystallized from ethanol-hexane).

Example 136

3-[2-(1H-benzimidazol-1-yl)-4-(4-chlorophenyl)-5-oxazolyl]-N-(2-phenylethyl)propionamide yield: 84%. colorless prism crystals, melting point: 164–165° C. (recrystallized from acetone-hexane).

Example 137

3-[2-(1H-benzimidazol-1-yl)-4-(4-chlorophenyl)-5-oxazolyl]-N-(2-fluorobenzyl)propionamide yield: 61%. colorless prism crystals, melting point: 202–203° C. (recrystallized from ethanol-hexane).

Example 138

3-[2-(1H-benzimidazol-1-yl)-4-(4-chlorophenyl)-5-oxazolyl]-N-[4-(trifluoromethyl)benzyl]propionamide yield: 55%. colorless prism crystals, melting point: 194–195° C. (recrystallized from ethanol-hexane).

Example 139

2-[4-(N-{3-[2-(1H-benzimidazol-1-yl)-4-(4-chlorophenyl)-5-oxazolyl]propanoyl}amino)phenyl]-N-(2-methoxyphenyl)acetamide yield: 79%. colorless prism crystals, melting point: 258–259° C. (recrystallized from tetrahydrofuran-hexane).

Example 140

2-[4-(N-{3-[2-(1H-benzimidazol-1-yl)-4-(4-chlorophenyl)-5-oxazolyl]propanoyl}amino)phenyl]-N-[4-(dimethylamino)phenyl]acetamide yield: 69%. colorless prism crystals, melting point: 169–170° C. (recrystallized from tetrahydrofuran-ethanol).

Example 141

3-[4-(4-chlorophenyl)-2-(2-methyl-1-imidazolyl)-5-oxazolyl]-N-[4-(cyanomethyl)phenyl]propionamide yield: 74%. colorless prism crystals, melting point: 187–188° C. (recrystallized from acetone-hexane).

Example 142

2-[4-({3-[2-(1H-benzimidazol-1-yl)-4-(4-chlorophenyl)-5-oxazolyl]propanoyl}amino)phenyl]-N,N-dimethylacetamide yield: 75%. colorless prism crystals, melting point: 207–208° C. (recrystallized from acetone-hexane).

Example 143

2-[4-({3-[2-(1H-benzimidazol-1-yl)-4-(4-chlorophenyl)-5-oxazolyl]propanoyl}amino)phenyl]-N-methylacetamide yield: 61%. colorless prism crystals, melting point: 219–221° C. (recrystallized from acetone-hexane).

Example 144

3-[2-(1H-benzimidazol-1-yl)-4-(4-chlorophenyl)-5-oxazolyl]-N-[4-tert-butylbenzyl]propionamide yield: 75%. colorless prism crystals, melting point: 170–171° C. (recrystallized from acetone-hexane).

Example 145

3-[2-(1H-benzimidazol-1-yl)-4-(4-chlorophenyl)-5-oxazolyl]-N-(4-methoxybenzyl)propionamide yield: 84%. colorless prism crystals, melting point: 210–212° C. (recrystallized from acetone-hexane).

Example 146

3-[2-(1H-benzimidazol-1-yl)-4-(4-chlorophenyl)-5-oxazolyl]-N-(4-methylbenzyl)propionamide yield: 86%. colorless prism crystals, melting point: 210–212° C. (recrystallized from tetrahydrofuran-hexane).

Example 147

3-[2-(1H-benzimidazol-1-yl)-4-(4-chlorophenyl)-5-oxazolyl]-N-(3,4-dichlorobenzyl)propionamide yield: 63%. colorless prism crystals, melting point: 190–191° C. (recrystallized from acetone-hexane).

Example 148

2-({3-[2-(1H-benzimidazol-1-yl)-4-(4-chlorophenyl)-5-oxazolyl]propanoyl}amino)-N-benzylacetamide yield: 78%. colorless prism crystals, melting point: 186–187° C. (recrystallized from acetone-hexane).

Example 149

2-({3-[2-(1H-benzimidazol-1-yl)-4-(4-chlorophenyl)-5-oxazolyl]propanoyl}amino)-N-phenylacetamide yield: 67%. colorless prism crystals, melting point: 250–251° C. (recrystallized from tetrahydrofuran-hexane).

Example 150

3-[2-(1H-benzimidazol-1-yl)-4-(4-chlorophenyl)-5-oxazolyl]-N-[4-(1,2,3-thiadiazol-4-yl)benzyl]propionamide yield: 74%. colorless prism crystals, melting point: 173–174° C. (recrystallized from acetone-hexane).

Example 151

N-[4-(aminosulfonyl)benzyl]-3-[2-(1H-benzimidazol-1-yl)-4-(4-chlorophenyl)-5-oxazolyl]propionamide yield: 77%. colorless prism crystals, melting point: 255–256° C. (recrystallized from tetrahydrofuran-hexane).

Example 152

3-[2-(1H-benzimidazol-1-yl)-4-(4-chlorophenyl)-5-oxazolyl]-N-(4-chlorobenzyl)propionamide yield: 80%. colorless prism crystals, melting point: 190–191° C. (recrystallized from acetone-hexane).

Example 153

3-[2-(1H-benzimidazol-1-yl)-4-(4-chlorophenyl)-5-oxazolyl]-N-(4-phenylbenzyl)propionamide yield: 76%. colorless prism crystals, melting point: 214–216° C. (recrystallized from tetrahydrofuran-hexane).

Example 154

3-[2-(1H-benzimidazol-1-yl)-4-(4-chlorophenyl)-5-oxazolyl]-N-(2-pyridinylmethyl)propionamide yield: 68%. colorless prism crystals, melting point: 157–158° C. (recrystallized from acetone-hexane).

Example 155

3-[2-(1H-benzimidazol-1-yl)-4-(4-chlorophenyl)-5-oxazolyl]-N-(4-pyridinylmethyl)propionamide yield: 70%. colorless prism crystals, melting point: 214–216° C. (recrystallized from acetone-hexane).

Example 156

3-[2-(1H-benzimidazol-1-yl)-4-(4-chlorophenyl)-5-oxazolyl]-N-(2,6-difluorobenzyl)propionamide yield: 97%. colorless prism crystals, melting point: 225–226° C. (recrystallized from acetone-hexane).

Example 157

3-[2-(1H-benzimidazol-1-yl)-4-(4-chlorophenyl)-5-oxazolyl]-N-[2-(trifluoromethyl)benzyl]propionamide yield: 97%. colorless prism crystals, melting point: 208–209° C. (recrystallized from acetone-hexane).

Example 158

3-[2-(1H-benzimidazol-1-yl)-4-(4-chlorophenyl)-5-oxazolyl]-N-(2,5-difluorobenzyl)propionamide yield: 90%. colorless prism crystals, melting point: 197–198° C. (recrystallized from acetone-hexane).

Example 159

3-[2-(1H-benzimidazol-1-yl)-4-(4-chlorophenyl)-5-oxazolyl]-N-(4-chloro-2-fluorobenzyl)propionamide yield: 94%. colorless prism crystals, melting point: 189–191° C. (recrystallized from acetone-hexane).

Example 160

3-[2-(1H-benzimidazol-1-yl)-4-(4-chlorophenyl)-5-oxazolyl]-N-(2,4-difluorobenzyl)propionamide yield: 98%. colorless prism crystals, melting point: 190–191° C. (recrystallized from acetone-hexane).

Example 161

3-[2-(1H-benzimidazol-1-yl)-4-(4-chlorophenyl)-5-oxazolyl]-N-(2,4,6-trimethoxybenzyl)propionamide yield: 95%. colorless prism crystals, melting point: 206–208° C. (recrystallized from acetone-hexane).

Example 162

3-[2-(1H-benzimidazol-1-yl)-4-(4-chlorophenyl)-5-oxazolyl]-N-(2-phenoxyethyl)propionamide yield: 95%. colorless prism crystals, melting point: 156–157° C. (recrystallized from acetone-hexane).

Example 163

3-[2-(1H-benzimidazol-1-yl)-4-(4-chlorophenyl)-5-oxazolyl]-N-[3-fluoro-5-(trifluoromethyl)benzyl]propionamide yield: 90%. colorless prism crystals, melting point: 198–200° C. (recrystallized from acetone-hexane).

Example 164

3-[2-(1H-benzimidazol-1-yl)-4-(4-chlorophenyl)-5-oxazolyl]-N-(3,5-difluorobenzyl)propionamide yield: 70%. colorless prism crystals, melting point: 155–156° C. (recrystallized from acetone-hexane).

Example 165

N-[4-(aminosulfonyl)benzyl]-3-[4-(4-chlorophenyl)-2-phenyl-5-oxazolyl]propionamide yield: 92%. colorless prism crystals, melting point: 225–227° C. (recrystallized from acetone-hexane).

Example 166

3-[4-(4-chlorophenyl)-2-phenyl-5-oxazolyl]-N-(4-methylbenzyl)propionamide yield: 98%. colorless prism crystals, melting point: 193–194° C. (recrystallized from acetone-hexane).

Example 167

3-[2-(1H-benzimidazol-1-yl)-4-(4-chlorophenyl)-5-oxazolyl]-N-(5-bromo-2-fluorobenzyl)propionamide yield: 96%. colorless prism crystals, melting point: 183–184° C. (recrystallized from acetone-hexane).

Example 168

3-[2-(1H-benzimidazol-1-yl)-4-(4-chlorophenyl)-5-oxazolyl]-N-(2-chloro-4-fluorobenzyl)propionamide yield: 92%. colorless prism crystals, melting point: 196–198° C. (recrystallized from acetone-hexane).

Example 169

3-[2-(1H-benzimidazol-1-yl)-4-(4-chlorophenyl)-5-oxazolyl]-N-(3,4,5-trimethoxybenzyl)propionamide yield: 87%. colorless prism crystals, melting point: 169–170° C. (recrystallized from acetone-hexane).

Example 170

3-[2-(1H-benzimidazol-1-yl)-4-(4-chlorophenyl)-5-oxazolyl]-N-(3-bromo-4-fluorobenzyl)propionamide yield: 75%. colorless needle crystals, melting point: 206–207° C. (recrystallized from acetone-hexane).

Example 171

3-[2-(1H-benzimidazol-1-yl)-4-(4-chlorophenyl)-5-oxazolyl]-N-(3-bromobenzyl)propionamide yield: 95%. colorless prism crystals, melting point: 181–183° C. (recrystallized from acetone-hexane).

Example 172

3-[2-(1H-benzimidazol-1-yl)-4-(4-chlorophenyl)-5-oxazolyl]-N-(4-bromobenzyl)propionamide yield: 84%. colorless prism crystals, melting point: 205–206° C. (recrystallized from acetone-hexane).

Example 173

3-[2-(1H-benzimidazol-1-yl)-4-(4-chlorophenyl)-5-oxazolyl]-N-(3-chloro-4-fluorobenzyl)propionamide yield: 83%. colorless prism crystals, melting point: 188–189° C. (recrystallized from acetone-hexane).

Example 174

3-[2-(1H-benzimidazol-1-yl)-4-(4-chlorophenyl)-5-oxazolyl]-N-(2,5-dichlorobenzyl)propionamide yield: 78%. colorless prism crystals, melting point: 205–207° C. (recrystallized from acetone-hexane).

Example 175

3-[2-(1H-benzimidazol-1-yl)-4-(4-chlorophenyl)-5-oxazolyl]-N-(2,4-dimethylbenzyl)propionamide yield: 76%. colorless prism crystals, melting point: 218–219° C. (recrystallized from acetone-hexane).

Example 176

3-[2-(1H-benzimidazol-1-yl)-4-(4-chlorophenyl)-5-oxazolyl]-N-(5-chloro-2-methylbenzyl)propionamide yield: 80%. colorless prism crystals, melting point: 217–219° C. (recrystallized from acetone-hexane).

Example 177

3-[2-(1H-benzimidazol-1-yl)-4-(4-chlorophenyl)-5-oxazolyl]-N-(3-phenylbenzyl)propionamide yield: 70%. colorless prism crystals, melting point: 201–202° C. (recrystallized from acetone-hexane).

Example 178

3-[2-(1H-benzimidazol-1-yl)-4-(4-chlorophenyl)-5-oxazolyl]-N-(4-chloro-2-methylbenzyl)propionamide yield: 80%. colorless prism crystals, melting point: 200–201° C. (recrystallized from acetone-hexane).

Example 179

3-[2-(1H-benzimidazol-1-yl)-4-(4-chlorophenyl)-5-oxazolyl]-N-(2,5-dimethoxybenzyl)propionamide yield: 68%. colorless prism crystals, melting point: 193–194° C. (recrystallized from acetone-hexane).

Example 180

3-[2-(1H-benzimidazol-1-yl)-4-(4-chlorophenyl)-5-oxazolyl]-N-(3,5-dimethoxybenzyl)propionamide yield: 40%. colorless prism crystals, melting point: 198–200° C. (recrystallized from acetone-hexane).

Example 181

3-[2-(1H-benzimidazol-1-yl)-4-(4-chlorophenyl)-5-oxazolyl]-N-(2,5-dimethylbenzyl)propionamide yield: 76%. colorless prism crystals, melting point: 218–219° C. (recrystallized from acetone-hexane).

Example 182

3-[2-(1H-benzimidazol-1-yl)-4-(4-chlorophenyl)-5-oxazolyl]-N-[2-(3,4-dimethoxyphenyl)ethyl]-N-methylpropionamide yield: 71%. amorphous.
elemental analysis: for $C_{30}H_{29}ClN_4O_4$ Calculated C, 66.11; H, 5.36; N, 10.28. Found C, 66.06; H, 5.28; N, 10.12.

Example 183

3-[2-(1H-benzimidazol-1-yl)-4-(4-chlorophenyl)-5-oxazolyl]-N-benzyl-N-methylpropionamide yield: 75%. amorphous.
elemental analysis: for $C_{27}H_{23}ClN_4O_2$ Calculated C, 68.86; H, 4.92; N, 11.90. Found C, 68.77; H, 4.89; N, 11.87.

Example 184

1-{3-[2-(1H-benzimidazol-1-yl)-4-(4-chlorophenyl)-5-oxazolyl]propanoyl}-2-(ethoxycarbonyl)piperidine yield: 96%. amorphous.
elemental analysis: for $C_{27}H_{27}ClN_4O_4$ Calculated C, 63.96; H, 5.37; N, 11.05. Found C, 63.77; H, 5.33; N, 10.99.

Example 185

1-{3-[2-(1H-benzimidazol-1-yl)-3–4-(4-chlorophenyl)-5-oxazolyl]propanoyl}piperazine hydrochloride yield: 52%. colorless prism crystals, melting point: 240–243° C. (recrystallized from ethanol-isopropyl ether).

Example 186

3-[4-(4-chlorophenyl)-2-(1H-benzimidazol-1-yl)-5-oxazolyl]-N-[2-(4-morpholinyl)ethyl]propionamide yield: 61%. a yellow oil. NMR(CDCl$_3$) delta: 2.3–2.5 (6H,m), 2.74 (2H, t, J=7.5 Hz), 3.3–3.4 (4H,m), 3.55–3.65 (4H,m), 7.4–7.5 (4H, m), 7.75 (2H, d, J=8.5 Hz), 7.85–7.9 (1H, m), 8.2–8.25 (1H, m), 8.57 (1H, s).

Example 187

3-[4-(4-chlorophenyl)-2-(1H-benzimidazol-1-yl)-5-oxazolyl]-N-[3-(4-morpholinyl)propyl]propionamide yield: 66%. a yellow oil. NMR(CDCl$_3$) delta: 1.5–1.7 (2H,m), 2.3–2.45 (6H,m), 2.63 (2H, t, J=7.5 Hz), 3.3–3.4 (4H,m), 3.55–3.65 (4H,m), 7.06 (1H, s), 7.4–7.55 (4H, m), 7.75 (2H, d, J=8.5 Hz), 7.85–7.9 (1H, m), 8.2–8.25 (1H, m), 8.57 (1H, s).

Example 188

3-[4-(4-chlorophenyl)-2-(1H-benzimidazol-1-yl)-5-oxazolyl]-N-[2-(1-piperidinyl)ethyl]propionamide yield: 55%. a yellow oil. NMR(CDCl$_3$) delta: 1.3–1.6 (4H,m), 2.25–2.45 (6H,m), 2.70 (2H, t, J=7.5 Hz), 3.3–3.4 (6H,m), 6.31 (1H, s), 7.4–7.55 (4H, m), 7.74 (2H, d, J=8.5 Hz), 7.85–7.9 (1H, m), 8.2–8.25 (1H, m), 8.58 (1H, s).

Example 189

3-[4-(4-chlorophenyl)-2-(1H-benzimidazol-1-yl)-5-oxazolyl]-N-[2-(1-pyrrolidinyl)ethyl]propionamide yield: 79%. a yellow oil. NMR(CDCl$_3$) delta: 1.9–2.1 (4H,m), 2.82 (2H, t, J=7.5 Hz), 2.9–3.1 (6H,m), 3.37 (2H, d,J=7.5 Hz), 3.5–3.6 (2H,m), 7.4–7.55 (4H, m), 7.76 (2H, d, J=8.5 Hz), 7.85–7.9 (1H, m), 8.25–8.3 (1H, m), 8.63 (1H, s).

Example 190

3-[4-(4-chlorophenyl)-2-(1H-benzimidazol-1-yl)-5-oxazolyl]-N-[3-(1-imidazolyl)propyl]propionamide yield: 59%. a yellow oil. NMR(CDCl$_3$) delta: 1.95–2.1 (2H,m), 2.65 (2H, t, J=7.5 Hz), 3.2–3.4 (4H,m), 3.9–4.0 (2H,m), 6.88 (1H,s), 7.11 (1H, s), 7.35–7.5 (4H,m), 7.74 (2H, d, J=8.5 Hz), 7.85–7.9 (1H, m), 8.2–8.25 (1H, m), 8.51 (1H, s).

Example 191

(3S)-1-{3-[2-(1H-benzimidazol-1-yl)-4-(4-chlorophenyl)-5-oxazolyl]propanoyl}-3-(trifluoroacetamide)pyrrolidine yield: 82%. colorless prism crystals, melting point: 190–191° C. (recrystallized from acetone-hexane).

Example 192

1-{3-[2-(1H-benzimidazol-1-yl)-4-(4-chlorophenyl)-5-oxazolyl]propanoyl}-4-piperidinol yield: 85%. colorless prism crystals, melting point: 182–183° C. (recrystallized from acetone-hexane).

Example 193

3-[2-(1H-benzimidazol-1-yl)-4-(4-chlorophenyl)-5-oxazolyl]-N-methyl-N-(1-methyl-4-piperidinyl)propionamide yield: 75%. colorless prism crystals, melting point: 133–134° C. (recrystallized from acetone-hexane).

Example 194

4-{3-[2-(1H-benzimidazol-1-yl)-4-(4-chlorophenyl)-5-oxazolyl]propanoyl}thiomorpholine-1,1-dioxide yield: 83%. colorless prism crystals, melting point: 227–228° C. (recrystallized from acetone-hexane).

Example 195

4-[2-(1H-benzimidazol-1-yl)-4-(4-chlorophenyl)-5-oxazolyl]-N-(5-bromo-2-fluorobenzyl)butanamide yield: 62%. colorless prism crystals, melting point: 196–198° C. (recrystallized from acetone-hexane).

Example 196

4-[2-(1H-benzimidazol-1-yl)-4-(4-chlorophenyl)-5-oxazolyl]-N-(4-methylbenzyl)butanamide yield: 60%. colorless prism crystals, melting point: 190–191° C. (recrystallized from acetone-hexane).

Example 197

4-[4-(4-chlorophenyl)-2-(1-pyrrolidinyl)-5-oxazolyl]-N-[4-(diethylphosphonomethyl)phenyl]butanamide yield: 25%. pale-yellow prism crystals, melting point: 127–128° C. (recrystallized from acetone-hexane).

Example 198

4-{4-(4-chlorophenyl)-2-[4-(2-pyridinyl)-1-piperazinyl]-5-oxazolyl}-N-[4-(diethylphosphonomethyl)phenyl]butanamide yield: 11%. pale-yellow prism crystals, melting point: 114–116° C. (recrystallized from acetone-hexane).

Example 199

4-{4-(4-chlorophenyl)-2-[4-(2-oxo-2,3-dihydro-1H-benzimidazol-1-yl)-1-piperazinyl]-5-oxazolyl}-N-[4-(diethylphosphonomethyl)phenyl]butanamide yield: 11%. pale-yellow prism crystals, melting point: 205–209° C. (recrystallized from acetone-hexane).

Example 200

4-[4-(4-chlorophenyl)-2-(N-benzyl-N-methylamino)-5-oxazolyl]-N-[4-(diethylphosphonomethyl)phenyl]butanamide yield: 39%. a yellow oil. NMR(CDCl$_3$) delta: 1.24 (6H, t,J=7 Hz), 2.05–2.15 (2H,m), 2.34 (2H,t,J=7 Hz), 2.88 (2H,t,J=7 Hz), 3.02 (3H,s), 3.11 (2H,d, J=22 Hz), 3.95–4.05 (4H,m), 4.61 (2H,s), 7.15–7.4 (12H,m), 7.57 (2H,d,J=8.5 Hz).

Example 201

3-[2-(1H-benzimidazol-1-yl)-4-(4-chlorophenyl)-5-thiazolyl]-N-[4-(diethylphosphonomethyl)phenyl]propionamide yield: 62%. colorless prism crystals, melting point: 150–151° C. (recrystallized from acetone-hexane).

Example 202

3-[2-(1H-benzimidazol-1-yl)-4-(4-chlorophenyl)-5-thiazolyl]-N-(5-bromo-2-fluorobenzyl)propionamide yield: 70%. colorless prism crystals, melting point: 188–189° C. (recrystallized from acetone-hexane).

Example 203

3-[2-(1H-benzimidazol-1-yl)-4-(4-chlorophenyl)-5-thiazolyl]-N-(4-methylbenzyl)propionamide yield: 70%. colorless prism crystals, melting point: 191–192° C. (recrystallized from tetrahydrofuran-hexane).

Example 204

3-[2-(1H-benzimidazol-1-yl)-4-phenyl-5-thiazolyl]-N-[4-(diethylphosphonomethyl)phenyl]propionamide yield: 64%. colorless prism crystals, melting point: 142–143° C. (recrystallized from acetone-hexane).

Example 205

1-{3-[4-(4-chlorophenyl)-2-(1H-benzimidazol-1-yl)-5-thiazolyl]propanoyl}-4-piperidinol yield: 92%. pale-yellow solid, HPLC analysis: purity 99.8% (retention time: 3.348 min.) MS (ESI+): 433 (M+H)

Example 206

1-{3-[4-(4-chlorophenyl)-2-(1H-benzimidazol-1-yl)-5-thiazolyl]propanoyl}thiomorpholine-1,1-dioxide yield: 92%. pale-yellow solid, HPLC analysis: purity 99.7% (retention time: 3.570 min.) MS (ESI+): 467 (M+H)

Example 207

1-{3-[4-(4-chlorophenyl)-2-(1H-benzimidazol-1-yl)-5-thiazolyl)propanoyl)thiomorpholine-1-oxide pale-yellow solid, HPLC analysis: purity 88.9% (retention time: 3.245 min.) MS (ESI+): 451 (M+H)

Example 208

(3S)-1-{3-[4-(4-chlorophenyl)-2-(1H-benzimidazol-1-yl)-5-thiazolyl}propanoyl)-3-(trifluoroacetamide)pyrrolidine yield: 92%. pale-yellow solid, HPLC analysis: purity 98.3% (retention time: 3.778 min.) MS (ESI+) : 514 (M+H)

Example 209

(2E)-3-[2-(1H-benzimidazol-1-yl)-4-methyl-5-thiazolyl)-N-[4-(diethylphosphonomethyl)phenyl]propenamide yield: 68%. colorless prism crystals, melting point: 150–151° C. (recrystallized from acetone-hexane).

Example 210

(2E)-3-[2-(1H-benzimidazol-1-yl)-4-tert-butyl-5-thiazolyl]-N-[4-(diethylphosphonomethyl)phenyl]propenamide yield: 67%. colorless prism crystals, melting point: 211–212° C. (recrystallized from acetone-hexane).

Example 211

(2E)-3-[2-(1H-benzimidazol-1-yl)-4-isopropyl-5-thiazolyl]-N-[4-(diethylphosphonomethyl)phenyl]propenamide yield: 49%. colorless prism crystals, melting point: 198–199° C. (recrystallized from acetone-hexane).

Example 212

(2E)-3-[2-(1H-benzimidazol-1-yl)-4-phenyl-5-thiazolyl]-N-[4-(diethylphosphonomethyl)phenyl]propenamide yield: 37%. yellow prism crystals, melting point: 229–230° C. (recrystallized from acetone-hexane).

Example 213

3-[2-(1H-benzimidazol-1-yl)-4-tert-butyl-5-thiazolyl]-N-[4-(diethylphosphonomethyl)phenyl]propionamide yield: 70%. colorless prism crystals, melting point: 155–156° C. (recrystallized from acetone-hexane).

Example 214

3-[2-(1H-benzimidazol-1-yl)-4-isopropyl-5-thiazolyl]-N-[4-(diethylphosphonomethyl)phenyl]propionamide yield: 71%. yellow prism crystals, melting point: 171–172° C. (recrystallized from acetone-hexane).

Example 215

4-[2-(1H-benzimidazol-1-yl)-4-(4-chlorophenyl)-5-thiazolyl]-N-[4-(diethylphosphonomethyl)phenyl]butanamide yield: 75%. colorless prism crystals, melting point: 140–141° C. (recrystallized from acetone-hexane).

Example 216

4-[2-(1H-benzimidazol-1-yl)-4-(4-chlorophenyl)-5-thiazolyl]-N-(5-bromo-2-fluorobenzyl)butanamide yield: 82%. colorless prism crystals, melting point: 160–161° C. (recrystallized from acetone-hexane).

Example 217

4-[2-(1H-benzimidazol-1-yl)-4-(4-chlorophenyl)-5-thiazolyl]-N-(4-methylbenzyl)butanamide yield: 73%. colorless prism crystals, melting point: 138–139° C. (recrystallized from acetone-hexane).

Example 218

2-[2-(1H-benzimidazol-1-yl)-4-(4-chlorophenyl)-5-thiazolyl]-N-[4-(diethylphosphonomethyl)phenyl]acetamide yield: 87%. colorless prism crystals, melting point: 154–155° C. (recrystallized from acetone-isopropyl ether).

Example 219

2-[2-(1H-benzimidazol-1-yl)-4-(4-chlorophenyl)-5-thiazolyl]-N-[4-(cyanomethyl)phenyl]acetamide yield: 75%. colorless prism crystals, melting point: 245–246° C. (recrystallized from tetrahydrofuran-isopropyl ether).

Example 220

6-[2-(1H-benzimidazol-1-yl)-4-(4-chlorophenyl)-5-thiazolyl]-N-[4-(diethylphosphonomethyl)phenyl]hexanamide yield: 70%. colorless prism crystals, melting point: 149–151° C. (recrystallized from ethanol-hexane).

Example 221

6-[4-(4-chlorophenyl)-2-phenyl-5-thiazolyl]-N-[4-(dimethylphosphonomethyl)phenyl]hexanamide yield: 81%. colorless prism crystals, melting point: 164–165° C. (recrystallized from ethanol-hexane).

Example 222

5-[2-(1H-benzimidazol-1-yl)-4-(4-chlorophenyl)-5-thiazolyl]-N-[4-(diethylphosphonomethyl)phenyl]pentanamide yield: 67%. colorless prism crystals, melting point: 168–169° C. (recrystallized from ethanol-hexane).

Example 223

5-[2-(1H-benzimidazol-1-yl)-4-(4-chlorophenyl)-5-thiazolyl]-N-[4-(cyanomethyl)phenyl]pentanamide yield: 68%. colorless prism crystals, melting point: 187–188° C. (recrystallized from ethanol-hexane).

Example 224

A mixture of 3-[2-chloro-4-(4-chlorophenyl)-5-oxazolyl]-N-[4-(diethylphosphonomethyl)phenyl]propionamide (0.40 g), imidazole (0.20 g), potassium carbonate (0.41 g) and N,N-dimethylformamide (5 ml) was stirred at 120° C. for 2 hrs. The reaction mixture was poured into water, and the precipitated crystals were collected by filtration through a glass filter. The obtained crystals were washed with water and dried by ventilation. Recrystallization from acetone-isopropyl ether gave 3-[4-(4-chlorophenyl)-2-(1-imidazolyl)-5-oxazolyl]-N-[4-(diethylphosphonomethyl)phenyl]propionamide as pale-yellow prism crystals (0.33 g, 78%). melting point: 196–197° C.

In the same manner as in Example 224, the compounds of Examples 225 and 226 were synthesized.

Example 225

3-[2-(1H-1,2,3-benzotriazole-1-yl)-4-(4-chlorophenyl)-5-oxazolyl]-N-[4-(diethylphosphonomethyl)phenyl]propionamide yield: 33%. pale-yellow prism crystals, melting point: 91–92° C. (recrystallized from acetone-isopropyl ether).

Example 226

4-[2-(1H-benzimidazol-1-yl)-4-(4-chlorophenyl)-5-oxazolyl]-N-[(4-diethylphosphonomethyl)phenyl]butanamide yield: 19%. pale-yellow prism crystals, melting point: 177–179° C. (recrystallized from acetone-isopropyl ether).

Example 227A

To a solution of 2-amino-4-(4-chlorophenyl)-5-thiazolepropionic acid (8.35 g), diethyl cyanophosphate (5.78 g) and diethyl 4-aminobenzylphosphonate (7.18 g) in N,N-dimethylformamide (100 ml) was added triethylamine (3.0 g) at 0° C. and the mixture was stirred at room temperature for 16 hrs.

The reaction mixture was poured into water, and the mixture was extracted with ethyl acetate. The ethyl acetate layer was washed with water, dried over anhydrous magnesium sulfate, and concentrated to give 3-[2-amino-4-(4-chlorophenyl)-5-thiazolyl]-N-[4-(diethylphosphonomethyl)phenyl]propionamide as crystals (8.28 g, 55%). Recrystallization from ethyl acetate-ethanol gave colorless prism crystals. melting point: 177–178° C.

Example 227B

A mixture of 3-[2-amino-4-(4-chlorophenyl)-5-thiazolyl]propionic acid (2.67 g), diethyl cyanophosphate (1.69 g), thiomorpholine-1,1-dioxide hydrochloride (1.62 g), triethylamine (2.9 ml) and N,N-dimethylformamide (40 ml) was stirred at room temperature for 3 hrs. The reaction mixture as poured into water, extracted with ethyl acetate, washed with 0.1N aqueous sodium hydroxide solution and water, dried over anhydrous magnesium sulfate and concentrated. The precipitated solid was collected by filtration to give 4-{3-[2-amino-4-(4-chlorophenyl)-5-thiazolyl]propanoyl}thiomorpholine-1,1-dioxide as a colorless powder. Recrystallization from ethanol-isopropyl ether gave colorless prism crystals. melting point: 220–222° C.

Example 228

A mixture of 3-[2-amino-4-(4-chlorophenyl)-5-thiazolyl]-N-[4-(diethylphosphonomethyl)phenyl]propionamide (500 mg), N,N-dimethylformamidedimethylacetal (155 mg) and N,N-dimethylformamide (10 ml) was stirred at room temperature for 1 hr. The reaction mixture was poured into water, and the mixture was extracted with ethyl acetate. The ethyl acetate layer was washed with water, dried over anhydrous magnesium sulfate, and concentrated. The residue was purified by silica gel column chromatography and 3-(4-(4-chlorophenyl)-2-{(E)-[(dimethylamino)methylidene]amino}-5-thiazolyl)-N-[4-(diethylphosphonomethyl)phenyl]propionamide was obtained as crystals (510 mg, yield: 92%) from a fraction eluted with 5% methanol-ethyl acetate. Recrystallization from ethyl acetate gave colorless prism crystals. melting point: 150–151° C.

Example 229

A mixture of 3-[2-amino-4-(4-chlorophenyl)-5-thiazolyl]-N-[4-(diethylphosphonomethyl)phenyl]propionamide (500 mg), pyridine-2-carboxylic acid (145 mg), 1-hydroxybenzotriazole (180 mg), 1-ethyl-3-(3-dimethylaminopropyl)carbodiimide hydrochloride (225 mg) and N,N-dimethylformamide (10 ml) was stirred at room temperature for 24 hrs. The reaction mixture was poured into water, and the mixture was extracted with ethyl acetate. The ethyl acetate layer was washed with water, dried over anhydrous magnesium sulfate, and concentrated to give 3-{4-(4-chlorophenyl)-2-[(2-pyridinylcarbonyl)amino)-5-thiazolyl}-N-[4-(diethylphosphonomethyl)phenyl]propionamide was obtained as crystals (560 mg). Recrystallization from ethyl acetate gave colorless prism crystals (350 mg, yield: 58%). melting point: 184–185° C.

Example 230

A mixture of 3-[2-amino-4-(4-chlorophenyl)-5-thiazolyl)-N-[4-(diethylphosphonomethyl)phenyl]propionamide (400 mg), tert-butyl isocyanate (780 mg) and toluene (10 ml) was stirred at 70–80° C. for 20 hrs. The reaction mixture was concentrated. The residue was purified by silica gel column chromatography and 3-(4-(4-chlorophenyl)-2-([(tert-butylamino)carbonyl]amino}-5-thiazolyl)-N-[4-(diethylphosphonomethyl)phenyl]propionamide was obtained as crystals (395 mg, yield: 83%) from a fraction eluted with 3% methanol-ethyl acetate. Recrystallization from ethyl acetate gave colorless prism crystals. melting point: 180–181° C.

In the same manner as in Examples 229 and 230, a reaction of 3-[2-amino-4-(4-chlorophenyl)-5-thiazolyl]-N-[4-(diethylphosphonomethyl)phenyl]propionamide with carboxylic acid or isocyanate (thio isocyanate) was carried out to synthesize the compounds of Examples 231–239.

Example 231

3-(4-(4-chlorophenyl)-2-{[(methylamino)carbonyl]amino}-5-thiazolyl)-N-[4-(diethylphosphonomethyl)phenyl]propionamide yield: 61%. colorless prism crystals, melting point: 206–207° C. (recrystallized from ethyl acetate).

Example 232

3-[4-(4-chlorophenyl)-2-({[(dimethylamino)methyl]carbonyl}amino)-5-thiazolyl]-N-[4-(diethylphosphonomethyl)phenyl]propionamide yield: 54%. amorphous. elemental analysis: for $C_{27}H_{34}ClN_4O_5PS \cdot 0.5H_2O$ Calculated C, 53.86; H, 5.86; N, 9.31. Found C, 53.97; H, 5.73; N, 9.41.

Example 233

3-(4-(4-chlorophenyl)-2-{[(benzylamino)carbonyl]amino}-5-thiazolyl)-N-[4-(diethylphosphonomethyl)phenyl]propionamide yield: 97%. colorless needle crystals, melting point: 144–145° C. (recrystallized from methanol-ethyl acetate).

Example 234

3-(4-(4-chlorophenyl)-2-{[(phenylamino)carbonyl]amino}-5-thiazolyl)-N-[4-(diethylphosphonomethyl)phenyl]propionamide yield: 91%. colorless prism crystals, melting point: 175–176° C. (recrystallized from methanol-ethyl acetate).

Example 235

3-{4-(4-chlorophenyl)-2-[(phenylsulfonyl)amino]-5-thiazolyl}-N-[4-(diethylphosphonomethyl)phenyl]propionamide yield: 91%. colorless needle crystals, melting point: 213–214° C. (recrystallized from methanol-ethyl acetate).

Example 236

3-[2-(benzoylamino)-4-(4-chlorophenyl)-5-thiazolyl]-N-[4-(diethylphosphonomethyl)phenyl]propionamide yield: 91%. colorless prism crystals, melting point: 171–172° C. (recrystallized from ethyl acetate-isopropyl ether).

Example 237

3-(4-(4-chlorophenyl)-2-{[(benzylamino)thiocarbonyl]amino}-5-thiazolyl)-N-[4-(diethylphosphonomethyl)phenyl]propionamide yield: 39%. colorless prism crystals, melting point: 202–203° C. (recrystallized from methanol-ethyl acetate).

Example 238

3-(4-(4-chlorophenyl)-2-{[(benzoylamino)thiocarbonyl]amino}-5-thiazolyl)-N-[4-(diethylphosphonomethyl)phenyl]propionamide yield: 72%. pale-yellow prism crystals, melting point: 208–209° C. (recrystallized from acetone-isopropyl ether).

Example 239

3-{4-(4-chlorophenyl)-2-[(3-phenylpropanoyl)amino)-5-thiazolyl}-N-[4-(diethylphosphonomethyl)phenyl]propionamide yield: 72%. pale-yellow prism crystals, melting point: 208–209° C. (recrystallized from acetone-isopropyl ether).

Example 240

A mixture of 3-[4-(4-chlorophenyl)-2-methyl-5-oxazolyl]propionic acid (50 mg), 1-hydroxy-7-aza-1H-1,2,3-benzotriazole (37 mg), 1-ethyl-3-(3-dimethylaminopropyl)carbodiimide (42 mg) and N,N-dimethylformamide (0.5 ml) was stirred overnight at room temperature. To the reaction mixture was added 0.1N aqueous hydrochloric acid solution (2 ml) and the reaction mixture was extracted with ethyl acetate (5 ml). The organic layer was concentrated and purified by Mega Bond Elut SCX (manufactured by Varian Inc.) (developing solvent: developed with ethyl acetate and then with 2M ammonia methanol solution) to give 3-[4-(4-chlorophenyl)-2-methyl-5-oxazolyl]-N-[4-(diethylphosphonomethyl)phenyl]propionamide (78.0 mg, yield 79%). Recrystallization from ethyl acetate-hexane gave colorless prism crystals. melting point: 155–156° C. MS (ESI+): 491 (M+H)

In the same manner as in Example 240, the compounds of Examples 241–258 were synthesized.

Example 241

4-{3-[4-(4-chlorophenyl)-2-methyl-5-oxazolyl]propanoyl}thiomorpholine-1,1-dioxide yield: 65%. colorless prism crystals, melting point: 124–125° C. (recrystallized from ethyl acetate-hexane). MS (ESI+): 383 (M+H)

Example 242

1-{3-[4-(4-chlorophenyl)-2-methyl-5-oxazolyl]propanoyl)-4-piperidinol yield: 74% HPLC analysis: purity 96.0% (retention time: 3.243 min.) MS (ESI+): 349 (M+H)

Example 243

3-[2-(1H-benzoimidazol-1-yl)-4-phenyl-5-oxazolyl]-N-[4-(diethylphosphonomethyl)phenyl]propionamide yield: 60%. yellow prism crystals, melting point: 148–149° C. (recrystallized from ethyl acetate-hexane). HPLC analysis: purity 95.3% (retention time: 4.045 min.) MS (ESI+): 559 (M+H)

Example 244

3-[2-(1H-benzoimidazol-1-yl)-4-(4-methoxyphenyl)-5-oxazolyl]-N-[4-(diethylphosphonomethyl)phenyl]propionamide yield: 31%. yellow prism crystals, melting point: 143–144° C. (recrystallized from ethyl acetate-hexane). HPLC analysis: purity 97.5% (retention time: 4.025 min.) MS (ESI+): 589 (M+H)

Example 245

4-{3-[2-(1H-benzoimidazol-1-yl)-4-phenyl-5-oxazolyl]propanoyl}thiomorpholine-1,1'-dioxide yield: 28%. colorless prism crystals, melting point: 177–179° C. (recrystallized from ethyl acetate-hexane). HPLC analysis: purity 98.5% (retention time: 3.727 min.) MS (ESI+): 451 (M+H)

Example 246

4-{3-[2-(1H-benzoimidazol-1-yl)-4-(4-methoxyphenyl)-5-oxazolyl]propanoyl}thiomorpholine-1,1'-dioxide yield: 44%. yellow prism crystals, melting point: 214–215° C. (recrystallized from ethyl acetate-hexane). HPLC analysis: purity 98.0% (retention time: 3.725 min.) MS (ESI+): 481 (M+H)

Example 247

1-{3-[2-(1H-benzoimidazol-1-yl)-4-phenyl-5-oxazolyl]propanoyl}-4-piperidinol yield: 61%. colorless prism crystals, melting point: 157–158° C. (recrystallized from ethyl acetate-hexane). HPLC analysis: purity 96.8% (retention time: 3.588 min.) MS (ESI+): 417 (M+H)

Example 248

1-(3-[2-(1H-benzoimidazol-1-yl)-4-(4-methoxyphenyl)-5-oxazolyl]propanoyl)-4-piperidinol yield: 46%. yellow prism crystals, melting point: 161–162° C. (recrystallized from ethyl acetate-hexane). HPLC analysis: purity 97.7% (retention time: 3.581 min.) MS (ESI+): 447 (M+H)

Example 249

1-{3-[2-(1H-benzoimidazol-1-yl)-4-phenyl-5-oxazolyl]propanoyl}-4-[(1-methyl-4-piperidinyl)methyl]piperazine yield: 11% HPLC analysis: purity 99.0% (retention time: 2.981 min.) MS (ESI+): 513 (M+H)

Example 250

1-{3-[2-(1H-benzoimidazol-1-yl)-4-(4-methoxyphenyl)-5-oxazolyl]propanoyl}-4-[(1-methyl-4-piperidinyl)methyl]piperazine yield: 17%. yellow prism crystals, melting point: dec. at 170° C. (recrystallized from ethyl acetate-hexane). HPLC analysis: purity 94.3% (retention time: 2.979 min.) MS (ESI+) : 543 (M+H)

Example 251

1-{3-[2-(1H-benzoimidazol-1-yl)-4-phenyl-5-oxazolyl]propanoyl}-4-[(1-methylpiperidin-3-yl)methyl]piperazine yield: 24% HPLC analysis: purity 95.3% (retention time: 2.976 min.) MS (ESI+): 513 (M+H)

Example 252

1-{3-[2-(1H-benzoimidazol-1-yl)-4-(4-methoxyphenyl)-5-oxazolyl]propanoyl}-4-[(1-methylpiperidin-3-yl)methyl]piperazine yield: 26%. yellow prism crystals, melting point: 151–152° C. (recrystallized from ethyl acetate-hexane). HPLC analysis: purity 96.6% (retention time: 2.981 min.) MS (ESI+): 543 (M+H)

Example 253

3-[2-(1H-benzoimidazol-1-yl)-4-(3-chlorophenyl)-5-oxazolyl]-N-[4-(diethylphosphonomethyl)phenyl]propionamide yield: 64%. yellow prism crystals, melting point: 98–99° C. (recrystallized from ethyl acetate-hexane). MS (ESI+): 593 (M+H)

Example 254

3-[2-(1H-benzoimidazol-1-yl)-4-(4-fluorophenyl)-5-oxazolyl]-N-[4-(diethylphosphonomethyl)phenyl]propionamide yield: 61%. yellow prism crystals, melting point: 95–96° C. (recrystallized from ethyl acetate-hexane). MS (ESI+): 577 (M+H)

Example 255

4-{3-[2-(1H-benzoimidazol-1-yl)-4-(3-chlorophenyl)-5-oxazolyl)propanoyl}thiomorpholine-1,1'-dioxide yield: 53%. colorless prism crystals, melting point: 186–187° C. (recrystallized from ethyl acetate-hexane). MS (ESI+): 485 (M+H)

Example 256

4-{3-[2-(1H-benzoimidazol-1-yl)-4-(4-fluorophenyl)-5-oxazolyl]propanoyl}thiomorpholine-1,1'-dioxide yield: 59%. colorless prism crystals, melting point: 224–225° C. (recrystallized from ethyl acetate-hexane). MS (ESI+): 469 (M+H)

Example 257

1-{3-[2-(1H-benzoimidazol-1-yl)-4-(3-chlorophenyl)-5-oxazolyl]propanoyl}-4-piperidinol yield: 63%. colorless prism crystals, melting point: 97–98° C. (recrystallized from ethyl acetate-hexane). MS (ESI+): 451 (M+H)

Example 258

1-{3-[2-(1H-benzoimidazol-1-yl)-4-(4-fluorophenyl)-5-oxazolyl]propanoyl}-4-piperidinol yield: 58%. yellow prism crystals, melting point: 158–159° C. (recrystallized from ethyl acetate-hexane). MS (ESI+): 435 (M+H)

Example 259

A mixture of thiazolidine (145 mg), 3-{3-[2-(1H-benzoimidazol-1-yl)-4-(4-chlorophenyl}-5-oxazolyl]propionic acid (300 mg), 1-hydroxy-7-aza-1H-1,2,3-benzotriazole (222 mg), 1-ethyl-3-(3-dimethylaminopropyl)carbodiimide (253 mg) and N,N-dimethylformamide (1 ml) was stirred overnight at room temperature. To the reaction mixture was added 0.1N aqueous hydrochloric acid solution (16 ml) and the reaction mixture was extracted with ethyl acetate (5 ml). The organic layer was concentrated, introduced into preparative HPLC and purified to give 3-{3-[2-(1H-benzoimidazol-1-yl)-4-(4-chlorophenyl)-5-oxazolyl]propanoyl}thiazolidine (165 mg, 46%). Recrystallization from ethyl acetate-hexane gave yellow prism crystals. melting point: 125–126° C.

HPLC analysis: purity 100% (retention time: 4.291 min.) MS (ESI+) : 439 (M+H)

In the same manner as in Example 259, the compounds of Examples 260–296 were synthesized.

Example 260

1-[(1-methyl-4-piperidinyl)methyl]-4-[3-(4-phenyl-5-oxazolyl)propanoyl]piperazine bis trifluoroacetate yield: 29% HPLC analysis: purity 93.1% (retention time: 2.168 min.) MS (ESI+): 397 (M+H)

Example 261

1-[(1-methyl-4-piperidinyl)methyl]-4-(3-{4-phenyl-2-[(E)-2-phenylethenyl]-5-oxazolyl}propanoyl)piperazine bis trifluoroacetate yield: 46% HPLC analysis: purity 79.1% (retention time: 2.998 min.) MS (ESI+): 499 (M+H)

Example 262

1-[2-methyl-3-(2-methyl-4-phenyl-5-oxazolyl)propanoyl]-4-[(1-methyl-4-piperidinyl)methyl]piperazine bis trifluoroacetate yield: 45% HPLC analysis: purity 100% (retention time: 2.307 min.) MS (ESI+): 425 (M+H)

Example 263

1-[2,2-dimethyl-3-(2-methyl-4-phenyl-5-oxazolyl)propanoyl]-4-[(1-methyl-4-piperidinyl)methyl]piperazine bis trifluoroacetate yield: 44% HPLC analysis: purity 100% (retention time: 2.350 min.) MS (ESI+): 439 (M+H)

Example 264

1-[(1-methyl-4-piperidinyl)methyl]-4-[3-(2-pentyl-4-phenyl-5-oxazolyl)propanoyl]piperazine bis trifluoroacetate yield: 47% HPLC analysis: purity 95.1% (retention time: 2.898 min.) MS (ESI+): 467 (M+H)

Example 265

1-{3-[4-(4-chlorophenyl)-2-(propylsulfanyl)-5-oxazolyl]propanoyl}-4-[(1-methyl-4-piperidinyl)methyl]piperazine bis trifluoroacetate yield: 33% HPLC analysis: purity 77.8% (retention time: 3.105 min.) MS (ESI+): 505 (M+H)

Example 266

1-[(1-methyl-4-piperidinyl)methyl]-4-{3-[2-methyl-4-(5,6,7,8-tetrahydro-2-naphthalenyl)-5-oxazolyl]propanoyl}piperazine bis trifluoroacetate yield: 22% HPLC analysis: purity 92.4% (retention time: 2.708 min.) MS (ESI+): 465 (M+H)

Example 267

1-{3-[4-(4-chlorophenyl)-2-(4-methyl-1-piperazinyl)-5-oxazolyl]propanoyl)-4-[(1-methyl-4-piperidinyl)methyl]piperazine tris trifluoroacetate yield: 38% HPLC analysis: purity 91.7% (retention time: 2.198 min.) MS (ESI+): 529 (M+H)

Example 268

1-{3-[4-(4-chlorophenyl)-2-(1-pyrrolidinyl)-5-oxazolyl]propanoyl}-4-[(l-methyl-4-piperidinyl)methyl]piperazine tris trifluoroacetate yield: 43% HPLC analysis: purity 86.9% (retention time: 2.180 min.) MS (ESI+): 500 (M+H)

Example 269

1-{3-[4-(4-chlorophenyl)-2-(cyclohexylamino)-5-oxazolyl]propanoyl}-4-[(1-methyl-4-piperidinyl)methyl]piperazine tris trifluoroacetate yield: 27% HPLC analysis: purity 91.7% (retention time: 2.582 min.) MS (ESI+): 528 (M+H)

Example 270

1-(3-{4-(4-chlorophenyl)-2-[(2-pyridinylmethyl)sulfanyl)-5-oxazolyl}propanoyl)-4-[(1-methyl-4-piperidinyl)methyl]piperazine tris trifluoroacetate yield: 44% HPLC analysis: purity 94.5% (retention time: 2.488 min.) MS (ESI+): 554 (M+H)

Example 271

1-(3-{4-(4-chlorophenyl)-2-[(4-methyl-pyrimidin-2-yl)sulfanyl]-5-oxazolyl}propanoyl)-4-[(1-methyl-4-piperidinyl)methyl]piperazine tris trifluoroacetate yield: 33% HPLC analysis: purity 92.2% (retention time: 2.874 min.) MS (ESI+): 555 (M+H)

Example 272

1-(3-{4-(4-chlorophenyl)-2-[(4-methyl-4H-1,2,4-triazol-3-yl)sulfanyl]-5-oxazolyl}propanoyl)-4-[(l-methyl-4-piperidinyl)methyl]piperazine tris trifluoroacetate yield: 42% HPLC analysis: purity 90.6% (retention time: 2.566 min.) MS (ESI+): 544 (M+H)

Example 273

1-{3-[4-(4-chlorophenyl)-2-(2-isopropyl-1H-imidazol-1-yl)-5-oxazolyl]propanoyl}-4-[(1-methyl-4-piperidinyl)methyl]piperazine tris trifluoroacetate yield: 45% HPLC analysis: purity 96.3% (retention time: 2.597 min.) MS (ESI+): 539 (M+H)

Example 274

1-{3-[4-(4-chlorophenyl)-2-(3,5-dimethyl-1H-pyrazol-1-yl)-5-oxazolyl]propanoyl}-4-[(1-methyl-4-piperidinyl)methyl]piperazine tris trifluoroacetate yield: 22% HPLC analysis: purity 86.3% (retention time: 3.028 min.) MS (ESI+): 525 (M+H)

Example 275

1-(3-(4-(4-chlorophenyl)-2-[2-(methylsulfonyl)-1H-imidazol-1-yl]-5-oxazolyl)propanoyl)-4-[(1-methyl-4-piperidinyl)methyl]piperazine tris trifluoroacetate yield: 38% HPLC analysis: purity 94.7% (retention time: 2.737 min.) MS (ESI+): 575 (M+H)

Example 276

1-(3-[2-(1,3-benzodioxol-5-yl)-4-(4-chlorophenyl)-5-oxazolyl]propanoyl}-4-[(1-methyl-4-piperidinyl)methyl]piperazine bis trifluoroacetate yield: 18% HPLC analysis: purity 82.2% (retention time: 3.711 min.) MS (ESI+): 551 (M+H)

Example 277

1-{3-[2-benzyl-4-(4-chlorophenyl)-5-oxazolyl]propanoyl}-4-[(1-methyl-4-piperidinyl)methyl]piperazine bis trifluoroacetate yield: 9% HPLC analysis: purity 92.9% (retention time: 3.003 min.) MS (ESI+): 521 (M+H)

Example 278

1-{3-[4-(4-chlorophenyl)-2-(2-naphthyl)-5-oxazolyl]propanoyl}-4-[(1-methyl-4-piperidinyl)methyl]piperazine bis trifluoroacetate yield: 14% HPLC analysis: purity 78.8% (retention time: 3.391 min.) MS (ESI+): 557 (M+H)

Example 279

1-{3-[4-(4-chlorophenyl)-2-(2-thienyl)-5-oxazolyl]propanoyl}-4-[(1-methyl-4-piperidinyl)methyl]piperazine bis trifluoroacetate yield: 43% HPLC analysis: purity 80.6% (retention time: 3.020 min.) MS (ESI+): 513 (M+H)

Example 280

1-{3-[4-(4-chlorophenyl)-2-propyl-5-oxazolyl]propanoyl}-4-[(1-methyl-4-piperidinyl)methyl]piperazine bis trifluoroacetate yield: 35% HPLC analysis: purity 94.4% (retention time: 2.825 min.) MS (ESI+): 473 (M+H)

Example 281

3-[4-(4-chlorophenyl)-2-(1-naphthyl)-5-oxazolyl]-N-[4-(diethylphosphonomethyl)phenyl]propionamide yield: 13% HPLC analysis: purity 99.4% (retention time: 4.846 min.) MS (ESI+): 603 (M+H) NMR(CDCl$_3$) delta: 1.12–1.22 (6H, m), 2.29 (2H, t, J=7.5 Hz), 3.07 (2H, t, J=21.5 Hz), 3.47 (2H, t, J=7.5 Hz), 3.88–4.02 (4H, m), 7.12–7.22 (2H, m), 7.38–7.68 (7H, m), 7.81 (2H, d, J=9 Hz), 7.92 (2H, dd, J=13, 8 Hz), 8.16 (1H, d, J=7 Hz), 9.35 (1H, d, J=8.5 Hz)

Example 282

3-[4-(4-chlorophenyl)-2-(3,4-dichlorophenyl)-5-oxazolyl]-N-[4-(diethylphosphonomethyl)phenyl]propionamide yield: 22% HPLC analysis: purity 100% (retention time: 4.785 min.) MS (ESI+): 621 (M+H)

Example 283

3-[4-(4-chlorophenyl)-2-(1-methyl-1H-indol-3-yl)-5-oxazolyl]-N-[4-(diethylphosphonomethyl)phenyl]propionamide yield: 56% HPLC analysis: purity 99.7% (retention time: 4.395 min.) MS (ESI+): 606 (M+H)

Example 284

3-[4-(4-chlorophenyl)-2-(1H-indazol-3-yl)-5-oxazolyl]-N-[4-(diethylphosphonomethyl)phenyl]propionamide yield: 35% HPLC analysis: purity 98.8% (retention time: 4.216 min.) MS (ESI+): 593 (M+H)

Example 285

1-{3-[4-(4-chlorophenyl)-2-(1-naphthyl)-5-oxazolyl]propanoyl}-4-piperidinol yield: 48% HPLC analysis: purity 99.0% (retention time: 4.428 min.) MS (ESI+): 461(M+H)

Example 286

1-{3-[4-(4-chlorophenyl)-2-(3,4-dichlorophenyl)-5-oxazolyl]propanoyl}-4-piperidinol yield: 39% HPLC analysis: purity 99.4% (retention time: 4.358 min.) MS (ESI+): 479 (M+H)

Example 287

1-{3-[4-(4-chlorophenyl)-2-(1-methyl-1H-indol-3-yl)-5-oxazolyl]propanoyl}-4-piperidinol yield: 45% HPLC analysis: purity 99.7% (retention time: 3.939 min.) MS (ESI+): 464 (M+H) NMR (CDCl$_3$) delta: 1.40–1.52 (2H, m), 1.80–1.92 (2H, m), 2.87 (2H, t, J=7.5Hz), 3.18–3.30 (2H, m), 3.36 (2H, t, J=7.5 Hz), 3.66–3.80 (2H, m), 3.91 (3H, s), 4.00–4.10 (1H, m), 7.30–7.46 (3H, m), 7.45 (2H, d, J=8.5 Hz) 7.71 (2H, d, J=8.5 Hz), 8.15 (1H, s), 8.18(1H, d, J=7 Hz)

Example 288

1-{3-[4-(4-chlorophenyl)-2-(1H-indazol-3-yl)-5-oxazolyl]propanoyl}-4-piperidinol yield: 4% HPLC analysis: purity 100% (retention time: 3.719 min.) MS (ESI+): 451 (M+H)

Example 289

4-{3-[4-(4-chlorophenyl)-2-(1-naphthyl)-5-oxazolyl]propanoyl}thiomorpholine-1,1'-dioxide yield: 9% HPLC analysis: purity 100% (retention time: 4.595 min.) MS (ESI+): 495 (M+H)

Example 290

4-{3-[4-(4-chlorophenyl)-2-(3,4-dichlorophenyl)-5-oxazolyl]propanoyl}thiomorpholine-1,1'-dioxide yield: 16% HPLC analysis: purity 100% (retention time: 4.530 min) MS (ESI+): 513 (M+H)

Example 291

4-{3-[4-(4-chlorophenyl)-2-(1-methyl-1H-indol-3-yl)-5-oxazolyl]propanoyl}thiomorpholine-1,1'-dioxide yield: 54% HPLC analysis: purity 99.5% (retention time: 4.166 min.) MS (ESI+): 498 (M+H)

Example 292

4-{3-[4-(4-chlorophenyl)-2-(1H-indazol-3-yl)-5-oxazolyl]propanoyl}thiomorpholine-1,1'-dioxide yield: 44% HPLC analysis: purity 100% (retention time: 3.977 min.) MS (ESI+): 485 (M+H)

Example 293

1-{3-[4-(4-chlorophenyl)-2-(1-naphthyl)-5-oxazolyl]propanoyl}-4-[(1-methyl-4-piperidinyl)methyl]piperazine yield: 59% HPLC analysis: purity 99.7% (retention time: 3.413 min.) MS (ESI+): 557 (M+H)

Example 294

1-(3-[4-(4-chlorophenyl)-2-(3,4-dichlorophenyl)-5-oxazolyl]propanoyl}-4-[(1-methyl-4-piperidinyl)methyl]piperazine yield: 61% HPLC analysis: purity 99.9% (retention time: 3.347 min.) MS (ESI+): 575 (M+H)

Example 295

1-(3-[4-(4-chlorophenyl)-2-(1-methyl-1H-indol-3-yl)-5-oxazolyl]propanoyl}-4-[(1-methyl-4-piperidinyl)methyl]piperazine yield: 45% HPLC analysis: purity 100% (retention time: 3.188 min.) MS (ESI+): 560 (M+H)

Example 296

1-{3-[4-(4-chlorophenyl)-2-(1H-indazol-3-yl)-5-oxazolyl]propanoyl}-4-[(1-methyl-4-piperidinyl)methyl]piperazine yield: 3% HPLC analysis: purity 100% (retention time: 3.141 min.) MS (ESI+): 547 (M+H)

Example 297

To a solution of diethyl bromodifluoromethylphosphonate (4.8 g) in N,N-dimethylacetamide (9 ml) was added zinc powder (1.17 g) under a nitrogen stream and the reaction mixture was stirred at room temperature for 2 hrs. Insoluble material was filtered off and copper(I) bromide (2.58 g) was added to the filtrate under a nitrogen stream. After stirring the reaction mixture at room temperature for 30 min, tert-butyl 4-iodophenylcarbamate (2.87 g) was added, and the mixture was stirred overnight. Ethyl acetate was added to the reaction mixture and the insoluble material was filtered off. The filtrate was concentrated, introduced into preparative HPLC and purified. Ethyl acetate was added and 4N hydrochloric acid ethyl acetate solution (3 ml) was added, and the mixture was stirred overnight at room temperature. The reaction mixture was concentrated and crystals were collected by filtration to give diethyl α,α-difluoro-4-aminobenzylphosphonate hydrochloride (250 mg, yield 10%).

A mixture of the obtained hydrochloride (100 mg), 3-{3-[2-(1H-benzoimidazol-1-yl)-4-(4-chlorophenyl)-5-oxazolyl]propionic acid (30 mg), 1-hydroxy-7-aza-1H-1,2,3-benzotriazole (22 mg), 1-ethyl-3-(3-dimethylaminopropyl)carbodiimide (29 mg) and N,N-dimethylformamide (0.5 ml) was stirred overnight at room temperature. To the reaction mixture was added 0.1N aqueous hydrochloric acid solution (1 ml) and the reaction mixture was extracted with ethyl acetate (2 ml). The organic layer was concentrated, introduced into preparative HPLC and purified to give 3-[2-(1H-benzoimidazol-1-yl)-4-(4-chlorophenyl)-5-oxazolyl]-N-{4-[(diethylphosphono)(difluoro)methyl]phenyl}propionamide (51.4 mg, yield 50%). Recrystallization from ethyl acetate-isopropyl ether gave yellow prism crystals. melting point: 155–156° C.

Example 298

A mixture of diethyl 4-amino-α-hydroxybenzylphosphonate (50 mg), 3-{3-[2-(1H-benzoimidazol-1-yl)-4-(4-chlorophenyl)-5-oxazolyl]propionic acid (54 mg), 1-hydroxy-7-aza-1H-1,2,3-benzotriazole (38 mg), 1-ethyl-3-(3-dimethylaminopropyl)carbodiimide (43 mg) and N,N-dimethylformamide (0.5 ml) was stirred overnight at room temperature. To the reaction mixture was added 0.1N aqueous hydrochloric acid solution (2 ml) and the reaction mixture was extracted with ethyl acetate (2 ml). The organic layer was concentrated, introduced into preparative HPLC and purified to give 3-[2-(1H-benzoimidazol-1-yl)-4-(4-chlorophenyl)-5-oxazolyl]-N-(4-[(diethylphosphono)(hydroxy)methyl]phenyl}propionamide (52 mg, 58%). Recrystallization from ethyl acetate-isopropyl ether gave yellow prism crystals. melting point: 171–172° C. MS (ESI+): 609 (M+H)

In the same manner as in Example 298, the compounds of Examples 299–342 were synthesized.

Example 299

3-[2-(1H-benzoimidazol-1-yl)-4-(4-chlorophenyl)-5-oxazolyl]-N-{4-[(diethylphosphono)(methoxy)methyl]phenyl}propionamide yield: 65%. colorless prism crystals, melting point: 191–192° C. (recrystallized from ethyl acetate-isopropyl ether).
MS (ESI+): 623 (M+H)

Example 300

1-{3-[2-(1H-benzoimidazol-1-yl)-4-(4-chlorophenyl)-5-oxazolyl]propanoyl}-3-piperidinol yield 81%. colorless prism crystals, melting point: 104–105° C. (recrystallized from ethyl acetate-isopropyl ether).
MS (ESI+): 451 (M+H)

Example 301

3-[2-(1H-benzoimidazol-1-yl)-4-(4-chlorophenyl)-5-oxazolyl]-N-[2-(ethylsulfonyl)ethyl]propanamide yield 54%. colorless prism crystals, melting point: 182–183° C. (recrystallized from ethyl acetate-isopropyl ether). MS (ESI+): 487 (M+H)

Example 302

3-[2-(1H-benzoimidazol-1-yl)-4-(4-chlorophenyl)-5-oxazolyl]-N-[2-(methylsulfonyl)ethyl]propanamide was obtained.

yield 62%. colorless prism crystals, melting point: 194–195° C. (recrystallized from ethyl acetate-isopropyl ether). MS (ESI+): 473 (M+H)

Example 303

3-[2-(1H-benzoimidazol-1-yl)-4-(4-chlorophenyl)-5-oxazolyl]-N-[2-(methylsulfonyl)ethyl]-N-methylpropanamide yield 85%. colorless prism crystals, melting point: 141–142° C. (recrystallized from ethyl acetate-isopropyl ether). MS (ESI+): 487 (M+H)

Example 304

3-[2-(1H-benzoimidazol-1-yl)-4-(4-chlorophenyl)-5-oxazolyl]-N-(4-hydroxycyclohexyl)propanamide yield 70%. colorless prism crystals, melting point: 204–206° C. (recrystallized from ethyl acetate-isopropyl ether). MS (ESI+): 465 (M+H)

Example 305

(1-{3-[2-(1H-benzoimidazol-1-yl)-4-(4-chlorophenyl)-5-oxazolyl]propanoyl}-4-piperidinyl)methanol yield 86%. yellow prism crystals, melting point: 101–102° C. (recrystallized from ethyl acetate-isopropyl ether). MS (ESI+): 465 (M+H)

Example 306

1-{3-[2-(1H-benzoimidazol-1-yl)-4-(4-chlorophenyl)-5-oxazolyl]propanoyl}-4-bromopiperidine yield 78%. colorless prism crystals, melting point: 116–117° C. (recrystallized from ethyl acetate-isopropyl ether). MS (ESI+): 514 (M+H)

Example 307

1-{3-[2-(1H-benzoimidazol-1-yl)-4-(4-chlorophenyl)-5-oxazolyl]propanoyl}-4-(methylsulfonyl)piperidine yield 80%. colorless prism crystals, melting point: 215–216° C. (recrystallized from ethyl acetate-isopropyl ether). MS (ESI+): 513 (M+H)

Example 308

3-[2-(1H-benzoimidazol-1-yl)-4-(4-chlorophenyl)-5-oxazolyl]-N-(1,1-dioxidetetrahydro-2H-thiopyran-4-yl)propanamide yield 52%. yellow prism crystal, melting point: 236–238° C. (recrystallized from ethyl acetate-isopropyl ether). MS (ESI+): 499 (M+H)

Example 309

4-{3-[2-(1H-benzoimidazol-1-yl)-4-chlorophenyl-5-oxazolyl]propanoyl}1,4-thiazepan-1,1'-dioxide yield 90%. yellow prism crystals, melting point: 142–144° C. (recrystallized from ethyl acetate-isopropyl ether). MS (ESI+): 499 (M+H)

Example 310

1-(3-{4-phenyl-2-[(E)-2-phenylethenyl]-5-oxazolyl}propanoyl)-4-piperidinol yield: 27% HPLC analysis: purity 83.5% (retention time: 3.792 min.) MS (ESI+): 403 (M+H)

Example 311

1-{3-[4-(4-chlorophenyl)-2-(propylsulfanyl)-5-oxazolyl]propanoyl}-4-piperidinol yield: 49% HPLC analysis: purity 98.6% (retention time: 4.009 min.) MS (ESI+): 409 (M+H)

Example 312

1-{3-[4-(4-chlorophenyl)-2-(1-methylcyclohexyl)-5-oxazolyl]propanoyl}-4-piperidinol yield: 39% HPLC analysis: purity 96.3% (retention time: 4.360 min.) MS (ESI+): 431 (M+H)

Example 313

1-{3-[4-(4-chlorophenyl)-2-(cyclohexylsulfanyl)-5-oxazolyl]propanoyl}-4-piperidinol yield: 61% HPLC analysis: purity 96.6% (retention time: 4.491 min.) MS (ESI+): 449 (M+H)

Example 314

1-(3-{4-(4-chlorophenyl)-2-[(2-pyridinylmethyl)sulfanyl]-5-oxazolyl}propanoyl)-4-piperidinol yield: 21% HPLC analysis: purity 94.8% (retention time: 2.909 min.) MS (ESI+): 458 (M+H)

Example 315

1-{3-[4-(4-chlorophenyl)-2-(2-isopropyl-1H-imidazol-1-yl)-5-oxazolyl]propanoyl}-4-piperidinol yield: 82% HPLC analysis: purity 95.7% (retention time: 3.013 min.) MS (ESI+): 443 (M+H)

Example 316

1-(3-{4-(4-chlorophenyl)-2-[2-(methylsulfonyl)-1H-imidazol-1-yl]-5-oxazolyl}propanoyl)-4-piperidinol yield: 35% HPLC analysis: purity 96.3% (retention time: 3.316 min.) MS (ESI+): 479 (M+H)

Example 317

1-{3-[4-(4-chlorophenyl)-2-(3,5-dimethyl-1H-pyrazol-1-yl)-5-oxazolyl]propanoyl}-4-piperidinol yield: 44% HPLC analysis: purity 97.5% (retention time: 3.760 min.) MS (ESI+): 429 (M+H)

Example 318

1-{3-[2-benzyl-4-(4-chlorophenyl)-5-oxazolyl]propanoyl}-4-piperidinol yield: 7% HPLC analysis: purity 91.1% (retention time: 3.806 min.) MS (ESI+): 425 (M+H)

Example 319

1-{3-[4-(4-chlorophenyl)-2-(2-thienyl)-5-oxazolyl]propanoyl}-4-piperidinol yield: 12% HPLC analysis: purity 93.5% (retention time: 3.873 min.) MS (ESI+): 417 (M+H)

Example 320

1-{3-[4-(4-chlorophenyl)-2-propyl-5-oxazolyl]propanoyl}-4-piperidinol yield: 25% HPLC analysis: purity 97.2% (retention time: 3.544 min.) MS (ESI+): 377 (M+H)

Example 321

4-(3-{4-phenyl-2-[(E)-2-phenylethenyl]-5-oxazolyl}propanoyl)thiomorpholine-1,1-dioxide yield: 40% HPLC analysis: purity 99.0% (retention time: 4.038 min.) MS (ESI+): 437 (M+H)

Example 322

4-{3-[4-(4-chlorophenyl)-2-(propylsulfanyl)-5-oxazolyl]propanoyl}thiomorpholine-1,1-dioxide yield: 48% HPLC analysis: purity 100% (retention time: 4.285 min.) MS (ESI+): 443 (M+H)

Example 323

4-{3-[4-(4-chlorophenyl)-2-(1-methylcyclohexyl)-5-oxazolyl]propanoyl}thiomorpholine-1,1-dioxide yield: 47% HPLC analysis: purity 100% (retention time: 4.588 min.) MS (ESI+): 465 (M+H)

Example 324

4-{3-[4-(4-chlorophenyl)-2-(cyclohexylsulfanyl)-5-oxazolyl]propanoyl}thiomorpholine-1,1-dioxide yield: 31% HPLC analysis: purity 100% (retention time: 4.689 min.) MS (ESI+): 483 (M+H)

Example 325

4-{3-[4-(4-chlorophenyl)-2-(cyclohexylamino)-5-oxazolyl]propanoyl}thiomorpholine-1,1-dioxide yield: 35% HPLC analysis: purity 87.6% (retention time: 3.209 min.) MS (ESI+): 466 (M+H)

Example 326

4-(3-{4-(4-chlorophenyl)-2-[(2-pyridinylmethyl)sulfanyl]-5-oxazolyl}propanoyl)thiomorpholine-1,1-dioxide yield: 42% HPLC analysis: purity 99.8% (retention time: 3.073 min.) MS (ESI+): 492 (M+H)

Example 327

4-(3-{4-(4-chlorophenyl)-2-[(4-methyl-4H-1,2,4-triazol-3-yl)sulfanyl]-5-oxazolyl}propanoyl)thiomorpholine-1,1-dioxide yield: 32% HPLC analysis: purity 99.8% (retention time: 3.204 min.) MS (ESI+): 482 (M+H)

Example 328

4-{3-[4-(4-chlorophenyl)-2-(2-isopropyl-1H-imidazol-1-yl)-5-oxazolyl]propanoyl}thiomorpholine-1,1-dioxide yield: 59% HPLC analysis: purity 100% (retention time: 3.171 min.) MS (ESI+): 477 (M+H)

Example 329

4-(3-{4-(4-chlorophenyl)-2-[2-(hydroxymethyl)-1H-imidazol-1-yl]-5-oxazolyl}propanoyl)thiomorpholine-1,1-dioxide yield: 19% HPLC analysis: purity 99.6% (retention time: 2.893 min.) MS (ESI+): 465 (M+H)

Example 330

4-{3-[2-(4-tert-butylphenoxy)-4-(4-chlorophenyl)-5-oxazolyl]propanoyl}thiomorpholine-1,1-dioxide yield: 28% HPLC analysis: purity 93.1% (retention time: 4.856 min.) MS (ESI+): 517 (M+H)

Example 331

4-(3-{4-(4-chlorophenyl)-2-[2-(methylsulfonyl)-1H-imidazol-1-yl]-5-oxazolyl}propanoyl)thiomorpholine-1,1-dioxide yield: 14% HPLC analysis: purity 100% (retention time: 3.559 min.) MS (ESI+): 513 (M+H)

Example 332

4-{3-[4-(4-chlorophenyl)-2-(4-methyl-1-piperazinyl)-5-oxazolyl]propanoyl}thiomorpholine-1,1-dioxide yield: 25% HPLC analysis: purity 88.3% (retention time: 2.754 min.) MS (ESI+): 467 (M+H)

Example 333

4-{3-[4-(4-chlorophenyl)-2-(3,5-dimethyl-1H-pyrazol-1-yl)-5-oxazolyl]propanoyl}thiomorpholine-1,1-dioxide yield: 39% HPLC analysis: purity 100% (retention time: 4.033 min.) MS (ESI+): 463 (M+H)

Example 334

4-{3-[2-benzyl-4-(4-chlorophenyl)-5-oxazolyl]propanoyl}thiomorpholine-1,1-dioxide yield: 50% HPLC analysis: purity 99.8% (retention time: 4.043 min.) MS (ESI+): 459 (M+H)

Example 335

4-{3-[4-(4-chlorophenyl)-2-(2-thienyl)-5-oxazolyl]propanoyl}thiomorpholine-1,1-dioxide yield: 31% HPLC analysis: purity 99.0% (retention time: 4.115 min.) MS (ESI+): 451 (M+H)

Example 336

4-(3-[4-(4-chlorophenyl)-2-propyl-5-oxazolyl]propanoyl}thiomorpholine-1,1-dioxide yield: 25% HPLC analysis: purity 100% (retention time: 3.816 min.) MS (ESI+): 411 (M+H)

Example 337

3-[4-(4-chlorophenyl)-2-(1-methyl-1H-indol-2-yl)-5-oxazolyl]-N-[4-(diethylphosphonomethyl)phenyl]propionamide yield: 48% HPLC analysis: purity 100% (retention time: 4.958 min.) MS (ESI+): 606 (M+H)

Example 338

3-[4-(4-chlorophenyl)-2-(1H-indazol-1-yl)-5-oxazolyl]-N-[4-(diethylphosphonomethyl)phenyl]propionamide yield: 78% HPLC analysis: purity 99.7% (retention time: 4.576 min.) MS (ESI+): 593 (M+H)

Example 339

4-{3-[4-(4-chlorophenyl)-2-(1-methyl-1H-indol-2-yl)-5-oxazolyl]propanoyl}thiomorpholine-1,1'-dioxide yield: 73% HPLC analysis: purity 100% (retention time: 4.724 min.) MS (ESI+): 498 (M+H)

Example 340

4-{3-[4-(4-chlorophenyl)-2-(1H-indazol-1-yl)-5-oxazolyl]propanoyl}thiomorpholine-1,1'-dioxide yield: 71% HPLC analysis: purity 93.8% (retention time: 4.347 min.) MS (ESI+): 485 (M+H)

Example 341

1-{3-[4-(4-chlorophenyl)-2-(1-methyl-1H-indol-2-yl)-5-oxazolyl]propanoyl}-4-piperidinol yield: 51% HPLC analysis: purity 99.2% (retention time: 4.374 min.) MS (ESI+): 464 (M+H)

Example 342

1-{3-[4-(4-chlorophenyl)-2-(1-methyl-1H-indol-2-yl)-5-oxazolyl]propanoyl}-4-piperidinol yield: 65% HPLC analysis: purity 98.9% (retention time: 4.067 min.) MS (ESI+): 451 (M+H)

Example 343

To a mixture of 3-{3-[2-(1H-benzoimidazol-1-yl)-4-(4-chlorophenyl)-5-oxazolyl]propanoyl}thiazolidine (25 mg) and tetrahydrofuran (10 mL) was added m-chloroperbenzoic acid (14.4 mg) with stirring under ice-cooling, and the mixture was stirred overnight at room temperature. The reaction mixture was poured into water, and the mixture was extracted with ethyl acetate. The ethyl acetate layer was washed with saturated aqueous sodium hydrogen carbonate and then with saturated brine, dried (MgSO$_4$) and concentrated. The residue was introduced into preparative HPLC and purified to give 3-{3-[2-(1H-benzoimidazol-1-yl)-4-(4-chlorophenyl)-5-oxazolyl]propanoyl}thiazolidine-1-oxide (7.3 mg, yield 28%).

HPLC analysis: purity 98.5% (retention time: 3.628 min.)
MS (ESI+): 455 (M+H)

Example 344

To a mixture of 3-{3-[2-(1H-benzoimidazol-1-yl)-4-(4-chlorophenyl)-5-oxazolyl]propanoyl}thiazolidine (25 mg) and tetrahydrofuran (10 mL) was added m-chloroperbenzoic acid (28.8 mg) with stirring under ice-cooling, and the mixture was stirred overnight at room temperature. The reaction mixture was poured into water, and the mixture was extracted with ethyl acetate. The ethyl acetate layer was washed with saturated aqueous sodium hydrogen carbonate and then with saturated brine, dried (MgSO$_4$) and concentrated. The residue was introduced into preparative HPLC and purified to give 3-{3-[2-(1H-benzoimidazol-1-yl)-4-(4-chlorophenyl)-5-oxazolyl]propanoyl}thiazolidine-1,1-dioxide (10.7 mg, yield 40%). Recrystallization from ethyl acetate-hexane gave yellow prism crystals. melting point: 136–137° C.

HPLC analysis: purity 94.8% (retention time: 4.053 min.)
MS (ESI+): 471 (M+H)

Example 345

A mixture of 4-[(diethylphosphono)(fluoro)methyl]nitrobenzene (74 mg), 10% Pd—C (10 mg) and ethanol (2 ml) was stirred at room temperature under a hydrogen stream for 1 hr. Pd—C was removed from the reaction mixture by filtration and the filtrate was concentrated. To the residue were added 3-{3-[2-(1H-benzoimidazol-1-yl)-4-(4-chlorophenyl)-5-oxazolyl]propanoic acid (25 mg), 1-hydroxy-7-aza-1H-1,2,3-benzotriazole (20 mg), 1-ethyl-3-(3-dimethylaminopropyl)carbodiimide (27 mg) and N,N-dimethylformamide (0.5 ml), and the mixture was stirred overnight at room temperature. The reaction mixture was poured into water, and the mixture was extracted with ethyl acetate. The ethyl acetate layer was concentrated, introduced into preparative HPLC and purified to give 3-[2-(1H-benzoimidazol-1-yl)-4-(4-chlorophenyl)-5-oxazolyl]-N-{4-[(diethylphosphono)(fluoro)methyl]phenyl}propionamide. Recrystallization from ethyl acetate-isopropyl ether gave colorless prism crystals (5 mg, yield 12%). melting point: 152–155° C.

MS (ESI+): 611 (M+H)

Example 346

A mixture of 3-[4-(4-chlorophenyl)-2-propyl-5-oxazolyl]propionic acid (41.7 mg), 1-hydroxy-7-aza-1H-1,2,3-benzotriazole (41 mg), 1-ethyl-3-(3-dimethylaminopropyl)carbodiimide (46 mg), 4-[(1-methyl-4-piperidinyl)methyl]piperazine (60 mg) and N,N-dimethylformamide (0.5 ml) was stirred overnight at room temperature. The reaction mixture was poured into water, and the mixture was extracted with ethyl acetate. The ethyl acetate layer was concentrated, introduced into preparative HPLC and purified. To the obtained oil was added ethyl acetate, and the mixture was washed with saturated aqueous sodium hydrogen carbonate. A 4N hydrochloric acid ethyl acetate solution was added to the ethyl acetate layer and the mixture was concentrated to give 1-{3-[4-(4-chlorophenyl)-2-propyl-5-oxazolyl]propanoyl}-4-[(1-methyl-4-piperidinyl)methyl]piperazine dihydrochloride (25.0 mg, yield 32%). Recrystallization from ethanol-isopropyl ether gave colorless prism crystals. melting point: 218° c (dec.).

MS (ESI+): 473 (M+H)

Example 347

A mixture of 3-[4-(4-chlorophenyl)-2-(3,5-dimethyl-1H-pyrazol-1-yl)-5-oxazolyl]propionic acid (51.5 mg), 1-hydroxy-7-aza-1H-1,2,3-benzotriazole (41 mg), 1-ethyl-3-(3-dimethylaminopropyl)carbodiimide (46 mg), 4-[(1-methyl-4-piperidinyl)methyl]piperazine (60 mg) and N,N-dimethylformamide (0.5 ml) was stirred overnight at room temperature. The reaction mixture was poured into water and extracted with ethyl acetate. The ethyl acetate layer was concentrated, introduced into preparative HPLC and purified. Ethyl acetate was added to the obtained oil and the mixture was washed with saturated aqueous sodium hydrogen carbonate. The ethyl acetate layer was washed with saturated brine, dried (MgSO$_4$), and concentrated to give 1-{3-[4-(4-chlorophenyl)-2-(3,5-dimethyl-1H-pyrazol-1-yl)-5-oxazolyl]propanoyl}-4-[(1-methyl-4-piperidinyl)methyl]piperazine (54.5 mg, yield 72%). Recrystallization from ethanol-isopropyl ether gave colorless prism crystals. melting point: 126–127° c.

MS (ESI+): 525 (M+H)

Example 348

A mixture of 3-{4-(4-chlorophenyl)-2-[2-(methylsulfonyl)-1H-imidazol-1-yl]-5-oxazolyl}propionic acid (50 mg), 1-hydroxy-7-aza-1H-1,2,3-benzotriazole (41 mg), 1-ethyl-3-(3-dimethylaminopropyl)carbodiimide (46 mg), 4-[(1-methyl-4-piperidinyl)methyl]piperazine (60 mg) and N,N-dimethylformamide (0.5 ml) was stirred overnight at room temperature. The reaction mixture was poured into water, and the mixture was extracted with ethyl acetate. The ethyl acetate layer was concentrated, introduced into preparative HPLC and purified. Ethyl acetate was added to the obtained oil and the mixture was washed with saturated aqueous sodium hydrogen carbonate. A 4N hydrochloric acid ethyl acetate solution was added to the ethyl acetate layer and the mixture was concentrated to give 1-(3-{4-(4-chlorophenyl)-2-[2-(methylsulfonyl)-1H-imidazol-1-yl]-5-oxazolyl}propanoyl)-4-[(1-methyl-4-piperidinyl)methyl]piperazine 3 hydrochloric acid (65.0 mg, yield 66%).

HPLC analysis: purity 100% (retention time: 2.737 min.)
MS (ESI+): 575 (M+H)

Example 349

A mixture of 2-(1H-benzimidazol-1-yl)-4-(4-chlorophenyl)-5-oxazolepropionic acid (19 mg), (S)-3-(N-Boc-amino) pyrrolidine (10 mg), 1-hydroxybenzotriazole (8 mg), 1-ethyl-3-(3-dimethylaminopropyl)carbodiimide hydrochloride (10 mg) and N,N-dimethylformamide (1 ml) was shaken at room temperature for 8 hrs. The reaction mixture was poured into water, and the mixture was extracted with ethyl acetate. The ethyl acetate layer was filtered and concentrated. The residue was dissolved in 4N hydrochloric acid ethyl acetate solution, left standing for 5 min. and concentrated. To the residue were added benzoic acid (10 mg), 1-hydroxy-7-azabenzotriazole (8 mg), 1-ethyl-3-(3-dimethylaminopropyl)carbodiimide hydrochloride (10 mg) and N,N-dimethylformamide (1 ml), and the mixture was shaken at room temperature for 16 hrs. The reaction mixture was directly introduced into preparative HPLC and purified to give the object compound.

Examples 350–394

In the same manner as in Example 349, the object compounds were obtained.

The structure and purity of the object compounds of Examples 349–394 were confirmed by LC-MS, HPLC. The yield, structure, purity and mass spectrum data of the object compounds are shown in [Table 1-1]–[Table 1-4].

TABLE 1-1 basic structure

Rx―C(=O)―Ry

| Ry | Rx | |
|---|---|---|
| phenyl (*) | Example 349<br>19.5 mg, 99%<br>540 (M + 1) | Example 350<br>22.7 mg, 98%<br>540 (M + 1) |
| 2-furyl | Example 354<br>16.6 mg, 99%<br>530 (M + 1) | Example 355<br>17.2 mg, 98%<br>530 (M + 1) |
| N-methylpyrrolyl | Example 360<br>16.9 mg, 99%<br>543 (M + 1) | Example 361<br>18.8 mg, 99%<br>543 (M + 1) |
| 3-furyl | Example 366<br>15.1 mg, 99%<br>530 (M + 1) | Example 367<br>18.1 mg, 95%<br>530 (M + 1) |

| Ry | Rx |
|---|---|
| phenyl | Example 351<br>19.4 mg, 99%<br>554 (M + 1) |

TABLE 1-1-continued
basic structure
| Ry | | |
|---|---|---|
| 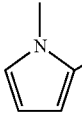 | Example 356<br>14.4 mg, 98%<br>544 (M + 1) | |
| 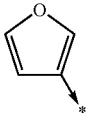 | Example 362<br>14.3 mg, 98%<br>557 (M + 1) | |
| 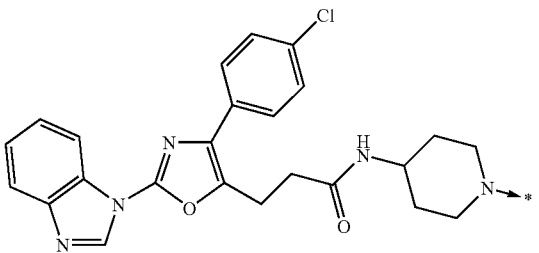 | Example 368<br>15.9 mg, 95%<br>544 (M + 1) | |
upper line: Example No.
middle line: yield, LC-MS purity (220 nm)
lower line: MS (ESI+, m/e)
TABLE 1-2
basic structure
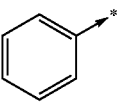
| Ry | Rx |
|---|---|
| 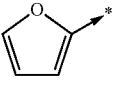 | 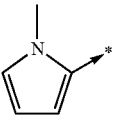 |
| 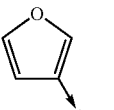 | |
| Example 357<br>3.1 mg, 98%<br>544 (M + 1) | |
| Example 363<br>14.3 mg, 95%<br>557 (M + 1) | |
| Example 369<br>6.7 mg, 95%<br>544 (M + 1) | |

TABLE 1-2-continued basic structure

Rx—C(=O)—Ry

| Ry | Rx |
|---|---|
| (4-chlorophenyl-benzimidazolyl-oxazole with propanamide-N-butyl-NH* linker) | |
| phenyl | Example 352<br>15.3 mg, 95%<br>542 (M + 1) |
| furan-2-yl | Example 358<br>16.8 mg, 99%<br>532 (M + 1) |
| 1-methylpyrrol-2-yl | Example 364<br>16.2 mg, 95%<br>545 (M + 1) |
| furan-3-yl | Example 370<br>16.4 mg, 98%<br>532 (M + 1) |

| Ry | Rx |
|---|---|
| (4-chlorophenyl-benzimidazolyl-oxazole with propanamide-N-ethyl-NH* linker) | |
| phenyl | Example 353<br>23.2 mg, 99%<br>514 (M + 1) |
| furan-2-yl | Example 359<br>18.1 mg, 99%<br>504 (M + 1) |
| 1-methylpyrrol-2-yl | Example 365<br>18.2 mg, 97%<br>517 (M + 1) |

TABLE 1-2-continued
basic structure
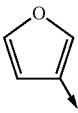
| Rx | Example |
|---|---|
| 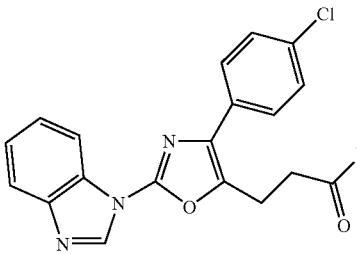 | Example 371<br>12.2 mg, 98%<br>504 (M + 1) |
upper line: Example No.
middle line: yield, LC-MS purity (220 nm)
lower line: MS (ESI+, m/e)
TABLE 1-3
basic structure
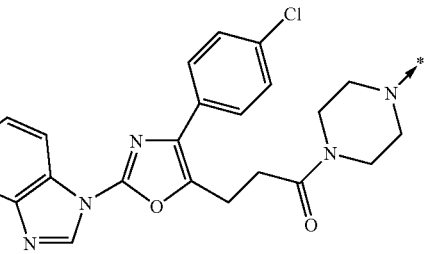
| Ry | Rx: 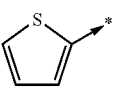 | Rx: 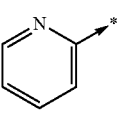 |
|---|---|---|
| 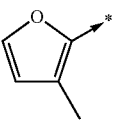 | Example 372<br>20.1 mg, 99%<br>546 (M + 1) | Example 373<br>22.9 mg, 98%<br>546 (M + 1) |
| 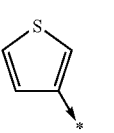 | Example 377<br>23.6 mg, 94%<br>541 (M + 1) | Example 378<br>28.1 mg, 97%<br>541 (M + 1) |
| | Example 383<br>23 mg, 99%<br>544 (M + 1) | Example 384<br>22.6 mg, 98%<br>544 (M + 1) |
| | Example 389<br>21.6 mg, 92%<br>546 (M + 1) | Example 390<br>20 mg, 99%<br>546 (M + 1) |

TABLE 1-3-continued basic structure

Rx—C(=O)—Ry

| Ry | Rx |
|---|---|
| | [benzimidazole-oxazole-(4-chlorophenyl)-piperidin-4-ylamine structure with NH—* attachment] |

| Ry | Rx | |
|---|---|---|
| thiophen-2-yl—* | | Example 374<br>18.2 mg, 98%<br>560 (M + 1) |
| pyridin-2-yl—* | | Example 379<br>18.4 mg, 98%<br>555 (M + 1) |
| 3-methylfuran-2-yl—* | | Example 385<br>19.6 mg, 98%<br>558 (M + 1) |
| thiophen-3-yl—* | | Example 391<br>16.9 mg, 97%<br>560 (M + 1) | upper line: Example No.
middle line: yield, LC-MS purity (220 nm)
lower line: MS (ESI+, m/e)

TABLE 1-4 basic structure

Rx—C(=O)—Ry

| Ry | Rx |
|---|---|
| | [benzimidazole-oxazole-(4-chlorophenyl)-propanamide-N-piperidin-4-yl structure with N—* attachment] |

TABLE 1-4-continued basic structure

Rx—C(=O)—Ry

| Rx group | Example info |
|---|---|
| thiophen-2-yl | |
| pyridin-2-yl | Example 380<br>4.4 mg, 90%<br>555 (M + 1) |
| 3-methylfuran-2-yl | Example 386<br>15.6 mg, 95%<br>558 (M + 1) |
| thiophen-3-yl | Example 392<br>13.7 mg, 95%<br>560 (M + 1) |

Ry — Rx:

[structure: 1-(benzimidazol-1-yl)-4-(4-chlorophenyl)oxazol-5-yl connected via -CH2CH2-C(=O)-NH-(CH2)4-NH-* ]

| Rx group | Example info |
|---|---|
| thiophen-2-yl | Example 375<br>16.9 mg, 94%<br>548 (M + 1) |
| pyridin-2-yl | Example 381<br>17.9 mg, 97%<br>543 (M + 1) |
| 3-methylfuran-2-yl | Example 387<br>20.2 mg,<br>546 (M + 1) |
| thiophen-3-yl | Example 393<br>15.9 mg, 98%<br>548 (M + 1) |

TABLE 1-4-continued basic structure

Rx—C(=O)—Ry

| Ry | Rx |
|---|---|
| (4-chlorophenyl-oxazole-benzimidazole-propanamide-ethylamine structure) | |
| thiophen-2-yl (*) | Example 376<br>26.3 mg, 98%<br>520 (M + 1) |
| pyridin-2-yl (*) | Example 382<br>15.6 mg, 85%<br>515 (M + 1) |
| 3-methylfuran-2-yl (*) | Example 388<br>18.1 mg, 95%<br>518 (M + 1) |
| thiophen-3-yl (*) | Example 394<br>19.4 mg, 85%<br>520 (M + 1) | upper line: Example No.
middle line: yield, LC-MS purity (220 nm)
lower line: MS (ESI+, m/e)

Example 395

A mixture of 2-(1H-benzimidazol-1-yl)-4-(4-chlorophenyl)-5-oxazolepropionic acid (22 mg), 3-amino-1-Boc-pyrrolidine (12 mg), 1-hydroxy-7-azabenzotriazole (10 mg), 1-ethyl-3-(3-dimethylaminopropyl)carbodiimide hydrochloride (12 mg) and N,N-dimethylformamide (1 ml) was shaken at room temperature for 8 hrs. The reaction mixture was poured into 1N hydrochloric acid, and the mixture was extracted with ethyl acetate. The ethyl acetate layer was filtered and concentrated. The residue was dissolved in 4N hydrochloric acid ethyl acetate solution, left standing for 5 min. and concentrated. To the residue were added (2R)-tetrahydrofuran-2-carboxylic acid (12 mg), 1-hydroxybenzotriazole (20 mg), dicyclohexylcarbodiimide (13 mg), N,N-dimethylformamide (1 ml), and the mixture was shaken at room temperature for 16 hrs. The reaction mixture was poured into Mega Bond Elut SCX column (1 g) (manufactured by Varian Inc.) equilibrated in advance with acetonitrile and impurities were washed out with acetonitrile. The object compound was eluted with 2N ammonia methanol solution and concentrated.

Examples 396–454

In the same manner as in Example 395, the object compounds were obtained.

The structure and purity of the object compounds of Examples 395–454 were confirmed by LC-MS, HPLC. The yield, structure, purity and mass spectrum data of the object compounds are shown in [Table 2-1]–[Table 2-8].

TABLE 2-1
basic structure
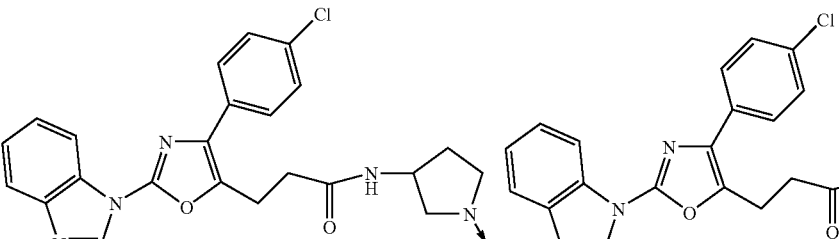
| Ry | Rx | |
|---|---|---|
| | 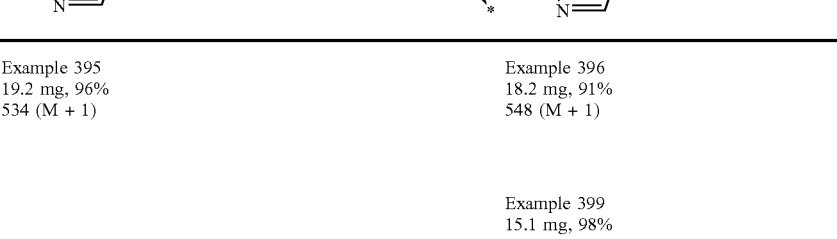 Example 395<br>19.2 mg, 96%<br>534 (M + 1) | 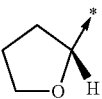 Example 396<br>18.2 mg, 91%<br>548 (M + 1) |
| 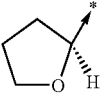 | | |
| 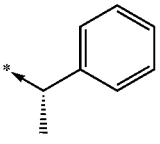 | | Example 399<br>15.1 mg, 98%<br>548 (M + 1) |
|  | Example 402<br>13.3 mg, 80%<br>568 (M + 1) | Example 403<br>13.5 mg, 83%<br>582 (M + 1) |
| 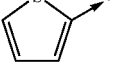 | Example 405<br>12.7 mg, 90%<br>546 (M + 1) | Example 406<br>11.1 mg, 91%<br>560 (M + 1) |
upper line: Example No.
middle line: yield, LC-MS purity (220 nm)
lower line: MS (ESI+, m/e)
TABLE 2-2
basic structure
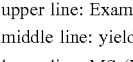
| Ry | Rx |
|---|---|
| |  |

TABLE 2-2-continued basic structure

Rx—C(=O)—Ry

| Rx | | |
|---|---|---|
| (tetrahydrofuran-2-yl, *) | Example 397<br>23.2 mg, 85%<br>562 (M + 1) | |
| (tetrahydrofuran-2-yl, *) | Example 400<br>19.9 mg, 87%<br>562 (M + 1) | |
| (1-phenylethyl, *) | | |
| (thiophen-2-yl, *) | Example 407<br>15.2 mg, 91%<br>574 (M + 1) | |

| Ry | Rx | |
|---|---|---|

Ry: benzimidazole-oxazole(4-chlorophenyl)-propanamide-N-methyl-ethylamine

| Rx | | |
|---|---|---|
| (tetrahydrofuran-2-yl, *) | Example 398<br>23.3 mg, 91%<br>522 (M + 1) | |
| (tetrahydrofuran-2-yl, *) | Example 401<br>21.3 mg, 94%<br>522 (M + 1) | |
| (1-phenylethyl, *) | Example 404<br>20.8 mg, 80%<br>556 (M + 1) | |
| (thiophen-2-yl, *) | Example 408<br>18.1 mg, 80%<br>534 (M + 1) | |

TABLE 2-2-continued basic structure

Rx—C(=O)—Ry

| Ry | Rx |
|---|---|
| (tetrahydrofuran-2-yl, *H) | (benzimidazol-1-yl / 4-(4-chlorophenyl)oxazol-5-yl / propanamide / pyrrolidin-3-ylmethyl, N*) |
| (tetrahydrofuran-2-yl, *H, opposite stereo) | |
| (1-phenylethyl, *) | |
| (thiophen-2-yl, *) | Example 409<br>10.2 mg, 94%<br>560 (M + 1) | upper line: Example No.
middle line: yield, LC-MS purity (220 nm)
lower line: MS (ESI+, m/e)

TABLE 2-3 basic structure

Rx—C(=O)—Ry

| Ry | Rx |
|---|---|
| | (benzimidazol-1-yl / 4-(4-chlorophenyl)oxazol-5-yl / propanamide / pyrrolidin-3-yl, N*)    (benzimidazol-1-yl / 4-(4-chlorophenyl)oxazol-5-yl / propanamide / piperidin-2-ylmethyl, N*) |

TABLE 2-3-continued
basic structure
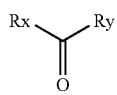
| | |
|---|---|
| 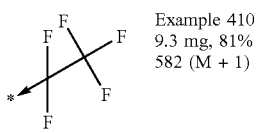 Example 410<br>9.3 mg, 81%<br>582 (M + 1) | Example 411<br>15.2 mg, 80%<br>610 (M + 1) |
| 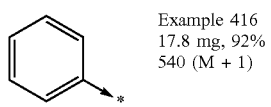 Example 416<br>17.8 mg, 92%<br>540 (M + 1) | |
| 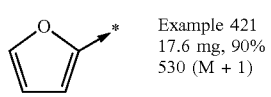 Example 421<br>17.6 mg, 90%<br>530 (M + 1) | |
Ry     Rx
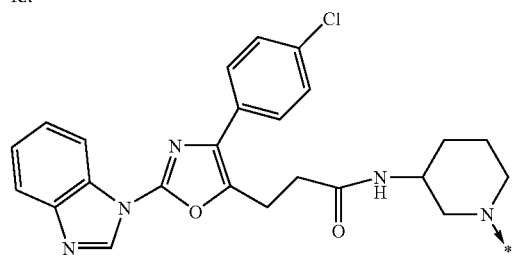
| | |
|---|---|
| | 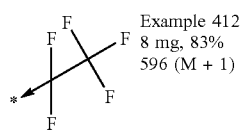 Example 412<br>8 mg, 83%<br>596 (M + 1) |
| | 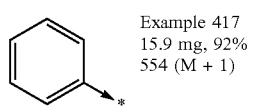 Example 417<br>15.9 mg, 92%<br>554 (M + 1) |
| | 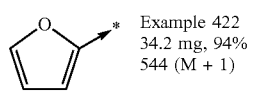 Example 422<br>34.2 mg, 94%<br>544 (M + 1) |
upper line: Example No.
middle line: yield, LC-MS purity (220 nm)
lower line: MS (ESI+, m/e)

TABLE 2-4 basic structure

Rx—C(=O)—Ry

| Ry | Rx (structure 1: benzimidazole-oxazole-(4-chlorophenyl)-CH2CH2C(=O)NH-CH2-piperidinyl-*) | Rx (structure 2: benzimidazole-oxazole-(4-chlorophenyl)-CH2CH2C(=O)NH-CH2CH2-N(CH3)-*) |
|---|---|---|
| CF3-CF2-* (F,F,F,F,F) | Example 413<br>14.7 mg, 80%<br>610 (M + 1) | Example 414<br>4 mg, 90%<br>570 (M + 1) |
| phenyl-* | Example 418<br>22 mg, 93%<br>568 (M + 1) | Example 419<br>22 mg, 83%<br>528 (M + 1) |
| 2-furyl-* | Example 423<br>24 mg, 91%<br>558 (M + 1) | Example 424<br>32 mg, 94%<br>518 (M + 1) |

| Ry | Rx (structure 3: benzimidazole-oxazole-(4-chlorophenyl)-CH2CH2C(=O)NH-CH2-pyrrolidinyl-*) |
|---|---|
| CF3-CF2-* | Example 415<br>4.7 mg, 80%<br>596 (M + 1) |
| phenyl-* | Example 420<br>10.9 mg, 85%<br>554 (M + 1) |
| 2-furyl-* | Example 425<br>17.5 mg, 87%<br>544 (M + 1) | upper line: Example No.
middle line: yield, LC-MS purity (220 nm)
lower line: MS (ESI+, m/e)

TABLE 2-5 basic structure

Rx—C(=O)—Ry

| Ry | Rx |
|---|---|
| (4-chlorophenyl-benzimidazolyl-oxazolyl)-CH₂CH₂-C(=O)-NH-CH₂-(piperidin-4-yl)-N* | |
| (S)-tetrahydrofuran-2-yl (*,H) | Example 426<br>21.4 mg, 93%<br>562 (M + 1) |
| (R)-tetrahydrofuran-2-yl (*,H) | Example 432<br>19.8 mg, 96%<br>562 (M + 1) |
| (S)-1-phenylethyl | Example 437<br>19.5 mg, 80%<br>596 (M + 1) |
| thiophen-2-yl | Example 443<br>22.3 mg, 95%<br>574 (M + 1) |

| Ry | Rx |
|---|---|
| (4-chlorophenyl-benzimidazolyl-oxazolyl)-CH₂CH₂-C(=O)-NH-CH₂-(thiazolidin-4-yl)-N* | |
| (S)-tetrahydrofuran-2-yl (*,H) | Example 427<br>19.6 mg, 90%<br>566 (M + 1) |
| (R)-tetrahydrofuran-2-yl (*,H) | |
| (S)-1-phenylethyl | Example 438<br>23.2 mg, 90%<br>600 (M + 1) |

TABLE 2-5-continued basic structure

Rx—C(=O)—Ry

| Ry | Rx | Example No. / yield, LC-MS purity / MS |
|---|---|---|
| thiophen-2-yl | | Example 444<br>19.2 mg, 91%<br>578 (M + 1) |
| | [benzimidazol-1-yl-oxazole-pyrrolidine structure with 4-chlorophenyl] | |
| (S)-tetrahydrofuran-2-yl | | Example 428<br>36.6 mg, 97%<br>534 (M + 1) |
| (R)-tetrahydrofuran-2-yl | | Example 433<br>26.6 mg, 96%<br>534 (M + 1) |
| 1-phenylethyl | | Example 439<br>27.9 mg, 97%<br>568 (M + 1) |
| thiophen-2-yl | | | upper line: Example No.
middle line: yield, LC-MS purity (220 nm)
lower line: MS (ESI+, m/e)

TABLE 2-6 basic structure

Rx—C(=O)—Ry

| Ry | Rx |
|---|---|
| (tetrahydrofuran-2-yl, *) | [benzimidazole-oxazole(4-chlorophenyl)-CH2CH2-C(=O)-piperazine-N*] Example 429 23.5 mg, 93% 534 (M + 1) |
| (tetrahydrofuran-2-yl, *) | Example 434 19.7 mg, 94% 534 (M + 1) |
| (1-phenylethyl, *) | Example 440 20.2 mg, 97% 568 (M + 1) |

| Ry | Rx |
|---|---|
| (tetrahydrofuran-2-yl, *) | [benzimidazole-oxazole(4-chlorophenyl)-CH2CH2-C(=O)-NH-(CH2)4-NH*] Example 430 33.7 mg, 82% 536 (M + 1) |
| (tetrahydrofuran-2-yl, *) | Example 435 28 mg, 88% 536 (M + 1) |
| (1-phenylethyl, *) | Example 441 28.5 mg, 91% 570 (M + 1) |

TABLE 2-6-continued basic structure

Rx—C(=O)—Ry

| Ry | Rx | |
|---|---|---|
| (tetrahydrofuran-2-yl, *R*) | [benzimidazole-oxazole-(4-chlorophenyl)-propanoyl-piperidin-4-yl-NH-*] | Example 431<br>33.5 mg, 93%<br>548 (M + 1) |
| (tetrahydrofuran-2-yl, *S*) | | Example 436<br>26.1 mg, 88%<br>548 (M + 1) |
| (1-phenylethyl) | | Example 442<br>25.6 mg, 94%<br>582 (M + 1) | upper line: Example No.
middle line: yield, LC-MS purity (220 nm)
lower line: MS (ESI+, m/e)

TABLE 2-7 basic structure

Rx—C(=O)—Ry

| Ry | Rx | |
|---|---|---|
| (CF$_3$–CF$_2$–*) | [benzimidazole-oxazole-(4-chlorophenyl)-propanoyl-NH-piperidin-4-yl-N-*] ; [benzimidazole-oxazole-(4-chlorophenyl)-propanoyl-NH-CH$_2$-thiazolidinyl-*] | Example 445<br>19.2 mg, 89%<br>610 (M + 1) |

TABLE 2-7-continued
basic structure
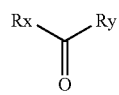
| Rx | Ry | | |
|---|---|---|---|
| 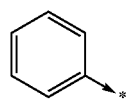 | Example 449<br>24.4 mg, 94%<br>568(M + 1) | | Example 450<br>43.1 mg, 89%<br>572(M + 1) |
| 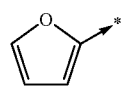 | Example 451<br>38.9 mg, 97%<br>558(M + 1) | | Example 452<br>28.1 mg, 83%<br>562(M + 1) |
| 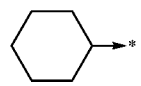 | | | |
Rx
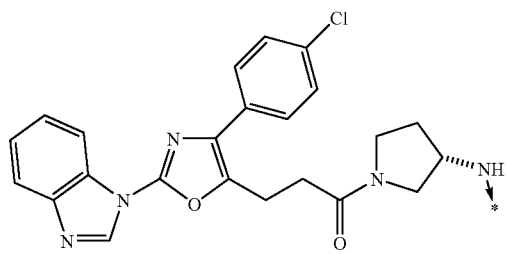
| Ry | |
|---|---|
| 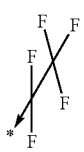 | Example 446<br>28.8 mg, 92%<br>582(M + 1) |
| 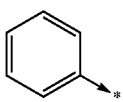 | |
| 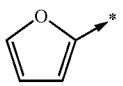 | |
| 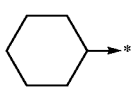 | Example 453<br>2.1 mg, 80%<br>546(M + 1) |
upper line: Example No.
middle line: yield, LC-MS purity(220 nm)
lower line: MS (ESI+, m/e)

TABLE 2-8
basic structure
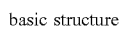
| | Rx |
|---|---|
| Ry | 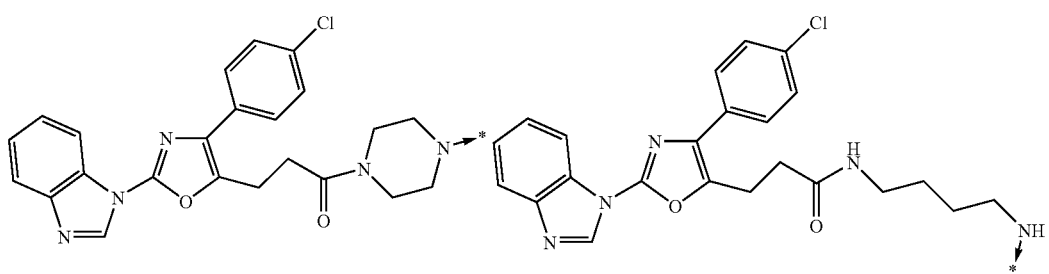 |
| 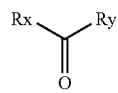 | Example 447<br>25.6 mg, 88%<br>584(M + 1) |
| 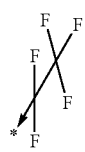 | Example 454<br>5 mg, 92%<br>546(M + 1) |
| | Rx |
|---|---|
| Ry | 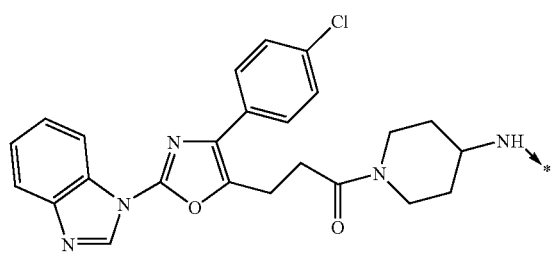 |
| 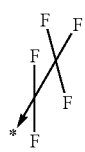 | Example 448<br>23.6 mg, 90%<br>596(M + 1) |
upper line: Example No.
middle line: yield, LC-MS purity(220 nm)
lower line: MS(ESI+, m/e)

Example 455

A mixture of 2-(1H-benzimidazol-1-yl)-4-(4-chlorophenyl)-5-oxazolepropionic acid (37 mg), 4-(2-cyanoethyl)piperazine (20 mg), 1-hydroxy-7-azabenzotriazole (20 mg), 1-ethyl-3-(3-dimethylaminopropyl)carbodiimide (20 mg) and N,N-dimethylformamide (1 ml) was shaken at room temperature for 8 hrs. The reaction mixture was directly poured into preparative HPLC and purified to give the object compound.

Examples 456–461

In the same manner as in Example 455, the object compounds were obtained.

The structure and purity of the object compounds of Examples 455–461 were confirmed by LC-MS, HPLC. The yield, structure, purity and mass spectrum data of the object compounds are shown in [Table 3].

TABLE 3

| basic structure |
|---|

Rx, Ry substituents on a carbonyl (C=O) group.

Rx = benzimidazolyl-oxazole(4-chlorophenyl)-ethyl group (common to all examples)

| Ry | Example |
|---|---|
| 2-cyanoethyl-piperazinyl | Example 455, 30.4 mg, 95%, 489(M + 1) |
| (1-methylpiperidin-4-yl)methyl-piperazinyl | Example 456, 7.7 mg, 94%, 547(M + 1) |
| ethanesulfonyl-piperazinyl | Example 457, 10 mg, 99%, 528(M + 1) |
| cinnamoyl-piperazinyl | Example 458, 13.5 mg, 93%, 566(M + 1) |
| 3-(N-methyl-N-Boc-amino)propylamino | Example 459, 20 mg, 97%, 538(M + 1) |

TABLE 3-continued

| basic structure |
|---|
| Rx⏥Ry with C=O |

| Rx |
|---|
| benzimidazole-oxazole-(4-chlorophenyl) ethyl linker structure |

| Ry | |
|---|---|
| *–N(piperazine)N–CH2–(N-methylpiperidine) | Example 460<br>32.9 mg, 99%<br>547(M + 1) |
| *–N(piperidine)–CH2CH2–NH–C(=O)–O–C(CH3)3 | Example 461<br>18.5 mg, 94%<br>578(M + 1) | upper line: Example No.
middle line: yield, LC-ms purity(220 nm)
lower line: MS(ESI+, m/e)

Example 462

A mixture of 4-(4-chlorophenyl)-2-phenyl-5-oxazolebutanoic acid (35 mg), N,N-dimethylethylenediamine (15 mg), 1-hydroxy-7-azabenzotriazole (20 mg), 1-ethyl-3-(3-dimethylaminopropyl)carbodiimide (20 mg) and N,N-dimethylformamide (1 ml) was shaken at room temperature for 8 hrs. The reaction mixture was directly poured into preparative HPLC and purified to give the object compound.

Examples 463–502

In the same manner as in Example 462, the object compounds were obtained.

The structure and purity of the object compounds of Examples 462–502 were confirmed by LC-MS, HPLC. The structure, purity (HPLC retention time) and mass spectrum data of the object compounds are shown in [Table 4-1]–[Table 4-5].

TABLE 4-1
basic structure
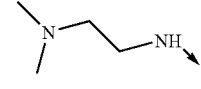
| Ry | Rx | |
|---|---|---|
| | 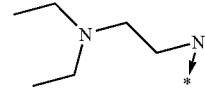 | 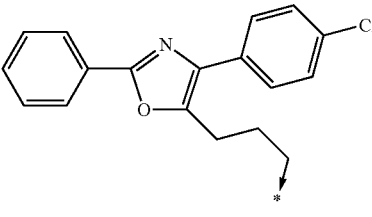 |
| 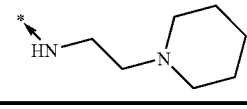 | Example 462<br>100%, 3.366<br>412(M + 1) | Example 463<br>94%, 3.431<br>454(M + 1) |
| Ry | Rx | |
|---|---|---|
| | 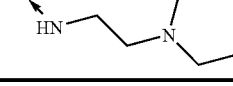 | 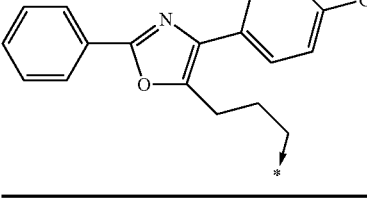 |
| 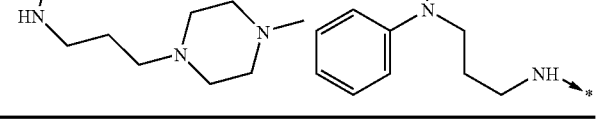 | Example 464<br>98%, 3.463<br>452(M + 1) | Example 465<br>99%, 3.354<br>454(M + 1) |
| Ry | Rx | |
|---|---|---|
| | 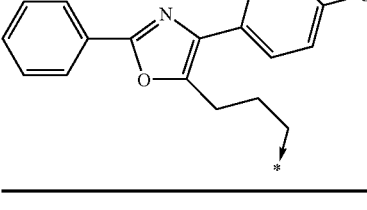 | 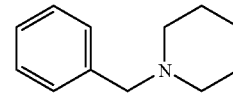 |
| 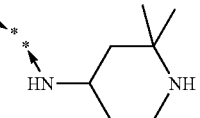 | Example 466<br>100%, 3.08<br>481(M + 1) | Example 467<br>95%, 3.692<br>488(M + 1) |
| Ry | Rx |
|---|---|
| | |

TABLE 4-1-continued basic structure

Rx—C(=O)—Ry

| Rx | Ry examples |
|---|---|
| [2-phenyl-4-(4-chlorophenyl)oxazol-5-yl]propyl–* | Example 468<br>92%, 3.643<br>514(M + 1) | Example 469<br>99%, 3.482<br>480(M + 1) | upper line: Example No.
middle line: HPLC purity(220 nm), retention time(min)
lower line: MS(APCI+, m/e)

TABLE 4-2 basic structure

Rx—C(=O)—Ry

| Ry | Rx |
|---|---|
| | *–HN–CH₂CH₂–NH–C₆H₅ | *–HN–CH₂–(2-pyridyl) | (4-pyridyl)–CH₂CH₂–NH–* |
| [2-phenyl-4-(4-chlorophenyl)oxazol-5-yl]propyl–* | Example 470<br>98%, 3.946<br>460(M + 1) | Example 471<br>99%, 3.42<br>432(M + 1) | Example 472<br>99%, 3.347<br>446(M + 1) |

| Ry | Rx |
|---|---|
| | *–HN–(CH₂)₃–(1-imidazolyl) | (iPr)₂N–CH₂CH₂–NH–* | (Me)₂N–CH₂C(Me)₂CH₂–NH–* |
| [2-phenyl-4-(4-chlorophenyl)oxazol-5-yl]propyl–* | Example 473<br>98%, 3.36<br>449(M + 1) | Example 474<br>91%, 3.634<br>468(M + 1) | Example 475<br>97%, 3.503<br>454(M + 1) |

TABLE 4-2-continued basic structure: Rx-C(=O)-Ry

| Ry | Rx: HN-CH2CH2CH2-(2-methylpiperidin-1-yl) | Rx: HN-CH2CH2CH2-morpholin-4-yl |
|---|---|---|
| 2-phenyl-4-(4-chlorophenyl)oxazol-5-yl-(CH2)3- | Example 476<br>95%, 3.551<br>480(M + 1) | Example 477<br>99%, 3.369<br>468(M + 1) | upper line: Example No.
middle line: HPLC purity(220 nm), retention time(min)
lower line: MS(APCI+, m/e)

TABLE 4-3 basic structure: Rx-C(=O)-Ry

| Ry | Rx: HN-CH2CH2-pyrrolidin-1-yl | Rx: HN-CH2CH2-N(ethyl)(3-methylphenyl) |
|---|---|---|
| 2-phenyl-4-(4-chlorophenyl)oxazol-5-yl-(CH2)3- | Example 478<br>99%, 3.426<br>438(M + 1) | Example 479<br>99%, 3.874<br>502(M + 1) |

| Ry | Rx: 1-benzylpyrrolidin-3-ylamino | Rx: N,N-bis(2-hydroxyethyl)-N'-propyl-diamine |
|---|---|---|

TABLE 4-3-continued basic structure

Rx—C(=O)—Ry

| Ry | Rx | |
|---|---|---|
| [2-phenyl-4-(4-chlorophenyl)oxazol-5-yl]propyl- | Example 480<br>93%, 3.707<br>500(M + 1) | Example 481<br>98%, 3.271<br>486(M + 1) |
| | *-HN-CH2CH2-NH-(pyridin-2-yl)<br>(5-N-oxide) | 4-(aminomethyl)pyridine NH-* |
| [2-phenyl-4-(4-chlorophenyl)oxazol-5-yl]propyl- | Example 482<br>86%, 4.42<br>506(M + 1) | Example 483<br>99%, 3.374<br>432(M + 1) |
| | 3-(aminomethyl)pyridine<br>NH-* | 3-(2-aminoethyl)pyridine<br>NH-* |
| [2-phenyl-4-(4-chlorophenyl)oxazol-5-yl]propyl- | Example 484<br>100%, 3.378<br>432(M + 1) | Example 485<br>99%, 3.361<br>446(M + 1) | upper line: Example No.
middle line: HPLC purity(220 nm), retention time(min)
lower line: MS(APCI+, m/e)

TABLE 4-4 basic structure

Rx—C(=O)—Ry

| Ry | Rx: *–NH–phenyl | Rx: 3,5-dimethoxy-phenyl-NH–* | Rx: *–NH–(4-benzylphenyl) |
|---|---|---|---|
| 2-phenyl-4-(4-chlorophenyl)oxazol-5-yl-butyl-* | Example 486<br>100%, 4.877<br>417(M + 1) | Example 487<br>100%, 4.844<br>477(M + 1) | Example 488<br>97%, 5.331<br>507(M + 1) |

| Ry | Rx: *–HN–(biphenyl-3-yl) | Rx: pyridin-4-yl–NH–* | Rx: quinolin-6-yl–NH–* |
|---|---|---|---|
| 2-phenyl-4-(4-chlorophenyl)oxazol-5-yl-butyl-* | Example 489<br>99%, 5.308<br>493(M + 1) | Example 490<br>99%, 3.534<br>418(M + 1) | Example 491<br>100%, 3.628<br>468(M + 1) |

| Ry | Rx: *–NH–benzothiazol-2-yl | Rx: *–NH–(2-fluorophenyl) |
|---|---|---|
| 2-phenyl-4-(4-chlorophenyl)oxazol-5-yl-butyl-* | Example 492<br>95%, 5.026<br>474(M + 1) | Example 493<br>96%, 4.923<br>435(M + 1) | upper line: Example No.
middle line: HPLC purity(220 nm), retention time(min)
lower line: MS(APCI+, m/e)

TABLE 4-5
basic structure
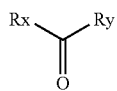
| Ry | Rx | | |
|---|---|---|---|
| | 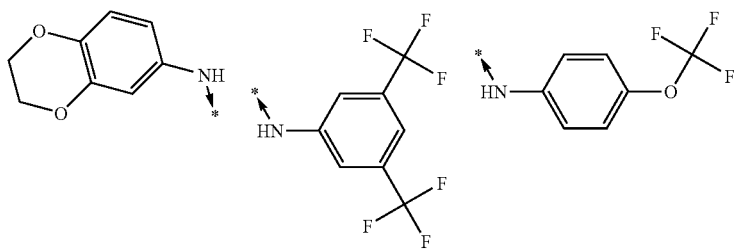 | | |
| 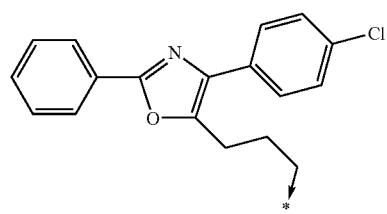 | Example 494<br>98%, 4.707<br>475(M + 1) | Example 495<br>95%, 5.488<br>553(M + 1) | Example 496<br>100%, 5.216<br>501(M + 1) |
| Ry | Rx | | |
|---|---|---|---|
| | 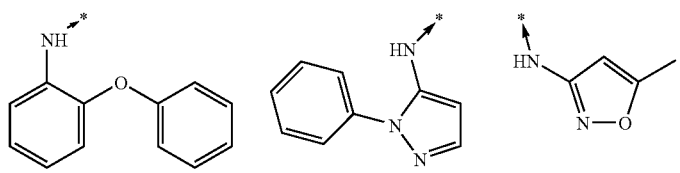 | | |
| 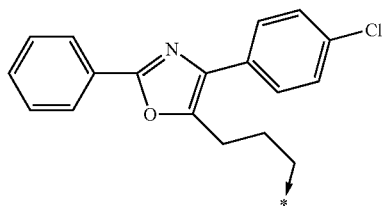 | Example 497<br>100%, 5.355<br>509(M + 1) | Example 498<br>90%, 4.623<br>483(M + 1) | Example 499<br>88%, 4.611<br>422(M + 1) |
| Ry | Rx | | |
|---|---|---|---|
| | 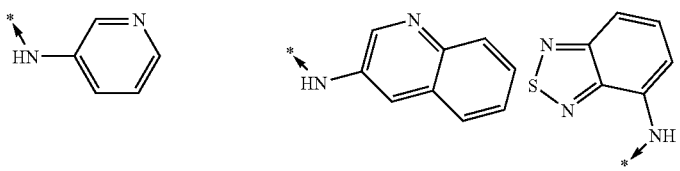 | | |
| 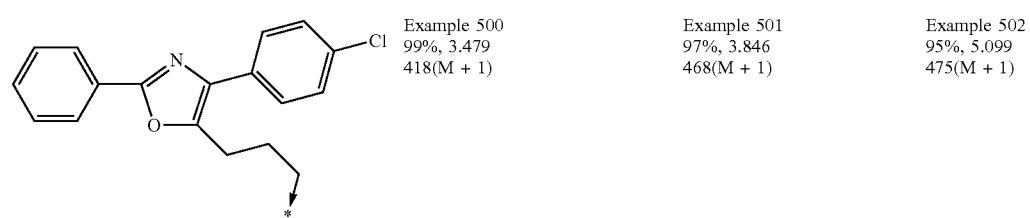 | Example 500<br>99%, 3.479<br>418(M + 1) | Example 501<br>97%, 3.846<br>468(M + 1) | Example 502<br>95%, 5.099<br>475(M + 1) |

TABLE 4-5-continued basic structure

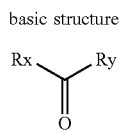

upper line: Example No.
middle line: HPLC purity(220 nm), retention time(min)
lower line: MS(APCI+, m/e)

Example 503

A mixture of 2-(1H-benzimidazol-1-yl)-4-(4-chlorophenyl)-5-oxazolepropionic acid (37 mg), 4-[(2,4-dioxo-1,3-thiazolidin-5-yl)methyl]aniline (35 mg), 1-hydroxy-7-azabenzotriazole (20 mg), 1-ethyl-3-(3-dimethylaminopropyl)carbodiimide (20 mg) and N,N-dimethylformamide (1 ml) was shaken at room temperature for 8 hrs. The reaction mixture was directly poured into preparative HPLC and purified to give the object compound.

Examples 504–508

In the same manner as in Example 503, the object compounds were obtained.

The structure and purity of the object compounds of Examples 503–508 were confirmed by LC-MS, HPLC. The structure, purity (HPLC retention time) and mass spectrum data of the object compounds are shown in [Table 5].

TABLE 5 basic structure

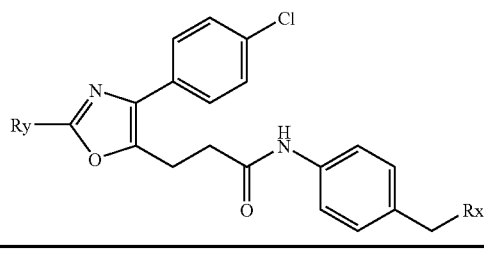

| Ry | Rx | |
|---|---|---|
| | 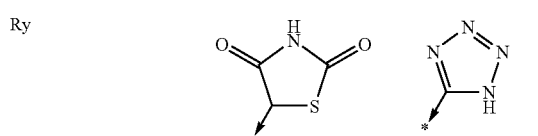 | |
| 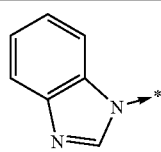 | Example 503<br>100%, 4.278<br>572(M + 1) | Example 504<br>99%, 3.998<br>525(M + 1) |
| 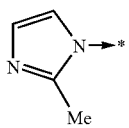 | Example 505<br>98%, 3.299<br>536(M + 1) | Example 506<br>97%, 3.055<br>489(M + 1) |
| 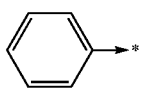 | Example 507<br>100%, 4.647<br>546(M + 1) | Example 508<br>99%, 4.315<br>499(M + 1) | upper line: Example No.
middle line: HPLC purity(220 nm), retention time
lower line: MS(APCI+, m/e)

Examples 509–874

A mixture of carboxylic acid (0.06 mmol), amine (0.06 mmol), PS-carbodiimide resin (0.94 meq/g, 96 mg) manufactured by Argonaut Technologies Inc. and dichloromethane (0.7 ml) was shaken for 20 hrs. using a 96 well plate with Flex Chem filter. The resin was removed by filtration and the filtrate was concentrated. The residue was purified by preparative HPLC to give the object compound.

The structure and purity (HPLC retention time) and mass spectrum data of the object compounds are shown in [Table 6-1]–[Table 6-4], [Table 7-1]–[Table 7-4], [Table 8-1]–[Table 8-2], [Table 9-1]–[Table 9-4], [Table 10-1]–[Table 10-4], [Table 11-1]–[Table 11-4], [Table 12-1]–[Table 12-4], [Table 13-1]–[Table 13-4] and [Table 14].

TABLE 6-1 basic structure

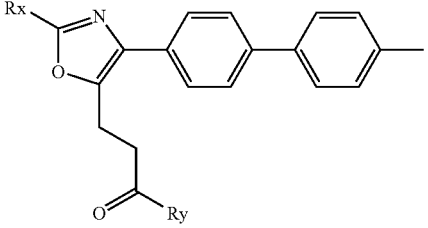

| Ry | Rx | | | |
|---|---|---|---|---|
| |  CH₃ | 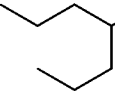 | 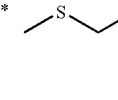 | 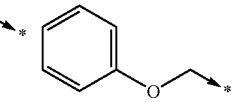 |
| 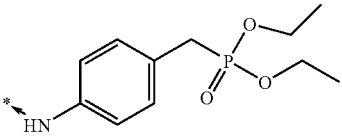 | Example 509<br>92%, 3.91 min<br>547(M + 1) | Example 510<br>99%, 4.64 min<br>631(M + 1) | Example 511<br>98%, 4.13 min<br>607(M + 1) | Example 512<br>100%, 4.32 min<br>639(M + 1) |
| 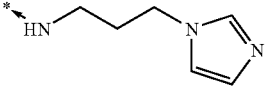 | Example 516<br>93%, 2.99 min<br>429(M + 1) | Example 517<br>100%, 3.68 min<br>513(M + 1) | Example 518<br>98%, 3.21 min<br>489(M + 1) | Example 519<br>97%, 3.45 min<br>521(M + 1) |
| 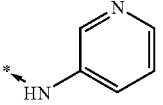 | Example 523<br>100%, 3.08 min<br>398(M + 1) | Example 524<br>99%, 3.78 min<br>482(M + 1) | Example 525<br>95%, 3.31 min<br>458(M + 1) | Example 526<br>98%, 3.53 min<br>490(M + 1) |
| 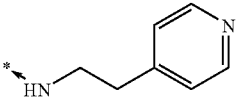 | Example 530<br>94%, 2.98 min<br>426(M + 1) | Example 531<br>99%, 3.67 min<br>510(M + 1) | Example 532<br>96%, 3.20 min<br>486(M + 1) | Example 533<br>99%, 3.44 min<br>518(M + 1) | upper line: Example No.
middle line: HPLC purity(220 nm), retention time
lower line: MS(APCI+, m/e)

TABLE 6-2 basic structure

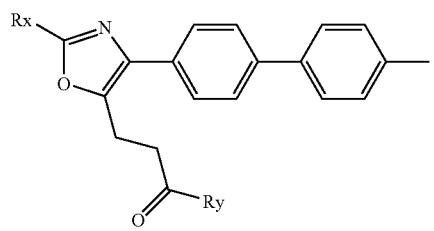

| Ry | Rx | | |
|---|---|---|---|
| | 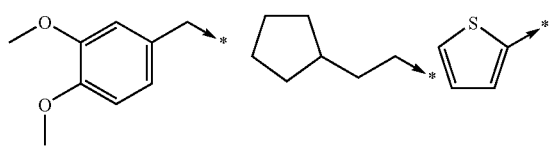 | | |
| 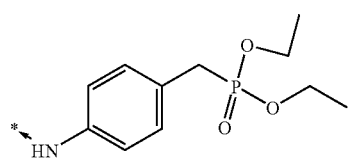 | Example 513<br>100%, 4.14 min<br>683(M + 1) | Example 514<br>99%, 4.62 min<br>629(M + 1) | Example 515<br>95%, 4.38 min<br>615(M + 1) |
| 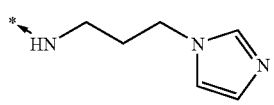 | Example 520<br>100%, 3.30 min<br>565(M + 1) | Example 521<br>87%, 3.65 min<br>511(M + 1) | Example 522<br>99%, 3.42 min<br>497(M + 1) |
| 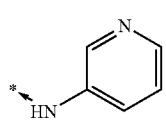 | Example 527<br>100%, 3.37 min<br>534(M + 1) | Example 528<br>98%, 3.74 min<br>480(M + 1) | Example 529<br>95%, 3.53 min<br>466(M + 1) |
| 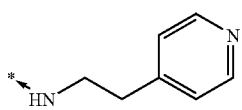 | Example 534<br>99%, 3.28 min<br>562(M + 1) | Example 535<br>97%, 3.64 min<br>508(M + 1) | Example 536<br>99%, 3.41 min<br>494(M + 1) | upper line: Example No.
middle line: HPLC purity(220 nm), retention time
lower line: MS(APCI+, m/e)

TABLE 6-3 basic structure

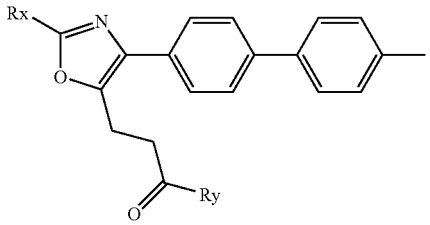

| Ry | Rx |  |  |  |
|---|---|---|---|---|
|  | CH₃—* |  | 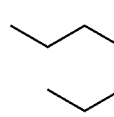 |  |
| 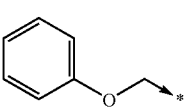 | Example 537<br>99%, 3.49 min<br>427(M + 1) | Example 538<br>99%, 4.40 min<br>511(M + 1) | Example 539<br>100%, 3.77 min<br>487(M + 1) | Example 540<br>99%, 4.03 min<br>519(M + 1) |
| 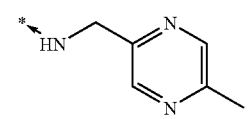 | Example 544<br>89%, 3.01 min<br>434(M + 1) | Example 545<br>99%, 3.70 min<br>518(M + 1) | Example 546<br>99%, 3.23 min<br>494(M + 1) | Example 547<br>99%, 3.47 min<br>526(M + 1) |
| 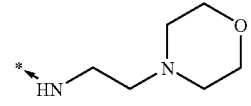 | Example 550<br>91%, 3.00 min<br>404(M + 1) | Example 551<br>98%, 3.70 min<br>488(M + 1) | Example 552<br>96%, 3.23 min<br>464(M + 1) | Example 553<br>97%, 3.47 min<br>496(M + 1) | upper line: Example No.
middle line: HPLC purity(220 nm), retention time
lower line: MS(APCI+, m/e)

TABLE 6-4 basic structure

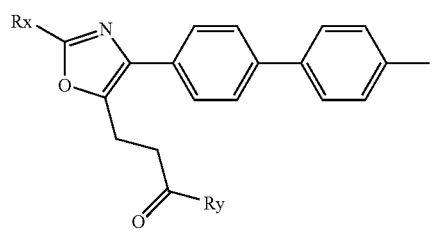

| Ry | Rx | | |
|---|---|---|---|
| | 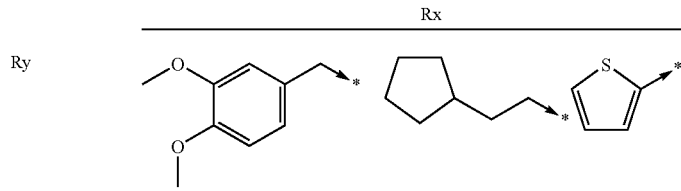 | | |
| 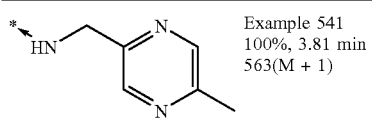 | Example 541<br>100%, 3.81 min<br>563(M + 1) | Example 542<br>98%, 4.35 min<br>509(M + 1) | Example 543<br>100%, 4.04 min<br>495(M + 1) |
| 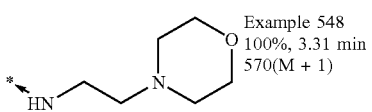 | Example 548<br>100%, 3.31 min<br>570(M + 1) | Example 549<br>100%, 3.68 min<br>516(M + 1) | |
| 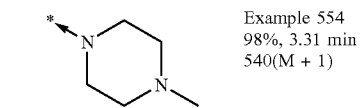 | Example 554<br>98%, 3.31 min<br>540(M + 1) | Example 555<br>84%, 3.68 min<br>486(M + 1) | Example 556<br>94%, 3.45 min<br>472(M + 1) | upper line: Example No.
middle line: HPLC purity(220 nm), retention time
lower line: MS(APCI+, m/e)

TABLE 7-1 basic structure

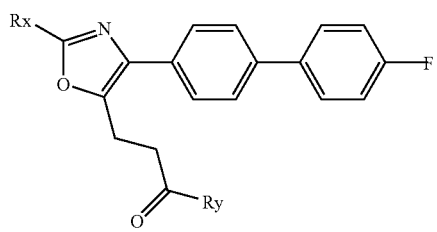

| Ry | Rx | | | |
|---|---|---|---|---|
| | 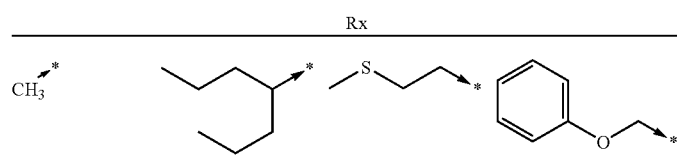 | | | |
| 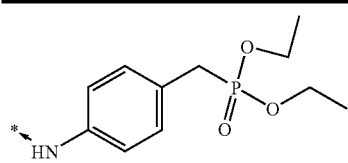 | Example 557<br>96%, 3.81 min<br>551(M + 1) | Example 558<br>99%, 4.53 min<br>635(M + 1) | Example 559<br>100%, 4.02 min<br>611(M + 1) | Example 560<br>100%, 4.21 min<br>643(M + 1) |

TABLE 7-1-continued

| | | | | |
|---|---|---|---|---|
| 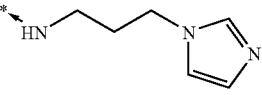 | Example 564<br>98%, 2.88 min<br>433(M + 1) | Example 565<br>90%, 3.59 min<br>517(M + 1) | Example 566<br>99%, 3.12 min<br>493(M + 1) | Example 567<br>93%, 3.36 min<br>525(M + 1) |
| 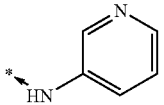 | Example 571<br>96%, 2.97 min<br>402(M + 1) | Example 572<br>100%, 3.69 min<br>486(M + 1) | Example 573<br>94%, 3.20 min<br>462(M + 1) | Example 574<br>98%, 3.44 min<br>494(M + 1) |
| 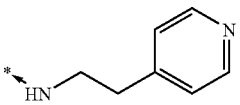 | Example 578<br>93%, 2.88 min<br>430(M + 1) | Example 579<br>91%, 3.58 min<br>514(M + 1) | Example 580<br>96%, 3.11 min<br>490(M + 1) | Example 581<br>89%, 3.34 min<br>522(M + 1) | upper line: Example No.

middle line: HPLC purity(220 nm), retention time lower line: MS(APCI+, m/e)

TABLE 7-2 basic structure

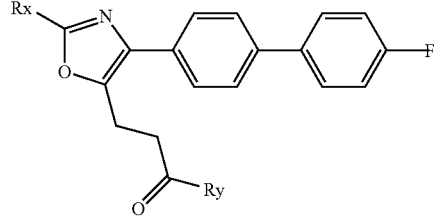

| | Rx | | |
|---|---|---|---|
| Ry | 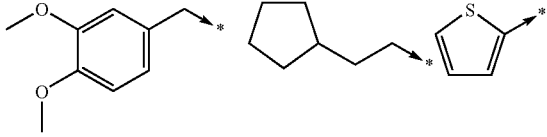 | 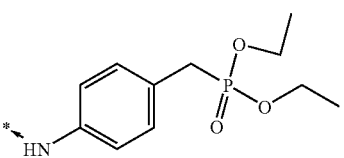 | 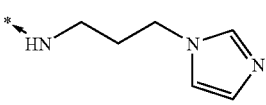 |
| 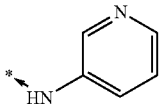 | Example 561<br>100%, 4.04 min<br>687(M + 1) | Example 562<br>96%, 4.51 min<br>633(M + 1) | Example 563<br>100%, 4.27 min<br>619(M + 1) |
| 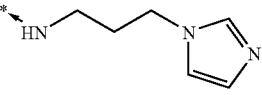 | Example 568<br>95%, 3.21 min<br>569(M + 1) | Example 569<br>88%, 3.57 min<br>515(M + 1) | Example 570<br>100%, 3.33 min<br>501(M + 1) |
| 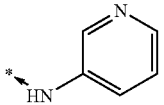 | Example 575<br>98%, 3.28 min<br>538(M + 1) | Example 576<br>97%, 3.67 min<br>484(M + 1) | Example 577<br>98%, 3.44 min<br>470(M + 1) |

TABLE 7-2-continued

| Ry | | | |
|---|---|---|---|
| *HN-CH2-pyridyl | Example 582 92%, 3.20 min 566(M + 1) | Example 583 89%, 3.56 min 512(M + 1) | Example 584 98%, 3.33 min 498(M + 1) | upper line: Example No.
middle line: HPLC purity(220 nm), retention time
lower line: MS(APCI+, m/e)

TABLE 7-3 basic structure

| | Rx | | | |
|---|---|---|---|---|
| Ry | CH₃-* | *-CH(CH₂CH₂CH₃)₂ | CH₃-S-CH₂CH₂-* | PhO-CH₂-* |
| *HN-CH₂-(5-methylpyrazin-2-yl) | Example 585 100%, 3.38 min 431(M + 1) | Example 586 97%, 4.28 min 515(M + 1) | Example 587 100%, 3.66 min 491(M + 1) | Example 588 99%, 3.92 min 523(M + 1) |
| *HN-CH₂CH₂-morpholinyl | Example 592 92%, 2.90 min 438(M + 1) | Example 593 94%, 3.62 min 522(M + 1) | Example 594 93%, 3.14 min 498(M + 1) | Example 595 99%, 3.38 min 530(M + 1) |
| *-(4-methylpiperazin-1-yl) | Example 599 89%, 2.90 min 408(M + 1) | Example 600 91%, 3.61 min 492(M + 1) | Example 601 92%, 3.14 min 468(M + 1) | Example 602 98%, 3.38 min 500(M + 1) | upper line: Example No.
middle line: HPLC purity(220 nm), retention time
lower line: MS(APCI+, m/e)

TABLE 7-4 basic structure

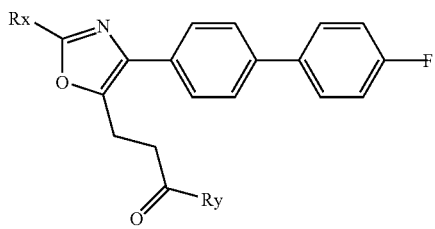

| Ry | Rx | | |
|---|---|---|---|
| | 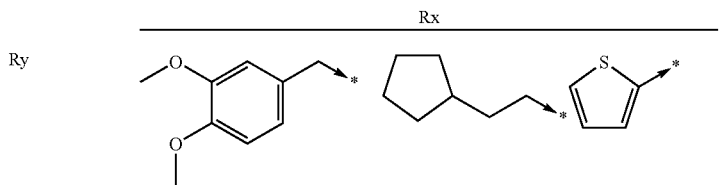 | | |
| 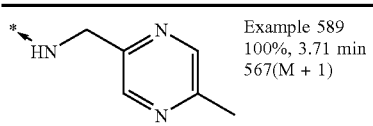 | Example 589<br>100%, 3.71 min<br>567(M + 1) | Example 590<br>97%, 4.24 min<br>513(M + 1) | Example 591<br>100%, 3.92 min<br>499(M + 1) |
| 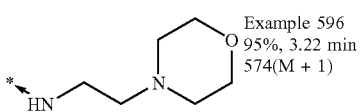 | Example 596<br>95%, 3.22 min<br>574(M + 1) | Example 597<br>90%, 3.59 min<br>520(M + 1) | Example 598<br>98%, 3.35 min<br>506(M + 1) |
| 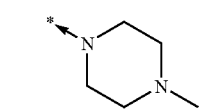 | Example 603<br>91%, 3.23 min<br>544(M + 1) | Example 604<br>91%, 3.58 min<br>490(M + 1) | Example 605<br>92%, 3.35 min<br>476(M + 1) | upper line: Example No.
middle line: HPLC purity(220 nm), retention time
lower line: MS(APCI+, m/e)

TABLE 8-1 basic structure

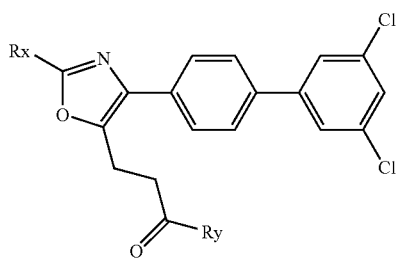

| | Rx | | |
|---|---|---|---|
| | 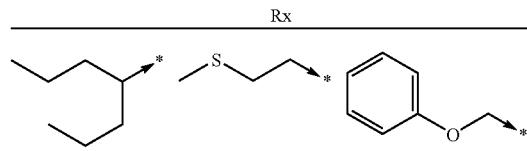 | | |
| Ry | | | |
| 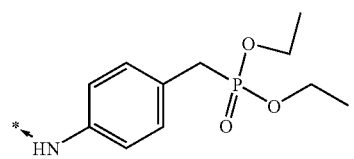 | | | Example 606<br>100%, 4.61 min<br>693(M + 1) |

TABLE 8-1-continued basic structure

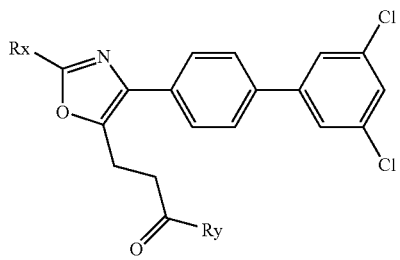

| Ry | Rx | | |
|---|---|---|---|
| 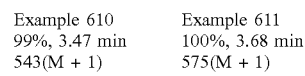 | Example 609<br>98%, 3.95 min<br>567(M + 1) | Example 610<br>99%, 3.47 min<br>543(M + 1) | Example 611<br>100%, 3.68 min<br>575(M + 1) |
| 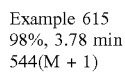 | | Example 614<br>94%, 3.58 min<br>512(M + 1) | Example 615<br>98%, 3.78 min<br>544(M + 1) |
| 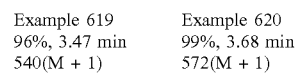 | Example 618<br>99%, 3.95 min<br>564(M + 1) | Example 619<br>96%, 3.47 min<br>540(M + 1) | Example 620<br>99%, 3.68 min<br>572(M + 1) |

| | Rx | |
|---|---|---|
| | 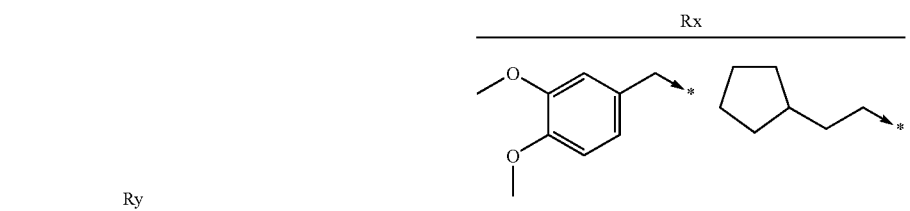 | |
| Ry | | |
| 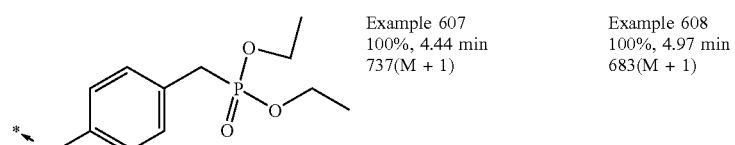 | Example 607<br>100%, 4.44 min<br>737(M + 1) | Example 608<br>100%, 4.97 min<br>683(M + 1) |
| 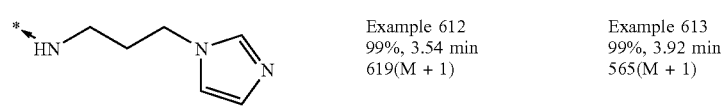 | Example 612<br>99%, 3.54 min<br>619(M + 1) | Example 613<br>99%, 3.92 min<br>565(M + 1) |
| 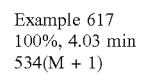 | Example 616<br>98%, 3.63 min<br>588(M + 1) | Example 617<br>100%, 4.03 min<br>534(M + 1) |
| 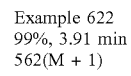 | Example 621<br>100%, 3.53 min<br>616(M + 1) | Example 622<br>99%, 3.91 min<br>562(M + 1) | upper line: Example No.
middle line: HPLC purity(220 nm), retention time
lower line: MS(APCI+, m/e)

TABLE 8-2 basic structure

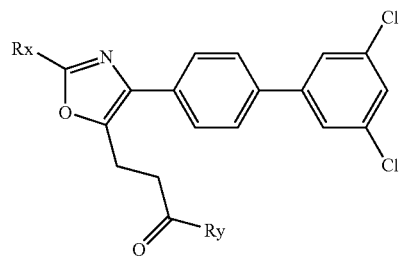

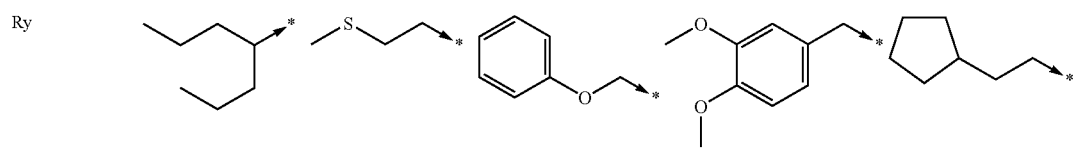

| Ry | | | | | |
|---|---|---|---|---|---|
| 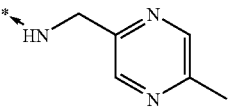 | Example 623<br>98%, 4.76 min<br>565(M + 1) | Example 624<br>94%, 4.12 min<br>541(M + 1) | Example 625<br>100%, 4.34 min<br>573(M + 1) | Example 626<br>100%, 4.14 min<br>617(M + 1) | Example 627<br>98%, 4.71 min<br>563(M + 1) |
| 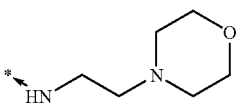 | Example 628<br>100%, 3.97 min<br>572(M + 1) | Example 629<br>99%, 3.48 min<br>548(M + 1) | Example 630<br>99%, 3.70 min<br>580(M + 1) | Example 631<br>100%, 3.55 min<br>624(M + 1) | Example 632<br>95%, 3.94 min<br>570(M + 1) |
| 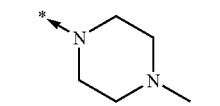 | Example 633<br>99%, 3.97 min<br>542(M + 1) | Example 634<br>96%, 3.49 min<br>518(M + 1) | Example 635<br>98%, 3.70 min<br>550(M + 1) | Example 636<br>98%, 3.55 min<br>594(M + 1) | Example 637<br>97%, 3.93 min<br>540(M + 1) | upper line: Example No.
middle line: HPLC purity(220 nm), retention time
lower line: MS(APCI+, m/e)

TABLE 9-1 basic structure

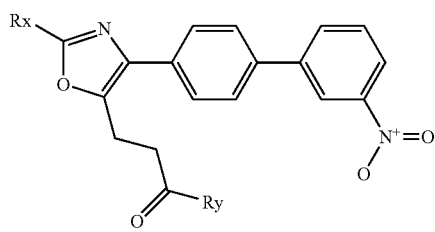

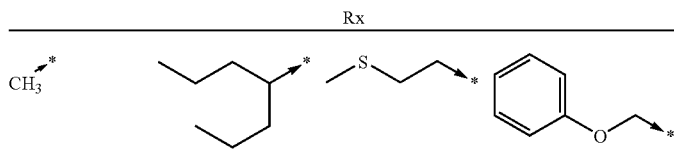

| Ry | | | | |
|---|---|---|---|---|
| 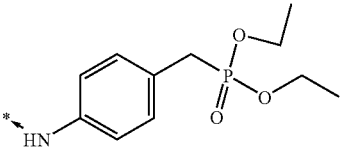 | Example 638<br>100%, 3.77 min<br>578(M + 1) | Example 639<br>98%, 4.49 min<br>662(M + 1) | Example 640<br>88%, 3.98 min<br>638(M + 1) | Example 641<br>100%, 4.16 min<br>670(M + 1) |

TABLE 9-1-continued

| | Example 645 100%, 2.88 min 460(M + 1) | Example 646 94%, 3.59 min 544(M + 1) | Example 647 90%, 3.11 min 520(M + 1) | Example 648 90%, 3.34 min 552(M + 1) |
|---|---|---|---|---|
| 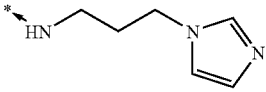 | | | | |
| 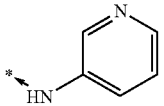 | Example 652 92%, 2.95 min 429(M + 1) | Example 653 89%, 3.67 min 513(M + 1) | Example 654 87%, 3.19 min 489(M + 1) | Example 655 94%, 3.41 min 521(M + 1) |
| 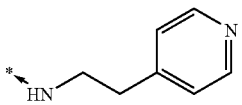 | Example 659 96%, 2.87 min 457(M + 1) | Example 660 89%, 3.58 min 541(M + 1) | Example 661 90%, 3.10 min 517(M + 1) | Example 662 91%, 3.34 min 549(M + 1) | upper line: Example No.
middle line: HPLC purity(220 nm), retention time
lower line: MS(APCI+, m/e)

TABLE 9-2 basic structure

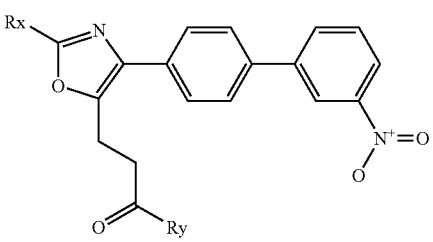

| | Rx | | |
|---|---|---|---|
| | 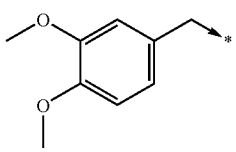 | 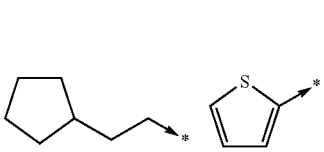 | 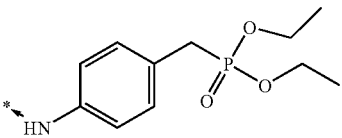 |
| Ry | | | |
| 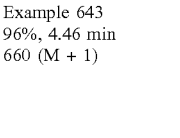 | Example 642 100%, 3.99 min 714 (M + 1) | Example 643 96%, 4.46 min 660 (M + 1) | Example 644 100%, 4.22 min 646 (M + 1) |
| 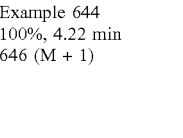 | Example 649 100%, 3.20 min 596 (M + 1) | Example 650 93%, 3.55 min 542 (M + 1) | Example 651 100%, 3.32 min 528 (M + 1) |
| 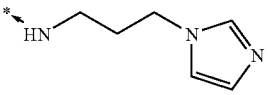 | Example 656 98%, 3.26 min 565 (M + 1) | Example 657 90%, 3.65 min 511 (M + 1) | Example 658 100%, 3.42 min 497 (M + 1) |
|  | Example 663 100%, 3.19 min 593 (M + 1) | Example 664 91%, 3.55 min 539 (M + 1) | Example 665 100%, 3.31 min 525 (M + 1) | upper line: Example No.
middle line: HPLC purity (220 nm), retention time
lower line: MS (APCI+, m/e)

TABLE 9-3 basic structure

| Ry | Rx 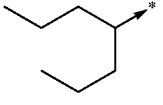 CH₃ |  | 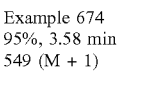 S |  O |
|---|---|---|---|---|
| 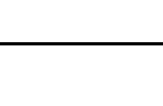 | Example 666<br>100%, 3.35 min<br>458 (M + 1) | Example 667<br>92%, 4.25 min<br>542 (M + 1) | Example 668<br>98%, 3.62 min<br>518 (M + 1) | Example 669<br>98%, 3.86 min<br>550 (M + 1) |
|  | Example 673<br>96%, 2.87 min<br>465 (M + 1) | Example 674<br>95%, 3.58 min<br>549 (M + 1) | Example 675<br>90%, 3.10 min<br>525 (M + 1) | Example 676<br>89%, 3.34 min<br>557 (M + 1) |
| 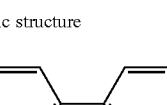 | Example 680<br>95%, 2.86 min<br>435 (M + 1) | Example 681<br>92%, 3.59 min<br>519 (M + 1) | Example 682<br>92%, 3.10 min<br>495 (M + 1) | Example 683<br>90%, 3.35 min<br>527 (M + 1) | upper line: Example No.
middle line: HPLC purity (220 nm), retention time
lower line: MS (APCI+, m/e)

TABLE 9-4 basic structure

| Ry | Rx  |  | 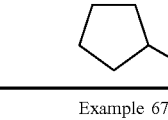 |
|---|---|---|---|
|  | Example 670<br>100%, 3.68 min<br>594 (M + 1) | Example 671<br>97%, 4.20 min<br>540 (M + 1) | Example 672<br>97%, 3.88 min<br>526 (M + 1) |

TABLE 9-4-continued basic structure

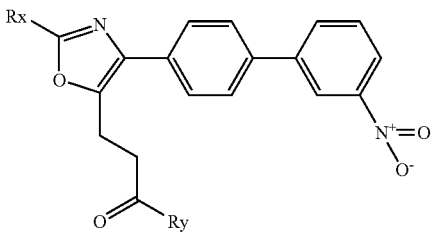

| Ry | Rx 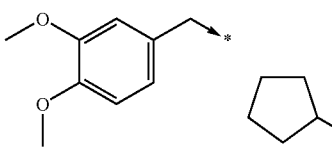 | 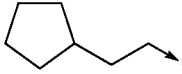 | 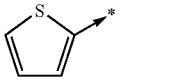 |
|---|---|---|---|
| 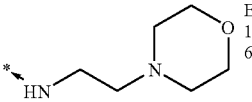 | Example 677<br>100%, 3.21 min<br>601 (M + 1) | Example 678<br>97%, 3.57 min<br>547 (M + 1) | Example 679<br>100%, 3.34 min<br>533 (M + 1) |
| 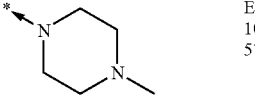 | Example 684<br>100%, 3.20 min<br>571 (M + 1) | Example 685<br>90%, 3.56 min<br>517 (M + 1) | Example 686<br>100%, 3.34 min<br>503 (M + 1) | upper line: Example No.
middle line: HPLC purity (220 nm), retention time
lower line: MS (APCI+, m/e)

TABLE 10-1 basic structure

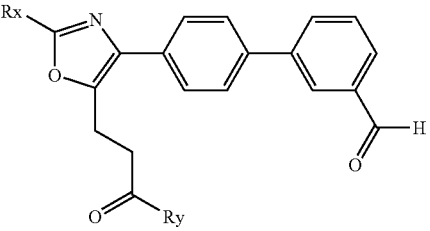

| Ry | Rx CH$_3$—* |  | 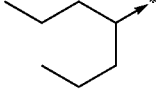 | 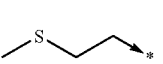 |
|---|---|---|---|---|
| 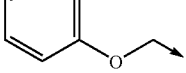 | Example 687<br>94%, 3.60 min<br>561 (M + 1) | Example 688<br>86%, 4.33 min<br>645 (M + 1) | Example 689<br>94%, 3.81 min<br>621 (M + 1) | Example 690<br>95%, 4.02 min<br>653 (M + 1) |
| 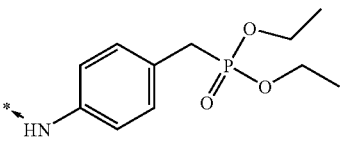 | Example 694<br>96%, 2.70 min<br>443 (M + 1) | Example 695<br>99%, 3.43 min<br>527 (M + 1) | Example 696<br>96%, 2.94 min<br>503 (M + 1) | Example 697<br>96%, 3.20 min<br>535 (M + 1) |

TABLE 10-1-continued basic structure

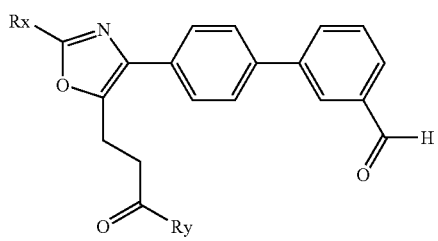

| Ry | Rx | | | |
|---|---|---|---|---|
| | CH₃—* | 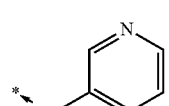 | —S—CH₂CH₂—* | Ph—O—CH₂—* |
| 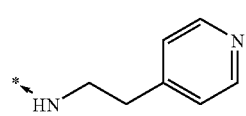 (3-pyridyl-NH-*) | Example 701<br>97%, 2.77 min<br>412 (M + 1) | Example 702<br>95%, 3.52 min<br>496 (M + 1) | Example 703<br>88%, 3.01 min<br>472 (M + 1) | Example 704<br>96%, 3.26 min<br>504 (M + 1) |
| 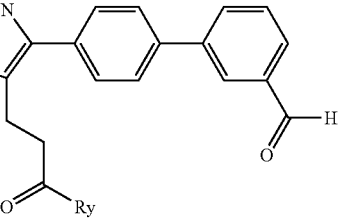 (4-pyridyl-CH₂CH₂-NH-*) | Example 708<br>97%, 2.69 min<br>440 (M + 1) | Example 709<br>97%, 3.43 min<br>524 (M + 1) | Example 710<br>94%, 2.93 min<br>500 (M + 1) | Example 711<br>96%, 3.18 min<br>532 (M + 1) | upper line: Example No.
middle line: HPLC purity (220 nm), retention time
lower line: MS (APCI+, m/e)

TABLE 10-2 basic structure

| Ry | Rx | | |
|---|---|---|---|
| | 3,4-dimethoxybenzyl-* | cyclopentyl-CH₂CH₂-* | 2-thienyl-* |
| 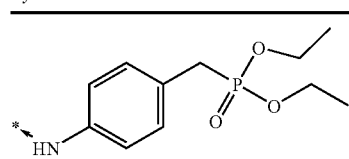 | Example 691<br>91%, 3.85 min<br>697 (M + 1) | Example 692<br>95%, 4.30 min<br>643 (M + 1) | Example 693<br>100%, 4.05 min<br>629 (M + 1) |

TABLE 10-2-continued basic structure

| | Rx | | |
|---|---|---|---|
| Ry | 3,4-dimethoxybenzyl | 2-cyclopentylethyl | 2-thienyl |
| 3-(1H-imidazol-1-yl)propylamino | Example 698<br>96%, 3.04 min<br>579 (M + 1) | Example 699<br>100%, 3.42 min<br>525 (M + 1) | Example 700<br>98%, 3.16 min<br>511 (M + 1) |
| pyridin-3-ylamino | Example 705<br>92%, 3.10 min<br>548 (M + 1) | Example 706<br>99%, 3.49 min<br>494 (M + 1) | Example 707<br>84%, 3.27 min<br>480 (M + 1) |
| 2-(pyridin-4-yl)ethylamino | Example 712<br>93%, 3.04 min<br>576 (M + 1) | Example 713<br>100%, 3.41 min<br>522 (M + 1) | Example 714<br>91%, 3.14 min<br>508 (M + 1) | upper line: Example No.
middle line: HPLC purity (220 nm), retention time
lower line: MS (APCI+, m/e)

TABLE 10-3 basic structure

| | Rx | | | |
|---|---|---|---|---|
| Ry | CH₃ | 3-heptyl | 2-(methylthio)ethyl | phenoxymethyl |
| (5-methylpyrazin-2-yl)methylamino | Example 715<br>95%, 3.13 min<br>441 (M + 1) | Example 716<br>97%, 4.05 min<br>525 (M + 1) | Example 717<br>88%, 3.43 min<br>501 (M + 1) | Example 718<br>92%, 3.70 min<br>533 (M + 1) |

TABLE 10-3-continued basic structure

[Chemical structure: oxazole ring with Rx substituent, connected to biphenyl group with aldehyde, and side chain with C(O)Ry]

| Ry | Rx: CH₃–* | Rx: sec-pentyl–* | Rx: CH₃–S–CH₂CH₂–* | Rx: PhO–CH₂–* |
|---|---|---|---|---|
| *–HN–CH₂CH₂–N(morpholine) | Example 722<br>91%, 2.70 min<br>448 (M + 1) | Example 723<br>100%, 3.45 min<br>532 (M + 1) | Example 724<br>95%, 2.95 min<br>508 (M + 1) | Example 725<br>97%, 3.22 min<br>540 (M + 1) |
| *–N(N-methylpiperazine) | Example 729<br>92%, 2.70 min<br>418 (M + 1) | Example 730<br>97%, 3.45 min<br>502 (M + 1) | Example 731<br>94%, 2.95 min<br>478 (M + 1) | Example 732<br>93%, 3.22 min<br>510 (M + 1) | upper line: Example No.
middle line: HPLC purity (220 nm), retention time
lower line: MS (APCI+, m/e)

TABLE 10-4 basic structure

[Chemical structure: oxazole ring with Rx substituent, connected to biphenyl group with aldehyde, and side chain with C(O)Ry]

| Ry | Rx: 3,4-dimethoxybenzyl–* | Rx: cyclopentylethyl–* | Rx: 2-thienyl–* |
|---|---|---|---|
| *–HN–CH₂–(5-methylpyrazinyl) | Example 719<br>97%, 3.49 min<br>577 (M + 1) | Example 720<br>100%, 4.01 min<br>523 (M + 1) | Example 721<br>100%, 3.68 min<br>509 (M + 1) |
| *–HN–CH₂CH₂–N(morpholine) | Example 726<br>100%, 3.06 min<br>584 (M + 1) | Example 727<br>99%, 3.43 min<br>530 (M + 1) | Example 728<br>94%, 3.17 min<br>516 (M + 1) |

TABLE 10-4-continued basic structure

| | Rx | | |
|---|---|---|---|
| Ry | 3,4-dimethoxybenzyl | 2-cyclopentylethyl | 2-thienyl |
| N-methylpiperazinyl | Example 733<br>95%, 3.06 min<br>554 (M + 1) | Example 734<br>91%, 3.43 min<br>500 (M + 1) | Example 735<br>93%, 3.18 min<br>486 (M + 1) | upper line: Example No.
middle line: HPLC purity (220 nm), retention time
lower line: MS (APCI+, m/e)

TABLE 11-1 basic structure

| | Rx | | | |
|---|---|---|---|---|
| Ry | CH₃ | hexyl | methylthioethyl | phenoxymethyl |
| 4-(diethoxyphosphorylmethyl)anilino | Example 736<br>96%, 3.76 min<br>563 (M + 1) | Example 737<br>96%, 4.48 min<br>647 (M + 1) | Example 738<br>96%, 3.98 min<br>623 (M + 1) | Example 739<br>100%, 4.17 min<br>655 (M + 1) |
| 3-(imidazol-1-yl)propylamino | Example 743<br>98%, 2.86 min<br>445 (M + 1) | Example 744<br>98%, 3.56 min<br>529 (M + 1) | Example 745<br>100%, 3.09 min<br>505 (M + 1) | Example 746<br>100%, 3.34 min<br>537 (M + 1) |
| 3-pyridylamino | Example 750<br>100%, 2.94 min<br>414 (M + 1) | Example 751<br>88%, 3.66 min<br>498 (M + 1) | Example 752<br>98%, 3.26 min<br>474 (M + 1) | Example 753<br>96%, 3.49 min<br>506 (M + 1) |

TABLE 11-1-continued basic structure

| Ry | Rx | | | |
|---|---|---|---|---|
| | CH₃—* | (hexan-3-yl)—* | CH₃S-CH₂CH₂—* | PhO-CH₂—* |
| *HN-CH₂CH₂-(4-pyridyl) | Example 757<br>99%, 2.85 min<br>442 (M + 1) | Example 758<br>98%, 3.56 min<br>526 (M + 1) | Example 759<br>98%, 3.09 min<br>502 (M + 1) | Example 760<br>100%, 3.33 min<br>534 (M + 1) | upper line:
Example No.
middle line:
HPLC purity (220 nm), retention time
lower line:
MS (APCI+, m/e)

TABLE 11-2 basic structure

| Ry | Rx | | |
|---|---|---|---|
| | 3,4-dimethoxybenzyl—* | cyclopentyl-CH₂CH₂—* | 2-thienyl—* |
| *HN-C₆H₄-CH₂-P(O)(OEt)₂ | Example 740<br>100%, 4.00 min<br>699 (M + 1) | Example 741<br>99%, 4.45 min<br>645 (M + 1) | Example 742<br>100%, 4.21 min<br>631 (M + 1) |
| *HN-CH₂CH₂CH₂-(1-imidazolyl) | Example 747<br>100%, 3.19 min<br>581 (M + 1) | Example 748<br>86%, 3.54 min<br>527 (M + 1) | Example 749<br>100%, 3.31 min<br>513 (M + 1) |

TABLE 11-2-continued basic structure

[Structure: oxazole ring with Rx at 2-position, biphenyl-methoxy at 4-position, and -CH2CH2C(O)Ry at 5-position]

| Ry | Rx: 3,4-dimethoxybenzyl | Rx: cyclopentylethyl | Rx: 2-thienyl |
|---|---|---|---|
| 3-aminopyridine (HN-pyridin-3-yl) | Example 754<br>99%, 3.28 min<br>550 (M + 1) | Example 755<br>95%, 3.65 min<br>496 (M + 1) | Example 756<br>99%, 3.42 min<br>482 (M + 1) |
| 2-(pyridin-4-yl)ethylamine | Example 761<br>100%, 3.18 min<br>578 (M + 1) | Example 762<br>87%, 3.54 min<br>524 (M + 1) | Example 763<br>99%, 3.28 min<br>510 (M + 1) | upper line: Example No.
middle line: HPLC purity (220 nm), retention time
lower line: MS (APCI+, m/e)

TABLE 11-3 basic structure

[Structure: oxazole ring with Rx at 2-position, biphenyl-methoxy at 4-position, and -CH2CH2C(O)Ry at 5-position]

| Ry | Rx: CH3 | Rx: sec-butyl/pentyl | Rx: -S-CH2CH2- (methylthioethyl) | Rx: phenoxymethyl |
|---|---|---|---|---|
| (5-methylpyrazin-2-yl)methylamine | Example 764<br>96%, 3.33 min<br>443 (M + 1) | Example 765<br>84%, 4.22 min<br>527 (M + 1) | Example 766<br>100%, 3.61 min<br>503 (M + 1) | Example 767<br>100%, 3.88 min<br>535 (M + 1) |
| 2-morpholinoethylamine | Example 771<br>99%, 2.86 min<br>450 (M + 1) | Example 772<br>93%, 3.58 min<br>534 (M + 1) | Example 773<br>100%, 3.13 min<br>510 (M + 1) | Example 774<br>100%, 3.38 min<br>542 (M + 1) |

TABLE 11-3-continued basic structure

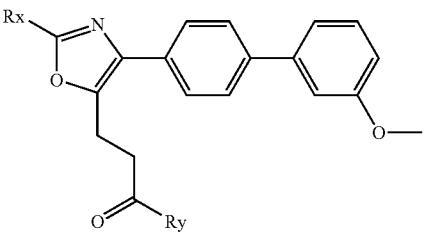

| Ry | Rx | | | |
|---|---|---|---|---|
| |  CH₃ | 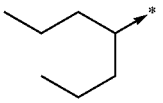 |  | 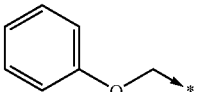 |
| 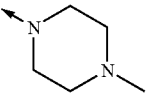 | Example 778<br>100%, 2.85 min<br>420 (M + 1) | Example 779<br>89%, 3.57 min<br>504 (M + 1) | Example 780<br>100%, 3.10 min<br>480 (M + 1) | Example 781<br>99%, 3.35 min<br>512 (M + 1) | upper line: Example No.
middle line: HPLC purity (220 nm), retention time
lower line: MS (APCI+, m/e)

TABLE 11-4 basic structure

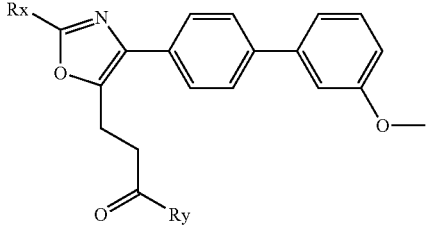

| Ry | Rx | | |
|---|---|---|---|
| | 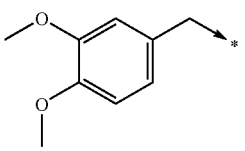 | 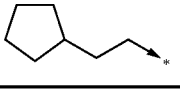 | 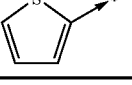 |
| 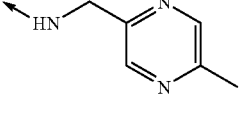 | Example 768<br>100%, 3.67 min<br>579 (M + 1) | Example 769<br>96%, 4.18 min<br>525 (M + 1) | Example 770<br>100%, 3.86 min<br>511 (M + 1) |
| 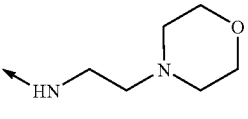 | Example 775<br>100%, 3.22 min<br>586 (M + 1) | Example 776<br>100%, 3.57 min<br>532 (M + 1) | Example 777<br>97%, 3.34 min<br>518 (M + 1) |
| 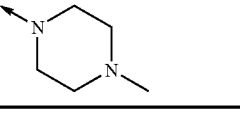 | Example 782<br>98%, 3.20 min<br>556 (M + 1) | Example 783<br>97%, 3.56 min<br>502 (M + 1) | Example 784<br>98%, 3.33 min<br>488 (M + 1) |

TABLE 11-4-continued
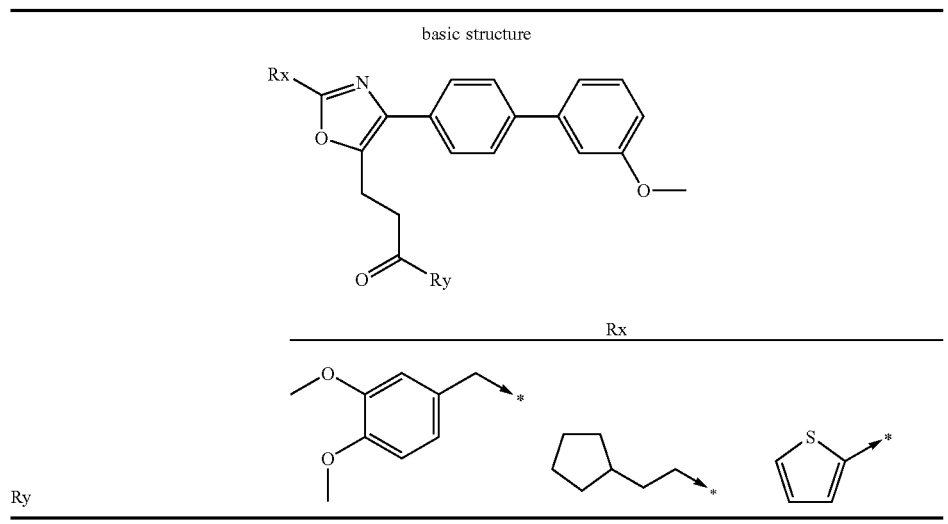
upper line: Example No.
middle line: HPLC purity (220 nm), retention time
lower line: MS (APCI+, m/e)
TABLE 12-1
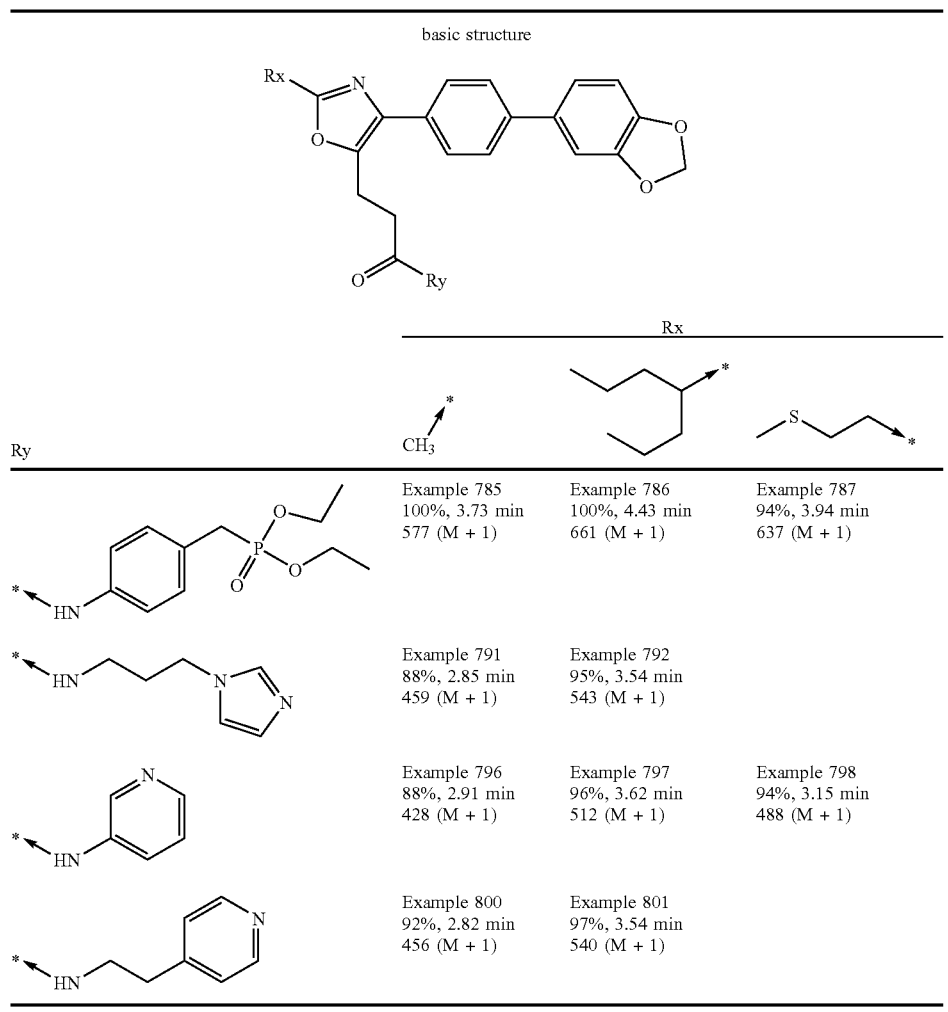
upper line: Example No.

TABLE 12-1-continued basic structure

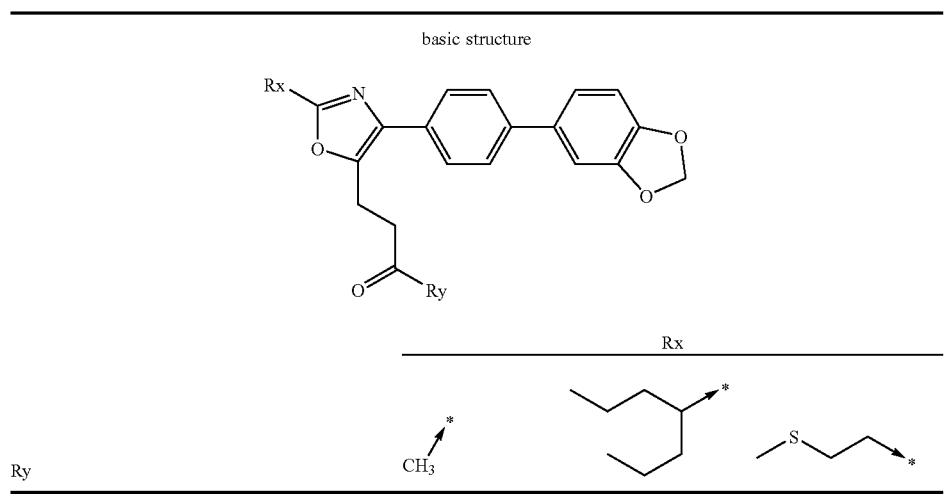

middle line: HPLC purity (220 nm), retention time
lower line: MS (APCI+, m/e)

TABLE 12-2

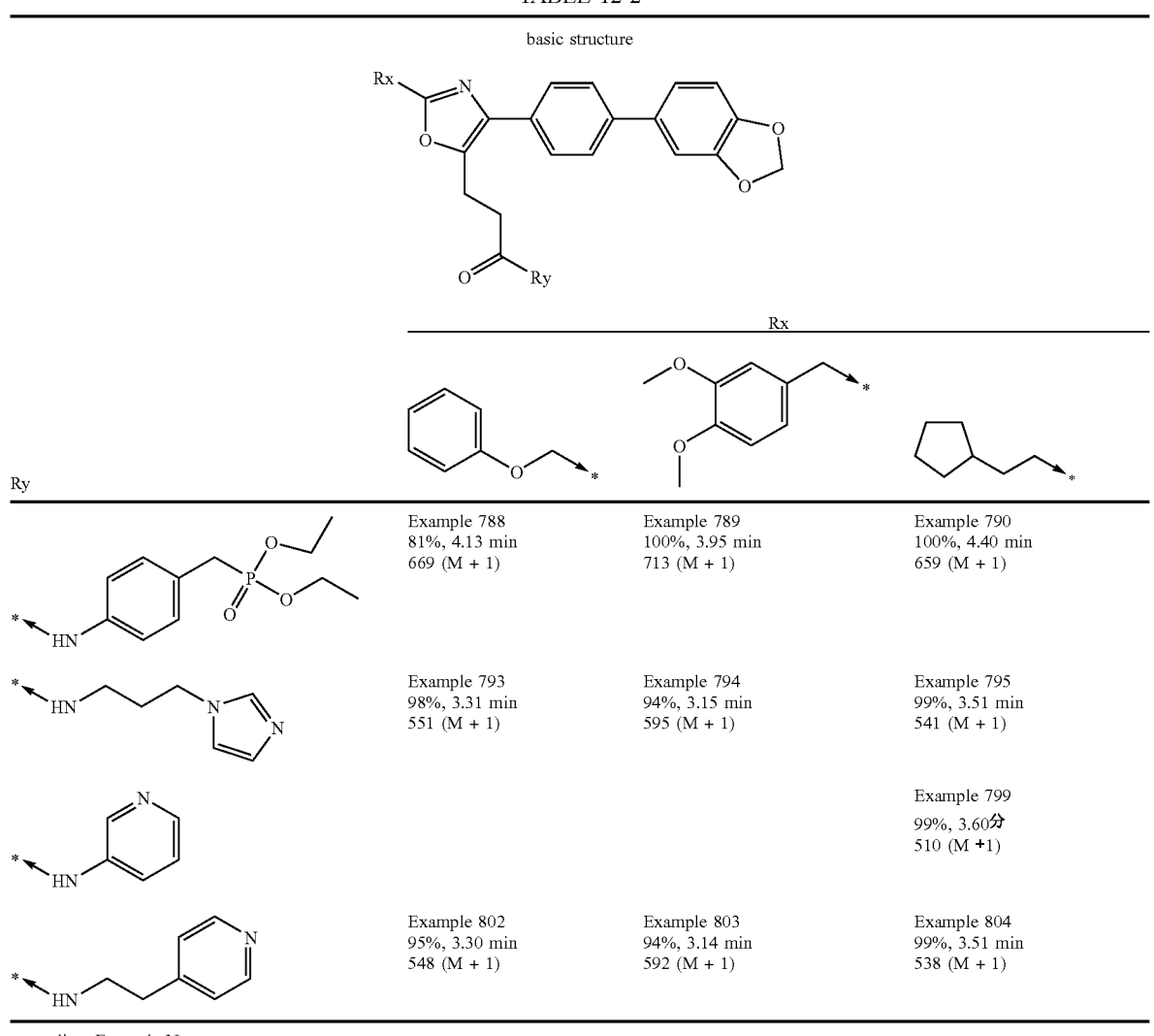

| Ry | Rx (PhOCH2-) | Rx (3,4-dimethoxybenzyl) | Rx (cyclopentylethyl) |
|---|---|---|---|
| 4-(diethoxyphosphorylmethyl)anilino | Example 788<br>81%, 4.13 min<br>669 (M + 1) | Example 789<br>100%, 3.95 min<br>713 (M + 1) | Example 790<br>100%, 4.40 min<br>659 (M + 1) |
| 3-(imidazol-1-yl)propylamino | Example 793<br>98%, 3.31 min<br>551 (M + 1) | Example 794<br>94%, 3.15 min<br>595 (M + 1) | Example 795<br>99%, 3.51 min<br>541 (M + 1) |
| pyridin-3-ylamino | | | Example 799<br>99%, 3.60 min<br>510 (M +1) |
| 2-(pyridin-4-yl)ethylamino | Example 802<br>95%, 3.30 min<br>548 (M + 1) | Example 803<br>94%, 3.14 min<br>592 (M + 1) | Example 804<br>99%, 3.51 min<br>538 (M + 1) | upper line: Example No.

TABLE 12-2-continued basic structure

[Structure: Rx-oxazole-phenyl-benzodioxole with CH2CH2C(=O)Ry substituent]

| | Rx | | |
|---|---|---|---|
| Ry | PhOCH2-* | 3,4-dimethoxybenzyl-* | cyclopentylethyl-* | middle line: HPLC purity (220 nm), retention time
lower line: MS (APCI+, m/e)

TABLE 12-3 basic structure

[Structure: Rx-oxazole-phenyl-benzodioxole with CH2CH2C(=O)Ry substituent]

| | Rx | | |
|---|---|---|---|
| Ry | CH3 | heptyl (sec) | CH3-S-CH2CH2-* |
| *—HN-CH2-(5-methylpyrazin-2-yl) | Example 805<br>100%, 3.29 min<br>457 (M + 1) | Example 806<br>91%, 4.17 min<br>541 (M + 1) | Example 807<br>100%, 3.57 min<br>517 (M + 1) |
| *—HN-CH2CH2-morpholino | Example 810<br>94%, 2.85 min<br>464 (M + 1) | Example 811<br>97%, 3.56 min<br>548 (M + 1) | Example 812<br>100%, 3.08 min<br>524 (M + 1) |
| *—N(4-methylpiperazin-1-yl) | Example 815<br>98%, 2.84 min<br>434 (M + 1) | Example 816<br>96%, 3.55 min<br>518 (M + 1) | Example 817<br>99%, 3.07 min<br>494 (M + 1) | upper line: Example No.
middle line: HPLC purity (220 nm), retention time
lower line: MS (APCI+, m/e)

TABLE 12-4 basic structure

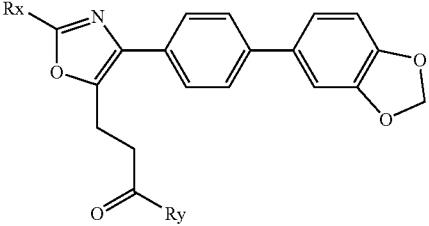

| Ry | Rx | |
|---|---|---|
| | 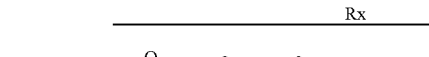 | 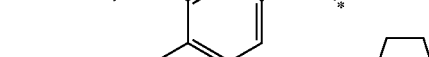 |
| 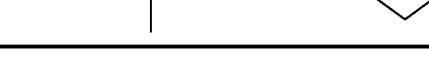 | Example 808<br>100%, 3.61 min,<br>593 (M + 1) | Example 809<br>96%, 4.12 min<br>539 (M + 1) |
| 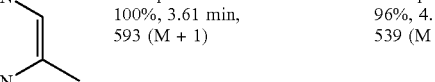 | Example 813<br>97%, 3.18 min,<br>600 (M + 1) | Example 814<br>99%, 3.54 min<br>546 (M + 1) |
| 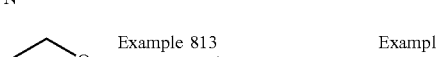 | Example 818<br>96%, 3.17 min<br>570 (M + 1) | Example 819<br>98%, 3.55 min<br>516 (M + 1) | upper line: Example No.
middle line: HPLC purity (220 nm), retention time
lower line: MS (APCI+, m/e)

TABLE 13-1 basic structure

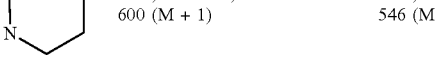

| Ry | Rx | | | |
|---|---|---|---|---|
| | 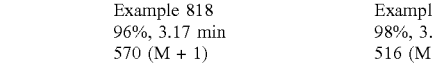 | 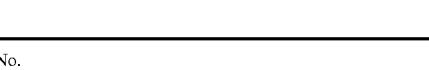 | 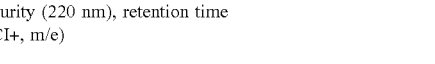 | 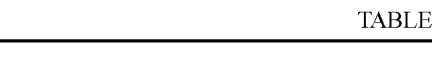 |
| 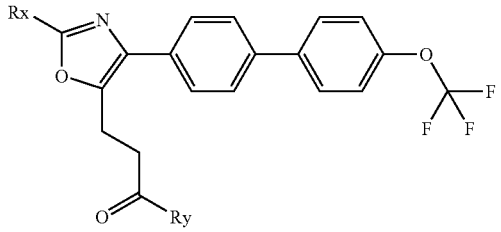 | Example 820<br>100%, 4.09 min<br>617 (M + 1) | Example 821<br>100%, 4.75 min<br>701 (M + 1) | Example 822<br>100%, 4.26 min<br>677 (M + 1) | Example 823<br>100%, 4.43 min<br>709 (M + 1) |

TABLE 13-1-continued

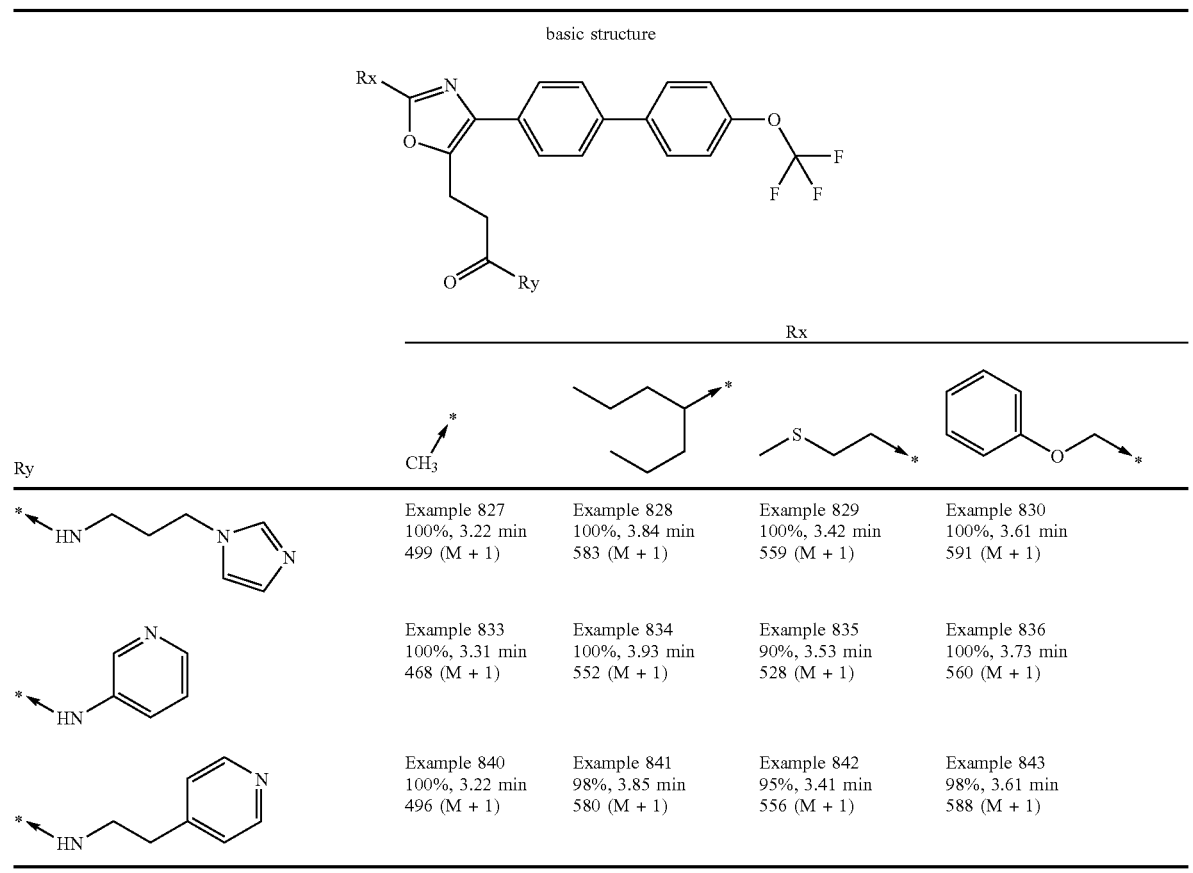

| Ry | Rx CH₃ | Rx (hexyl) | Rx SMe-ethyl | Rx PhO-methyl |
|---|---|---|---|---|
| *HN-propyl-imidazole | Example 827<br>100%, 3.22 min<br>499 (M + 1) | Example 828<br>100%, 3.84 min<br>583 (M + 1) | Example 829<br>100%, 3.42 min<br>559 (M + 1) | Example 830<br>100%, 3.61 min<br>591 (M + 1) |
| *HN-pyridin-3-yl | Example 833<br>100%, 3.31 min<br>468 (M + 1) | Example 834<br>100%, 3.93 min<br>552 (M + 1) | Example 835<br>90%, 3.53 min<br>528 (M + 1) | Example 836<br>100%, 3.73 min<br>560 (M + 1) |
| *HN-ethyl-pyridin-4-yl | Example 840<br>100%, 3.22 min<br>496 (M + 1) | Example 841<br>98%, 3.85 min<br>580 (M + 1) | Example 842<br>95%, 3.41 min<br>556 (M + 1) | Example 843<br>98%, 3.61 min<br>588 (M + 1) | upper line: Example No.
middle line: HPLC purity (220 nm), retention time
lower line: MS (APCI+, m/e)

TABLE 13-2

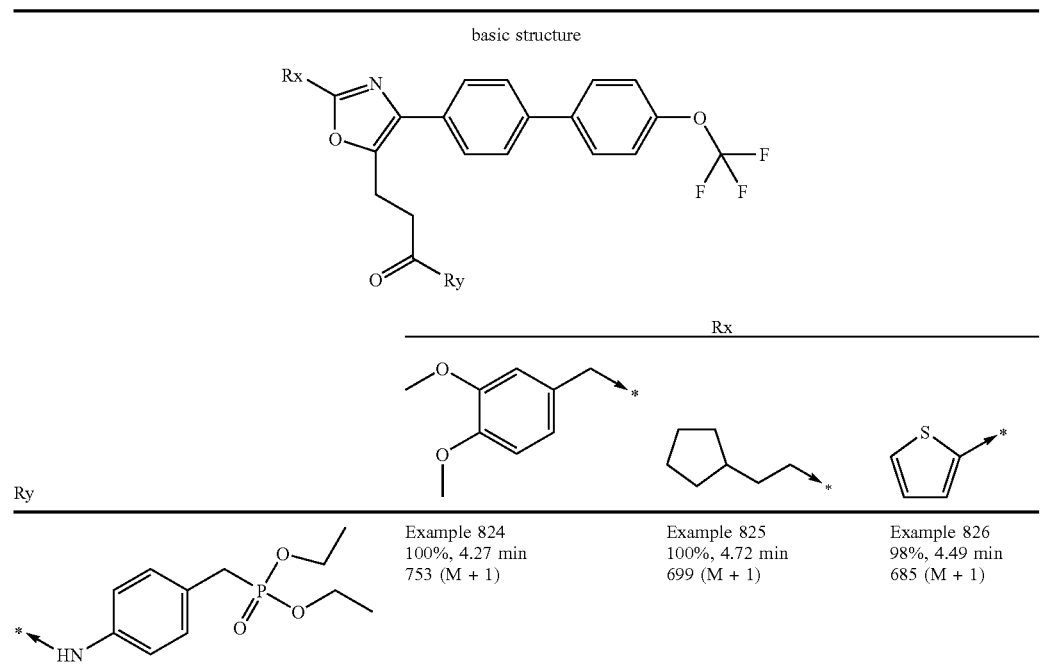

| Ry | Rx (dimethoxybenzyl) | Rx (cyclopentylethyl) | Rx (thienyl) |
|---|---|---|---|
| *HN-Ph-CH₂-P(O)(OEt)₂ | Example 824<br>100%, 4.27 min<br>753 (M + 1) | Example 825<br>100%, 4.72 min<br>699 (M + 1) | Example 826<br>98%, 4.49 min<br>685 (M + 1) |

TABLE 13-2-continued
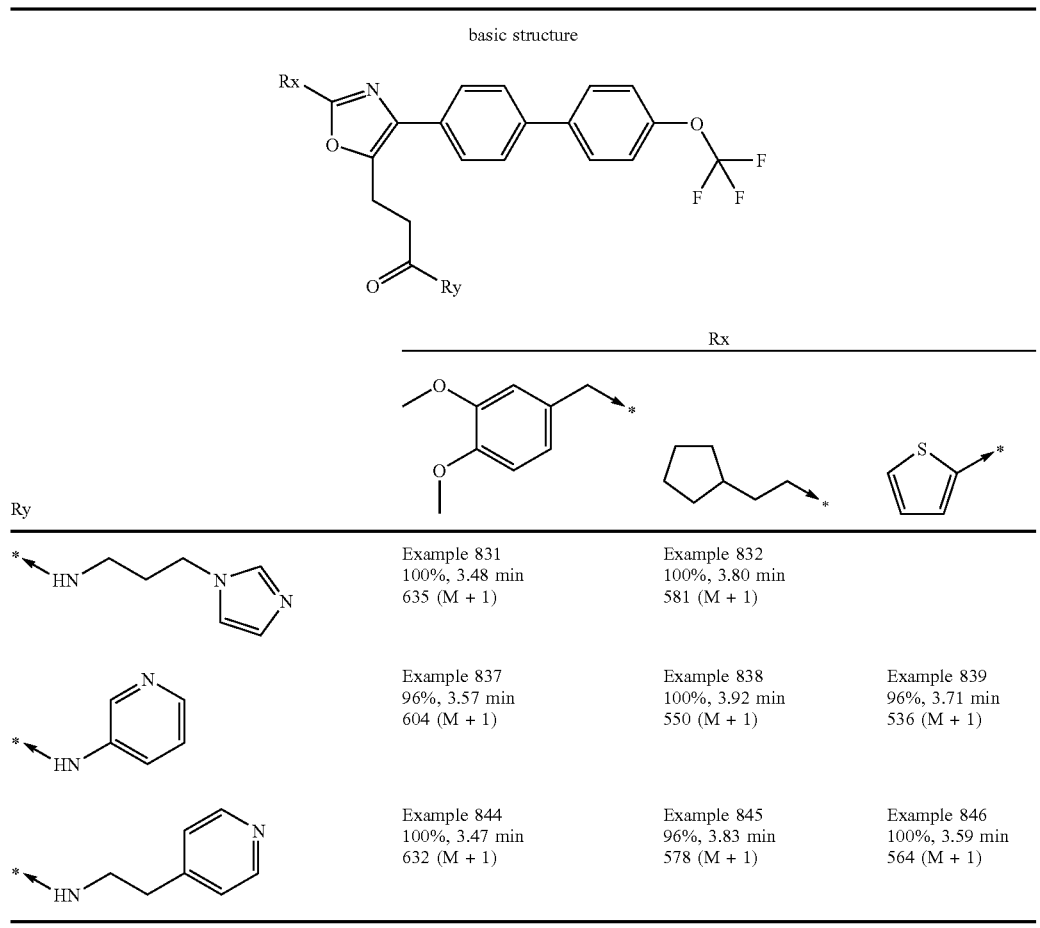
upper line: Example No.
middle line: HPLC purity (220 nm), retention time
lower line: MS (APCI+, m/e)
TABLE 13-3
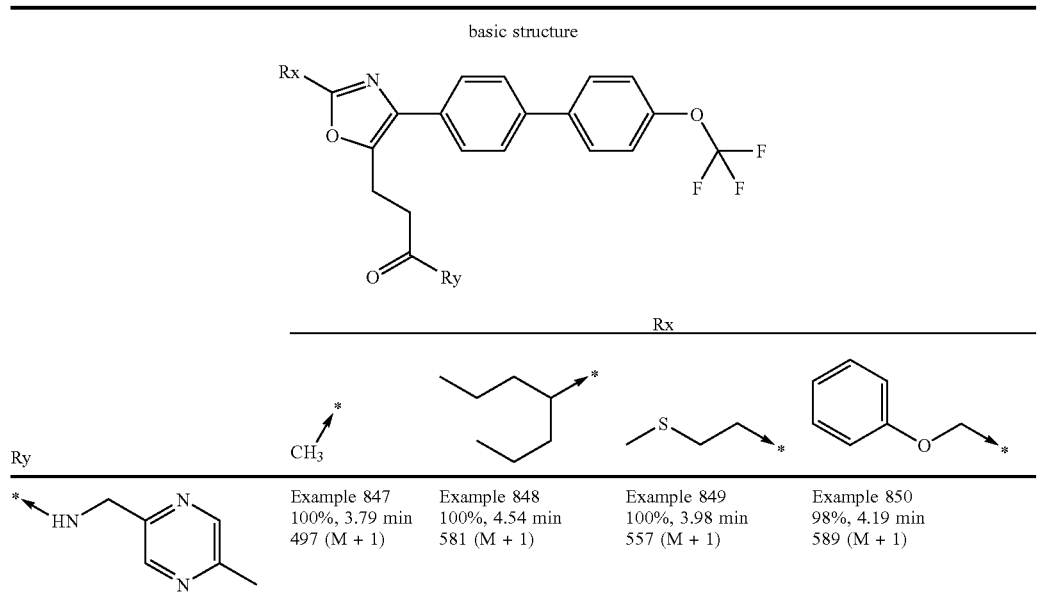

TABLE 13-3-continued basic structure

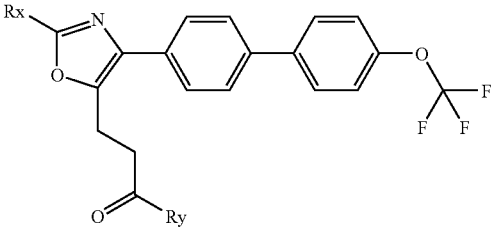

| Ry | Rx  CH₃ | 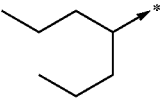 | 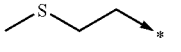 S | 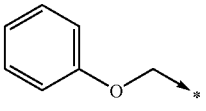 |
|---|---|---|---|---|
| 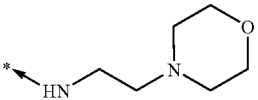 HN | Example 854<br>100%, 3.24 min<br>504 (M + 1) | Example 855<br>97%, 3.87 min<br>588 (M + 1) | Example 856<br>97%, 3.43 min<br>564 (M + 1) | Example 857<br>99%, 3.64 min<br>596 (M + 1) |
| 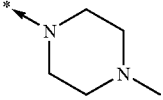 | Example 861<br>99%, 3.25 min<br>474 (M + 1) | Example 862<br>100%, 3.87 min<br>558 (M + 1) | Example 863<br>95%, 3.43 min<br>534 (M + 1) | Example 864<br>100%, 3.64 min<br>566 (M + 1) | upper line: Example No.
middle line: HPLC purity (220 nm), retention time
lower line: MS (APCI+, m/e)

TABLE 13-4 basic structure

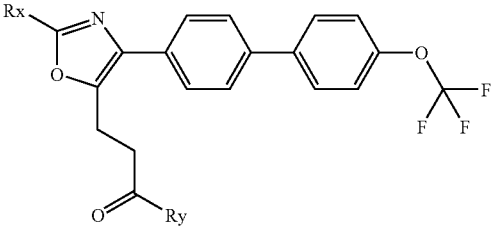

| Ry | Rx 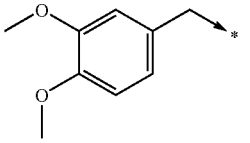 | 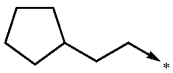 | 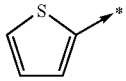 |
|---|---|---|---|
| 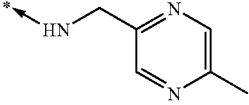 HN | Example 851<br>98%, 4.00 min<br>633 (M + 1) | Example 852<br>100%, 4.50 min<br>579 (M + 1) | Example 853<br>100%, 4.21 min<br>565 (M + 1) |
| 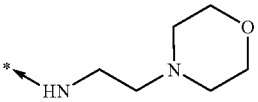 HN | Example 858<br>99%, 3.50 min<br>640 (M + 1) | Example 859<br>98%, 3.84 min<br>586 (M + 1) | Example 860<br>97%, 3.62 min<br>572 (M + 1) |

TABLE 13-4-continued basic structure

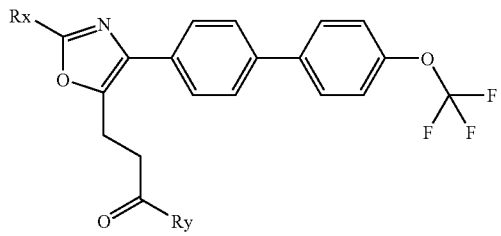

| Ry | Rx | | |
|---|---|---|---|
| | 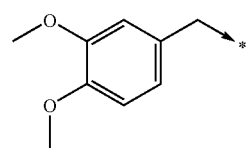 | 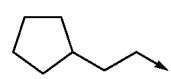 | 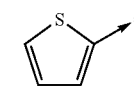 |
| 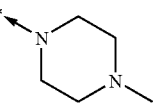 | Example 865<br>97%, 3.50 min<br>610 (M + 1) | Example 866<br>98%, 3.83 min<br>556 (M + 1) | Example 867<br>97%, 3.62 min<br>542 (M + 1) | upper line: Example No.
middle line: HPLC purity (220 nm), retention time
lower line: MS (APCI+, m/e)

TABLE 14 basic structure

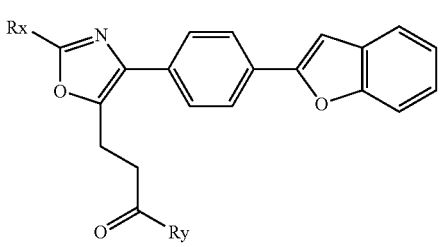

| Ry | Rx | | | | |
|---|---|---|---|---|---|
| |  | 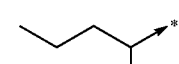 | 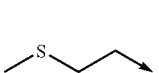 | 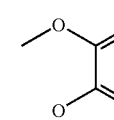 | 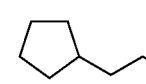 |
| 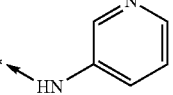 | Example 868<br>92%, 3.33 min<br>424 (M + 1) | Example 869<br>83%, 3.53 min<br>508 (M + 1) | Example 870<br>100%, 3.49 min<br>484 (M + 1) | Example 871<br>100%, 3.54 min<br>560 (M + 1) | Example 872<br>90%, 3.52 min<br>506 (M + 1) |
| 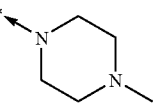 | | Example 873<br>80%, 3.44 min<br>514 (M + 1) | | | Example 874<br>89%, 3.42 min<br>512 (M + 1) | upper line: Example No.

TABLE 14-continued basic structure

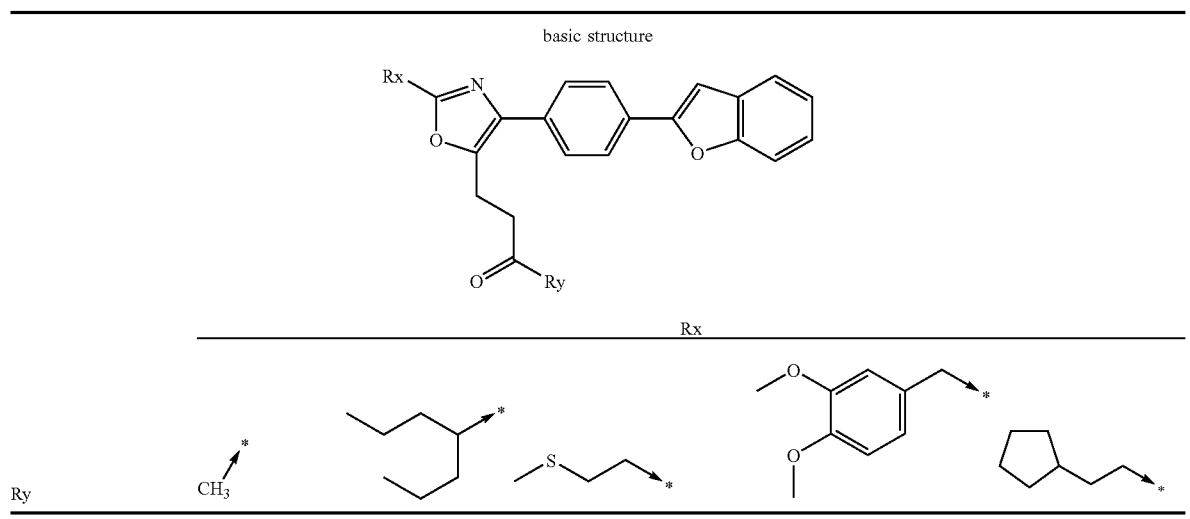

middle line: HPLC purity (220 nm), retention time
lower line: MS (APCI+, m/e)

Example 875

A mixture of diethyl [4-({3-[2-amino-4-(4-chlorophenyl)-1,3-thiazol-5-yl]propanoyl}amino)benzyl]phosphonate (100 mg), ethyl carbamate (50 mg), carbonyldiimidazole (38 mg), diisopropylethylamine (85 μl) and N,N-dimethylformamide (0.5 ml) was shaken at room temperature for 8 hrs. The reaction mixture was directly poured into preparative HPLC and purified to give the object compound.

Examples 876–953

In the same manner as in Example 875, the object compounds were obtained.

The structure and purity of the object compounds of Examples 875–953 were confirmed by LC-MS, HPLC. The yield, structure, purity and mass spectrum data of the object compounds are shown in [Table 15-1]–[Table 15-4], [Table 16-1]–[Table 16-4] and [Table 17].

TABLE 15-1 basic structure

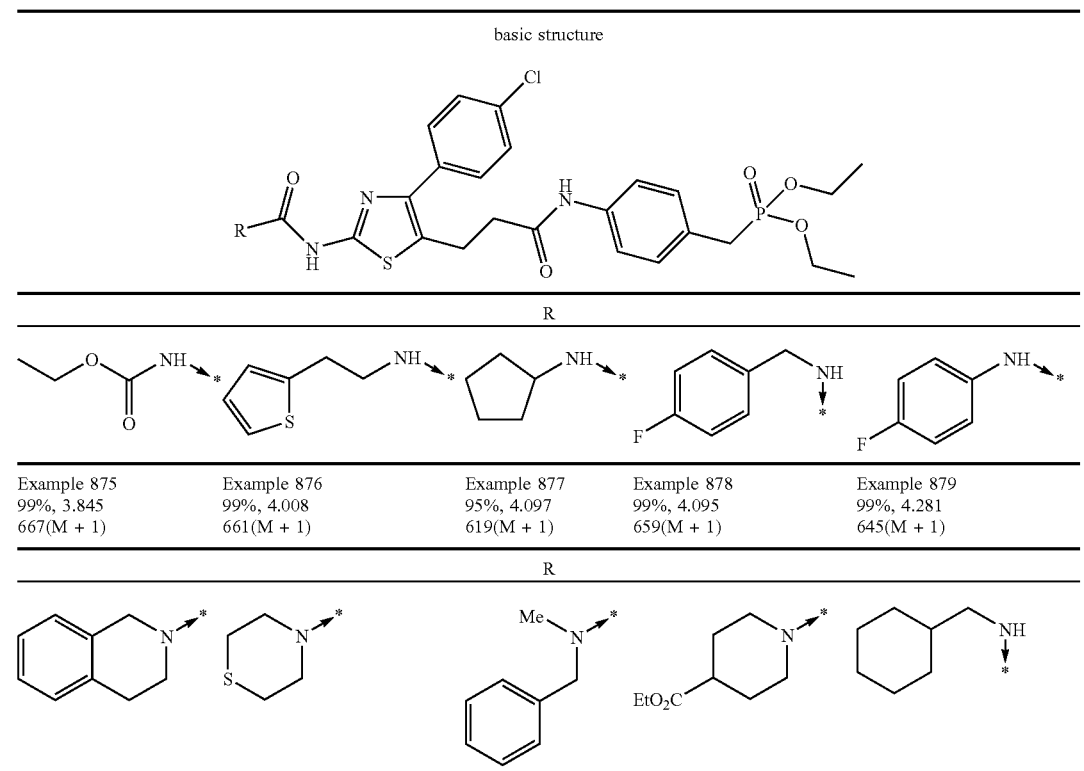

| Example 875 | Example 876 | Example 877 | Example 878 | Example 879 |
|---|---|---|---|---|
| 99%, 3.845 | 99%, 4.008 | 95%, 4.097 | 99%, 4.095 | 99%, 4.281 |
| 667(M + 1) | 661(M + 1) | 619(M + 1) | 659(M + 1) | 645(M + 1) |

TABLE 15-1-continued basic structure

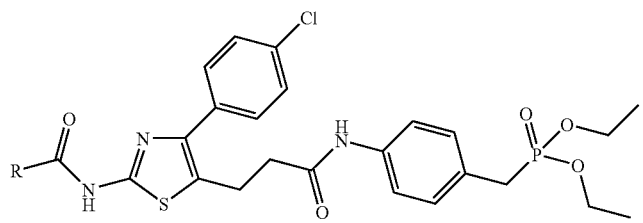

| Example 880 | Example 881 | Example 882 | Example 883 | Example 884 |
|---|---|---|---|---|
| 96%, 4.363 | 93%, 4.027 | 94%, 4.280 | 97%, 4.117 | 99%, 4.386 |
| 667(M + 1) | 637(M + 1) | 655(M + 1) | 691(M + 1) | 647(M + 1) | upper line: Example No.

middle line: HPLC purity(220 nm), retention time(min)

lower line: MS(APCI+, m/e)

TABLE 15-2 basic structure

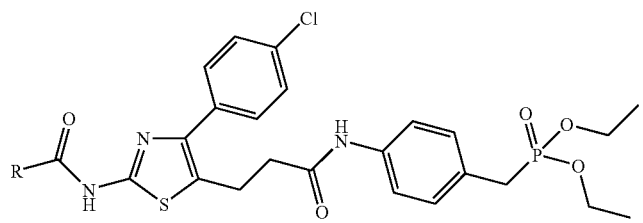

| R | | | | |
|---|---|---|---|---|
| Example 885 | Example 886 | Example 887 | Example 888 | Example 889 |
| 100%, 3.653 | 99%, 3.739 | 87%, 4.210 | 99%, 4.276 | 95%, 4.051 |
| 609(M + 1) | 653(M + 1) | 633(M + 1) | 667(M + 1) | 726(M + 1) |

| R | | | | |
|---|---|---|---|---|
| Example 890 | Example 891 | Example 892 | Example 893 | Example 894 |
| 96%, 3.538 | 94%, 4.170 | 97%, 4.352 | 98%, 3.417 | 98%, 3.524 |
| 662(M + 1) | 691(M + 1) | 633(M + 1) | 710(M + 1) | 712(M + 1) | upper line: Example No.
middle line: HPLC purity(220 nm), retention time(min)
lower line: MS(APCI+, m/e)

TABLE 15-3
basic structure
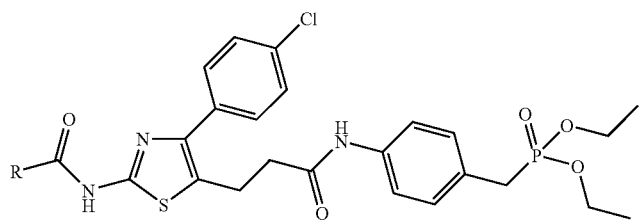
R
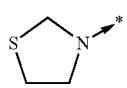  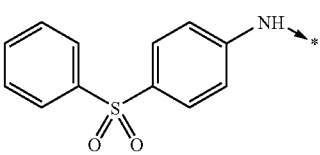
| Example 895 | Example 896 | Example 897 |
|---|---|---|
| 99%, 3.986 | 90%, 3.998 | 96%, 4.339 |
| 623(M + 1) | 777(M + 1) | 767(M + 1) |
R
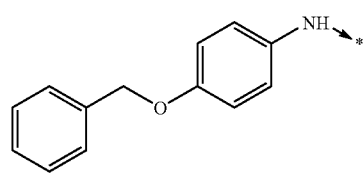 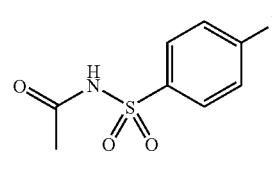 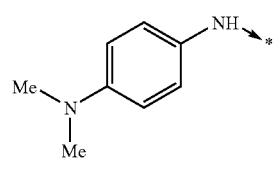
| Example 898 | Example 899 | Example 900 |
|---|---|---|
| 96%, 4.579 | 98%, 3.903 | 96%, 3.492 |
| 733(M + 1) | 748(M + 1) | 698(M + 1) |
R
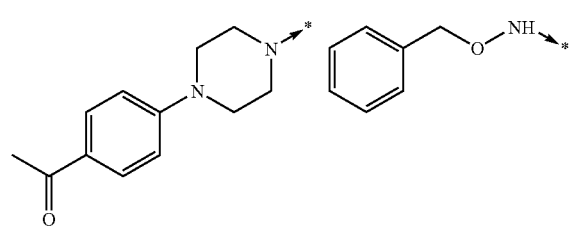 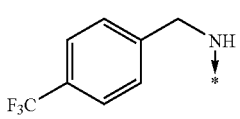
| Example 901 | Example 902 | Example 903 |
|---|---|---|
| 98%, 3.887 | 92%, 4.220 | 98%, 4.340 |
| 738(M + 1) | 657(M + 1) | 709(M + 1) |
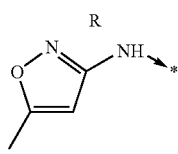
Example 904
98%, 4.054
632(M + 1)
upper line: Example No.
middle line: HPLC purity(220 nm), retention time(min)
lower line: MS(APCI+, m/e)

TABLE 15-4
basic structure
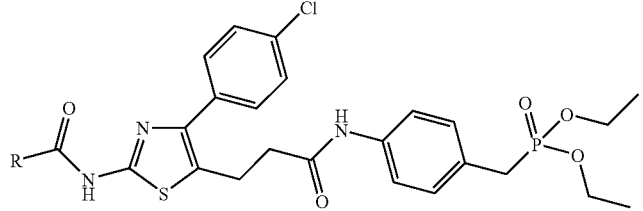
| R | | | |
|---|---|---|---|
| 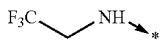 | 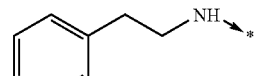 | 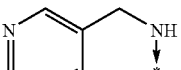 | 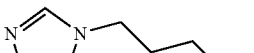 |
| Example 905 | Example 906 | Example 907 | Example 908 |
| 99%, 3.996 | 99%, 4.343 | 99%, 3.230 | 100%, 3.230 |
| 633(M + 1) | 689(M + 1) | 642(M + 1) | 659(M + 1) |
| R | | | |
|---|---|---|---|
| 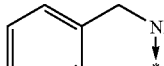 |  | 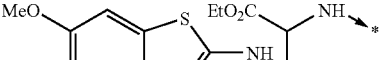 | |
| Example 909 | Example 910 | Example 911 | Example 912 |
| 86%, 4.362 | 97%, 4.407 | 99%, 4.150 | 97%, 4.133 |
| 709(M + 1) | 681(M + 1) | 714(M + 1) | 709(M + 1) |
| R | |
|---|---|
| | |
| Example 913 | Example 914 |
| 100%, 3.676 | 99%, 3.732 |
| 604(M + 1) | 734(M + 1) |
upper line: Example No.
middle line: HPLC purity(220 nm), retention time(min)
lower line: MS(APCI+, m/e)

TABLE 16-1 basic structure

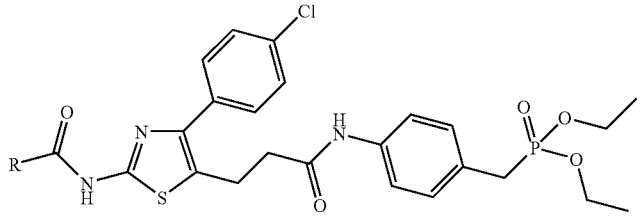

| R | | | | |
|---|---|---|---|---|
| 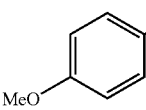 | 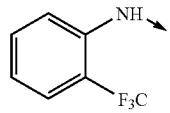 | 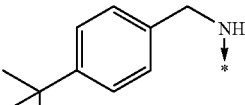 | 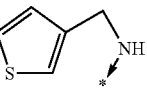 | 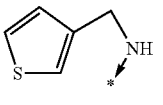 |
| Example 915<br>96%, 4.152<br>657(M + 1) | Example 916<br>100%, 4.317<br>657(M + 1) | Example 917<br>100%, 3.796<br>590(M + 1) | Example 918<br>98%, 4.609<br>697(M + 1) | Example 919<br>100%, 4.056<br>647(M + 1) |

| R | | | | |
|---|---|---|---|---|
| 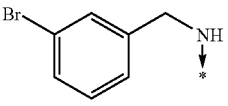 | 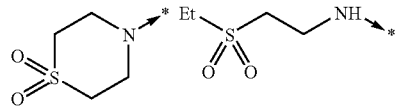 | 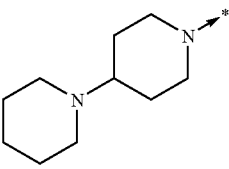 | 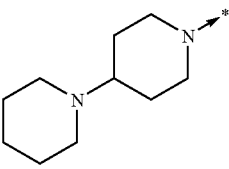 | 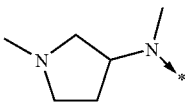 |
| Example 920<br>100%, 4.314<br>720(M + 1) | Example 921<br>100%, 3.696<br>669(M + 1) | Example 922<br>100%, 3.641<br>671(M + 1) | Example 923<br>100%, 3.284<br>702(M + 1) | Example 924<br>100%, 3.243<br>648(M + 1) | upper line: Example No.
middle line: HPLC purity(220 nm), retention time(min)
lower line: MS(APCI+, m/e)

TABLE 16-2 basic structure

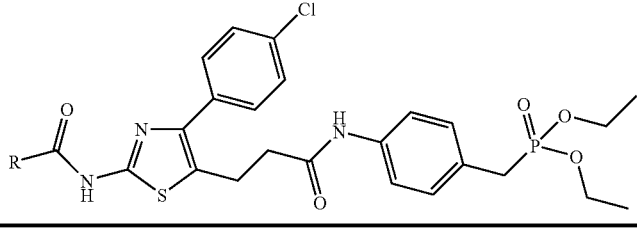

| R | | | |
|---|---|---|---|
| 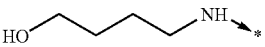 | 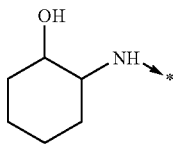 |  | |
| Example 925<br>99%, 3.488<br>623(M + 1) | Example 926<br>95%, 3.762<br>649(M + 1) | Example 927<br>80%, 4.136<br>736(M + 1) | Example 928<br>99%, 3.227<br>664(M + 1) |

| R |
|---|

TABLE 16-2-continued
basic structure
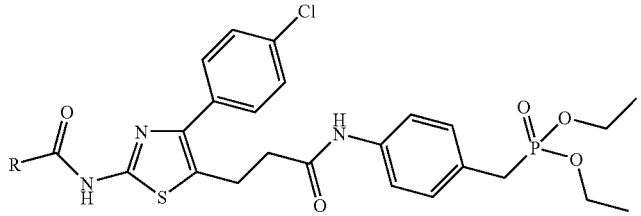
| 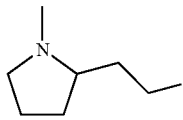 | 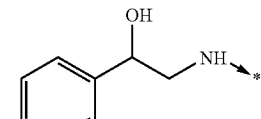 | 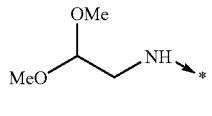 | 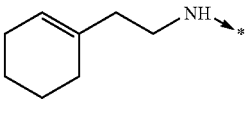 |
|---|---|---|---|
| Example 929<br>100%, 3.245<br>662(M + 1) | Example 930<br>99%, 3.856<br>671(M + 1) | Example 931<br>89%, 3.735<br>639(M + 1) | Example 932<br>96%, 4.436<br>659(M + 1) |
R
| | | 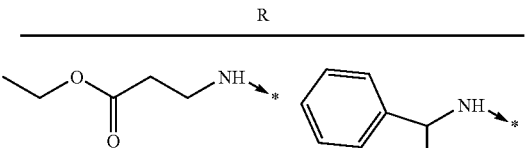 | 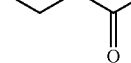 |
|---|---|---|---|
| | | Example 933<br>99%, 3.866<br>651(M + 1) | Example 934<br>99%, 4.300<br>667(M + 1) |
upper line: Example No.
middle line: HPLC purity(220 nm), retention time(min)
lower line: MS(APCI+, m/e)
TABLE 16-3
basic structure
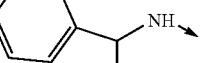
R
| 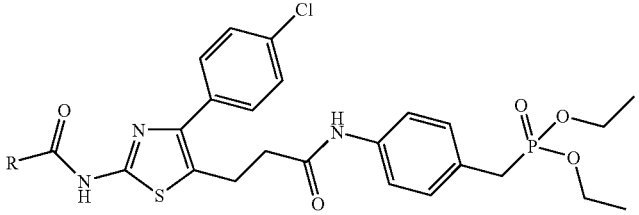 | 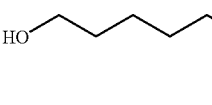 | 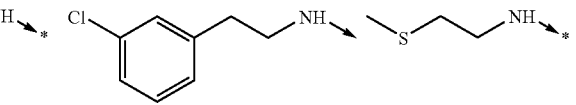 |
|---|---|---|
| Example 935<br>100%, 3.679<br>651(M + 1) | Example 936<br>100%, 4.357<br>689(M + 1) | Example 937<br>99%, 3.885<br>625(M + 1) |
R TABLE 16-3-continued
basic structure
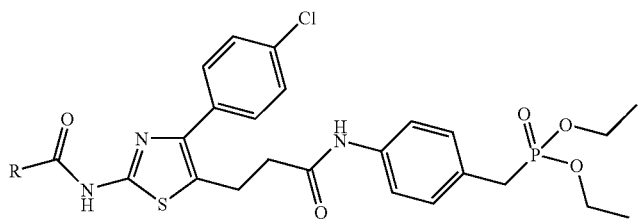
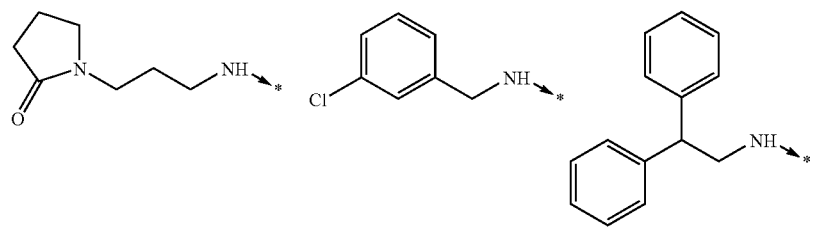
| Example 938 | Example 939 | Example 940 |
|---|---|---|
| 99%, 3.539 | 100%, 4.275 | 99%, 4.518 |
| 676(M + 1) | 675(M + 1) | 731(M + 1) |
R
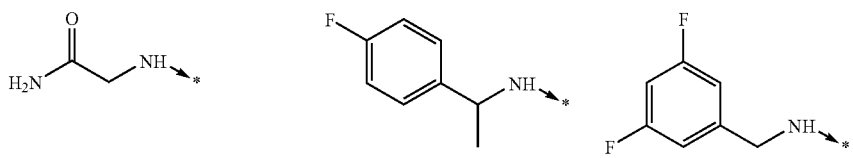
| Example 941 | Example 942 | Example 943 |
|---|---|---|
| 98%, 3.364 | 99%, 4.241 | 99%, 4.204 |
| 608(M + 1) | 673(M + 1) | 677(M + 1) |
R
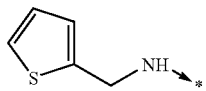
Example 944
99%, 4.057
647(M + 1)
upper line: Example No.
middle line: HPLC purity(220 nm), retention time(min)
lower line: MS(APCI+, m/e)

TABLE 16-4
basic structure
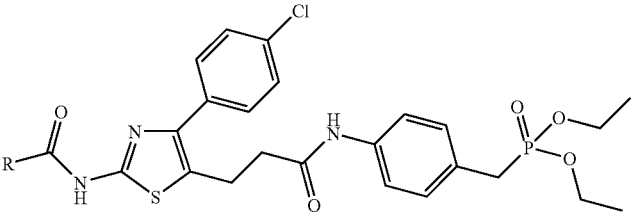
| R | | |
|---|---|---|
| 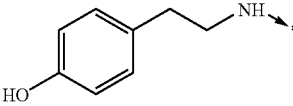 | 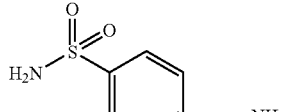 | 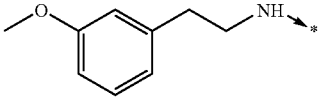 |
| Example 945 | Example 946 | Example 947 |
| 99%, 3.839 | 100%, 3.717 | 99%, 4.173 |
| 671(M + 1) | 720(M + 1) | 685(M + 1) |
| R | | |
|---|---|---|
| 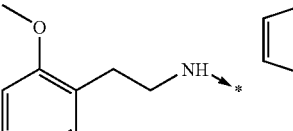 | 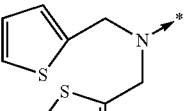 | 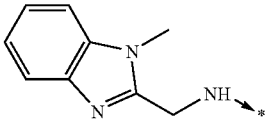 |
| Example 948 | Example 949 | Example 950 |
| 99%, 4.281 | 99%, 4.615 | 99%, 3.395 |
| 685(M + 1) | 743(M + 1) | 695(M + 1) |
| R |
|---|
| 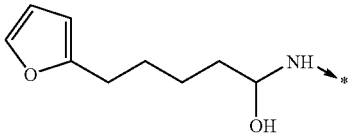 |
| Example 951 |
| 99%, 4.494 |
| 701(M + 1) |
upper line: Example No.
middle line: HPLC purity(220 nm), retention time(min)
lower line: MS(APCI+, m/e)

TABLE 17 basic structure

[Chemical structure: thiazole core with 4-chlorophenyl, R-NH-C(O)- group, and propanoyl-thiomorpholine-SO2]

R

[Structure 1: tetrahydronaphthalen-1-yl-NH-*]  [Structure 2: 2-(thiophen-2-yl)ethyl-NH-*]

| Example 952 | Example 953 |
|---|---|
| 99%, 4.005 | 99%, 3.885 |
| 573(M + 1) | 553(M + 1) | upper line: Example No.
middle line: HPLC purity(220 nm), retention time(min)
lower line: MS(APCI+, m/e)

Example 954

A mixture of diethyl [4-({3-[2-amino-4-(4-chlorophenyl)-1,3-thiazol-5-yl]propanoyl}amino)benzyl]phosphonate (100 mg), cyclohexanecarboxylic acid (38 mg), 1-hydroxy-7-azabenzotriazole (31 mg), 1-ethyl-3-(3-dimethylaminopropyl)carbodiimide (76 mg) and N,N-dimethylformamide (0.4 ml) was shaken at room temperature for 8 hrs. The reaction mixture was directly poured into preparative HPLC and purified to give the object compound.

Examples 955–993

In the same manner as in Example 954, the object compounds were obtained.

The structure and purity of the object compounds of Examples 954–993 were confirmed by LC-MS, HPLC. The yield, structure, purity and mass spectrum data of the object compounds are shown in [Table 18-1]–[Table 18-2] and [Table 19-1]–[Table 19-2].

TABLE 18-1 basic structure

[Chemical structure: thiazole core with 4-chlorophenyl, R-C(O)-NH- group, and propanoyl-NH-phenyl-CH2-P(O)(OEt)2]

R

| Example 954 | Example 955 | Example 956 | Example 957 |
|---|---|---|---|
| [cyclohexylmethyl-*] | [(E)-3-(4-fluorophenyl)allyl-*] | [3-methoxybenzyl-*] | [(6-fluoropyridin-3-yl)methyl-*] |
| 100%, 4.413 | 100%, 3.447 | 100%, 3.982 | 100%, 4.259 |
| 618(M + 1) | 656(M + 1) | 642(M + 1) | 631(M + 1) |

R

[BocNH-CH2-cyclohexyl-CH2-*] [benzofuran-2-ylmethyl-*] [furan-3-ylmethyl-*] [thiophen-2-ylmethyl-*]

TABLE 18-1-continued
basic structure
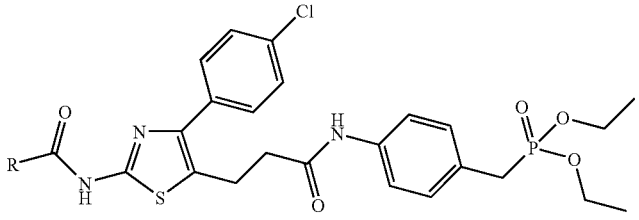
| Example 958 | Example 959 | Example 960 | Example 961 |
|---|---|---|---|
| 99%, 4.249 | 97%, 4.640 | 97%, 3.996 | 96%, 4.214 |
| 747(M + 1) | 652(M + 1) | 602(M + 1) | 618(M + 1) |
R
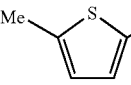
| | | Example 962 | Example 963 |
|---|---|---|---|
| | | 96%, 4.510 | 100%, 4.137 |
| | | 632(M + 1) | 602(M + 1) |
upper line: Example No.
middle line: HPLC purity(220 nm), retention time(min)
lower line: MS(APCI+, m/e)
TABLE 18-2
basic structure
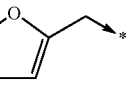
R
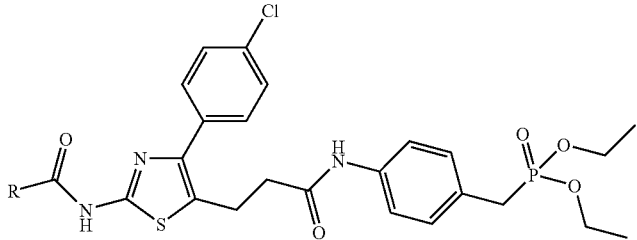
| Example 964 | Example 965 | Example 966 |
|---|---|---|
| 100%, 3.382 | 96%, 4.083 | 98%, 4.408 |
| 704 (M + 1) | 613 (M + 1) | 660 (M + 1) |
R
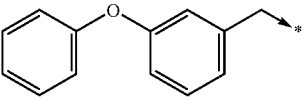
| Example 969 | Example 970 | Example 971 |
|---|---|---|
| 96%, 4.507 | 99%, 4.057 | 98%, 4.470 |
| 654 (M + 1) | 636 (M + 1) | 658 (M + 1) |
R
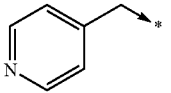

TABLE 18-2-continued basic structure

[Structure: 4-chlorophenyl-thiazole with R-C(O)NH- substituent and propanamide linker to 4-(diethylphosphonomethyl)aniline]

| Example 967 | Example 968 |
|---|---|
| 100%, 4.370 | 100%, 4.380 |
| 628 (M + 1) | 668 (M + 1) |

R

| [biphenyl-CH2CH2-*] | [2-bromobenzyl-CH2-*] |
|---|---|
| Example 972 | Example 973 |
| 98%, 4.363 | 97%, 4.118 |
| 702 (M + 1) | 705 (M + 1) | upper line: Example No.
middle line: HPLC purity (220 nm), retention time (min)
lower line: MS (APCI+, m/e)

TABLE 19-1 basic structure

[Structure: 4-chlorophenyl-thiazole with R-C(O)NH- substituent and propanamide linker to 4-(diethylphosphonomethyl)aniline]

R

| [NC-CH2CH2CH2-*] | [pyrenyl-CH2CH2-*] | [furan-2-yl-CH2CH2CH2-*] |
|---|---|---|
| Example 974 | Example 975 | Example 976 |
| 99%, 4.144 | 98%, 4.029 | 98%, 4.101 |
| 575 (M + 1) | 750 (M + 1) | 628 (M + 1) |

R

| [quinolin-2-yl-CH2-*] | [indol-3-yl-CH2CH2-*] | [isohexyl: Me2CH-CH2CH2CH2-*] |
|---|---|---|
| Example 979 | Example 980 | Example 981 |
| 93%, 4.047 | 87%, 4.460 | 100%, 4.139 |
| 663 (M + 1) | 679 (M + 1) | 606 (M + 1) |

TABLE 19-1-continued
basic structure
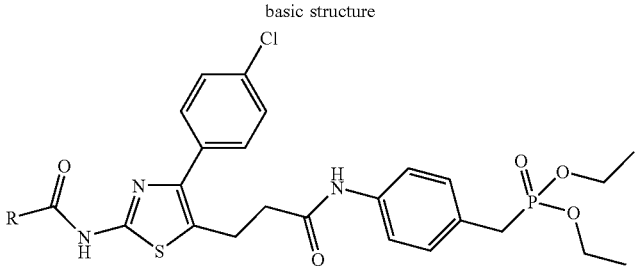
| R | |
|---|---|
| 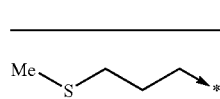 | 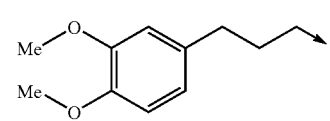 |
| Example 977 | Example 978 |
| 96%, 4.862 | 99%, 4.401 |
| 610 (M + 1) | 700 (M + 1) |
| R | |
|---|---|
| 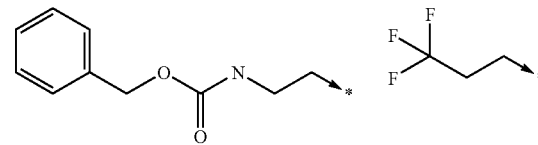 | 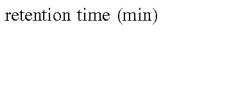 |
| Example 982 | Example 983 |
| 100%, 4.810 | 100%, 4.136 |
| 699 (M + 1) | 618 (M + 1) |
upper line: Example No.
middle line: HPLC purity (220 nm), retention time (min)
lower line: MS (APCI+, m/e)
TABLE 19-2
basic structure
| R | | |
|---|---|---|
| 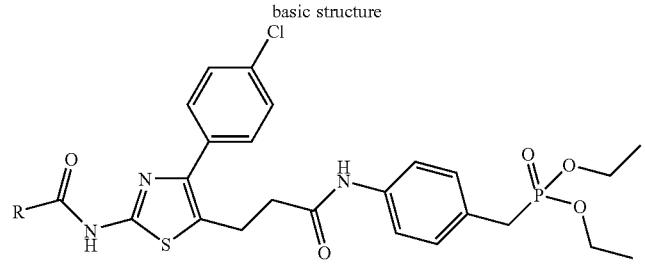 | 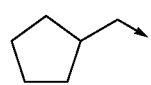 | 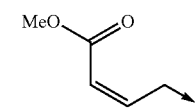 |
| Example 984 | Example 985 | Example 986 |
| 100%, 4.254 | 100%, 4.071 | 99%, 4.806 |
| 604 (M + 1) | 620 (M + 1) | 613 (M + 1) |
R TABLE 19-2-continued basic structure (as shown)

| Example 989 | Example 990 | Example 991 |
|---|---|---|
| 97%, 4.296 | 99%, 4.281 | 99%, 3.808 |
| 723 (M + 1) | 680 (M + 1) | 614 (M + 1) |

R

| Example 987 | Example 988 |
|---|---|
| 98%, 4.411 | 100%, 4.346 |
| 679 (M + 1) | 702 (M + 1) |

R

| Example 992 | Example 993 |
|---|---|
| 99%, 4.113 | 98%, 4.586 |
| 680 (M + 1) | 666 (M + 1) | upper line: Example No.
middle line: HPLC purity (200 nm), retention time (min)
lower line: MS (APCI+, m/e)

Experimental Example 1

To 6-week-old male SD rats (CLEA Japan, Inc.) was injected 70 mg/kg body weight of streptozotocin (STZ) from the tail vein to form a diabetic neuropathy model.

After raising for one month, 3 mg/kg of compound (compound of Example 5 or Example 226) suspended in 0.5% methyl cellulose was orally administered to the rats. For the control group, a 0.5% aqueous methyl cellulose suspension free of the aforementioned compound was administered.

After the completion of the administration, the rats were anesthetized with Nembutal, the body temperature was maintained at a constant level using a hot plate at 37° C. and a desk lamp, needle electrodes were placed on the above-knee region and ankle, stimulated using Neuropack 2 (NIHON KOHDEN CORPORATION) principally at 1.6 mA and the evoked potential was detected from the plantar part. The Motor Nerve Conduction Velocity (MNCV) was calculated from the distance between different electrodes and latency difference of waveforms.

After the evaluation of the nerve conduction velocity, the ischiadic nerve was taken from the rat, a lysis buffer (0.1M Tris-HCl buffer containing 1M sodium chloride, 2% BSA, 2 mM EDTA, 80 trypsin unit/L of aprotinin, pH 7.6) in a 20-fold amount of the wet weight of ischiadic nerve was added and the mixture was subjected to ultrasonication and centrifugal separation (15,000 rpm, 60 min.), and the BDNF content of the supernatant was measured.

The BDNF content was measured by sandwich ELISA Method using anti-BDNF polyclonal antibody (Promega) and biotinated anti-BDNF antibody (G1641, Promega). The results are shown in [Table 20].

TABLE 20

|  | MNCV (m/s) | BDNF (ng/g) |
| --- | --- | --- |
| control group | 45.1 ± 4.4 | 2.0 ± 0.4 |
| Compound of Example 5 administration group | 52.7 ± 5.0** | 2.6 ± 0.7** |
| Compound of Example 226 administration group | 52.3 ± 2.4** | 3.6 ± 0.4* | average value ± SD (n = 7–8)
*p < 0.05 vs. control group (t-test)
**p < 0.01 vs. control group (t-test)

As shown in [Table 20], the compound of the present invention increased motor nerve conduction velocity and nerve BDNF content.

Formulation Example 1 (Production of Capsule)

|  |  |  |
| --- | --- | --- |
| 1) compound of Example 1 | 30 mg |
| 2) cellulose fine powder | 10 mg |
| 3) lactose | 19 mg |
| 4) magnesium stearate | 1 mg |
| total | 60 mg |

1), 2), 3) and 4) are mixed and filled in gelatin capsules.

Formulation Example 2 (Production of Tablet)

|  |  |
| --- | --- |
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of 1), 2) and 3) and 30 g of 4) are kneaded with water and, after drying in vacuo, granulated. The granules are mixed with 14 g of 4) and 1 g of 5) and punched with a tableting machine. In this way, 1000 tablets containing 30 mg of the compound of Example 1 per tablet are obtained.

INDUSTRIAL APPLICABILITY

The compound of the present invention has a superior action of promoting production or secretion of a neurotrophic factor, and is useful for the prophylaxis or treatment of diabetic neuropathy and the like.

The invention claimed is:
1. A compound represented by the formula (I)

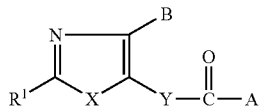

wherein $R^1$ is an optionally substituted heterocyclic group,
A is an optionally substituted cyclic amino group or —$NR^2$—W—D wherein $P^2$ is a hydrogen atom or an alkyl group,
W is a bond or a divalent acyclic hydrocarbon group,
D is an optionally substituted cyclic group, an optionally substituted amino group or an optionally substituted acyl group,
B is an optionally substituted hydrocarbon group or an optionally substituted heterocyclic group,
X is an oxygen atom, and
Y is a bond or a divalent acyclic hydrocarbon group,
or a salt thereof.

2. The compound of claim 1, wherein A is an optionally substituted cyclic amino group.

3. The compound of claim 1, wherein A is —$NR^2$—W—D wherein $R^2$ is a hydrogen atom or an alkyl group, W is a bond or a divalent acyclic hydrocarbon group, and D is an optionally substituted cyclic group, an optionally substituted amino group or an optionally substituted acyl group.

4. The compound of claim 3, wherein D is an optionally substituted cyclic group.

5. The compound of claim 1, wherein B is an optionally substituted $C_{6-14}$aryl group.

6. The compound of claim 1, wherein Y is $C_{1-4}$alkylene.

7. The compound of claim 1, which is 3-[2-(1H-benzimidazol-1-yl)-4-(4-chlorophenyl)-5-oxazolyl]-N-[4-(diethylphosphonomethyl)phenyl]propionamide;

3-[4-(4-chlorophenyl)-2-(4-morpholinyl)-5-oxazolyl]-N-[4-(diethylphosphonomethyl)phenyl]propionamide;

3-[2-(1H-benzimidazol-1-yl)-4-(4-chlorophenyl)-5-oxazolyl]-N-{4-[(2-oxide-1,3,2-dioxaphosphinan-2-yl)methyl]phenyl}propionamide;

4-[2-(1H-benzimidazol-1-yl)-4-(4-chlorophenyl)-5-oxazolyl]-N-[(4-dimethylphosphonomethyl)phenyl]butanamide;

1-{3-[2-(1H-benzimidazol-1-yl)-4-(4-chlorophenyl)-5-oxazolyl]propanoyl}-4-piperidinol;

4-{3-[2-(1H-benzimidazol-1-yl)-4-(4-chlorophenyl)-5-oxazolyl]propanoyl}thiomorpholine-1,1-dioxide;

4-[2-(1H-benzimidazol-1-yl)-4-(4-chlorophenyl)-5-oxazolyl]-N-[(4-diethylphosphonomethyl)phenyl]butanamide; or 4-{3-[4-(4-chlorophenyl)-2-(1-methyl-1H-indol-3-yl)-5-oxazolyl]propanoyl}thiomorpholine-1,1-dioxide.

8. A pharmaceutical agent comprising the compound of claim 1 or a prodrug thereof and a pharmaceutically acceptable carrier, excipient or diluent.

9. A method for the treatment of diabetic neuropathy in a mammal in need thereof, which comprises administering an effective amount of compound of claim 1 or a prodrug thereof to the mammal.

10. A method for the treatment of pain in a mammal in need thereof, which comprises administering an effective amount of compound of claim 1 or a prodrug thereof to the mammal.

* * * * *